(12) United States Patent
Gitman

(10) Patent No.: US 11,337,892 B2
(45) Date of Patent: May 24, 2022

(54) GRASPING FACILITATORS AND USES THEREOF AND KITS INVOLVING THE SAME

(71) Applicant: SCALPAL LLC, Wilmington, DE (US)

(72) Inventor: Eliot Robert Gitman, Jerusalem (IL)

(73) Assignee: SCALPAL LLC, Wilmington, DE (US)

( * ) Notice: Subject to any disclaimer, the term of this patent is extended or adjusted under 35 U.S.C. 154(b) by 292 days.

(21) Appl. No.: 16/396,997

(22) Filed: Apr. 29, 2019

(65) Prior Publication Data

US 2019/0247278 A1 Aug. 15, 2019

Related U.S. Application Data

(63) Continuation-in-part of application No. 15/977,431, filed on May 11, 2018, and a continuation-in-part of application No. 15/977,358, filed on May 11, 2018, now Pat. No. 11,234,899, and a continuation-in-part
(Continued)

(51) Int. Cl.
| | |
|---|---|
| *A61B 1/06* | (2006.01) |
| *A61J 1/20* | (2006.01) |
| *A61J 1/16* | (2006.01) |
| *A61M 5/31* | (2006.01) |

(Continued)

(52) U.S. Cl.
CPC .............. *A61J 1/2055* (2015.05); *A61J 1/16* (2013.01); *A61M 5/3137* (2013.01); *A61M 5/3213* (2013.01); *A61M 2005/3139* (2013.01); *A61M 2005/3215* (2013.01); *A61M 2209/04* (2013.01); *A61M 2209/084* (2013.01); *F16M 13/005* (2013.01)

(58) Field of Classification Search
CPC ........ A61J 1/2055; A61J 1/16; A61M 5/3137; A61M 5/3213; A61M 2005/3139; A61M 2005/3215; A61M 2209/04; A61M 2209/084; F16M 13/005
USPC ......................................................... 220/737
See application file for complete search history.

(56) References Cited

U.S. PATENT DOCUMENTS

| | | | | |
|---|---|---|---|---|
| 6,471,514 | B2 * | 10/2002 | Beck | ........................ A61C 3/00 433/141 |
| 8,745,825 | B2 | 6/2014 | Gitman et al. | |
| 8,844,099 | B2 | 9/2014 | Puig | |

(Continued)

FOREIGN PATENT DOCUMENTS

| | | |
|---|---|---|
| CN | 201023742 Y | 2/2008 |
| WO | 2010/037250 A1 | 4/2010 |

*Primary Examiner* — Don M Anderson
*Assistant Examiner* — Elizabeth J Volz
(74) *Attorney, Agent, or Firm* — Smith, Gambrell & Russell, LLP

(57) ABSTRACT

A grasping collar is featured that has a flexible main body having an exterior surface with surface cavities configured for finger reception; a hole extending within an interior region of the body along an X-axis direction and being a through-hole relative to the body; an elongated slit extending in the X-axis direction, and in a radially inward direction from an exterior surface of the body into communication with the hole, the elongated slit including a thinner slit section extending in the X-axis direction for a portion of an overall length of the body as well as a wider slit section extending in the X-axis direction for a remaining portion of the overall length of the body. Methods of utilizing and assembling the grasping collar are also featured.

38 Claims, 116 Drawing Sheets

Related U.S. Application Data of application No. 14/939,150, filed on Nov. 12, 2015, now Pat. No. 10,940,086.

(60) Provisional application No. 62/505,034, filed on May 11, 2017.

(51) Int. Cl.
*A61M 5/32* (2006.01)
*F16M 13/00* (2006.01)

(56) References Cited

U.S. PATENT DOCUMENTS

| | | |
|---|---|---|
| 9,179,975 B2 | 11/2015 | Gitman |
| 10,940,086 B2 | 3/2021 | Gitman et al. |
| 2008/0179353 A1 | 7/2008 | Maymon |
| 2010/0140431 A1 | 6/2010 | Van Horne |
| 2013/0197317 A1* | 8/2013 | Daniel .................. A61B 90/35 600/249 |
| 2015/0072304 A1 | 3/2015 | Swatton et al. |
| 2015/0148596 A1 | 5/2015 | Gitman |
| 2018/0325774 A1 | 11/2018 | Gitman et al. |
| 2018/0325776 A1 | 11/2018 | Gitman et al. |

\* cited by examiner

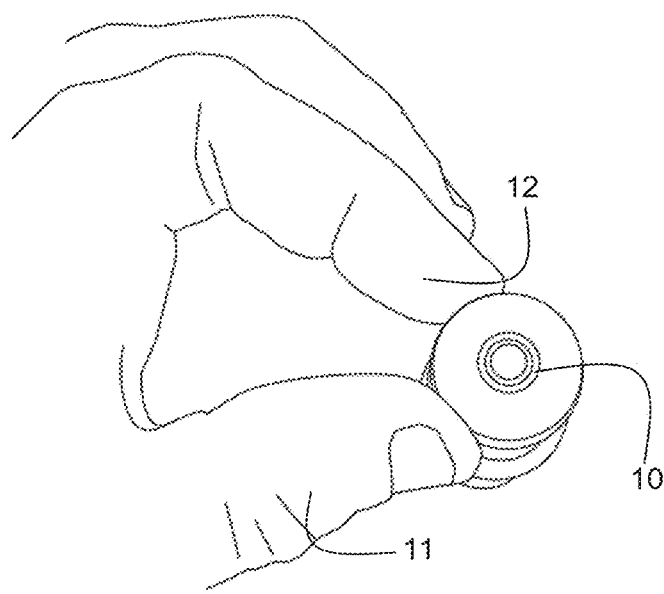
FIG. 1A (Prior Art)
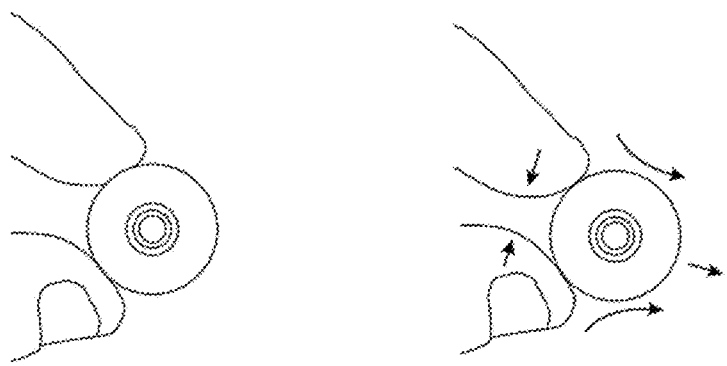
**FIG. 1B
(Prior Art)**
**FIG. 1C
(Prior Art)**
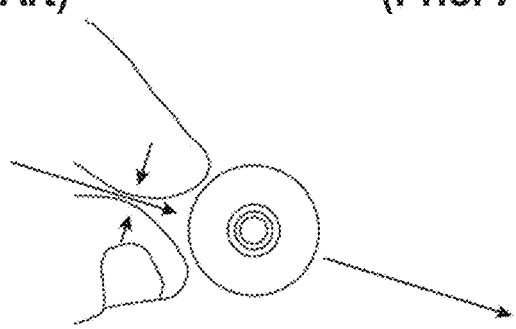
**FIG. 1D
(Prior Art)**

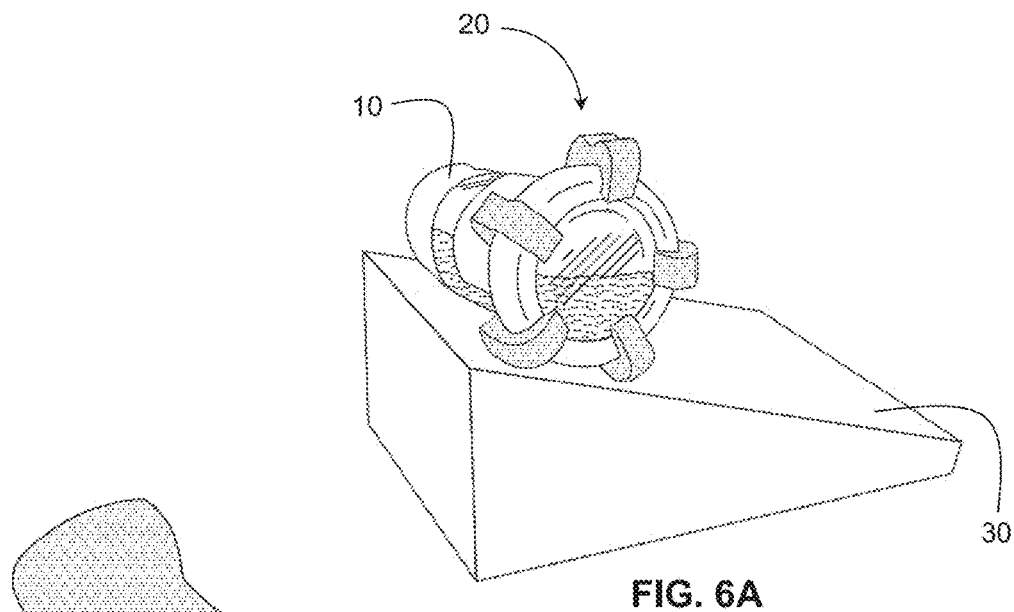
FIG. 6A
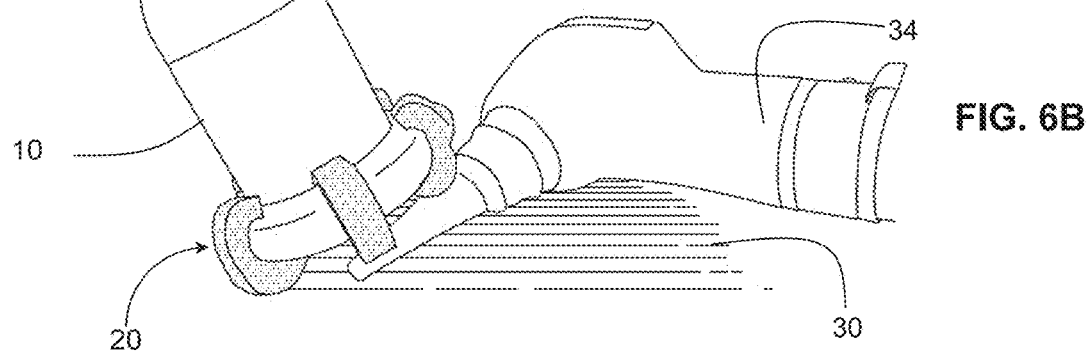
FIG. 6B
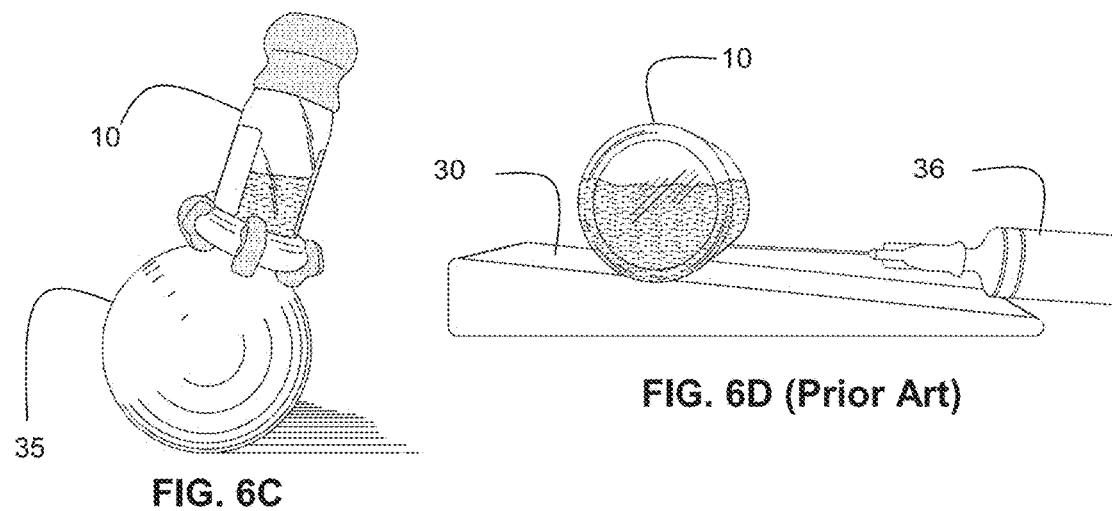
FIG. 6C
FIG. 6D (Prior Art)

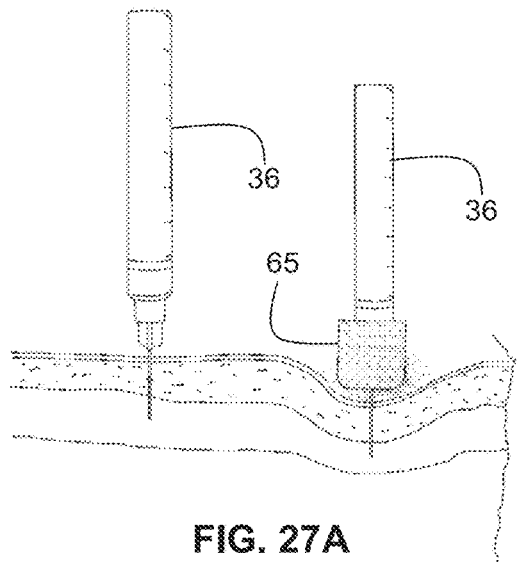
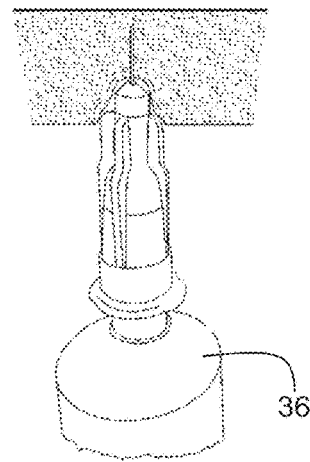
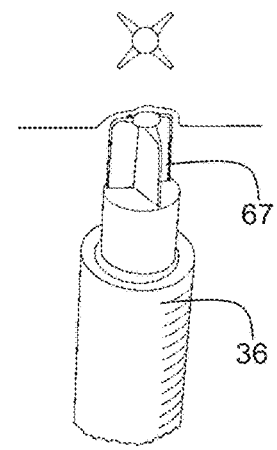
FIG. 27A  FIG. 27B (Prior art)  FIG. 27C (Prior art)
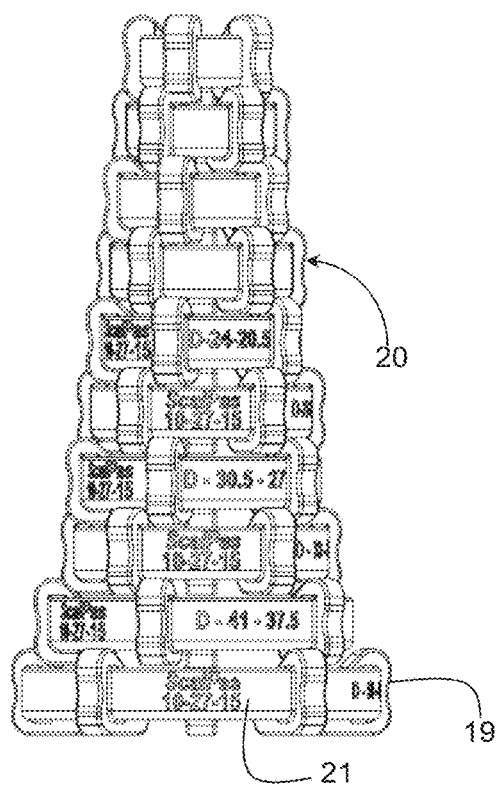
FIG. 28
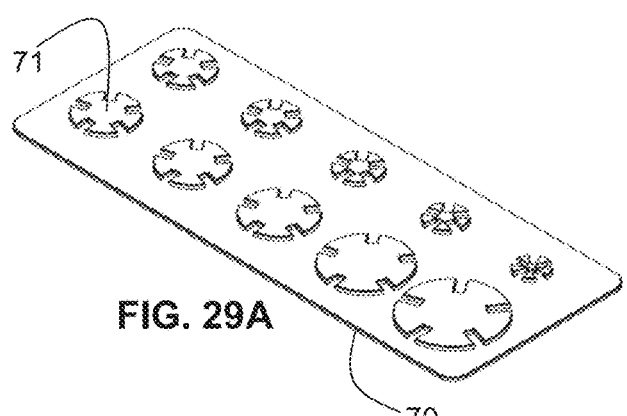
FIG. 29A
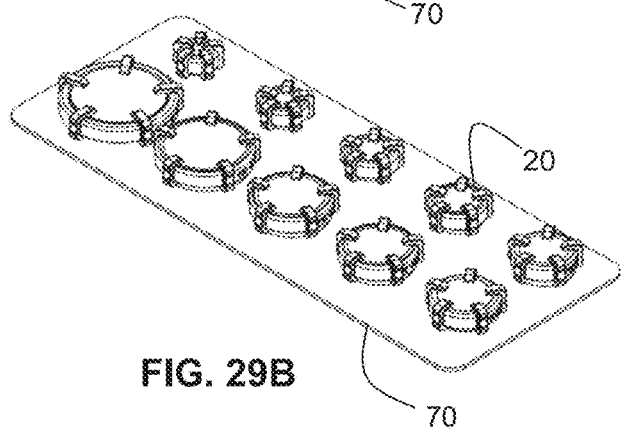
FIG. 29B

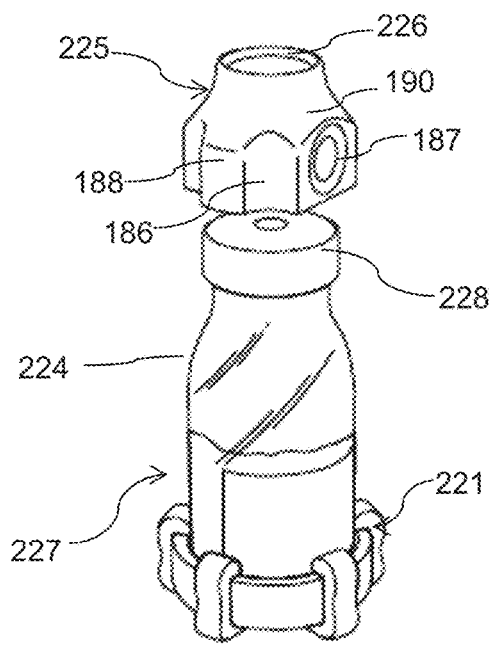
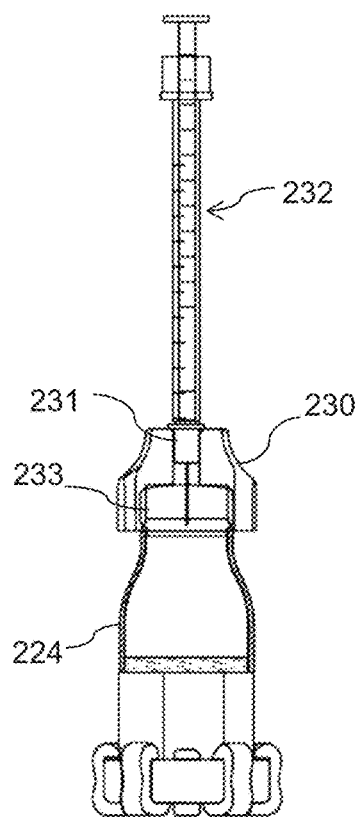
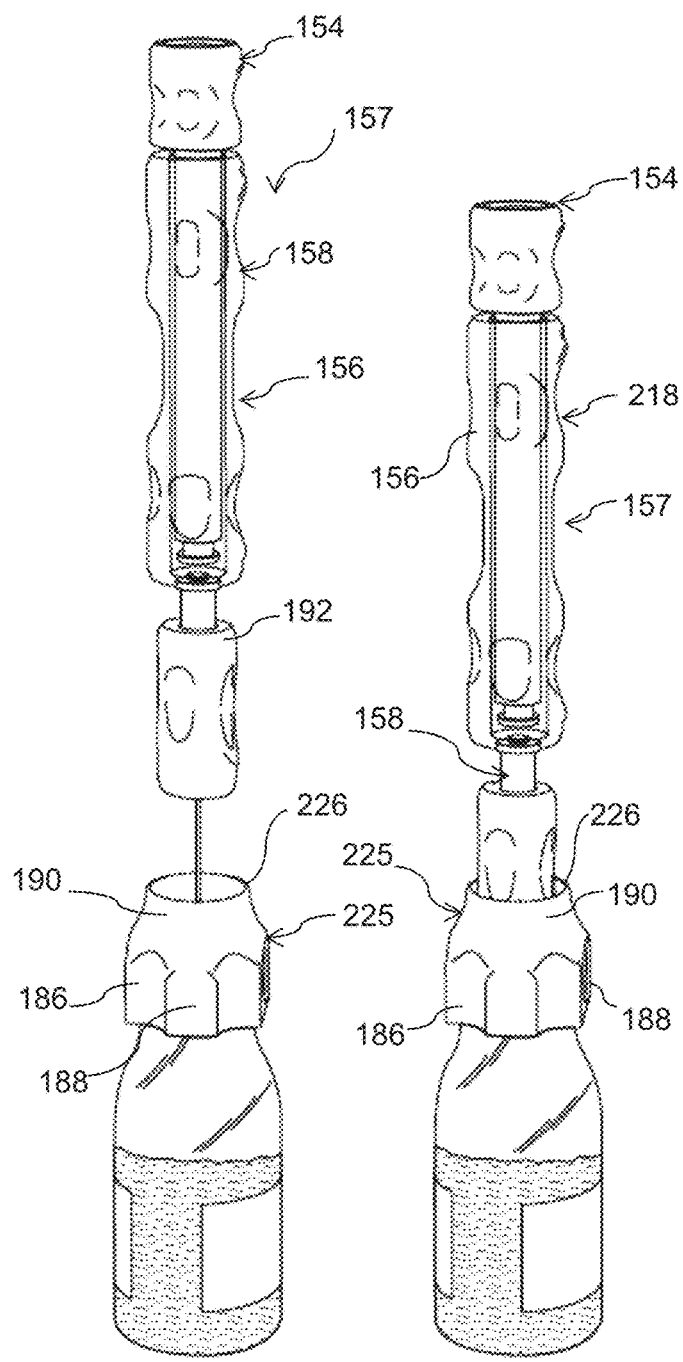
FIG. 59
FIG. 60
FIG. 61
FIG. 62

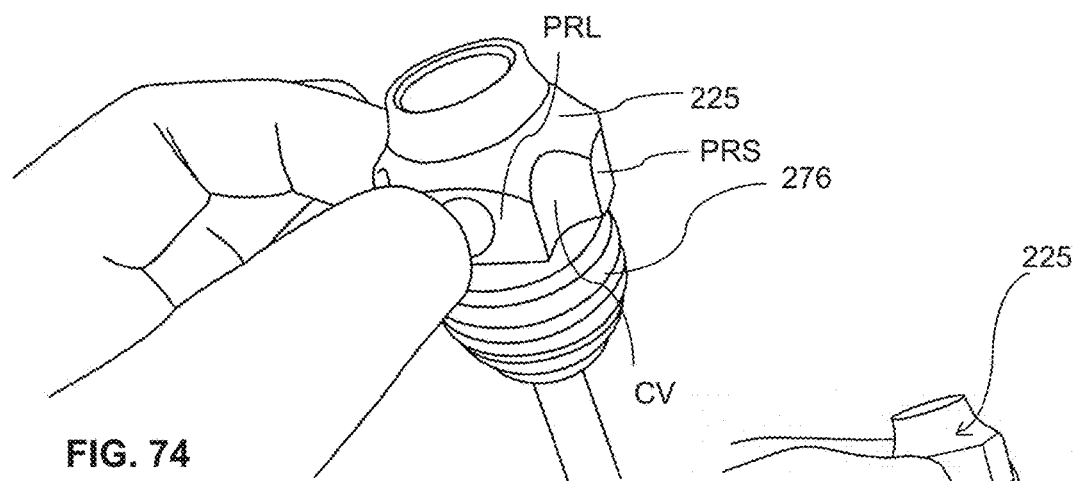
FIG. 74
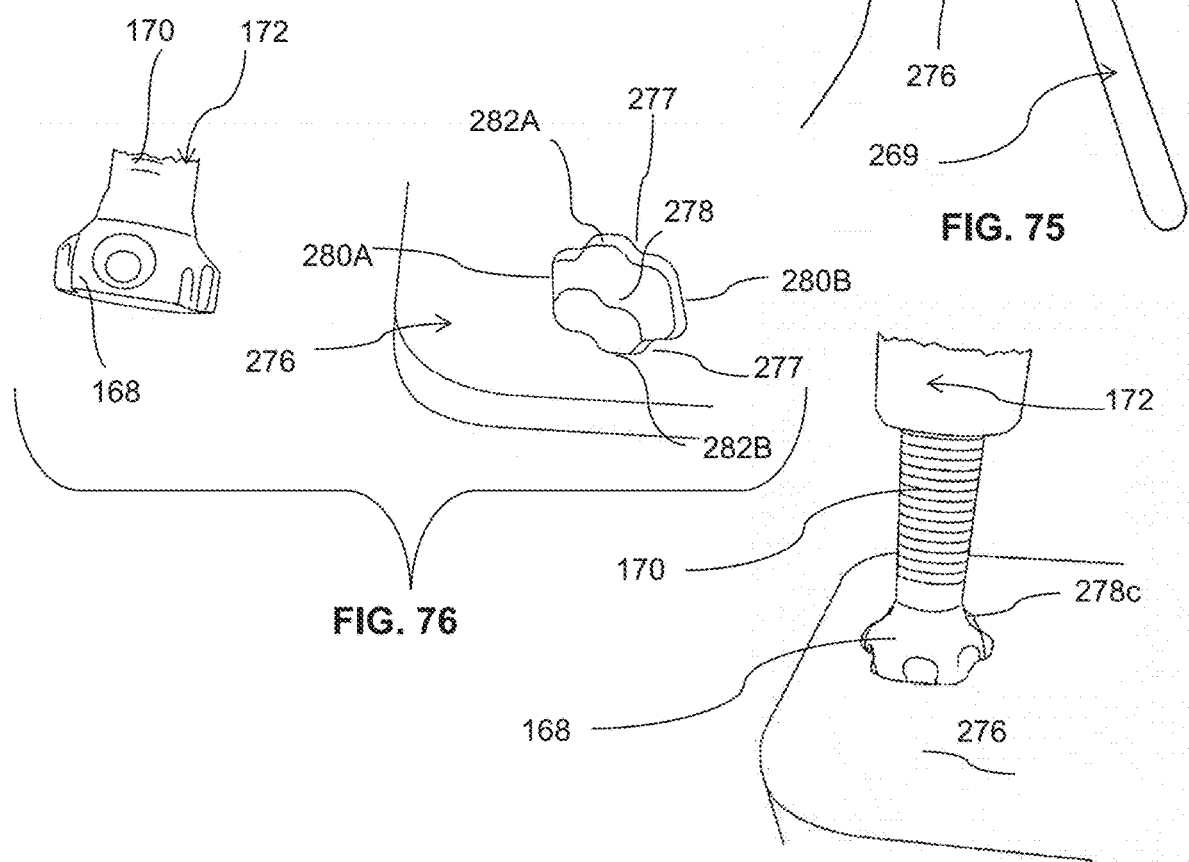
FIG. 75
FIG. 76
FIG. 77

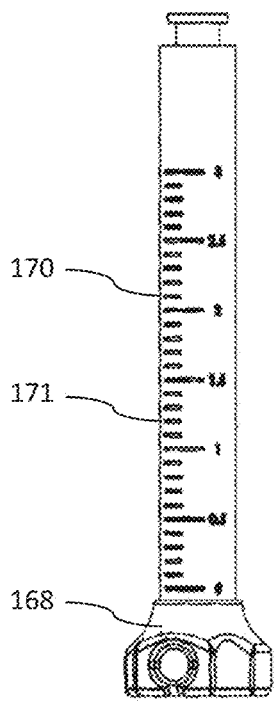
FIG. 77A
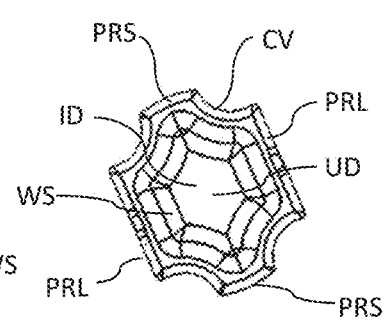
FIG. 77B
FIG. 77C
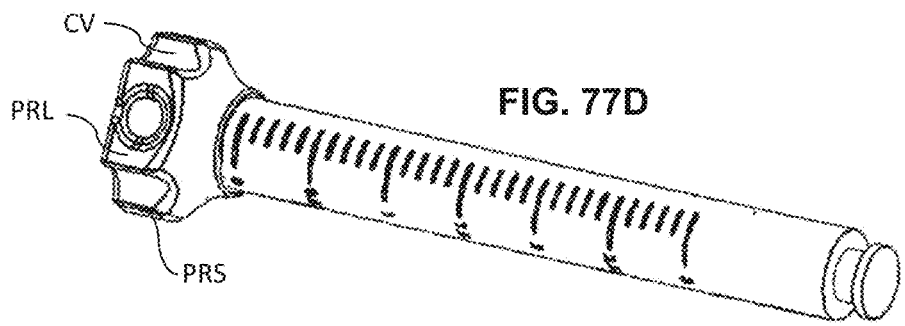
FIG. 77D
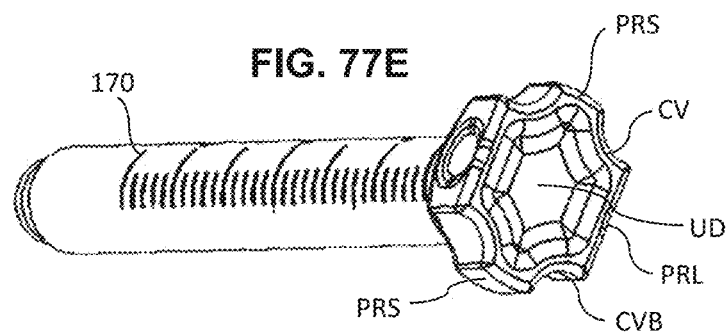
FIG. 77E

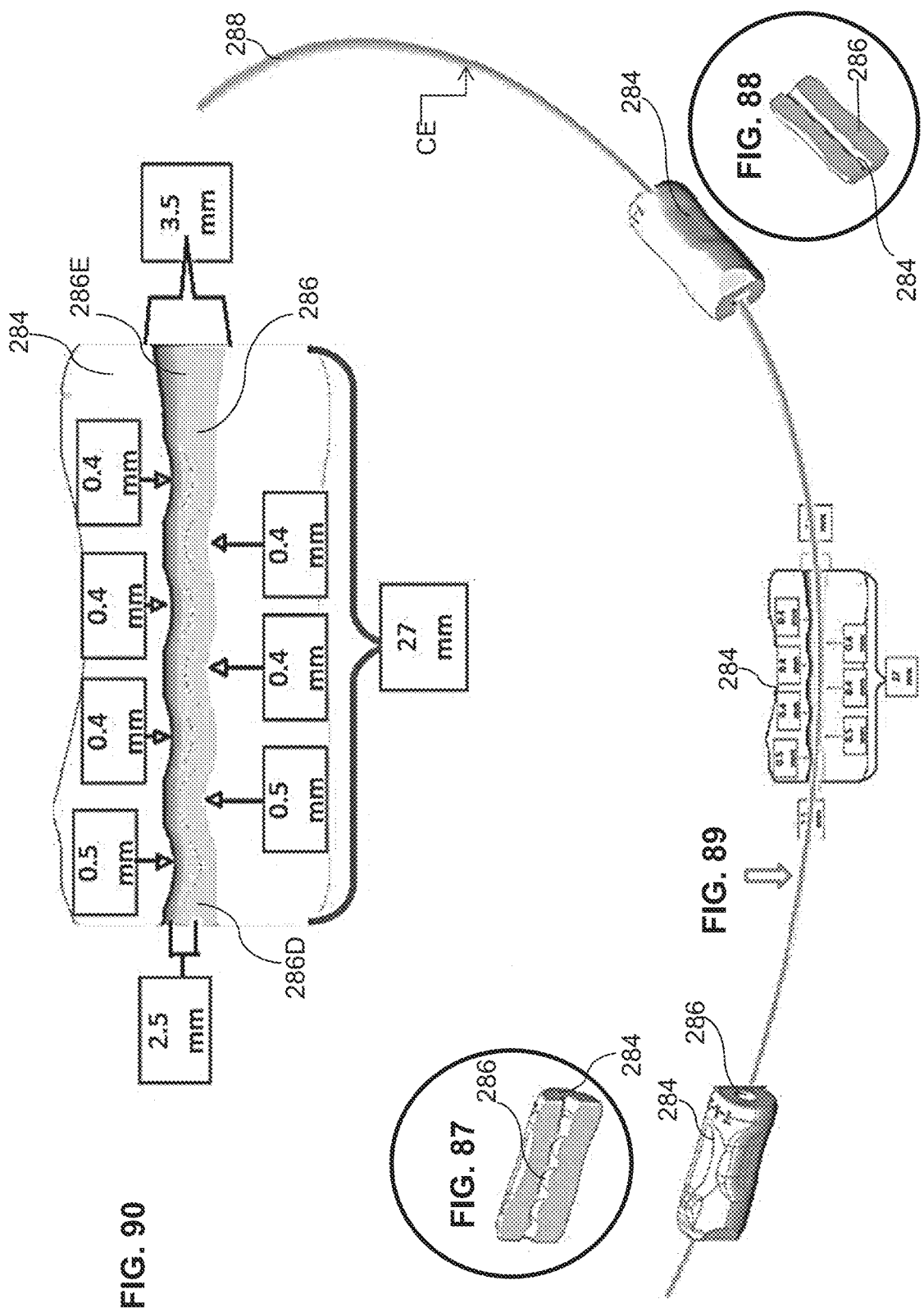

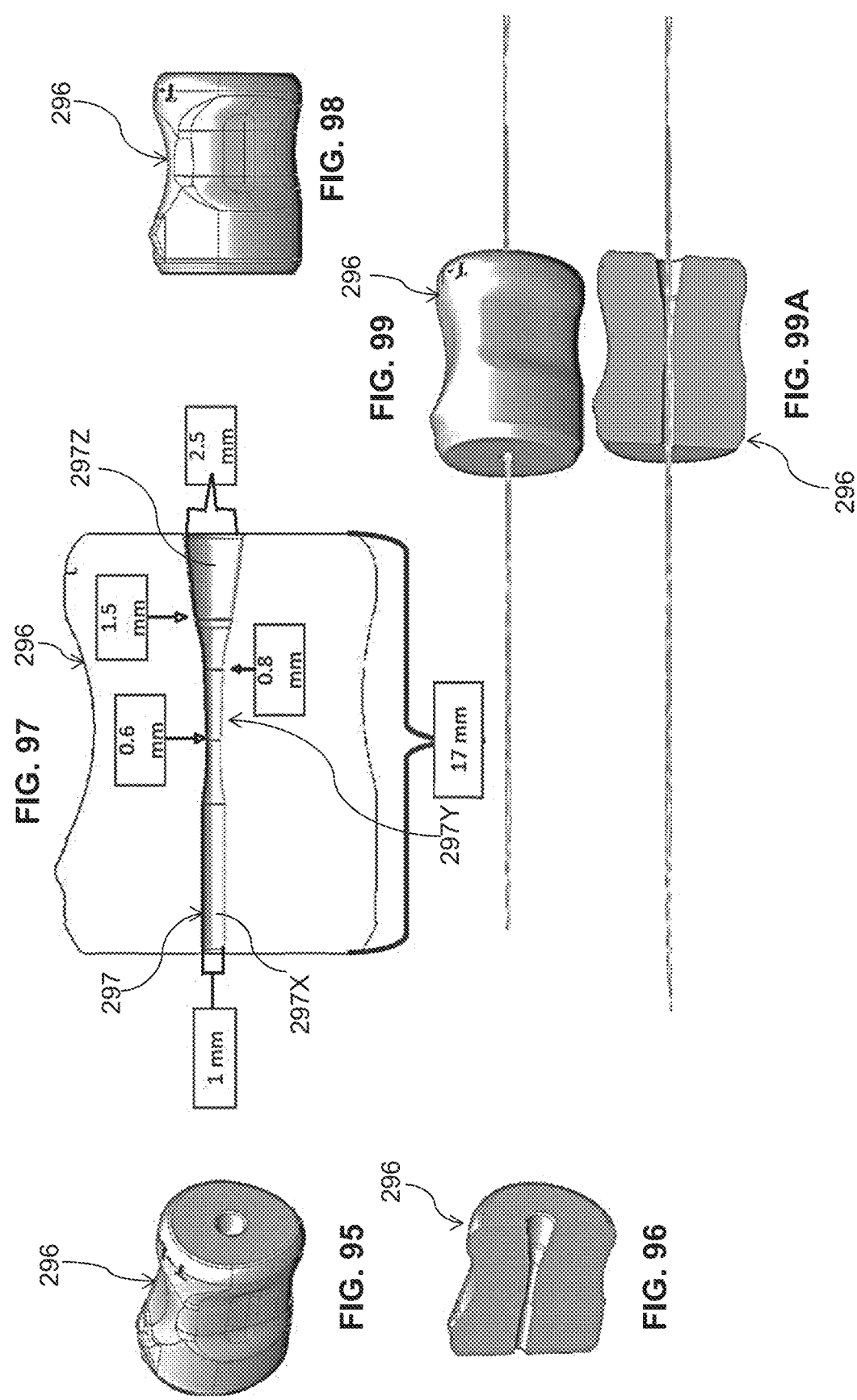

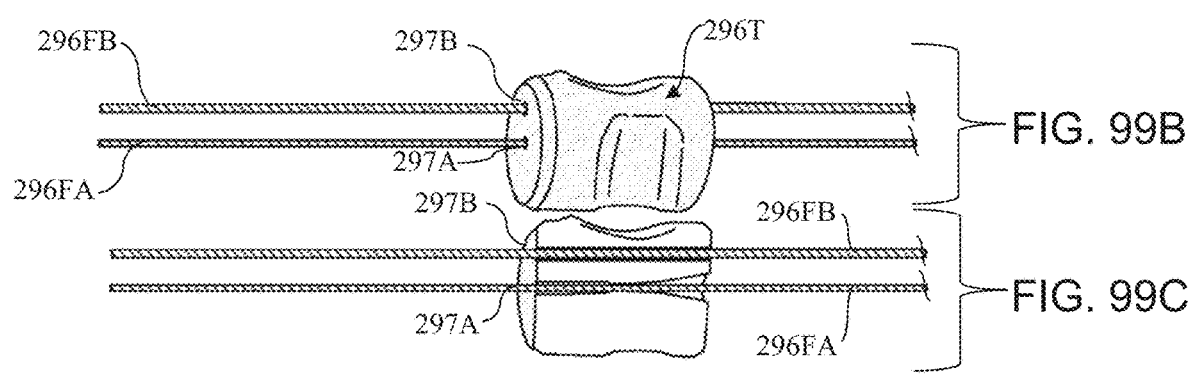

Sleeve Covered by one of more of the following Patents:
US 8,745,825

Total Length 22mm Entry angle 60-40 degrees

IV Needle Sleeve
Diameter: L12-D2-
L2D3-L4D3.5.
Total Length
18mm Entry angle
60-40 degrees Soft Shot Sleeve
Diameter: L12-D2-
L2D3L4D4-L4D6.
Total Length 22mm
Entry angle 60-40
degrees
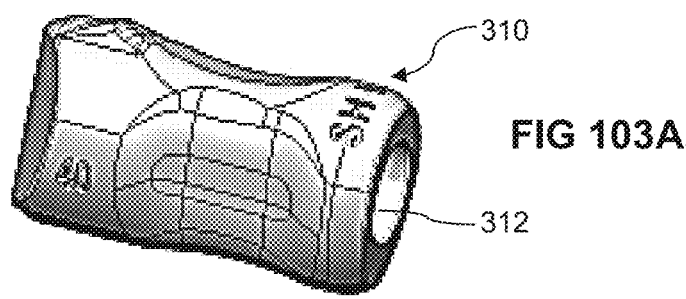
FIG 103A
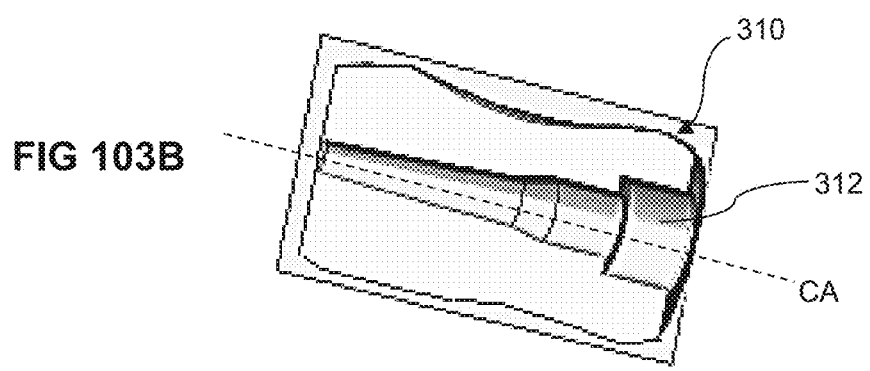
FIG 103B
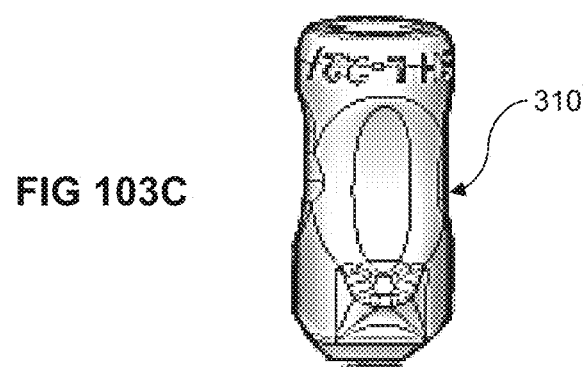
FIG 103C
FIG 103D

Soft Shot Sleeve:
Length 17?-14

Soft Shot Sleeve
Diameter: 3.8
Length 11mm
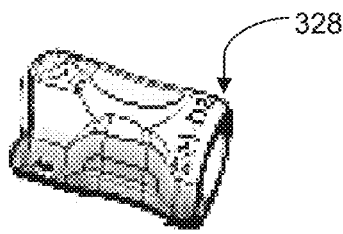
FIG 105A
FIG 105B
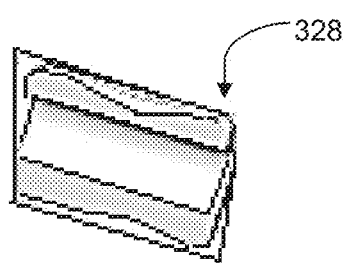
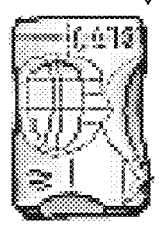
FIG 105C
FIG 105D
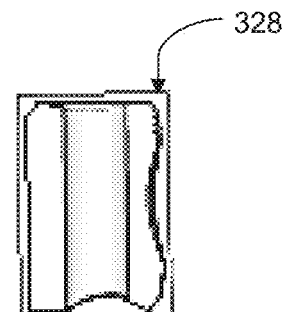

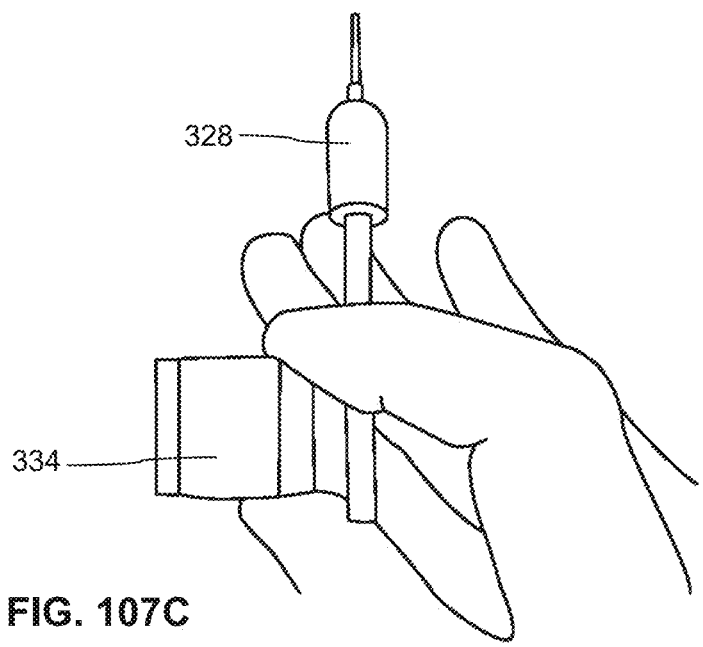
FIG. 107C
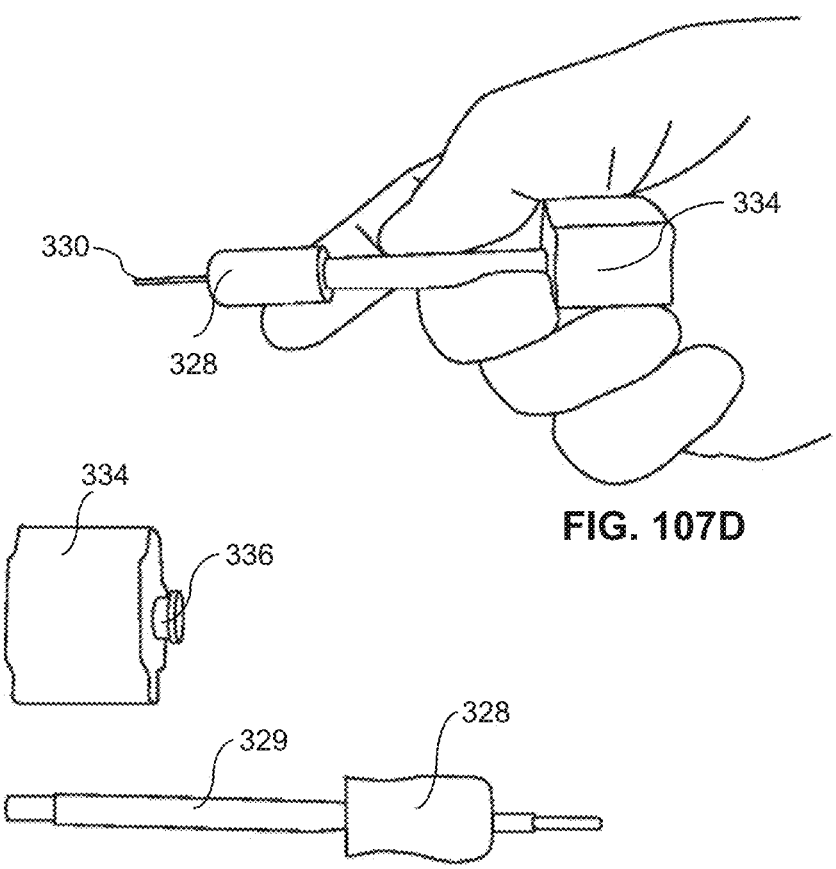
FIG. 107D
FIG. 107E

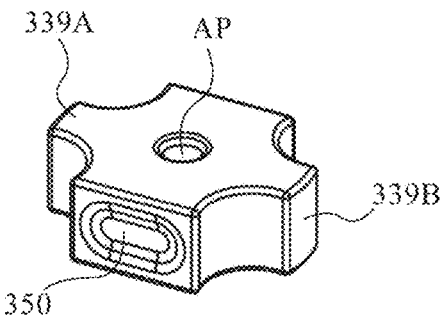
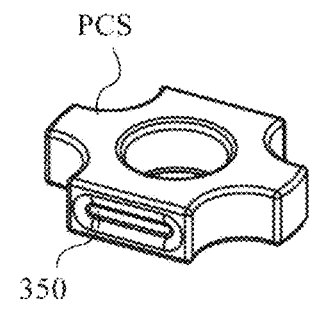
FIG. 109I    FIG. 109J
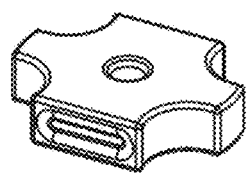
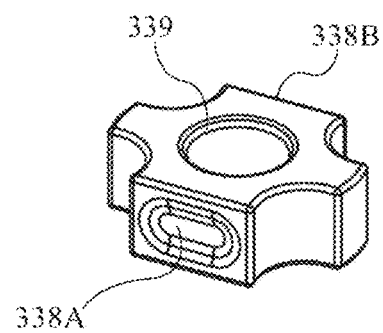
FIG. 109K    FIG. 109L
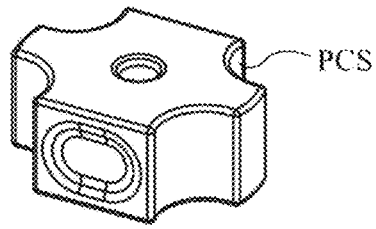
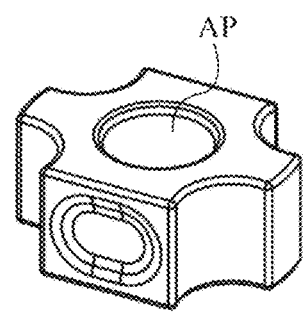
FIG. 109M    FIG. 109N

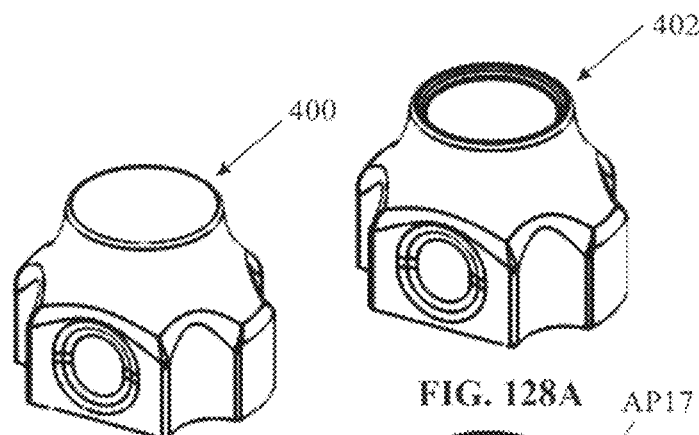
FIG. 127A  FIG. 128A
FIG. 127B  FIG. 128B
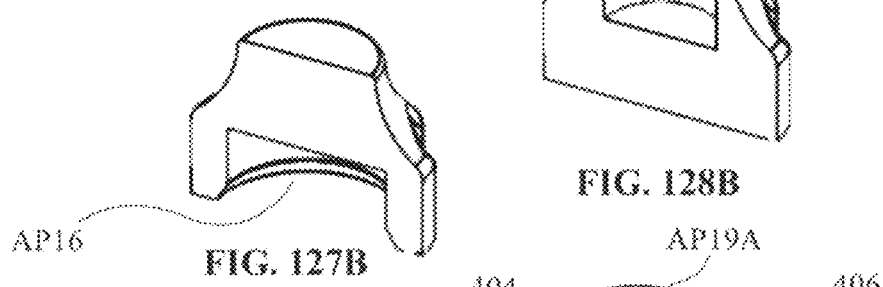
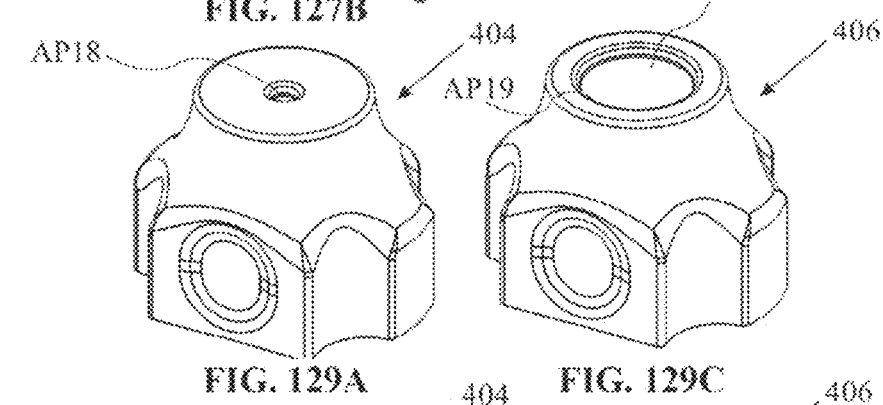
FIG. 129A  FIG. 129C
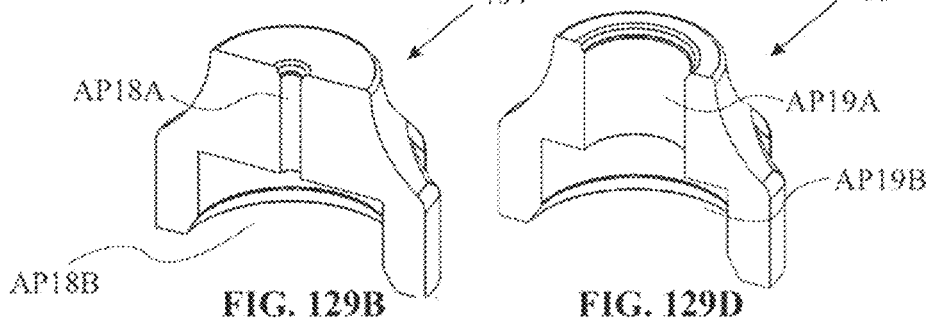
FIG. 129B  FIG. 129D

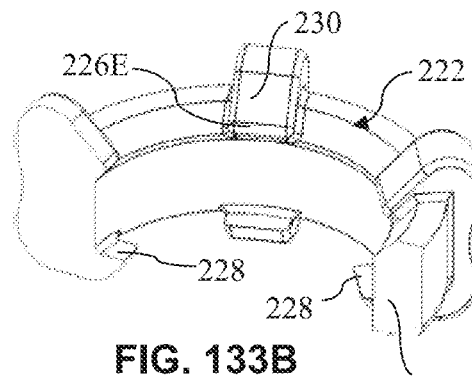
FIG. 133B
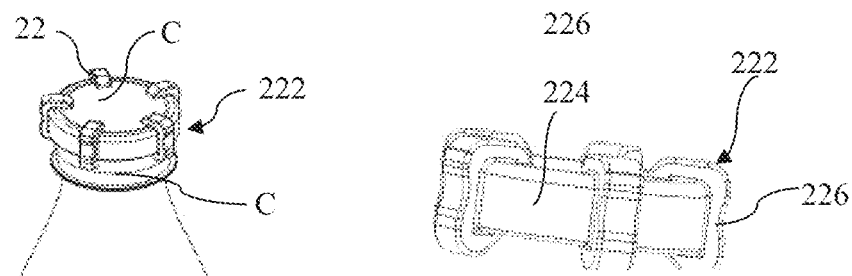
FIG. 133C
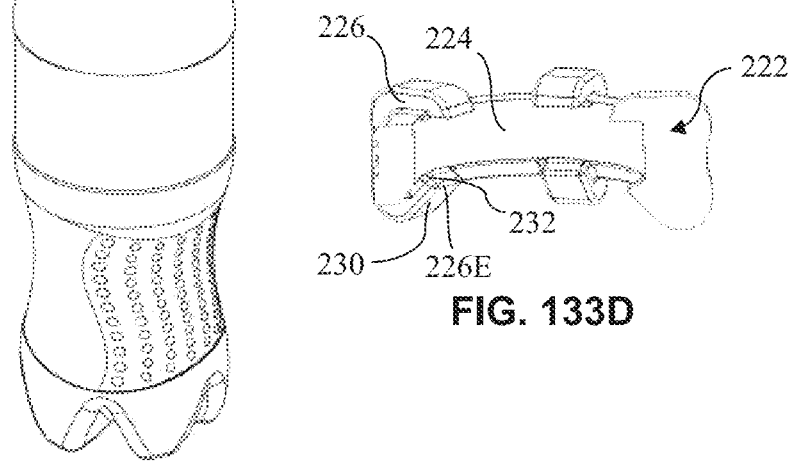
FIG. 133A
FIG. 133D
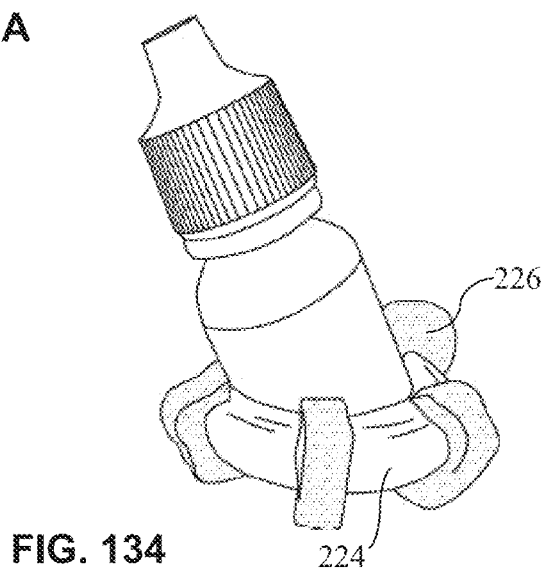
FIG. 134

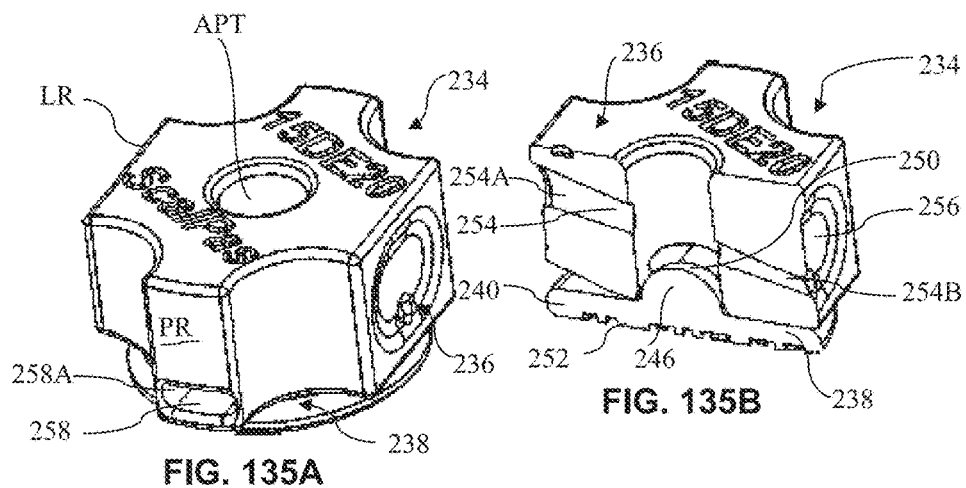
FIG. 135A
FIG. 135B
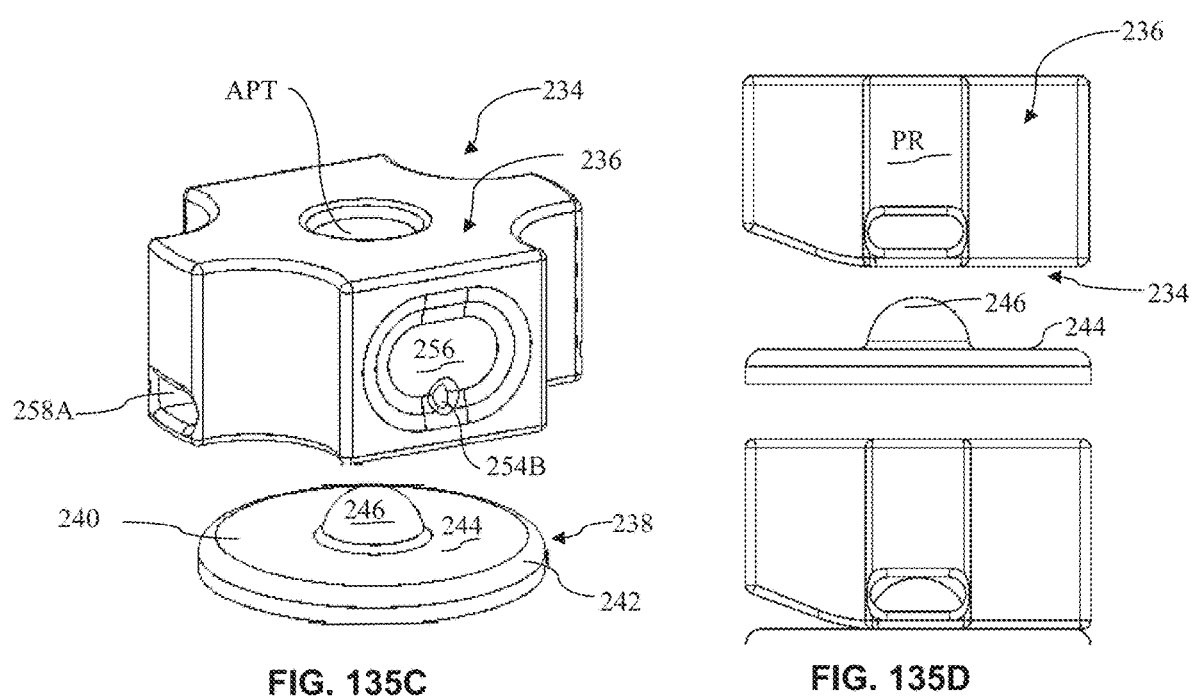
FIG. 135C
FIG. 135D

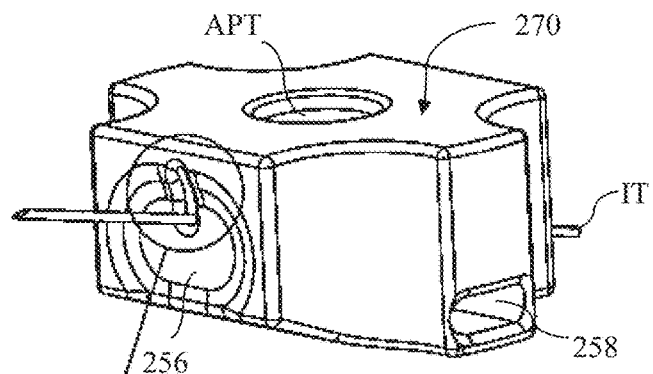
FIG. 137
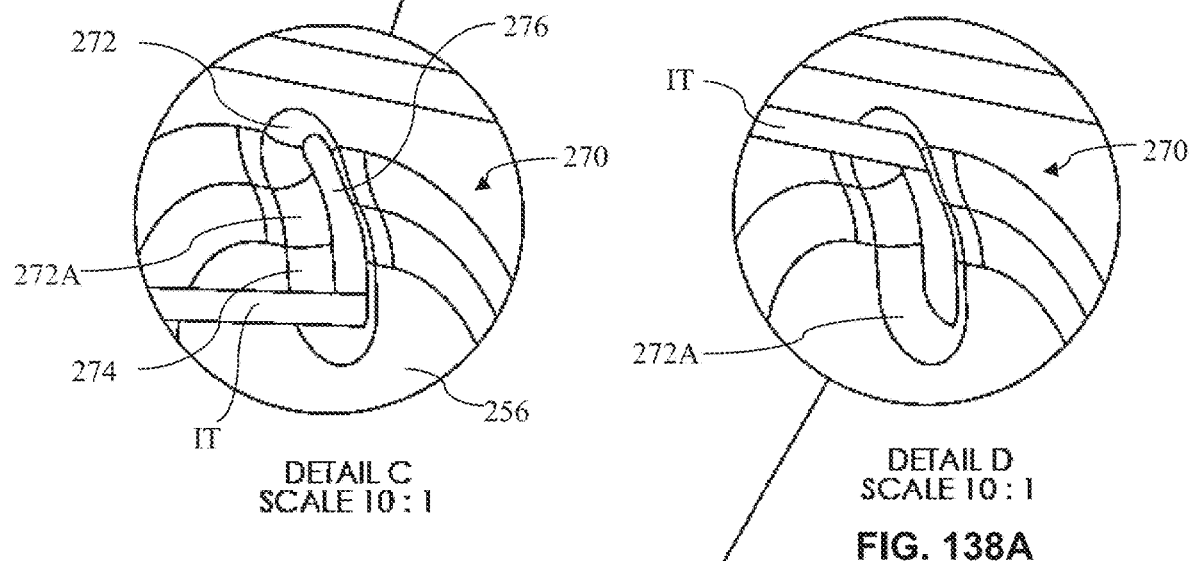
DETAIL C
SCALE 10 : 1
FIG. 137A
DETAIL D
SCALE 10 : 1
FIG. 138A
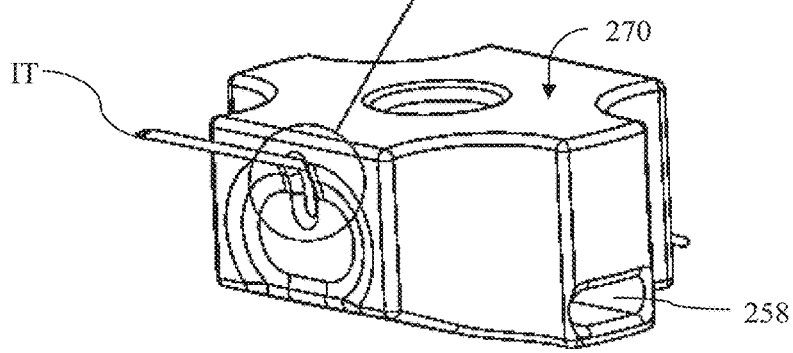
FIG. 138

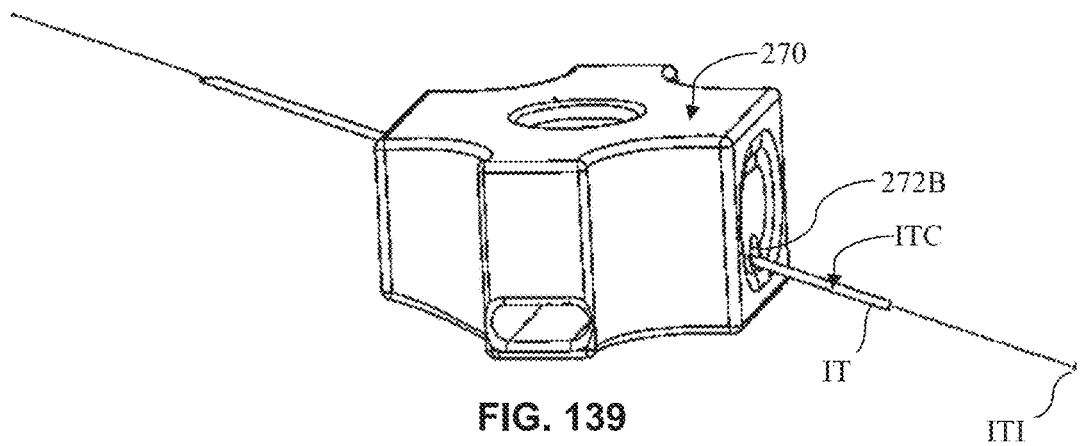
FIG. 139
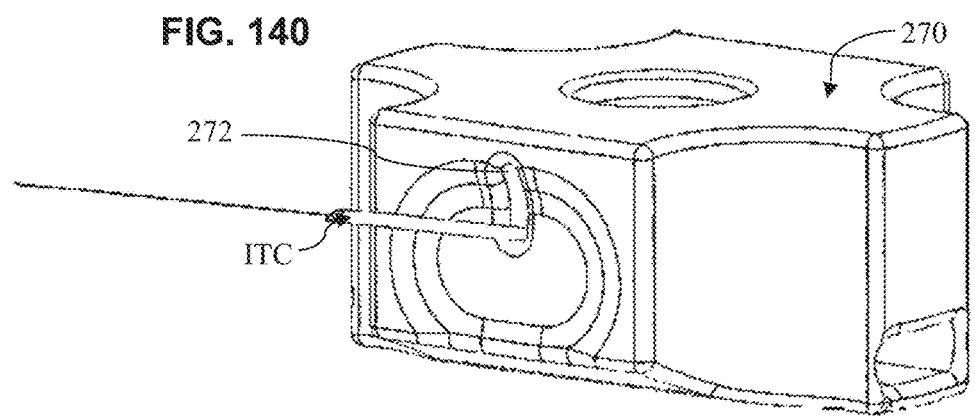
FIG. 140
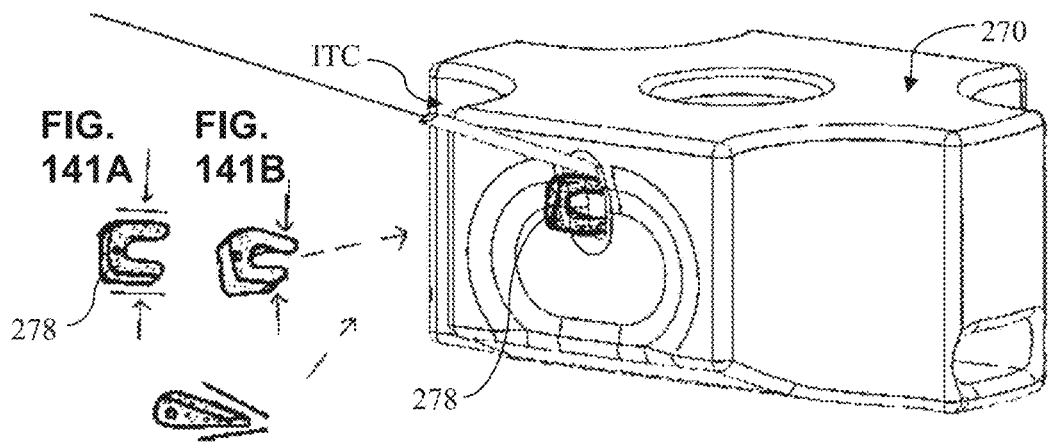
FIG. 141A  FIG. 141B
FIG. 141C
FIG. 141

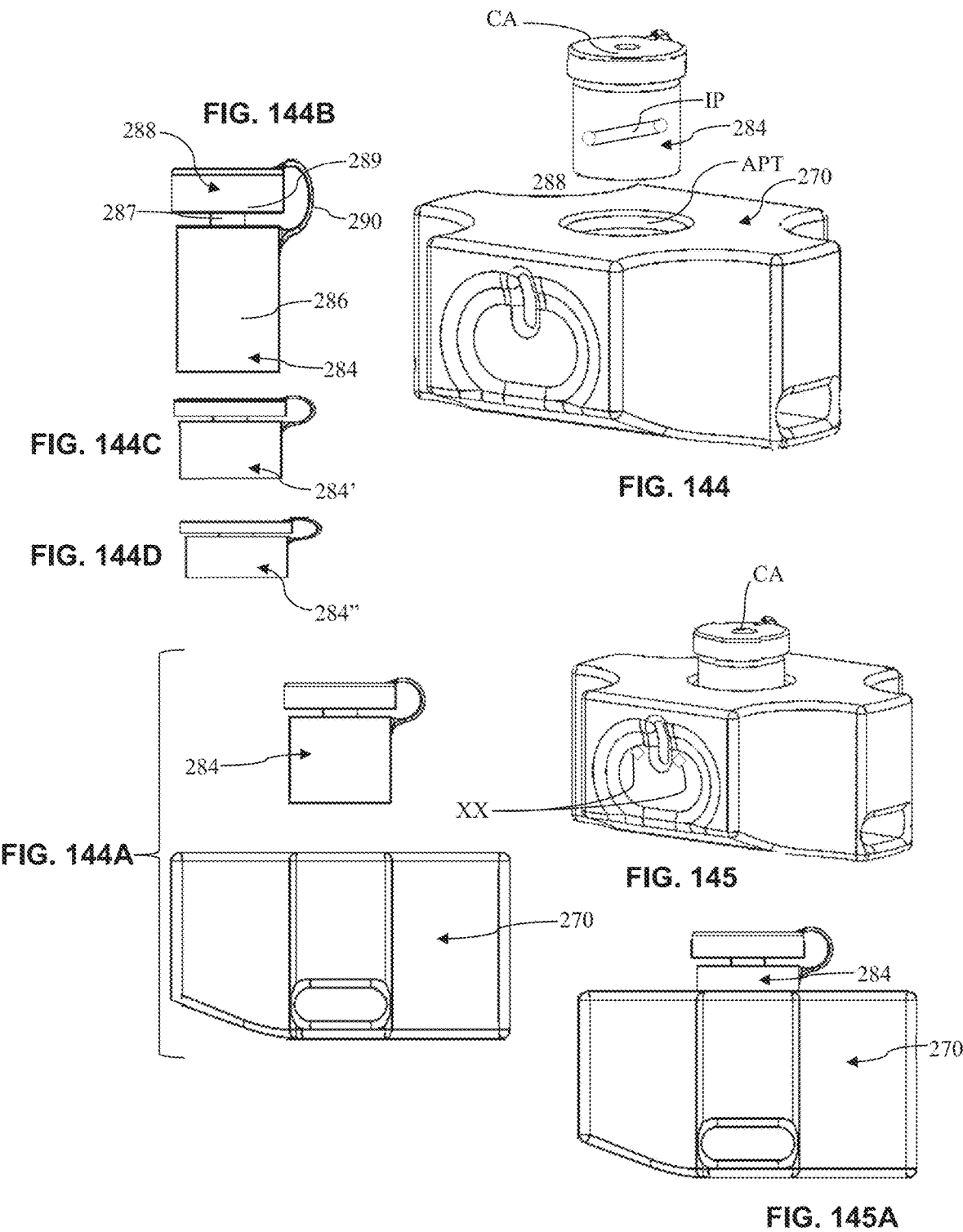

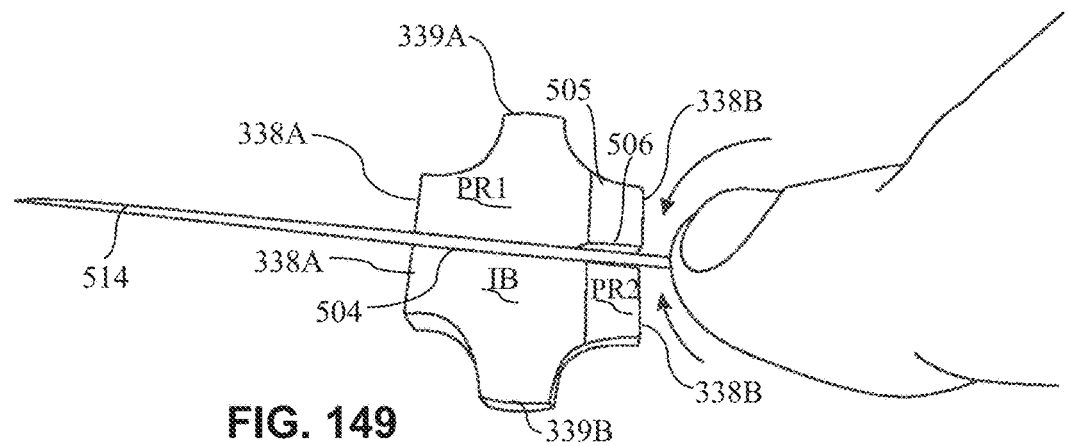
FIG. 149
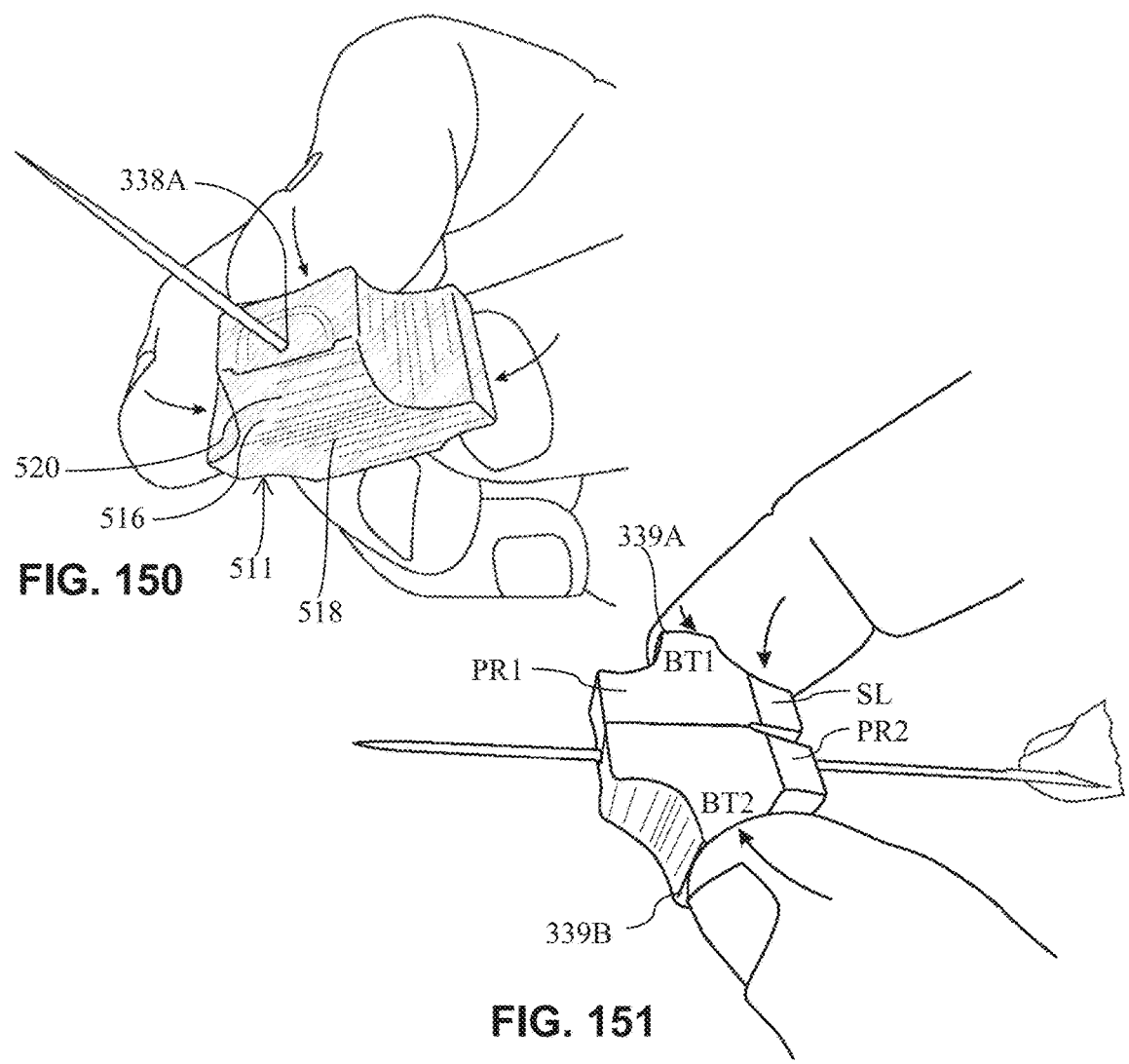
FIG. 150
FIG. 151

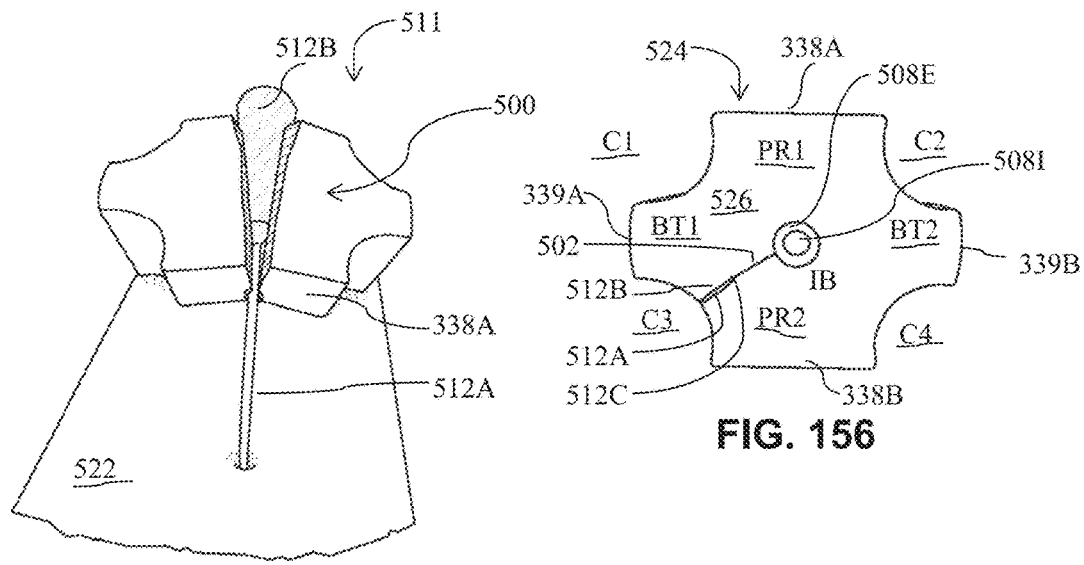
FIG. 155
FIG. 156
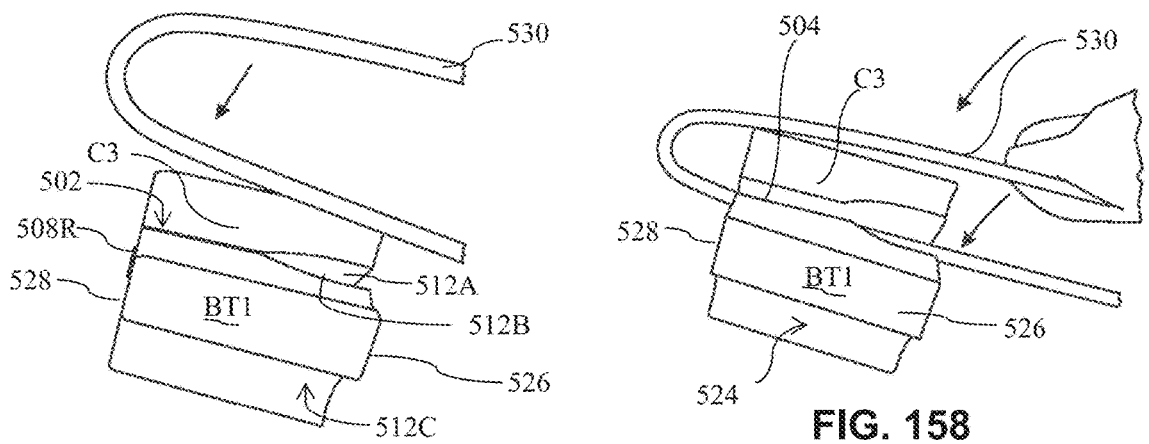
FIG. 157
FIG. 158
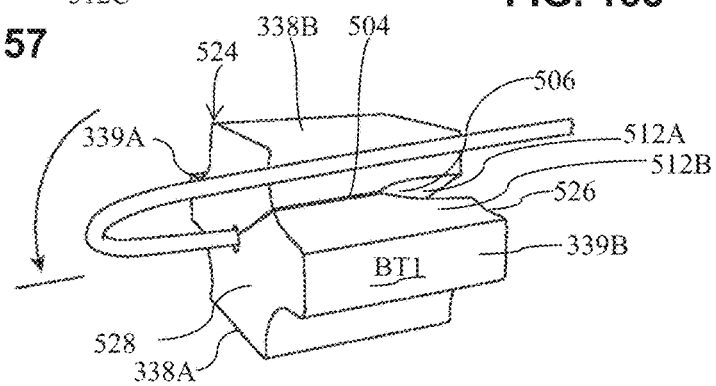
FIG. 159

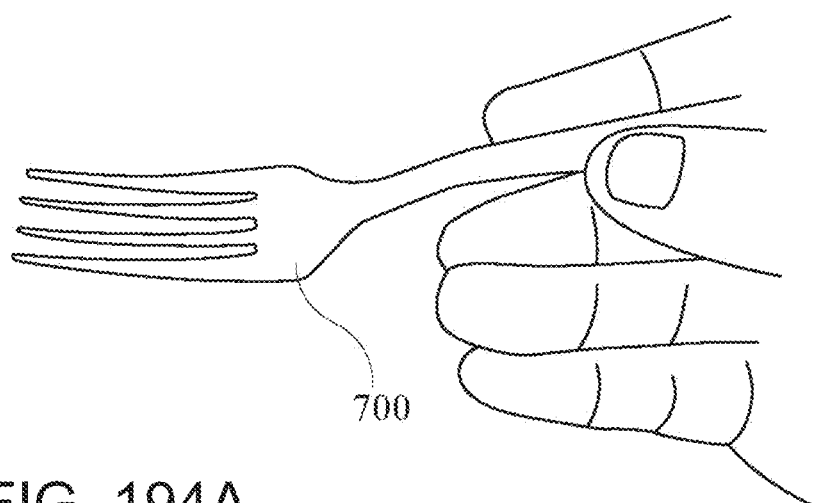
FIG. 194A
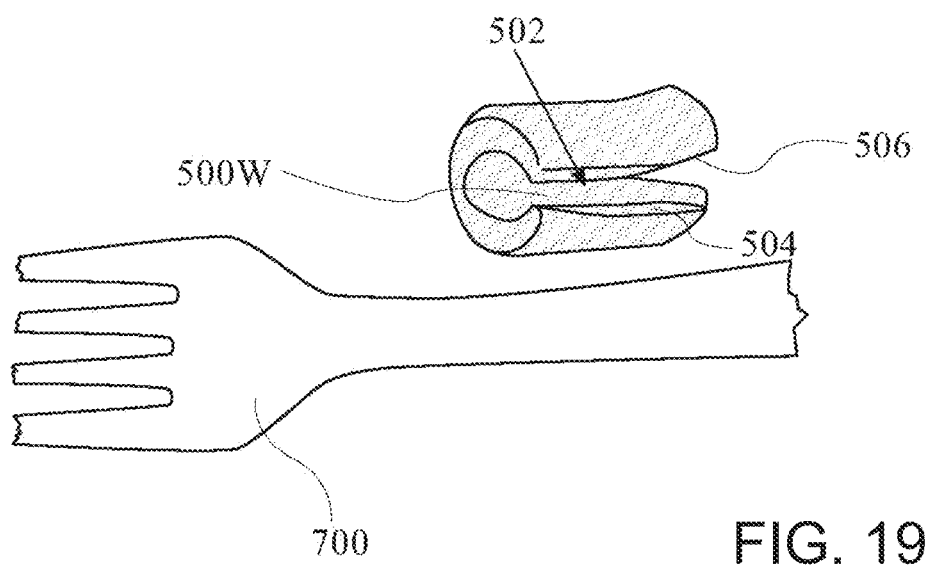
FIG. 194B1
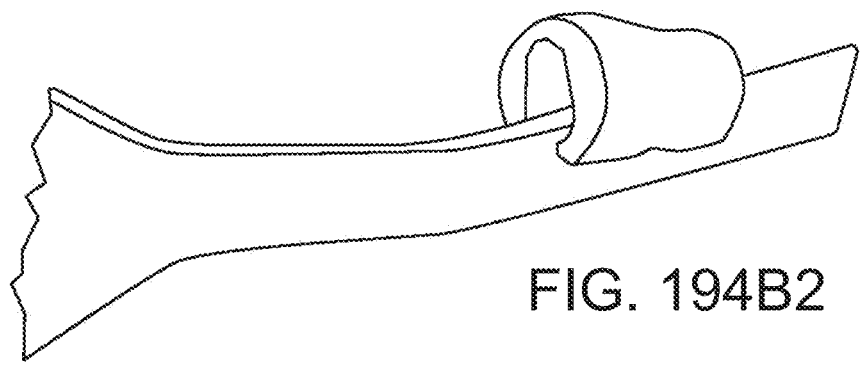
FIG. 194B2

GRASPING FACILITATORS AND USES THEREOF AND KITS INVOLVING THE SAME

PRIORITY

The present invention is a Continuation-in-Part of each of U.S. Ser. No. 15/977,358, filed May 11, 2018; U.S. Ser. No. 15/977,431, filed May 11, 2018, and U.S. Ser. No. 14/939,150 filed Nov. 12, 2015, each of which applications is incorporated herein by reference in its entirety. The present invention also claims priority to U.S. Provisional Patent Application Ser. No. 62/505,034; filed May 11, 2017, which is also incorporated herein by reference in its entirety.

FIELD OF THE INVENTION

This invention relates to grasping facilitators, inclusive of utensil or instrument support mounts and adaptable collars or sleeves, either alone or in combination, with embodiments of such grasping facilitators being usable in the medical field, for example.

BACKGROUND OF THE INVENTION

Various objects such as bottles (e.g., medical vials) are inherently unstable owing to their cylindrical geometry, which renders them prone to slip and roll. Likewise, if inadvertently tilted, they are apt to tip and spill their contents if open or insufficiently sealed. This is at best a nuisance but can be hazardous if the contents are chemicals or medicines. There are many different types of bottle supports in the prior art, some of which attempt to address these issues.

In addition to the need to support bottles of different sizes on a flat surface, there is also a need to lift and hold bottles securely. FIGS. 1A, 1B, 1C and 1D show pictorially the tendency for round and cylindrical objects 10 to slip when grasped between thumb 11 and forefinger 12. When a gripping force is applied as shown in FIG. 1C between points on the side surfaces of a cylindrical object 10 that are not diametrically opposite each other, a component of the gripping force acts to push the object out of the user's grip. This tendency is increased if friction between the user's fingers and the outer surface of the object is reduced, such as when a bottle is gripped with wet or soapy hands. This tendency to slip from the user's grip is equally true for bottle supports of the type described in US 2010/0140431 owing to the smooth side surface of the cylindrical ring.

FIGS. 2A and 2B show a bottle 10 gripped non-diametrically between the thumb 11 and forefinger 12 of a user's hand. If the segment that is closer to the center 13 of the oblique arch between thumb and forefinger and bound by the points at which the bottle is gripped has an area less than half that of the bottle's cross-section, the gripping force will have a tangential component that urges the bottle away from the center 13 of the oblique arch. The bottle 10 will then slip out of the user's hand. Conversely, if the area of this segment is greater than half that of the bottle's cross-section, the gripping force will have a tangential component that urges the bottle toward the center 13 of the oblique arch into the user's hand. In either case, the transverse grip on the bottle will be lost and the bottle will slip.

The need to support bottles stably becomes all the more urgent when the bottles contain medicines and other liquid contents that are required to be removed or injected. For example, liquid medicine bottles are often provided with a re-sealable cap through which a hypodermic needle is inserted in order to withdraw a quantity of liquid. Alternatively, liquid in a hypodermic syringe may need to be injected into a vial or other container. Both of these operations require that the vial or bottle be retained securely on a support surface, possibly inclined to the horizontal, in order to provide direct access to the cap and ensure visual alignment thereof to the tip of the hypodermic needle.

There is therefore a need for a device that allows the bottle to be disposed stably on a support surface while allowing it to be gripped securely and reliably without the associated risk of slippage, particularly when gripped using wet hands.

In addition to the problem of rolling and tilting of bottles and the like, there is another, and in some respects associated, problem of handling bottles securely when filling them or extracting liquids therefrom. This problem may at first seem quite dissociated from the stability issues that we have raised above, but frequently the very act of injecting liquid into a bottle or extracting liquid therefrom is what induces instability in the first place.

Thus, liquids may be extracted from bottles such as medicine vials or injected therein in one of two ways, which we will describe with reference to a typical medical scenario. In one way, the bottle is placed on a work surface and the needle of a hypodermic syringe is inserted into the neck of the bottle. Provided that the only force applied is vertical, this should avoid any tendency to skid. But in practice, this is difficult to achieve. Medical orderlies work under pressure and work surfaces are often wet, so that any slight displacement of the needle from the vertical induces a horizontal force component that causes the bottle to slip. Alternatively, the bottle is gripped in one hand by or toward the neck and the hypodermic syringe is operated with the other hand. Not infrequently this is done with wet hands or gloves and this causes the bottle or vial to slip from the user's grip in the same manner as explained above with reference to FIGS. 1A-1C and 2A-2C of the drawings. Furthermore, this technique requires axial alignment between the tip of the needle and the neck of the bottle. Under stress it is all too easy to miss the bottle and the exposed fingers of the user's other hand are then at risk of being pricked and possibly injected with the contents of the hypodermic syringe.

The tendency of bottles to slip from a user's grip has been addressed in the art. For example, CN 2010/23742 discloses a bottle sheath disposed between the neck and the middle portion of a bottle and fixed to the bottle body. WO 2010/037250 discloses a non-slip sleeve that is removably fitted around the neck of a bottle. US 2008/0179353 discloses a sleeve that is secured around the neck of a wine bottle for preventing dripping when pouring.

None of these references discloses, for instance, a non-slip sheath that may be removably attached to the neck of a bottle and is configured to coupling to a hypodermic syringe.

The invention also addresses a number of problems associated with handling of instruments such as hypodermic syringes and other medical utensils such as specimen vials (e.g., blood specimen vials), catheters, and the like. First, relative to hypodermic syringes, the sharp needle is a common source of injury to both patient and medical staff. Initially the needle is protected by a guard, which must be removed prior to use often under conditions that may be stressful for the patient. A patient who wriggles increases the risk that the medical orderly will inject the needle poorly, thus causing hardship to the patient; and will more easily render the medical orderly prone to self-injury. Hypodermic needles are typically injected into a blood vessel at an acute angle to the surface of the skin of, for example, about 15° or vertically at 90°, although they may be injected at other angles. For example, due to the relationship of different sized fingers, the angle of penetration will vary. However, by placing a predetermined angle on a sleeve one can standardize the angle desired despite different operator hand size (e.g., a pre-chosen and fixed needle insertion angles of 15°, 20°, or 40° within the 15° to 90° options noted above).

The manner of use typically requires use of both hands as shown in FIG. 2C. Alternatively, one hand may be used to hold the syringe and manipulate the plunger while a finger of the other hand is placed under the body of the syringe and serves as a fulcrum or pivot point that allows the medical orderly to guide the syringe at the appropriate angle with more control than could be achieved using only one hand. In either case, the close proximity of the other hand to the syringe renders it subject to self-injury, particularly if the patient moves unexpectedly.

Further problems relate to the extent to which the needle projects from the end of the syringe. Generally, the length of the needle determines the maximal depth of penetration, which itself is a function of the medical procedure. In other words, some procedures may require only superficial penetration while others may require that the needle be injected to a depth of over one-inch, i.e., more than 2.5 cm. The longer the needle, the higher is the risk of injury and the more frightening it is to the patient. This is why patient management often dictates that the needle guard be removed out of sight of the patient and that the needle not be brandished in the sight of the patient. But regardless of when the needle guard is removed, the needle must be exposed prior to use and it is during this exposure that the medical orderly is most at risk of self-injury.

Another common source of injury occurs when lifting a hypodermic syringe from a supine position. During medical procedures, a nurse typically hands the surgeon a tray on which there are disposed multiple instruments for carrying out the procedure and from which the surgeon selects the appropriate instrument. The hands of the surgeon may be wet and a hypodermic syringe being cylindrical can easily slip from the surgeon's grip. It should be borne in mind that optimal gripping is always achieved by the arch between thumb and forefinger, as explained above with reference to FIG. 2A. This is how screwdrivers, for example, are gripped in a manner that allows adequate torque to be applied. However, hypodermic syringes are not amenable to being grasped in this manner, and in practice a medical orderly is constrained to lift them using only his or her fingertips, thus vastly increasing the likelihood of slippage and self-injury. Also, the cylindrical barrel and plunger of a standard prior art syringe have end flanges that present obstacles relative to controlled holding and passing of syringes. Still further, there is a need in the field for an improved grasping device, wherein a user can readily position an instrument relative to that grasping device while the grasping device is well suited for instrument positioning.

There is also a need in the grasping field for a grasping device that can facilitate the insertion and retention of an instrument, inclusive of sharp pointed instruments. There is a further need in the grasping field for a grasping device that can switch readily between a secure grasping state and a general retention state that avoids finger grasping stress, as well as a grasping device that provides for slide repositioning of an instrument being grasped to a desired new position, inclusive of slit collar positioners that provide a stable platform despite outside influences and are suitable for a variety of fields such as medical fields, material working, craft works, or any field where instrument or tool support is desirable. As made clearer below, the prior art is lacking in providing an instrument with multi-function capabilities like those featured in the embodiments described in the present application.

SUMMARY OF THE INVENTION

The present invention is inclusive of a multi-functional grasping device that has an instrument reception split (or slit) and provides means for ready insertion and firm grasping when needed, as when pressure is applied to the exterior of the grasping collar, such as through use of finger compression in finger reception cavities and/or projections and/or contouring strategically positioned on the collar having the instrument reception slit.

In this regard, a first aspect of the invention includes a grasping device in the form of an instrument collar (or sleeve) comprising:
  a flexible body having an exterior surface preferably provided with surface cavities configured for finger reception;
  a hole extending within an interior region of the body along an X-axis direction and being a through-hole relative to the body;
  an elongated slit extending in the X-axis direction, and in a radially inward direction from an exterior surface of the body into communication with the hole, the elongated slit including a thinner slit section extending in the X-axis direction for a portion of an overall length of the body as well as a wider slit section extending in the X-axis direction for a remaining portion of the overall length of the body.

A second aspect of the invention includes the grasping collar of the first aspect wherein the wider slit section has side walls that diverge apart in going from a border region with the thinner slit section to a free end of the body and/or wider slit section side walls that converge in a direction going from the exterior of the body down to the through-hole.

A third aspect of the invention includes the grasping collar of the second aspect wherein the thinner slit section is longer than the wider slit section.

A fourth aspect of the invention includes the grasping collar of the first aspect wherein the thinner slit section is longer than the wider slit section (as in the thinner slit section representing 55% to 75% of the overall length of the body).

A fifth aspect of the invention includes the grasping collar of the first aspect wherein walls of the body defining the thinner slit section are in contact (e.g., full contact over all respective planar side wall surfaces up from the through-hole to the exterior surface) when the collar is in a natural state and/or the walls of the wider slit section are free of contact in a natural state for a least a majority of respective opposing surface regions.

A sixth aspect of the invention includes the grasping collar of the first aspect wherein wall surfaces defining the thinner slit extension extend into common side wall surfaces defining the wider slit extension in a smooth, non-interrupted fashion.

A seventh aspect of the invention includes the grasping collar of the first aspect wherein the collar is a monolithic component formed of a flexible material.

An eighth aspect of the invention includes the grasping collar of the third aspect wherein the flexible material comprises a medical grade polymer such as one selected from the group consisting of silicone rubber or elastomer, natural rubber, polyvinyl chloride (PVC), polyurethane, Polyethylene (PE), Polypropylene (PP), polyester, Polyetherketone (PEEK), polyphenylsulfone, nylon, or any combination of the same, with a latex free elastomer such as a silicone elastomer being illustrative of a suitable material.

A ninth aspect of the invention includes the grasping collar of the first aspect wherein the minimum diameter of the hole is larger than a gap thickness between opposing body walls defining the thinner slit section and, preferably also at least a border region of the wider slit section with the thinner slit section (as well as potentially the entire wider slit section).

A tenth aspect of the invention includes the grasping collar of the ninth aspect wherein the hole has a taper that converges in the X-axis direction from a proximal end of the collar to (or toward) a distal, working end of the collar, with the taper either being continuous for the full X-axis length or interrupted as with different tapered hole side wall regions and/or cylindrical sub-regions along the X-axis.

An eleventh aspect of the invention includes the grasping collar of the first aspect wherein the body includes four surface cavities which are corner recesses, and, between respective pairs of the corner recesses, projections, with the projections including an opposing pair of first length side wall projections and an opposing pair of second length side wall projections, which the second length side wall projections being shorter in length than the first length side wall projections.

A twelfth aspect of the invention includes the grasping collar of the eleventh aspect wherein the slit extends along the X-axis and intersects the longer length side wall projections.

A thirteenth aspect of the invention includes the grasping collar of the twelfth aspect wherein the projections having longer side walls extend out from a center of the body to a lesser extent than the projections having shorter length side walls.

A fourteenth aspect of the invention includes the grasping collar of the first aspect wherein the body has a pair of surface cavities to opposite sides of the slit formed in the body.

A fifteenth aspect of the invention includes the grasping collar of the fourteenth aspect wherein the body has a circular or oval shaped cross-sectional configuration.

A sixteenth aspect of the invention includes the grasping collar of the first aspect wherein the body has a first exposed surface in which is formed the slit and a second exposed surface opposing the first exposed surface in which the slit is not formed.

A seventeenth aspect of the invention includes the grasping collar of the first aspect wherein the body slit is formed within a corner recess that is elongated in the X-axis direction.

An eighteenth aspect of the invention includes the grasping collar of the fourteenth aspect wherein opposing first and second exposed surfaces include parallel sections.

A nineteenth aspect of the invention includes the grasping collar of the eighteenth aspect wherein the opposing first and second exposed surface include a tapered surface that slopes outward and inward to a free edge region of the body.

A twentieth aspect of the invention includes the grasping collar of the nineteenth aspect wherein each of the first and second exposed surfaces have a tapered surface that slopes outward and inward to respective free edge regions of the body.

A twenty first aspect of the invention includes a method of forming the grasping collar of the first aspect including molding the body and forming the slit therein after molding.

A twenty second aspect of the invention includes a method of forming the grasping collar of the first aspect wherein the slit is formed during the molding of the body.

A twenty third aspect of the invention includes a method of assembly an instrument assembly including inserting an instrument within the slit of the grasping collar of the first aspect of the invention.

A twenty fourth aspect of the invention includes the method of the twenty third aspect wherein the inserting of the instrument includes first inserting a portion of the instrument within the wider gap and then further forcing the instrument as to separate side walls of the thinner slit section until the instrument is at least partially received within the hole of the body (with this insertion typically being a single-handed insertion as that is all that is needed; and with the insertion also avoiding the need to thread through a tunnel extending through a body from one end to another which can lead to increased chance of instrument contact as in needle tip punctures).

In addition to the above described split grasping collar an additional embodiment of the present invention, that is independent of the split grasping collar embodiment or can be used in combination, as in a kit arrangement, is directed at providing an improved bottle support that allows bottles to be supported by either their base or their neck and to be retained in the bottle support at an angle without detracting from the stability of the support. Hence in a kit aspect there can be provided a medicament bottle and an instrument assembly that features the split grasping collar and a syringe for supplying or retrieving medicament from the medicine bottle or vial, and optionally an annular core bottle support as described below.

Another aspect of an embodiment of the invention is to address and alleviate some of the aforementioned problems relating to safe transfer of liquid from a bottle to another container, particularly albeit not only to hypodermic syringes.

Yet a further aspect of an embodiment of the invention is to address and alleviate some of the aforementioned problems relating to use of hypodermic syringes and other needed utensils.

To this end there is provided in accordance with the invention either or both of a bottle support and a collar having grasping facilitating.

In some embodiments the bottle support comprises: an annular core having an inner side surface defining a hollow opening, an outer side surface, a top surface and a base surface, and a plurality of pliable ribs each at least partially encircling the annular core so as to overlap the base surface, the top surface and the outer side surface such that at least an upper end of each rib where it overlaps the top surface extends into the hollow opening.

The ribs are mounted parallel to a longitudinal axis of the core but unlike the arrangement in US 2010/0140431 they cover at least partially the outer surface and project over the top surface. Furthermore, they extend into the hollow opening so as to be resiliently deformed by a bottle inserted therein and thereby grasp the bottle.

In some embodiments, the lower ends of the ribs extend into the hollow opening so as to provide a platform for supporting the base of the bottle and ensuring that it does not make direct contact with a surface on which the bottle support is disposed. This prevents contamination reaching a sterile bottle. Further, the mounts of the present invention can also be used on upper regions of objects either to facilitate grasping of the object in that area or in conjunction with an object's position retention, with the mounts vertical orientation being switchable to place ribs in either an underlying support orientation or an overlying clamping type orientation or both orientations through a pair of mounts working together.

Kits under the present application are also inclusive of the grasping collars described above in combination with an instrument (e.g., a medical instrument inclusive of a needle hub assembly, a fastener such as a threaded screw dimensioned for receipt in the grasping collar (split or non-split), etc.). Methods under the invention also include manipulation of the kit components as in securing an instrument within the grasping collar for position support and/or facilitated grasping, including grasping with slit collars in the manner described.

BRIEF DESCRIPTION OF THE DRAWINGS

In order to understand the invention and to see how it may be carried out in practice, embodiments will now be described, by way of non-limiting examples only, with reference to the accompanying drawings, in which:

FIGS. 1A to 1D show schematically the tendency of a cylindrical bottle to slip when gripped non-diametrically;

FIGS. 6A, 6B and 6C show the bottle support preventing rolling or tipping of an inclined bottle;

FIG. 6D shows an undesirable manner as to how a cylindrical bottle may be prevented from rolling without use of the bottle support according to the invention;

FIGS. 27A, 27B and 27C show comparisons of prior art syringes, with a syringe fitted with the collar of FIG. 21 shown only in FIG. 27A;

FIG. 28 shows multiple bottle supports stacked for easy display and packing; and FIG. 29A shows a tray for mounting multiple bottle supports; and FIG. 29B shows use of such a tray to mount multiple bottle supports.

FIG. 59 shows a combination of present invention components, inclusive of a base support mount of FIG. 3A and the collar of FIG. 11 (just prior to vial top attachment), with the FIG. 11 collar in this embodiment having a fully open, rimmed top for receipt of a syringe assembly or other interconnecting component.

FIG. 60 shows a schematic line drawing showing an interior review of the combination of the vial and a modified top collar, and the associated positioning of the syringe assembly.

FIG. 61 shows a syringe assembly that includes a first grasping collar at the plunger base, a second grasping collar along the syringe's cylinder, and a third grasping collar at the syringe's needle assembly that is configured for insertion into the FIG. 11 collar with the needle not yet having punctured through the vial's top seal.

FIG. 62 shows a similar view as that of FIG. 60 with the needle having been inserted through the vial's top seal and into the vial.

FIG. 74 shows the components of FIG. 73 in an engaged state and with the same offset, two finger grasping described above.

FIG. 75 shows the combined components of FIG. 74 and the ability for the pinch support to hold the combination in a suspended state with one hand (with either the cavity(s) or projection sidewall(s) being finger contacted).

FIG. 76 shows a modified tray embodiment featuring a reception aperture that has a common surrounding configuration for snug receipt of the integrated collar shown in the syringe plunger of FIG. 48.

FIG. 77 shows the integrated collar and plunger shown in FIG. 48 in a snug reception state relative to a supporting/transfer tray.

FIG. 77A shows a full view of the combination of a syringe plunger having a FIG. 11 collar at its base.

FIG. 77B shows a view of the collar of FIG. 77A in bottom perspective.

FIG. 77C shows a view of the collar of FIG. 77A in a bottom plan view.

FIG. 77D shows the combination of FIG. 77A from a different orientation.

FIG. 77E also shows the combination of FIG. 77A from a different orientation

FIG. 87 shows a cross section of the collar in FIG. 86 showing a non-truly-cylindrical cavity featuring, in the embodiment shown, a sequence of cavity constrictions and expansions along the longitudinal length of the cavity.

FIG. 88 shows a cross-sectional view from the opposite direction from that which is shown in FIG. 86.

FIG. 89 shows the grasping collar of FIG. 86 in three different positions on a catheter line and with the middle position showing being cut away to illustrate the haptic, generally sinusoidal (expansion/contraction) wave pattern of the through-hole cavity featured for the sleeve which has different clearance widths along the length as well as different outlet opening diameters in this embodiment.

FIG. 90 shows the intermediate positioned grasping collar presented in FIG. 89 in an expanded view such that the haptic promoting cavity configuration can be better seen together with some, non-limiting, illustrative cavity thickness values of the length of the collar for the catheter equipment embodiment featured.

FIG. 95 shows an additional embodiment of a catheter line grasping collar or sleeve in perspective view.

FIG. 96 shows the grasping collar of FIG. 95 with its central haptic cavity shown in cross-section.

FIG. 97 shows the cross-sectional view of FIG. 96 with some non-limiting, illustrative haptic cavity diameter values relative to the varying diametrical nature of the cavity along its length.

FIG. 98 shows a front elevation of the exterior contoured surface of the collar of FIG. 95.

FIG. 99 shows the collar of FIG. 95 in position on a catheter line with an exterior view.

FIG. 99A shows the collar of FIG. 95 in position on a catheter line with a cut away view showing the haptic cavity contact with the threaded catheter line extending therethough.

FIG. 99B shows a perspective view of a modified haptic collar such as shown in FIG. 99 with a two passageway configuration, and with each shown receiving therein a linear element.

FIG. 99C shows a similar view as seen in FIG. 99B but in cross-section such that there can be seen that, for this embodiment, the two holes in the collar include one featuring a non-varying through-hole passageway and the other one a varying (haptic facilitating) through hole passageway

FIG. 100F shows a different grasping relationship wherein the middle finger and thumb are compressed upon the haptic collar or sleeve and the index finger is free (while also providing for a fluid conduit guidance flow curve along the underside of the index finger), with the compression level on the haptic collar allowing for maximum or intermediate flow levels in the fluid passing out the free end of the conduit about the exterior of the tool positioned within the conduit.

FIGS. 100L and 100M show a different valve grasping collar embodiment sharing the natural state valve shut off configuration in FIG. 100L with FIG. 100M showing the multi-finger bending of collar ends about a central fulcrum to form a convex shape that places the collar valve in a flow through state.

FIG. 100N shows an assembly sequence for a different embodiment of the present invention wherein the kit features a haptic collar (a natural state closed haptic collar valve in this embodiment) together with a supply conduit and an exit conduit in the shape of a nozzle in this embodiment.

FIG. 100O shows the completed assembly shown in FIG. 100N in use wherein the convex compression forces provided by the fingers shown on the collar result in an opening of the valve collar for achieving fluid supply from the supply conduit to the outlet conduit (nozzle shown with a diverging spray output in this embodiment).

FIGS. 101A to 101D show a different grasping collar or sleeve embodiment featuring a through-hole well suited for needle assembly reception, with FIG. 101A showing a perspective view, FIG. 101B showing a central cut-away view; FIG. 101C showing a top plan view, and FIG. 101D showing the cavity configuration extending through the collar at an angle.

FIGS. 102A to 102D show yet a different grasping collar or sleeve embodiment featuring a through-hole well suited for needle assembly reception, with FIG. 102A showing a perspective view, FIG. 102B showing a central cut-away view; FIG. 102C showing a top plan view, and FIG. 102D showing the cavity configuration extending through the collar at an angle.

FIGS. 103A to 103D show another different grasping collar or sleeve embodiment featuring a through-hole well suited for needle assembly reception, with FIG. 103A showing a perspective view, FIG. 103B showing a view of the central cavity relative to the FIG. 103A orientation, FIG. 103C showing a top plan view of the collar, and FIG. 103D showing the cavity configuration extending through the collar relative to the orientation of FIG. 103C.

Figure 104A:
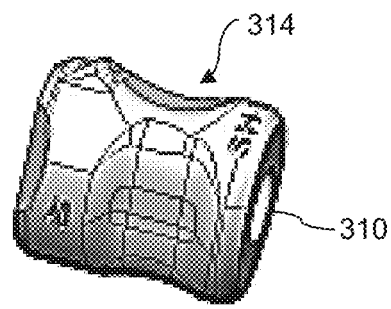
Figure 104B:
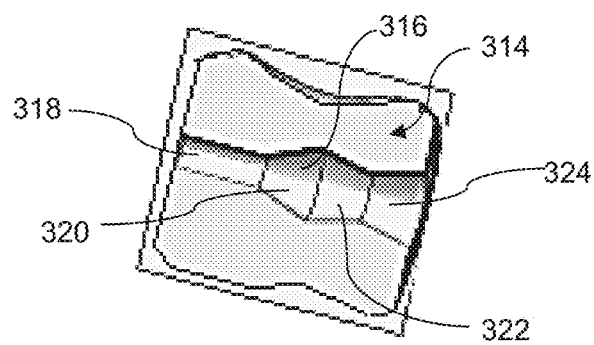
Figure 104C:
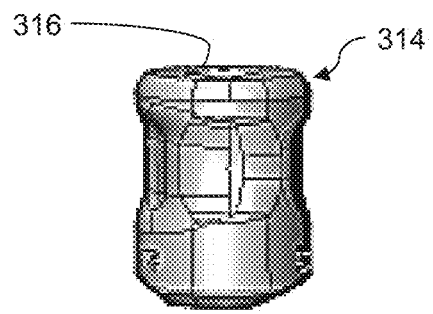
Figure 104D:
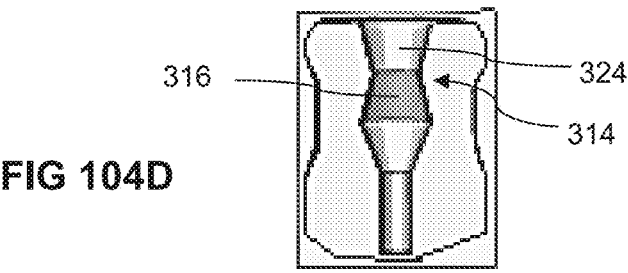

FIGS. 104A to 104D show another different grasping collar or sleeve embodiment featuring a through-hole well suited for needle assembly reception, with FIG. 104A showing a perspective view, FIG. 104B showing a view of the central cavity relative to the FIG. 104A orientation, FIG. 104C showing a top plan view of the collar, and FIG. 104D showing the cavity configuration extending through the collar relative to the orientation of FIG. 104C.

FIGS. 105A to 105D show another different grasping collar or sleeve embodiment featuring a through-hole well suited for syringe body attachment, with FIG. 105A showing a perspective view, FIG. 105B showing a view of the central cavity relative to the FIG. 105A orientation, FIG. 105C showing a top plan view of the collar, and FIG. 105D showing the cavity configuration extending through the collar relative to the orientation of FIG. 105C.

Figure 10A:
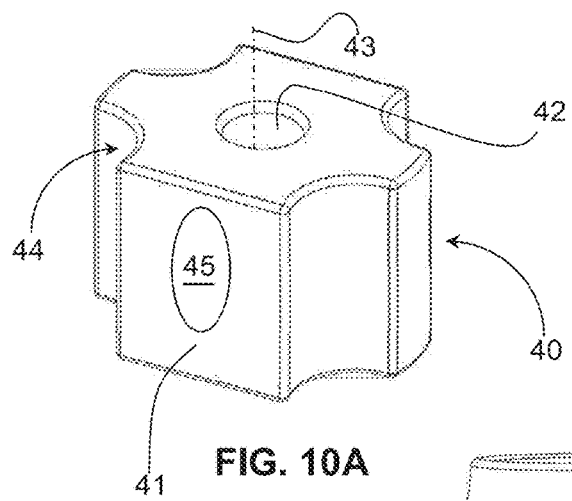
FIGS. 10A and 10B show a detail of the collar according to a first embodiment.
Figure 106A:
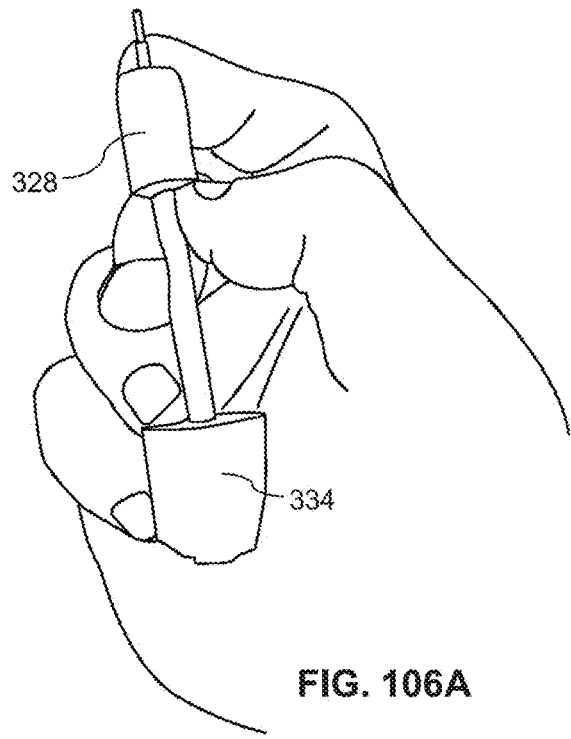
Figure 107A:
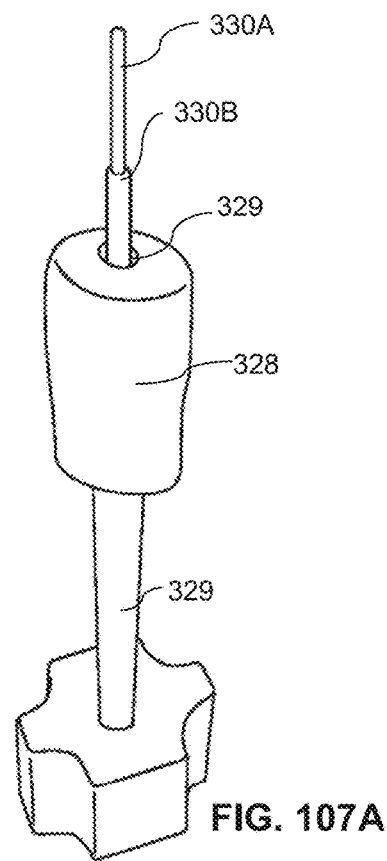
Figure 106B:
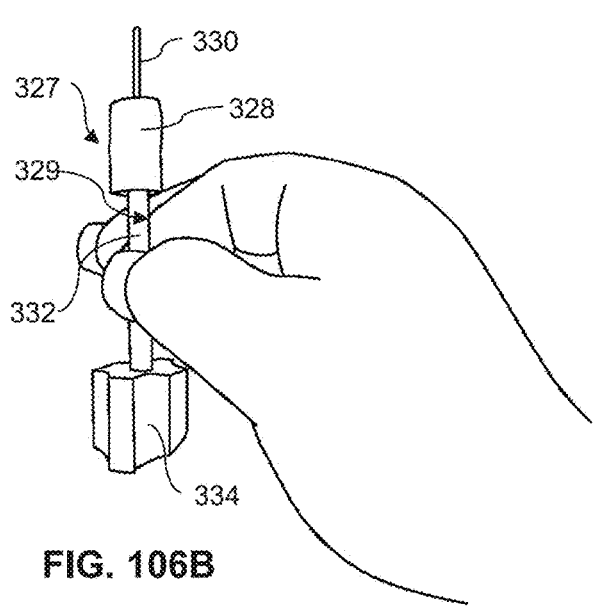
Figure 107B:
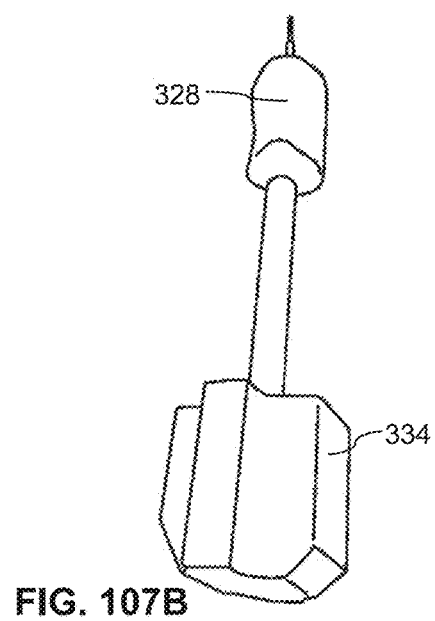

FIGS. 106A to 106B and FIGS. 107A to 107E show various views of a combination set of collars, featuring a first collar for securement to a distal end of an object such as the illustrated push, pull and/or torque (e.g., dental) tool and a second collar of FIG. 10A configuration for attachment to the base of the tool, with FIG. 106A showing the combination being held with one hand contact on each of the collars and the tool; and FIG. 106B showing a pinching holding of just the tool body; FIGS. 107A and 107B show different views of the combination of FIG. 106A, while FIG. 107C shows a one hand holding of all components, but with the base collar removed, FIG. 107D shows a single hand support of the combination in ready for non-rotative use position, while FIG. 107E shows the combination of FIG. 106A with an added adapter component received by the removed base collar.

Figure 3A:
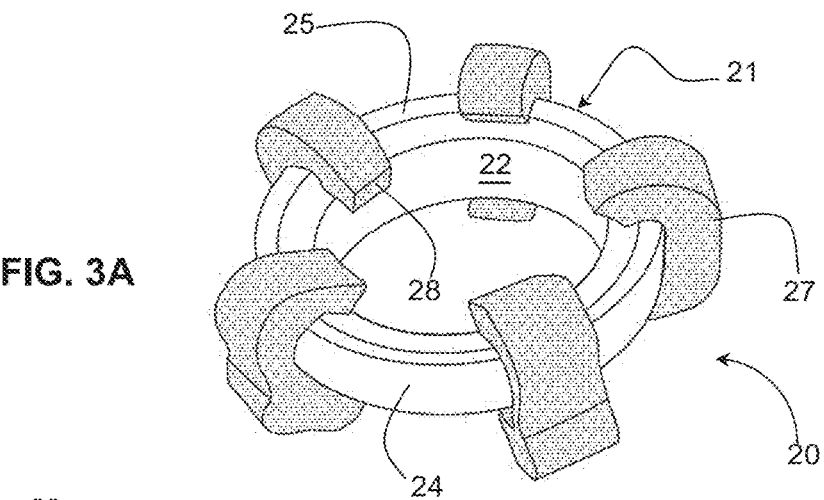
FIGS. 3A, 3B and 3C show details of a bottle support according to an embodiment of the invention.

FIGS. 108A to 108H illustrate a prior art view of a capped container and various views relative to an inventive combination of a collar (of FIG. 11 configuration) in use with and without a bottle mount of FIG. 3A; and some of the various hand positions and component positions utilized for bottle cap removal.

Figure 11:
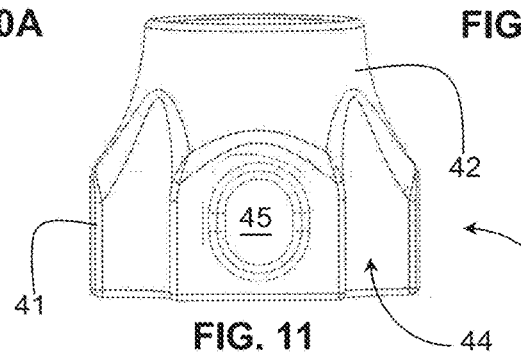
FIG. 11 shows a detail of the collar according to a second embodiment.
Figure 109:
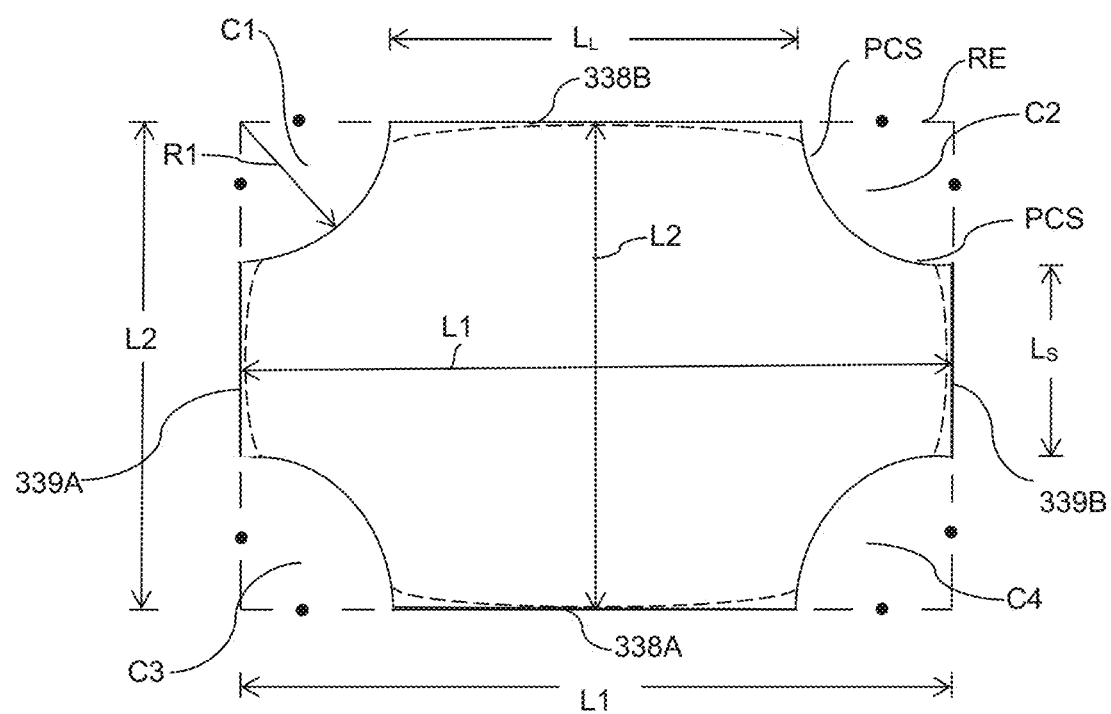

FIG. 109 shows a schematic depiction of a top plan view of a collar of FIG. 11 configuration with some of lengths and cavity depths demarcated.

Figure 109A:
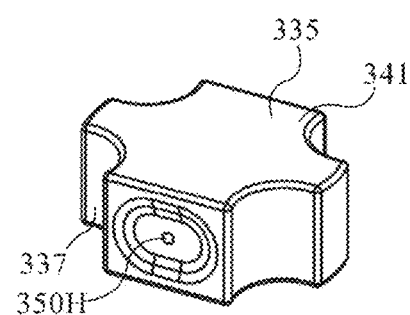

FIGS. 109A to 109N show a variety of different embodiments of thinner version collars of the FIG. 10A configuration.

Figure 110A:
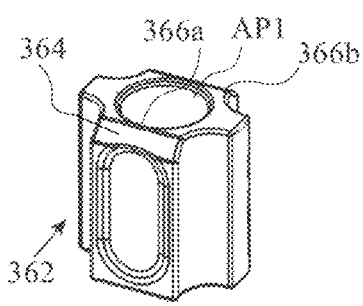
Figure 110B:
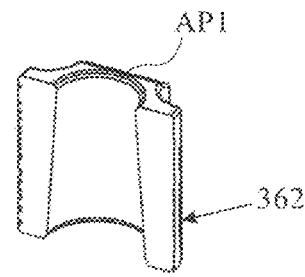

FIGS. 110A and 110B illustrate a longer or thicker version of the collar configuration of FIG. 10A with the former showing a perspective view and the latter showing a central vertical cross-section and the aperture configuration.

Figure 111A:
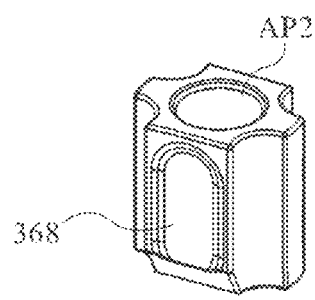
Figure 111B:
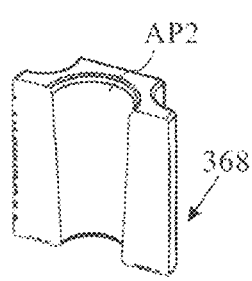

FIGS. 111A and 111B illustrate a longer or thicker version of the collar configuration of FIG. 10A with the former showing a perspective view and the latter showing a central vertical cross-section and the aperture configuration.

Figure 112A:
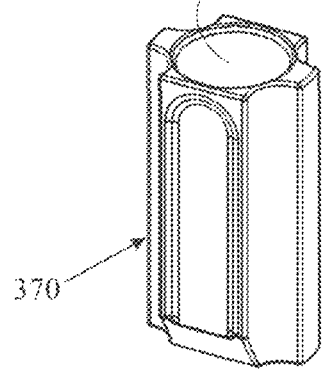
Figure 112B:
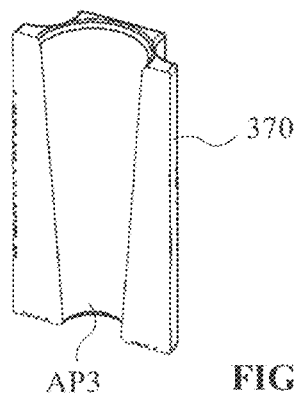

FIGS. 112A and 112B illustrate a longer or thicker version of the collar configuration of FIG. 10A with the former showing a perspective view and the latter showing a central vertical cross-section and the aperture configuration.

Figure 113A:
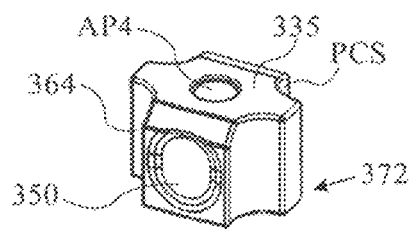
Figure 113B:
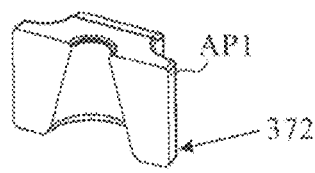

FIGS. 113A and 113B illustrate a longer or thicker version (as in an intermediate thickness level) of the collar configuration of FIG. 10A with the former showing a perspective view and the latter showing a central vertical cross-section and the aperture configuration.

Figure 114A:
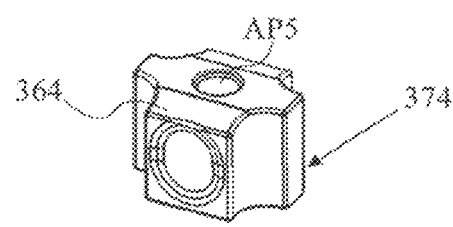
Figure 114B:

FIGS. 114A and 114B illustrate a longer or thicker version (as in an intermediate thickness level) of the collar configuration of FIG. 10A with the former showing a perspective view and the latter showing a central vertical cross-section and the aperture configuration.

Figure 115A:
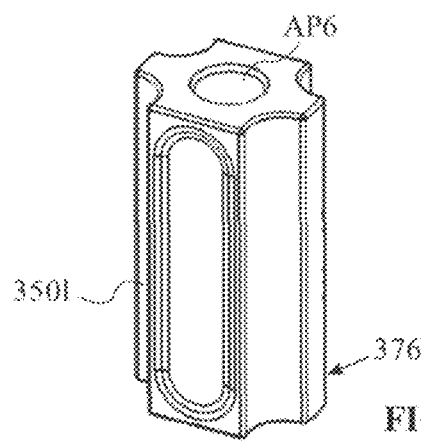
Figure 115B:
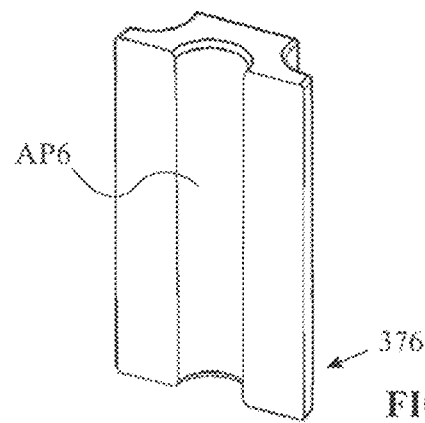

FIGS. 115A and 115B illustrate a much longer or thicker version of the collar configuration of FIG. 10A with the former showing a perspective view and the latter showing a central vertical cross-section and the aperture configuration.

Figure 116A:
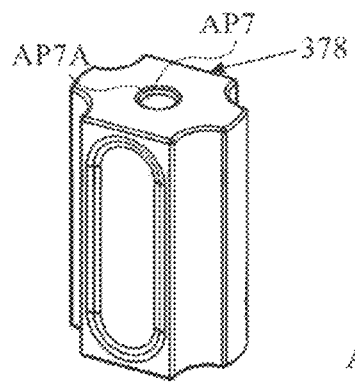
Figure 116B:
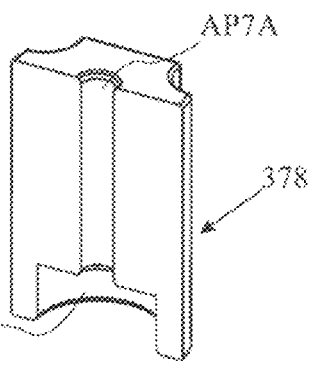

FIGS. 116A and 116B illustrate a longer or thicker version of the collar configuration of FIG. 10A with the former showing a perspective view and the latter showing a central vertical cross-section and the aperture configuration.

Figure 117A:
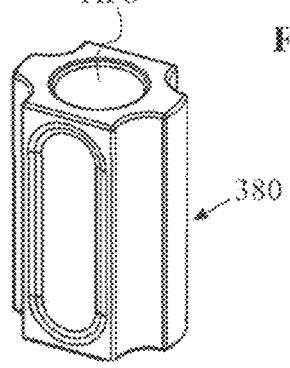
Figure 117B:
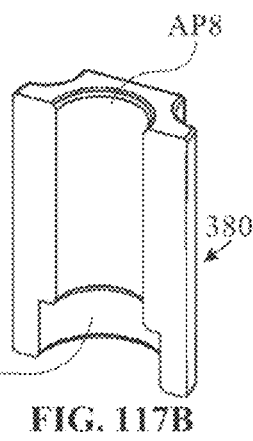

FIGS. 117A and 117B illustrate a longer or thicker version of the collar configuration of FIG. 10A with the former showing a perspective view and the latter showing a central vertical cross-section and the aperture configuration.

Figure 118A:
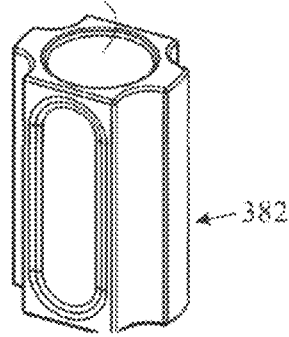
Figure 118B:
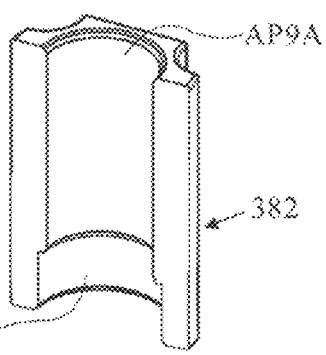

FIGS. 118A and 118B illustrate a longer or thicker version of the collar configuration of FIG. 10A with the former showing a perspective view and the latter showing a central vertical cross-section and the aperture configuration.

Figure 119A:
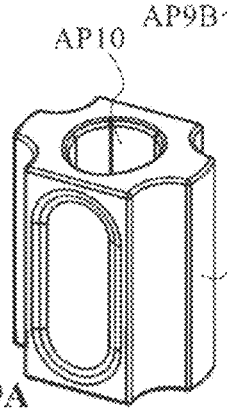
Figure 119B:
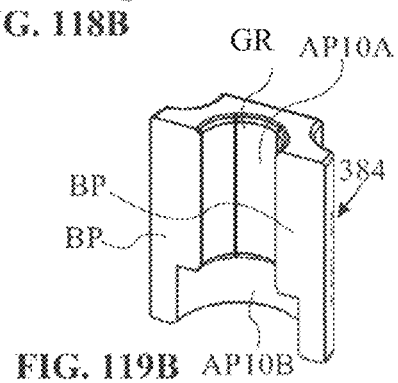

FIGS. 119A and 119B illustrate a longer or thicker version of the collar configuration of FIG. 10A with the former showing a perspective view and the latter showing a central vertical cross-section and the aperture configuration.

Figure 120A:
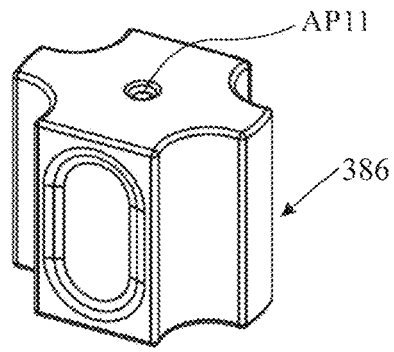
Figure 120B:
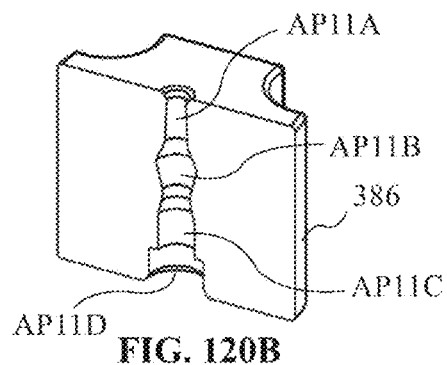

FIGS. 120A and 120B illustrate a longer or thicker version of the collar configuration of FIG. 10A with the former showing a perspective view and the latter showing a central vertical cross-section and the aperture configuration.

Figure 121A:
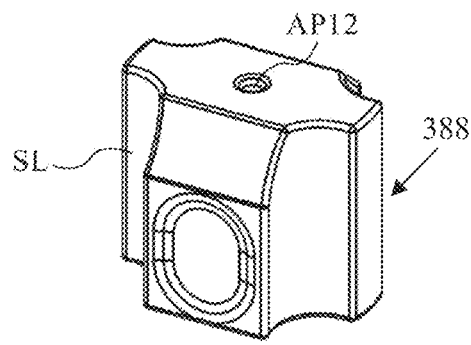
Figure 121B:
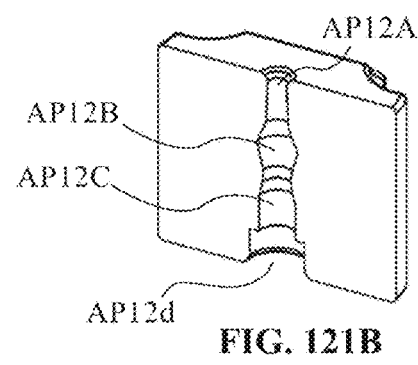

FIGS. 121A and 121B illustrate a longer or thicker version of the collar configuration of FIG. 10A with the former showing a perspective view and the latter showing a central vertical cross-section and the aperture configuration.

Figure 122A:
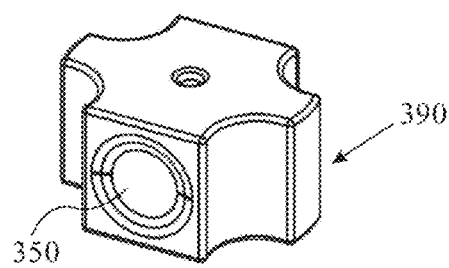
Figure 122B:
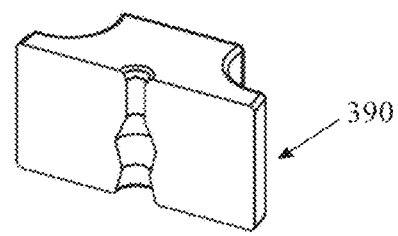

FIGS. 122A and 122B illustrate a longer or thicker version (as in an intermediate thickness) of the collar configuration of FIG. 10A with the former showing a perspective view and the latter showing a central vertical cross-section and the aperture configuration.

Figure 123A:
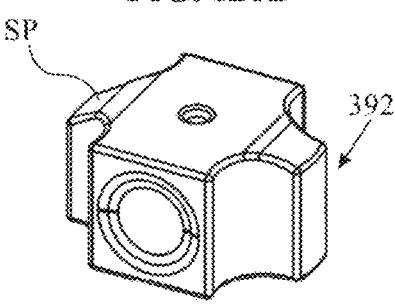
Figure 123B:
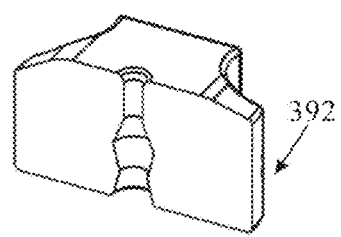

FIGS. 123A and 123B illustrate a longer or thicker version (as in an intermediate thickness) of the collar configuration of FIG. 10A with the former showing a perspective view and the latter showing a central vertical cross-section and the aperture configuration.

Figures 124A, 124B:
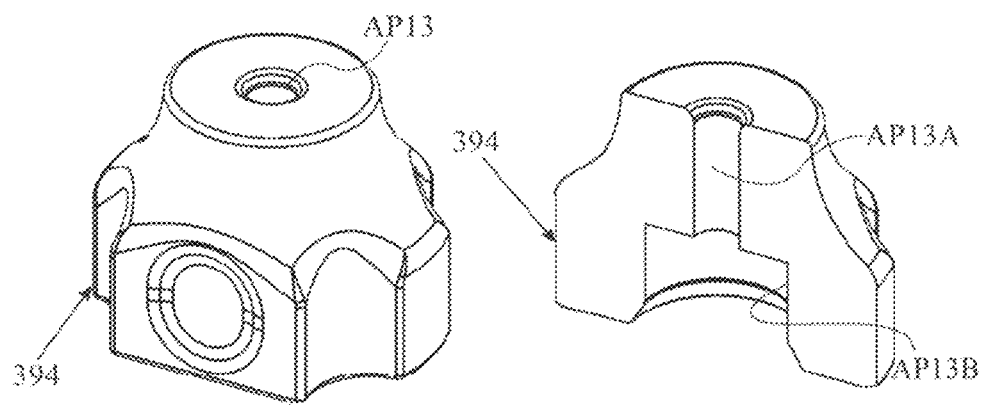

FIGS. 124A and 124B illustrate a version of the collar configuration of FIG. 11 with the former showing a perspective view and the latter showing a central vertical cross-section and the stepped aperture configuration.

Figures 125A, 125B:
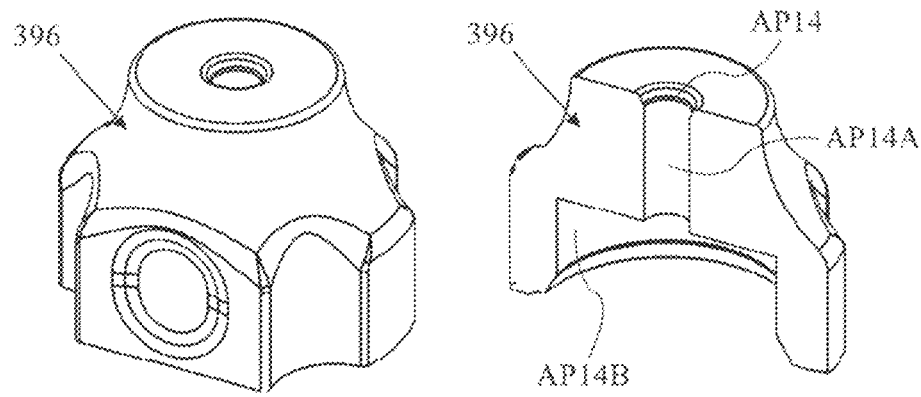

FIGS. 125A and 125B illustrate a version of the collar configuration of FIG. 11 with the former showing a perspective view and the latter showing a central vertical cross-section and the stepped aperture configuration.

Figures 126A, 126B:
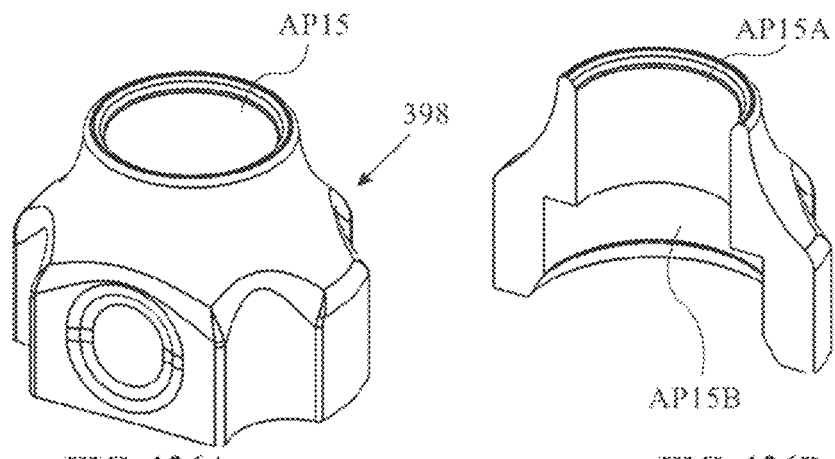

FIGS. 126A and 126B illustrate a version of the collar configuration of FIG. 11 with the former showing a perspective view and the latter showing a central vertical cross-section and the stepped aperture configuration.

FIGS. 127A and 127B illustrate a closed top version of the collar configuration of FIG. 11 with the former showing a perspective view and the latter showing a central vertical cross-section and the aperture configuration.

FIGS. 128A and 128B illustrate a closed bottom version of the collar configuration of FIG. 11 with the former showing a perspective view and the latter showing a central vertical cross-section and the aperture configuration.

FIGS. 129A and 129B illustrate a version of the collar configuration of FIG. 11 with the former showing a perspective view and the latter showing a central vertical cross-section and the stepped aperture configuration.

FIGS. 129C and 129D illustrate a version of the collar configuration of FIG. 11 with the former showing a perspective view and the latter showing a central vertical cross-section and the stepped aperture configuration.

Figure 130A:
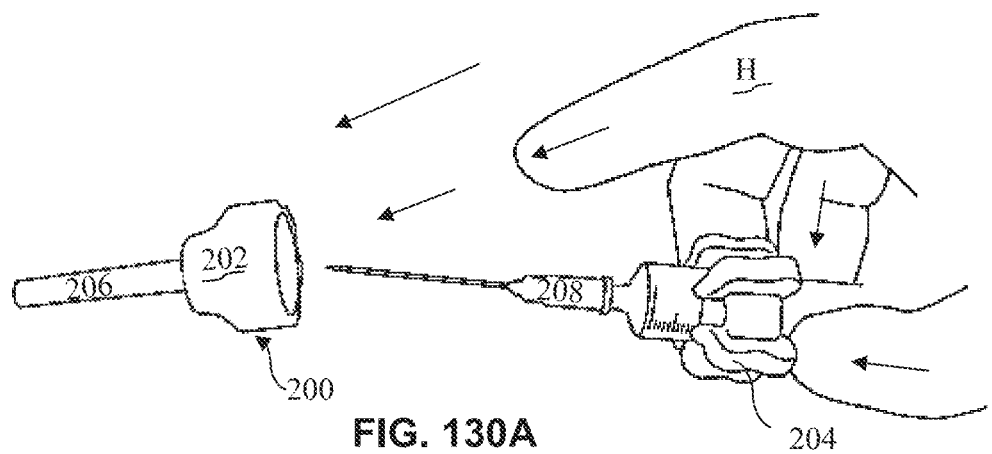
Figure 130B:
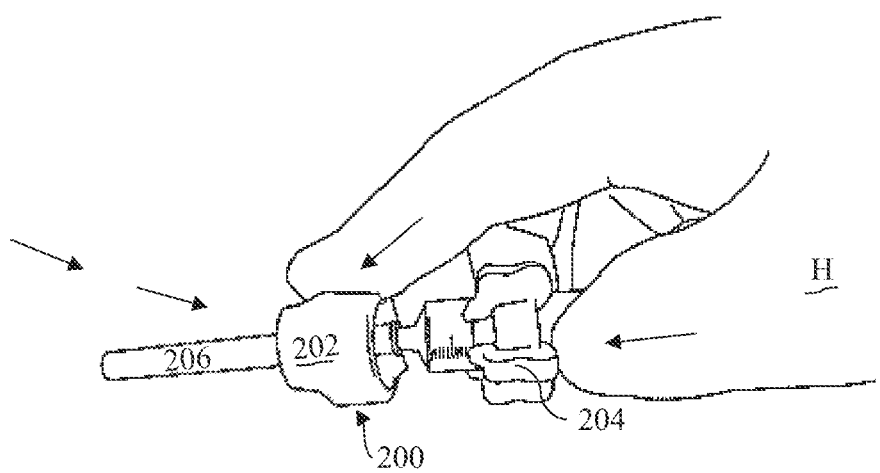
Figure 130C:
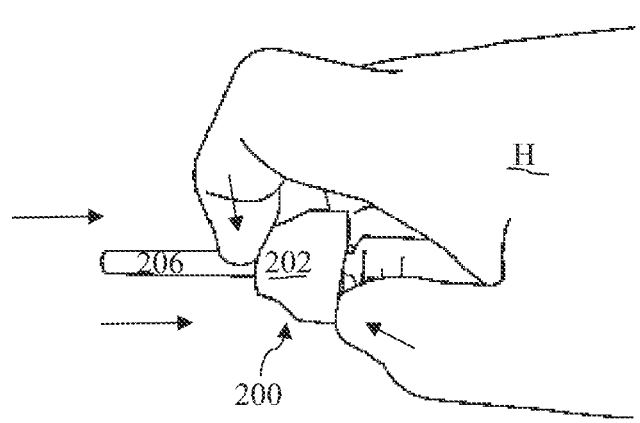

FIGS. 130A to 130C, provide an example of a combination collar of FIG. 11 and mount of FIG. 3A being used to hold a needle cover in position for safe insertion of the needle into the needle cover and to snap on with one hand the needle cover through use of the combination, with FIG. 130B also showing an alternative initial stage of separation of the two with one hand.

Figure 131A:
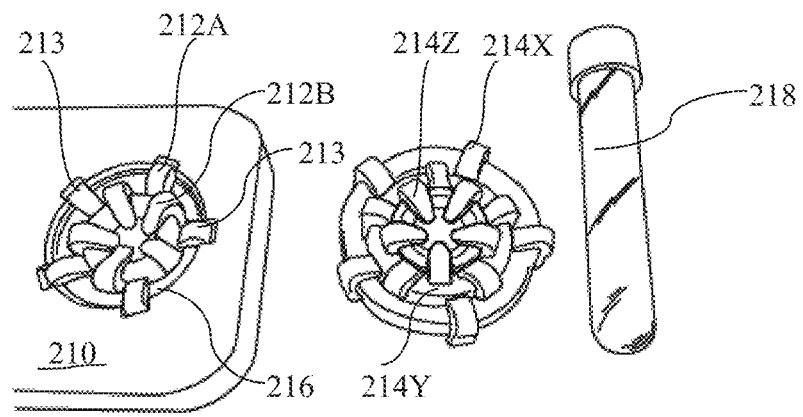
Figure 131B:
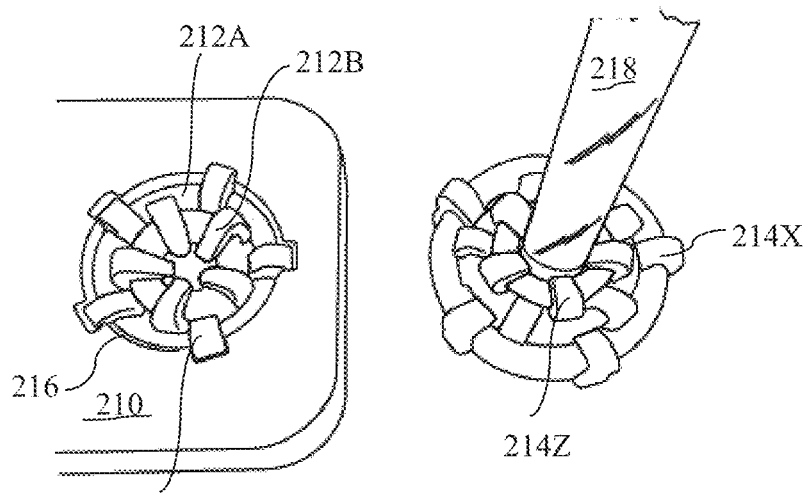
Figure 131C:
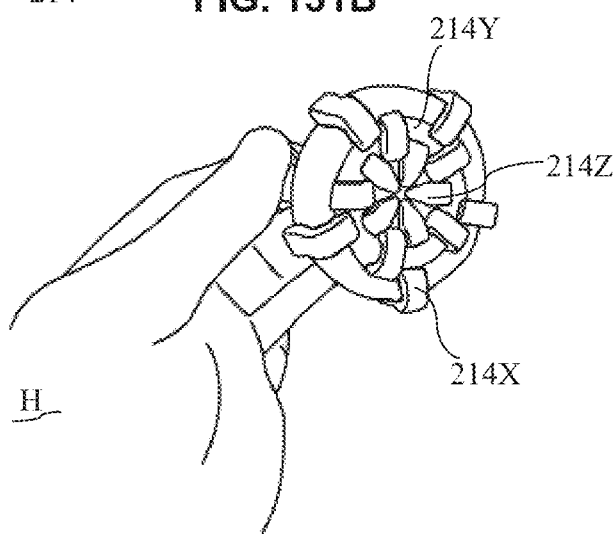

FIGS. 131A to 131C show a circumferential set of different size mounts of FIG. 3A configuration used to adjust the size of a tray aperture (e.g., see FIG. 39 example tray) such that a smaller utensil can fit in a larger aperture, and also to provide a more stable (larger diameter contact with support) as when the combination is put on a vibrating plate or surface to avoid specimen settling or coagulation.

Figure 132A:
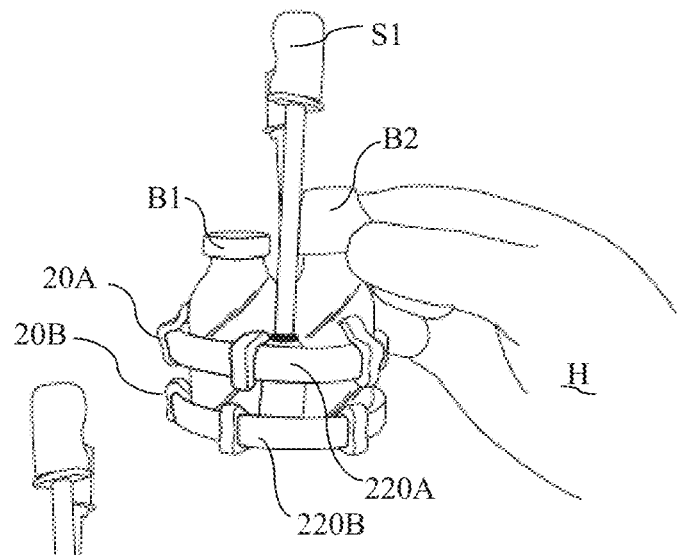
Figure 132B:
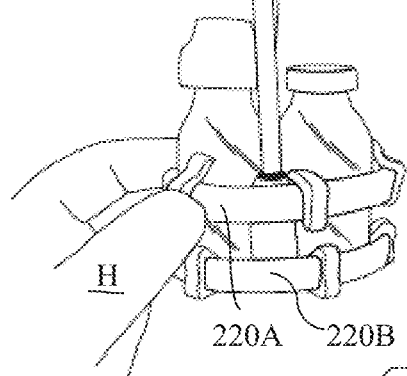
Figure 132C:
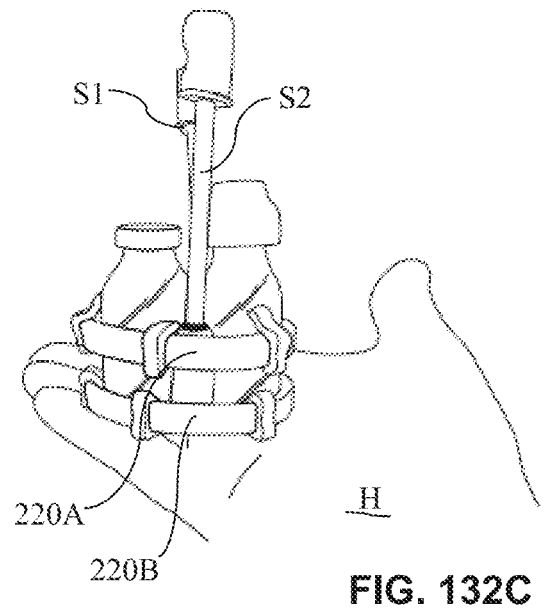

FIGS. 132A to 132C show a double set kit of same size mounts of the configuration of FIG. 3A used to hold together a plurality of different components to provide for transport with one hand, either by holding one of the more upper regions of the trapped components (132a), holding one or more of the mounts (FIG. 132B); or holding the bottom region of the trapped components (FIG. 132C).

FIGS. 133A to 133D show the mount of FIG. 3A configuration mounted on a cap of a bottle such as a soda bottle, with cross-sectional views showing how the mount mounted on the cap of the bottle has an annular core and ribs designed for bottle cap engagement (and thus inherently providing an expanded circumference torque generation cap removal means).

FIG. 134 shows a view of a pliable mount of FIG. 3A configuration which is able to accommodate a large tilt due to missed insertion of a medicine dropper bottle or an intentional tilted orientation for presenting the top at a more desired orientation to the user.

FIGS. 135A to 135J illustrate various views of an alternate combination of features of the invention featuring a collar having FIG. 10A configuration with added side porting, with FIGS. 135A to 135D showing the turret combination of collar and underlying spin platform, and 135E to 135J showing the turret collar alone in various perspective and cut-away views.

Figures 135E, 135F:
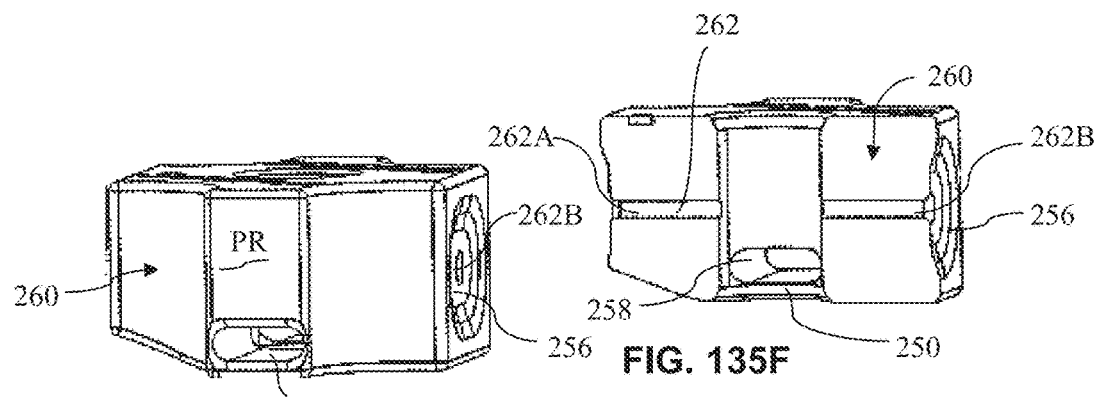
Figure 136A:
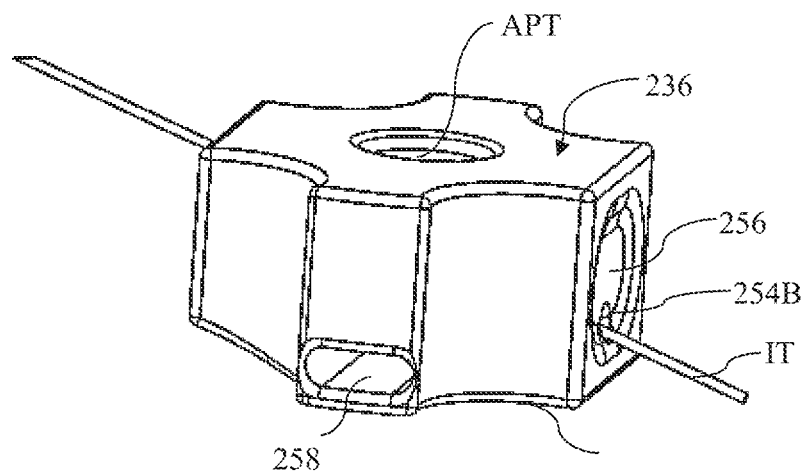
Figure 136B:
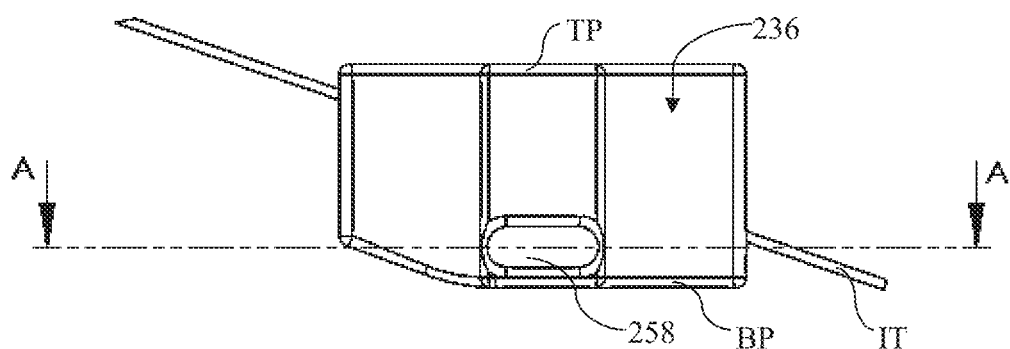
Figure 136C:
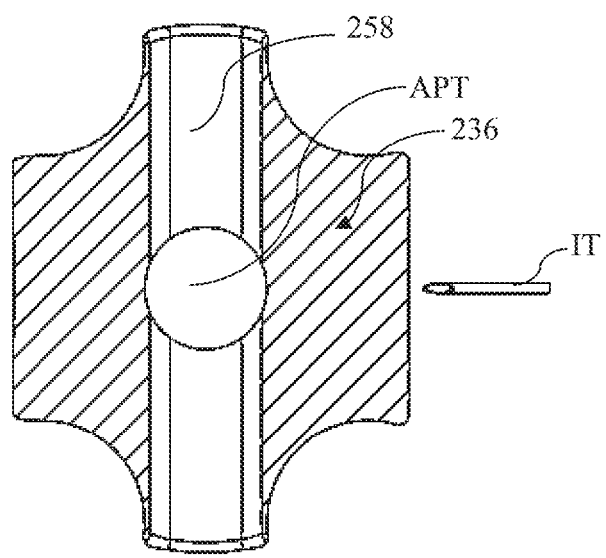

FIGS. 136A to 136C illustrate the collar of FIG. 135A removed from its mount, with FIG. 135A showing a perspective view of the collar with an angled thin tool inserted as in a needle insertion, catheter sheath, wire, fluid tube, etc. insertion, FIG. 136B shows a front elevational view of that which is shown in FIGS. 136A, and 136C shows a cross-sectional view along cross-section A-A in FIG. 136B.

FIG. 137 shows a rotated view of the collar shown in FIG. 135A and with the inserted tool being at a shallower angle relative to the underlying surface of the collar such that it rests in the lower part of the illustrated oblong exit (or entry groove) that is detailed in the enlarged view shown in FIG. 137A which shows an enlarged view of the circled section of FIG. 137.

FIG. 138 shows a rotated view of the collar shown in FIG. 135A and with the inserted tool being at a steeper angle relative to the underlying surface of the collar such that the tool (e.g., sheath) abuts the upper part of the illustrated oblong exit (or entry groove) that is detailed in the enlarged view shown in FIG. 138A which shows an enlarged view of the circled section of FIG. 138.

FIG. 139 also shows a rotated view of the collar shown in FIG. 135A and with the inserted tool being a combination sheath and interior wire, with the collar providing the desired angle of orientation.

FIG. 140 shows the collar of FIG. 139 with inserted sheath and wire tool received but from a different angle.

FIG. 141 shows a similar view as that of FIG. 140 but with a position retainer insert added.

FIGS. 141A to 141C show different variants of the position retainer insert designed to hold the tool at a desired orientation within the receiving oblong or oval shaped opening provided in the collar for tool positioning flexibility.

Figure 142A:
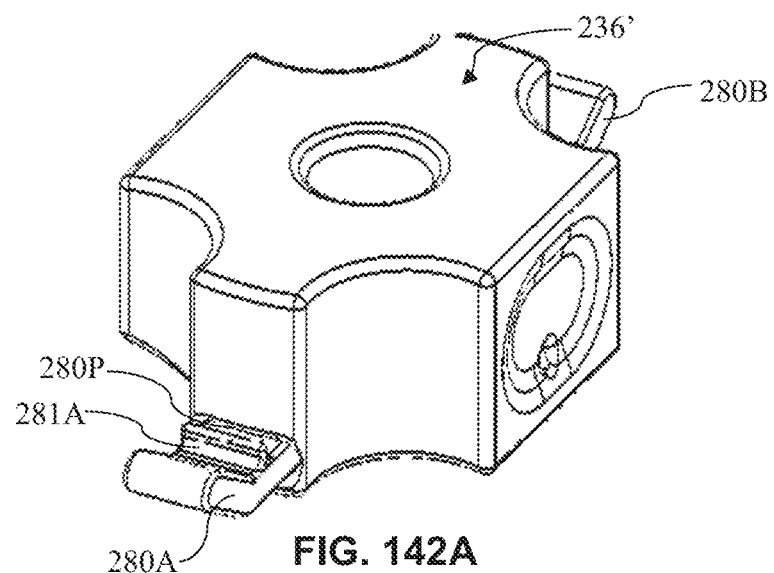
Figure 142B:
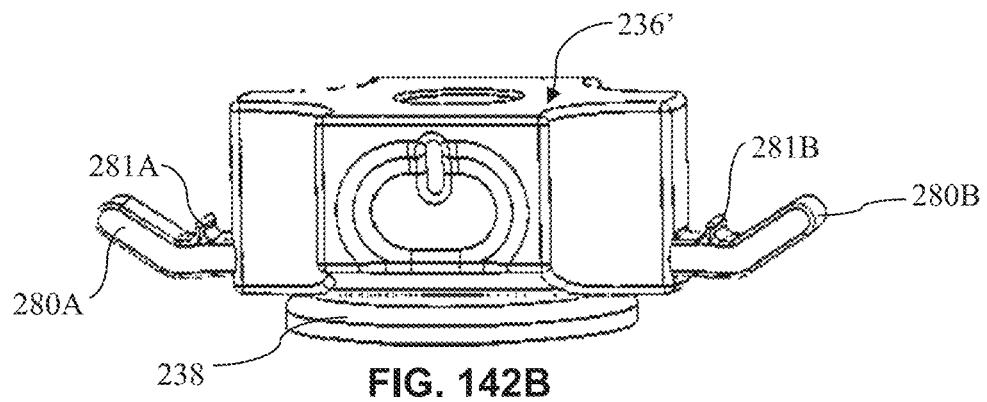

FIGS. 142A and 142B show different views of a swivel mounted collar similar to FIG. 135A, but with a pair of clamp down wings extending out from the collar main body (e.g., after insertion into respective passageway sections of the turret collar).

Figure 143:
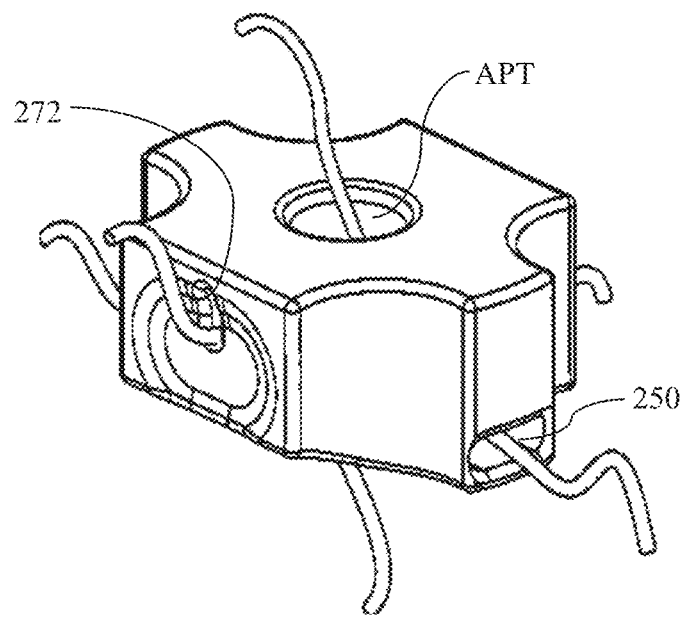

FIG. 143 shows a swivel mounted collar similar to FIG. 135A with a plurality of different utensils or one utensil having a plurality of different offshoots (e.g., instrument wiring or tubing) received therein and coming out of the different porting.

FIG. 144 illustrates the collar of FIG. 135A further comprising a plug member having a central aperture, which plug provides for hold down functioning of items received in the collar and/or alignment for needle insertion etc., relative to a central hole in the plug, and or deflecting a received thin instrument as to brake from further movement or stop flow in valve stop like fashion.

FIG. 144A shows the collar and plug arrangement shown in FIG. 144 but from a side view.

FIGS. 144B to 144D show different length plugs with integrated pin caps that can be inserted to seal off the plug itself received by the collar.

FIG. 145 shows the same collar as FIG. 144 but with the plug inserted into the collar and with the plug cap in place.

FIG. 145A shows that which is shown in FIG. 145 but in side view.

Figure 109B:
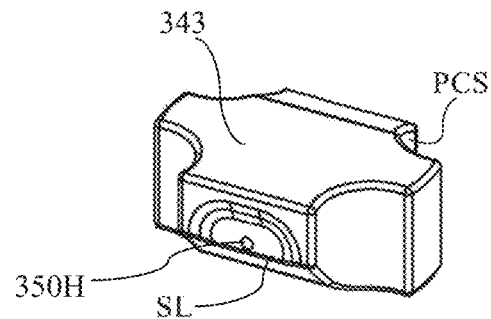
Figure 146:
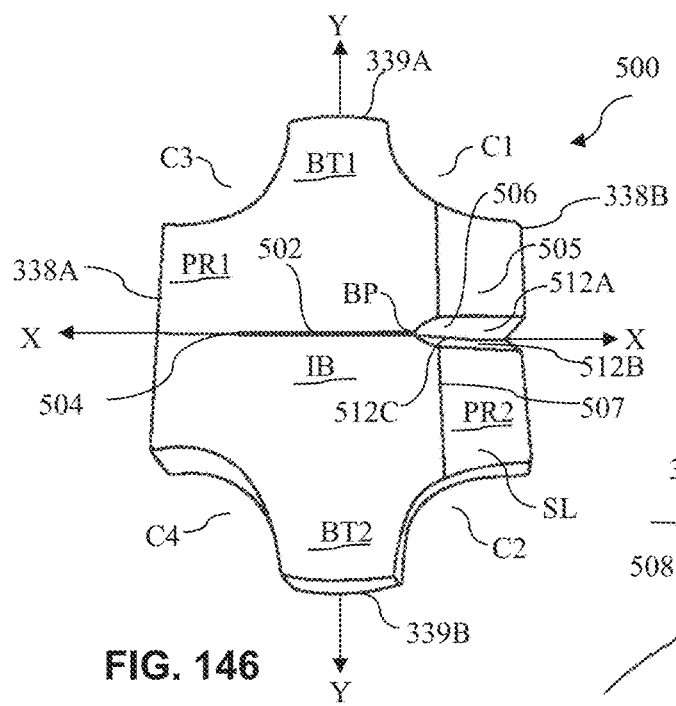

FIG. 146 shows a top plan view of a modified, "split" embodiment of the collar shown in FIG. 109B.

Figure 147:
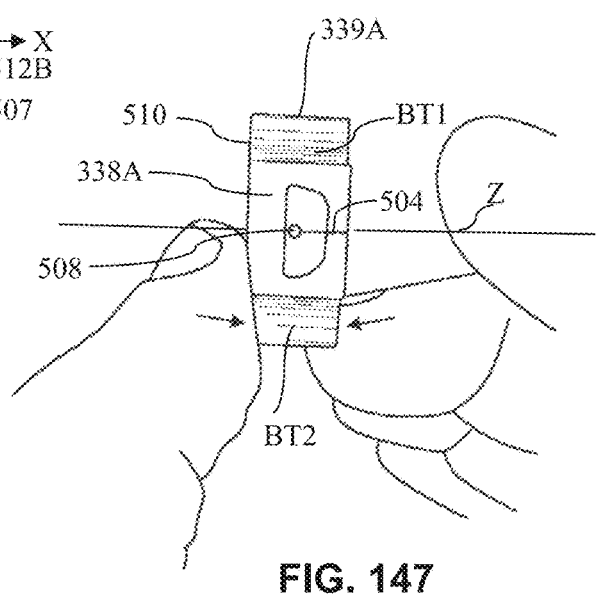

FIG. 147 shows a side view of the collar shown in FIG. 146 being held in a non-flexed state.

Figure 148:
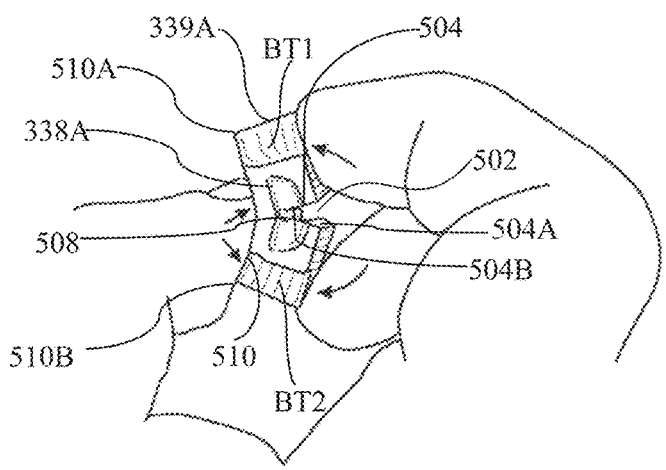

FIG. 148 shows a side view of the collar shown in FIG. 146 being held in a flexed, concave state.

FIG. 149 shows a top plan view of the collar similar to FIG. 146 but with an instrument in an initial state of insertion as to place the collar in an initial stage of flexing.

FIG. 150 shows a first perspective view from a bottom front orientation with the instrument of FIG. 149 fully inserted.

FIG. 151 shows a second perspective view from a top side orientation with the instrument of FIG. 149 fully inserted.

Figure 152:
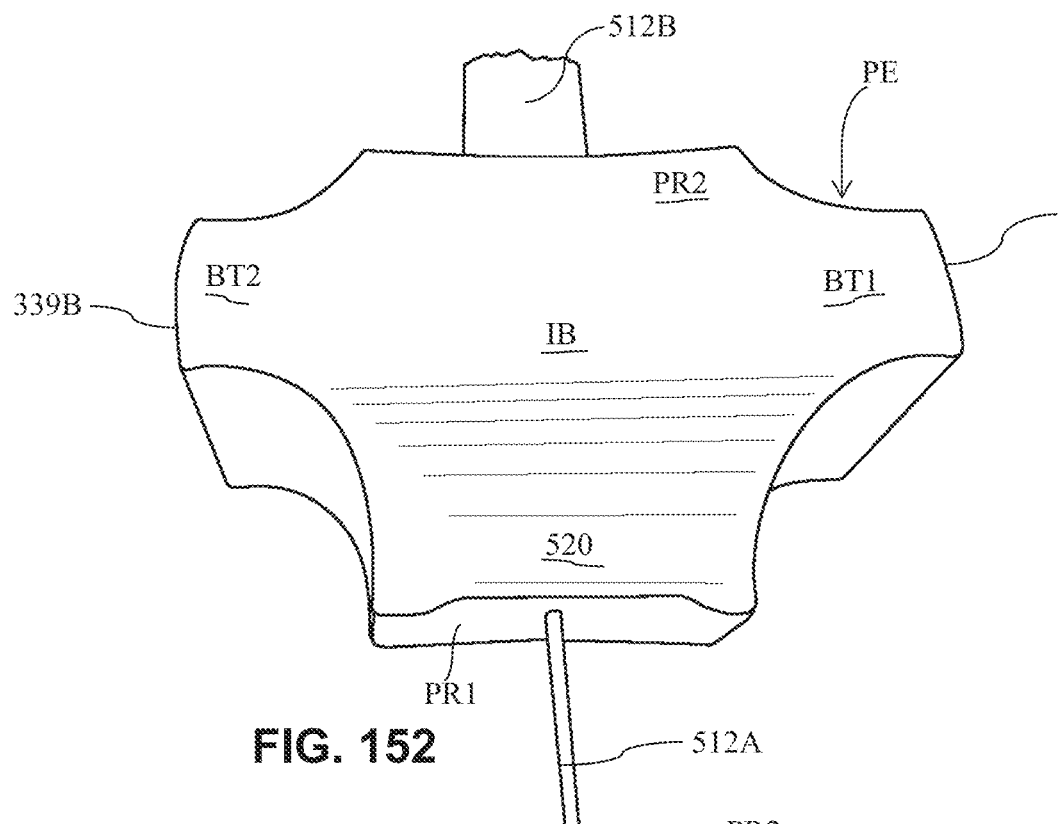

FIG. 152 shows another bottom perspective view of that which is shown in FIG. 151.

Figure 153:
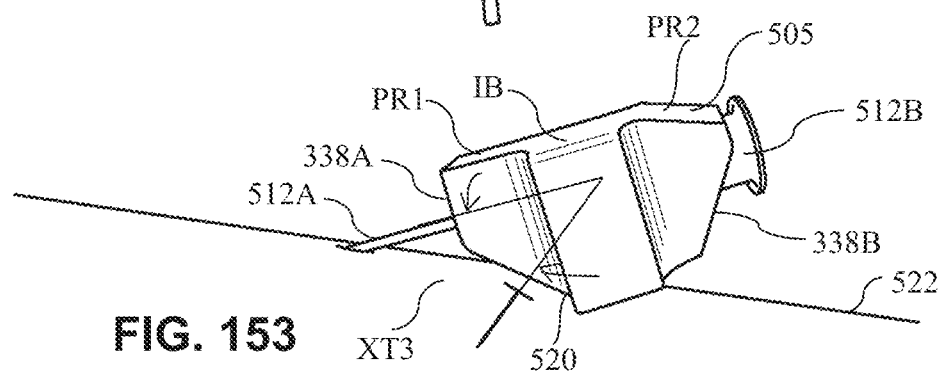

FIG. 153 shows the collar with a received instrument in the form of a needle assembly, with the needle puncturing a surface at an angle.

Figure 154:
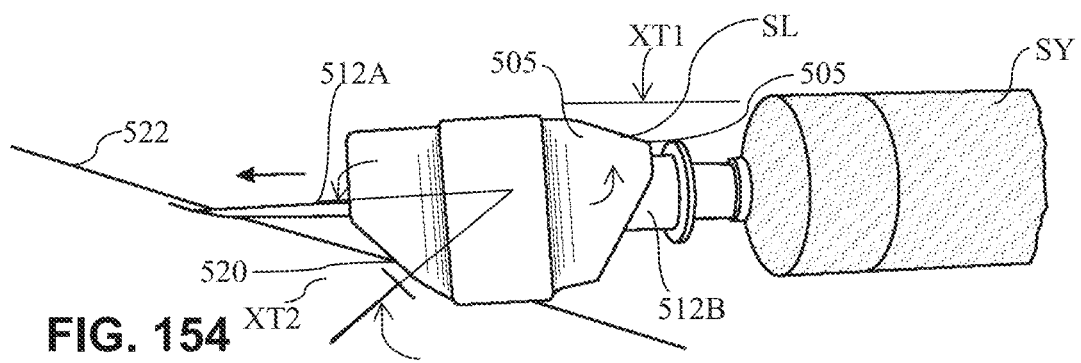

FIG. 154 shows that which is shown in FIG. 153 with an added syringe cylinder (shown broken away) in a locked engagement with the needle assembly received in the collar.

FIG. 155 shows a top view of the collar of FIG. 146 with needle assembly fully received and the collar fully flexed relative to the needle assembly.

FIG. 156 shows a receiving (or proximal) end view of a modified, "split" embodiment of the type of collar shown in FIG. 120A.

FIG. 157 shows a perspective view of the "split" collar embodiment shown in FIG. 156 just prior to receipt of an instrument.

FIG. 158 shows the same perspective view of the "split" collar embodiment shown in FIG. 157 with the instrument having just been received and the collar having gone from a flexed reception state to a "reformed neutral" state with the instrument supported.

FIG. 159 shows a working (or distal) end perspective view of the "split" collar embodiment shown in FIG. 158 with the instrument having been received and the collar in a reception state.

Figure 160:
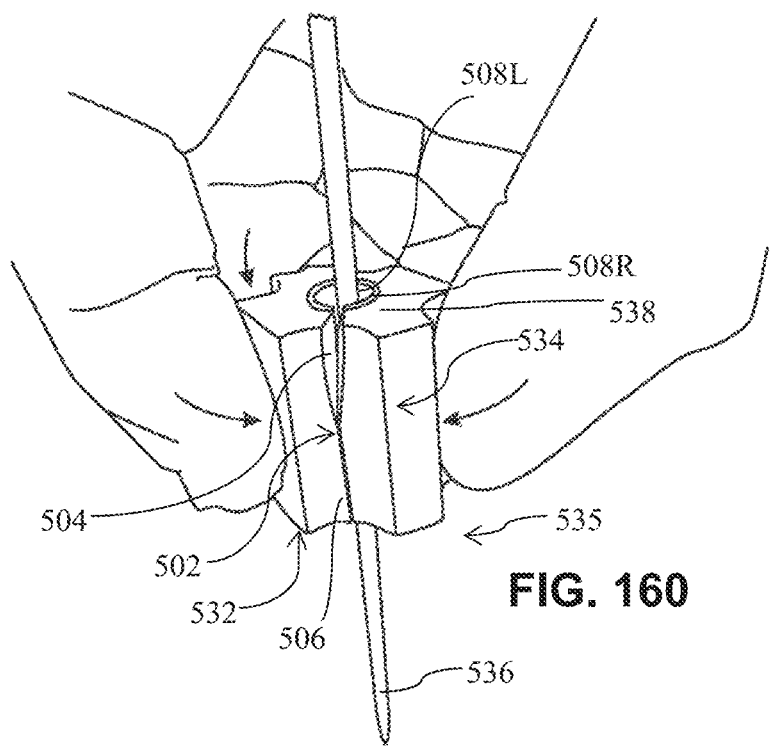

FIG. 160 shows a receiving end perspective (in use) illustration of another "split" embodiment featuring a tapered through-hole somewhat similar to that shown in FIG. 114B.

Figure 161:
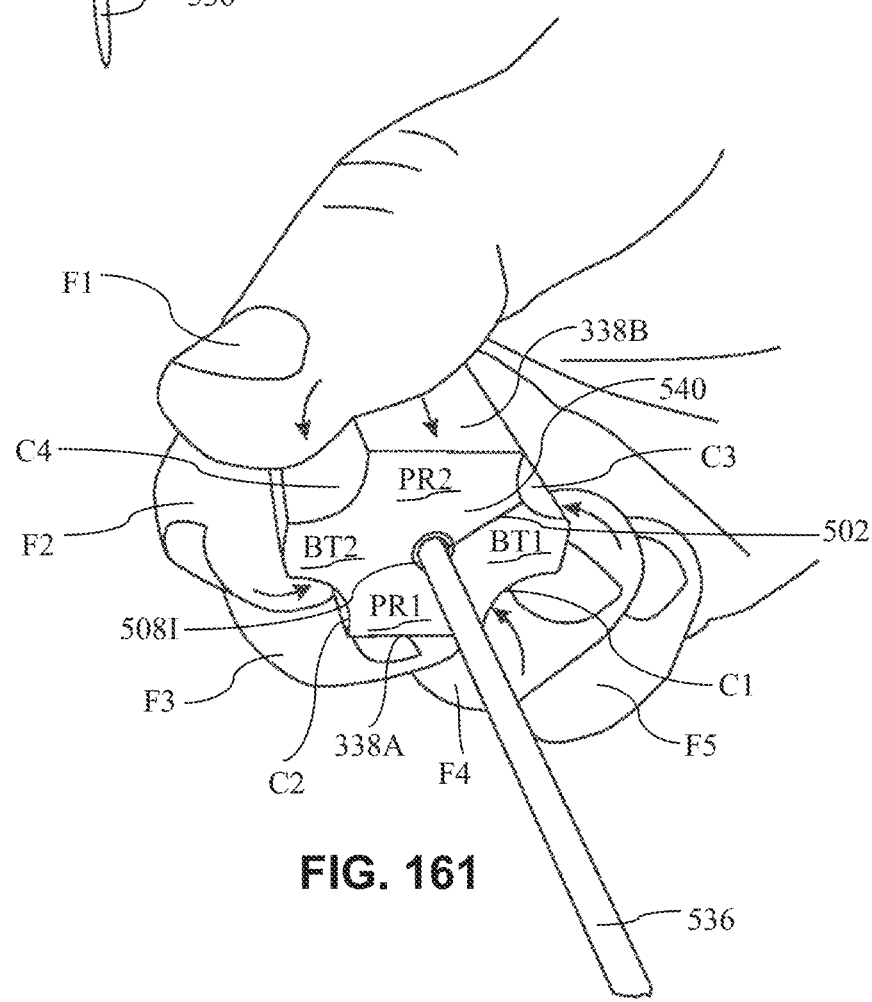

FIG. 161 shows the embodiment of FIG. 160 from an alternate working end view point.

Figure 162:
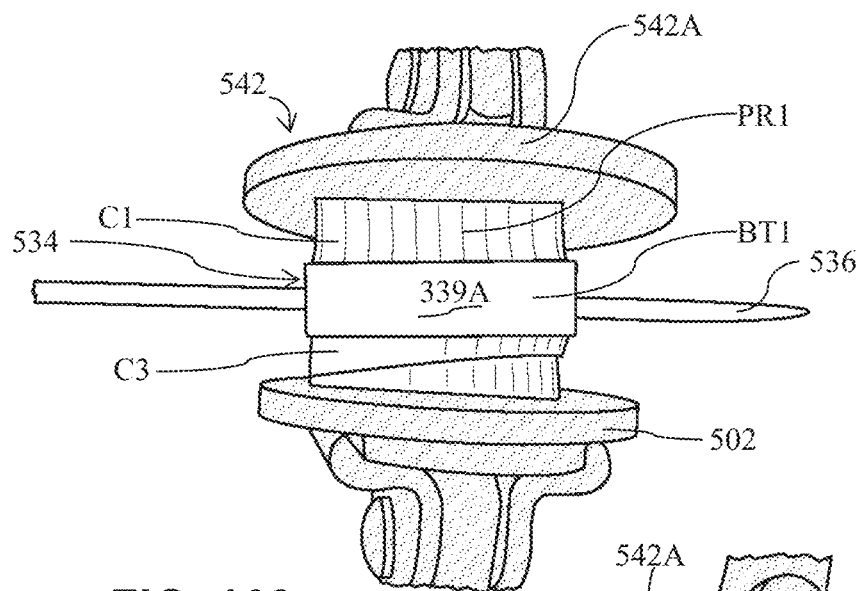
Figure 163:
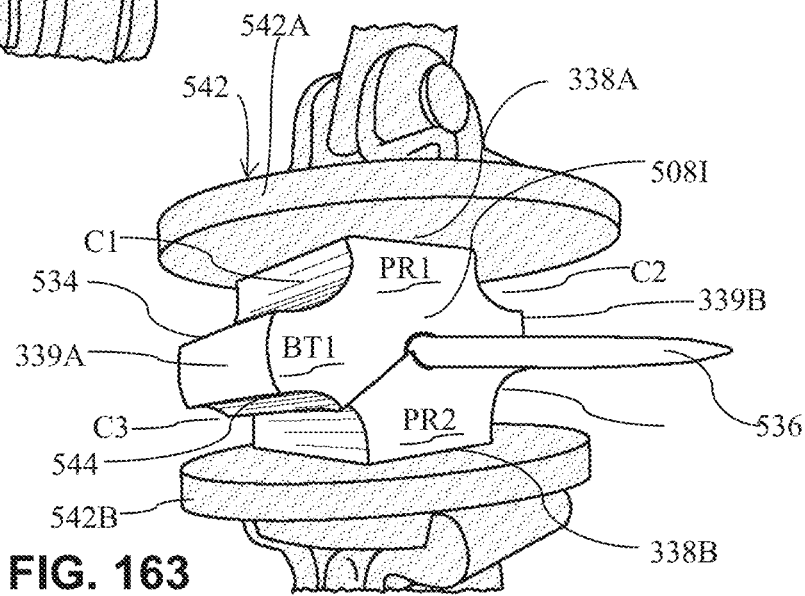
Figure 164:
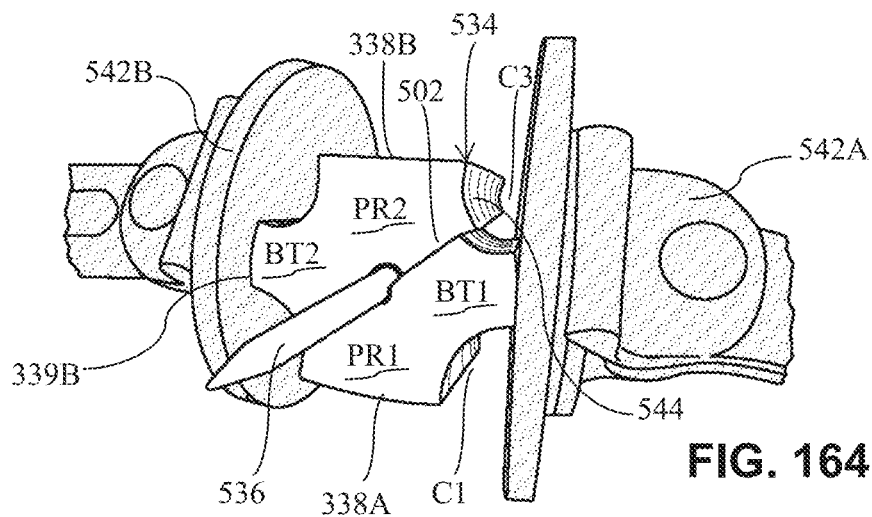

FIGS. 162 to 164 show various views of the embodiment of FIG. 161 subject to a clamping assembly to help visualize the unique compression grasping quality of split collar embodiments of the present invention with the clamping pressure shown (without total collapse) being at an exaggerated applied pressure beyond finger grasp capacity.

Figure 165:
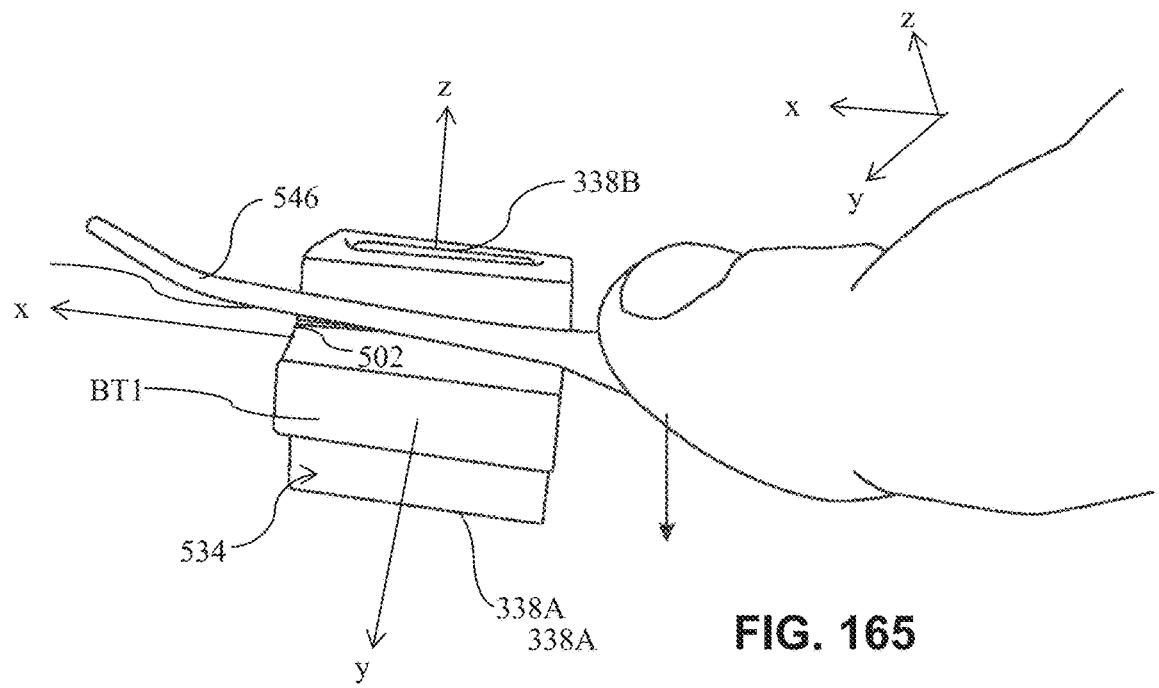
Figure 166:
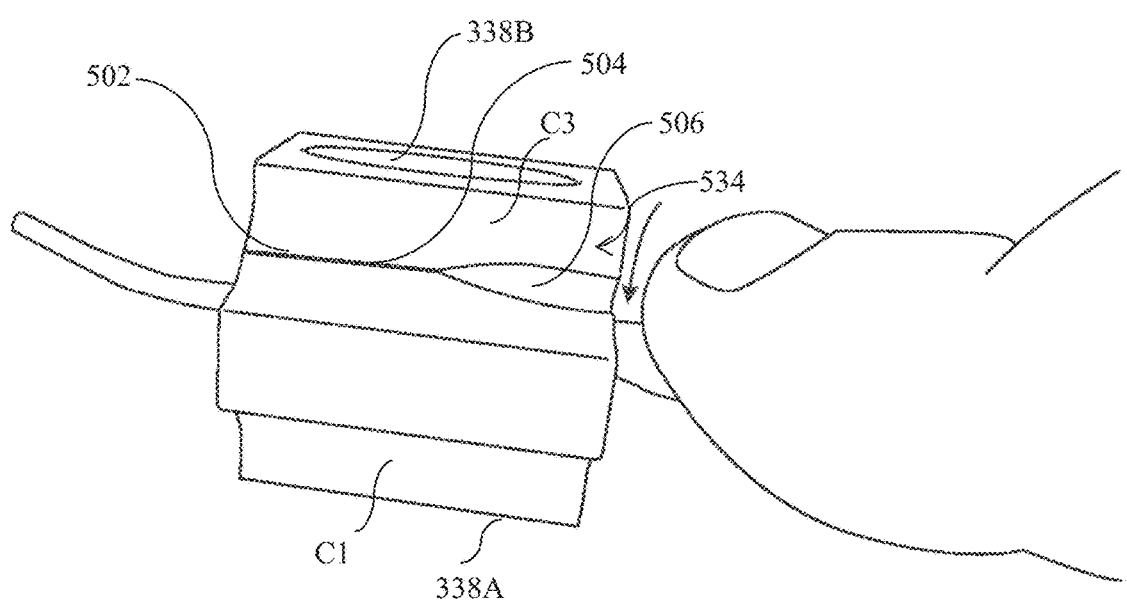

FIGS. 165 and 166 show a split collar embodiment similar to that of FIG. 157, but with a different instrument in both an initial contact state of insertion and a fully inserted state, respectively.

Figure 167:
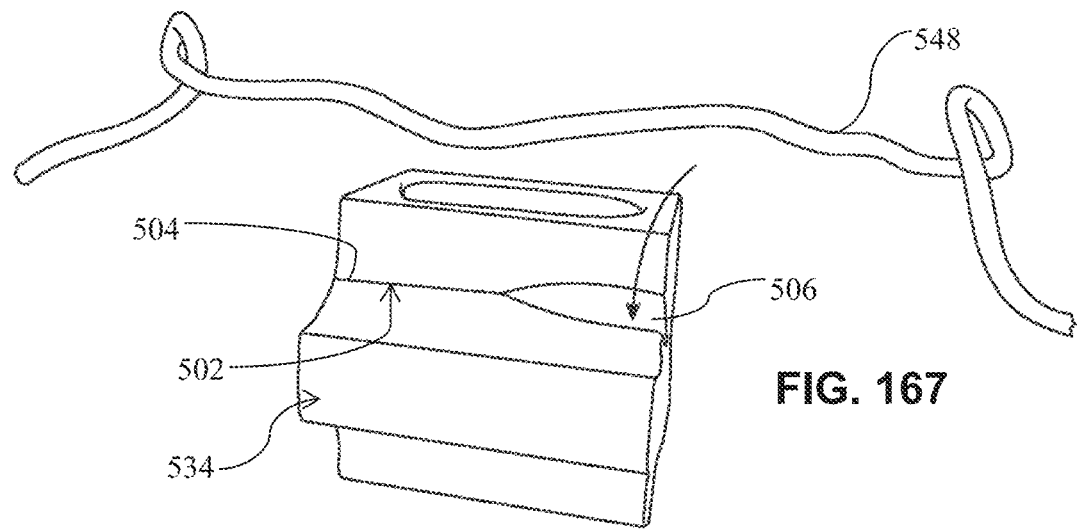
Figure 168:
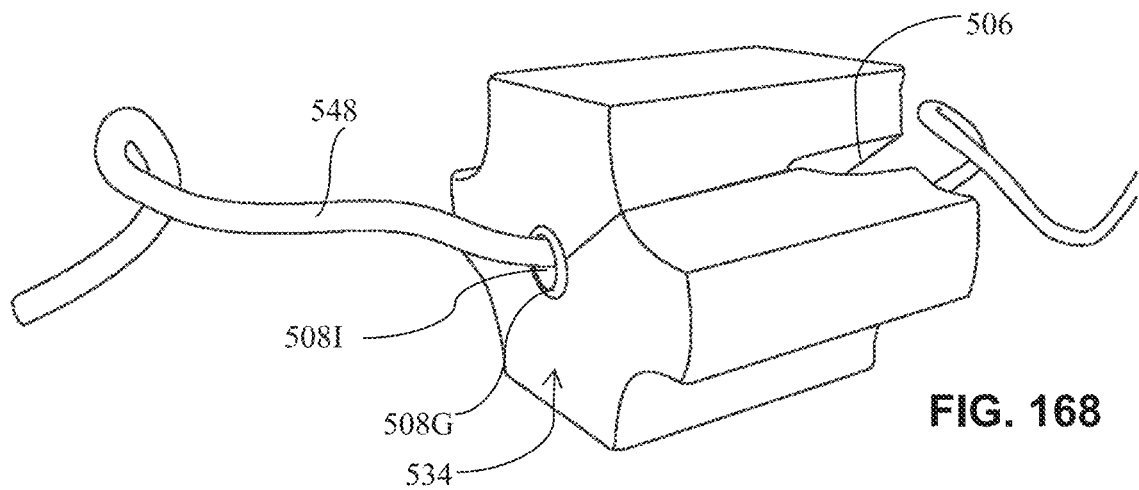

FIGS. 167 and 168 show a split collar embodiment similar to that of FIG. 157, but with a different instrument in both a pre-insertion state and a fully inserted state, respectively.

Figure 167A:
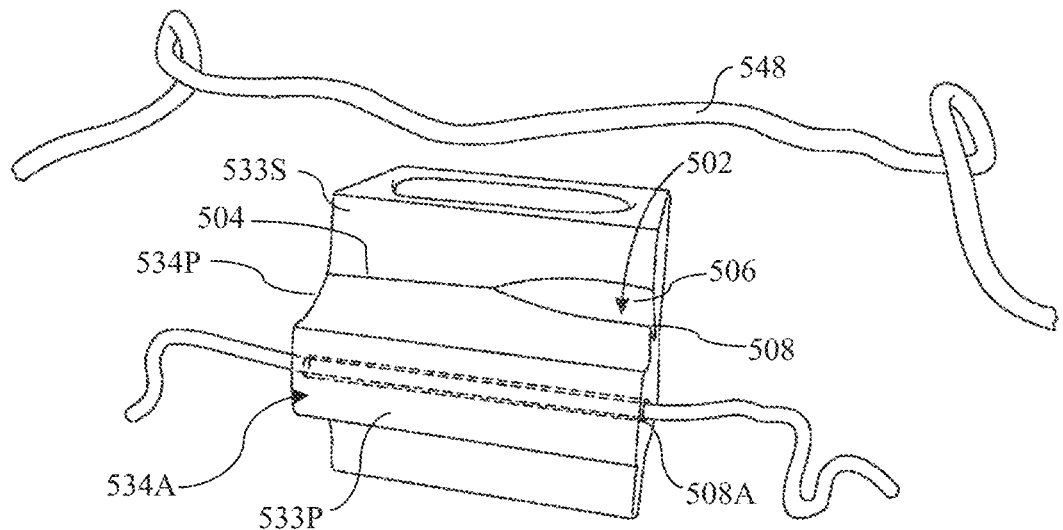
Figure 168A:
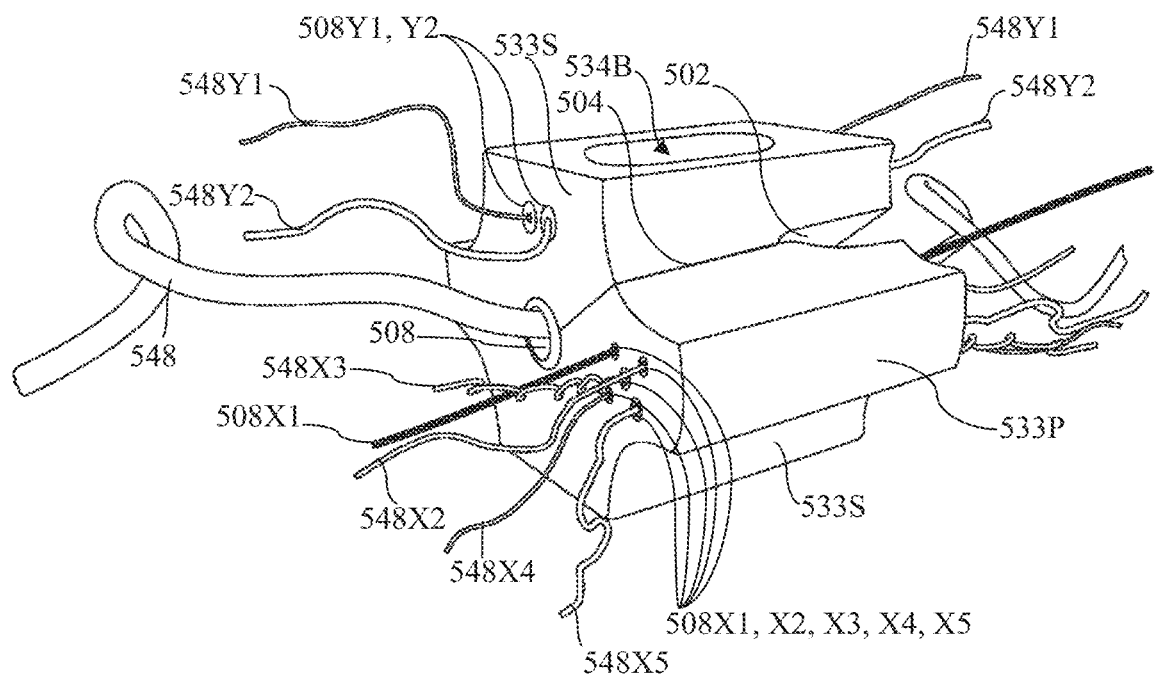

FIGS. 167A and 168A show a split collar embodiment similar to that of FIGS. 167 and 168, but with additional collar conduits added for receipt of additional linear elements such as wires (e.g., electronic or medical usage as in catheter wires), fluid (gas or liquid) passageways.

Figure 169:
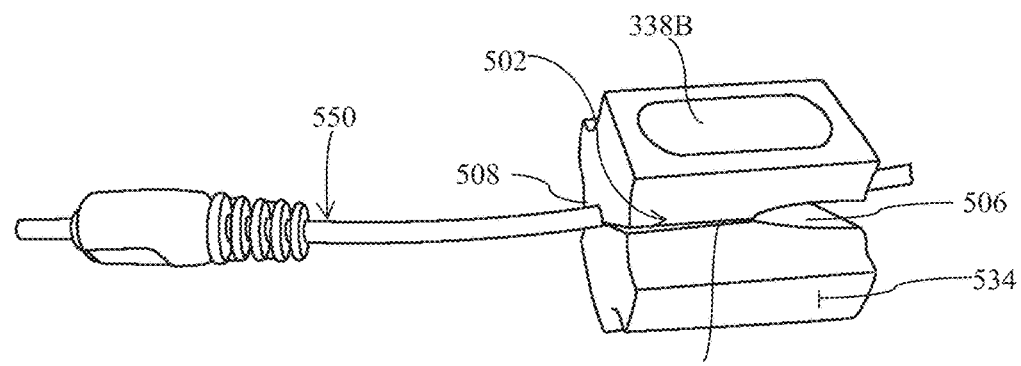

FIG. 169 shows a split collar embodiment similar to that of FIG. 157 (non-tapered through-hole) but with a different instrument, with FIG. 169 showing the instrument receiving collar in a flexed shut, but uncompressed state that is able to maintain the closure capacity of the collar without external force.

Figure 170:
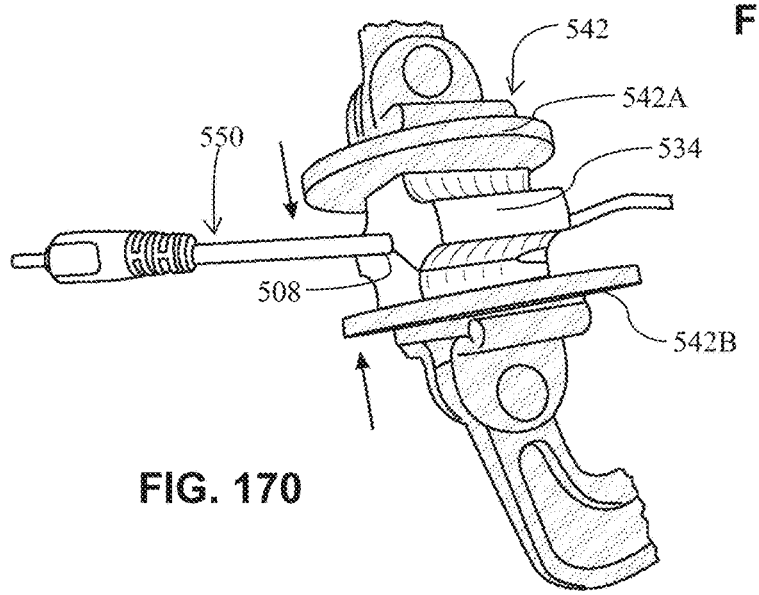

FIG. 170 shows the collar under a mechanical compression assembly.

Figure 170A:
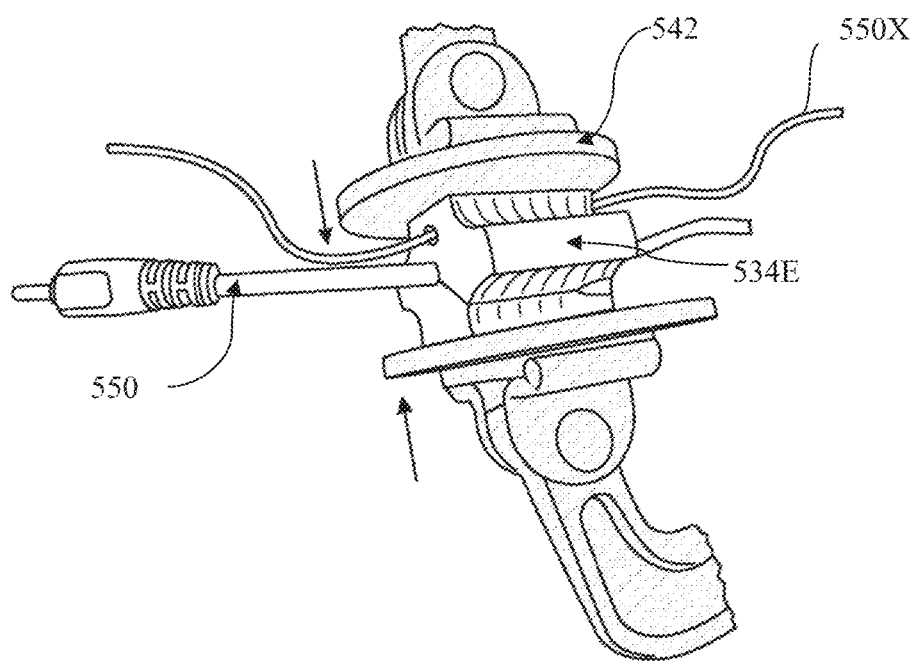

FIG. 170A shows a similarly configured collar as that shown in FIG. 170 but with an added passageway through which a linear element extends out at each end.

Figure 170B:
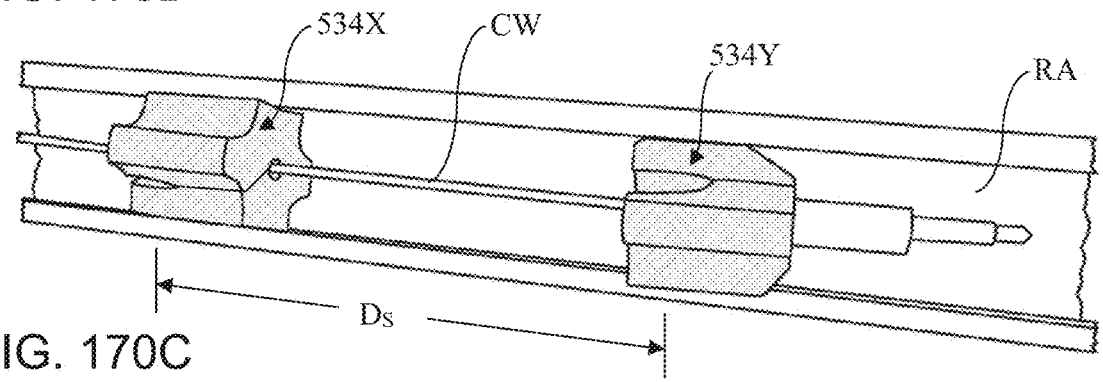

FIG. 170B shows as assembly featuring multiple collars of the FIG. 170 type arranged in a common reception area, with each collar having a slit and reception cavity combination, but in a different orientation as to facilitate blockage of a continuous release of a linear element that is received by each of the multiple collars when only a pull-out from one or some is desired.

Figure 170C:
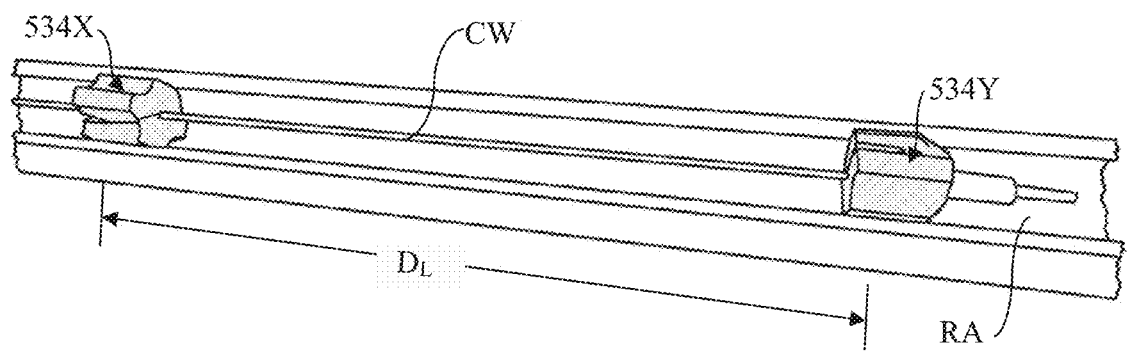

FIG. 170C shows a similar arrangement as in FIG. 170B but with the relative spacing between the two collars shown increased within the common reception cavity.

Figure 170D:
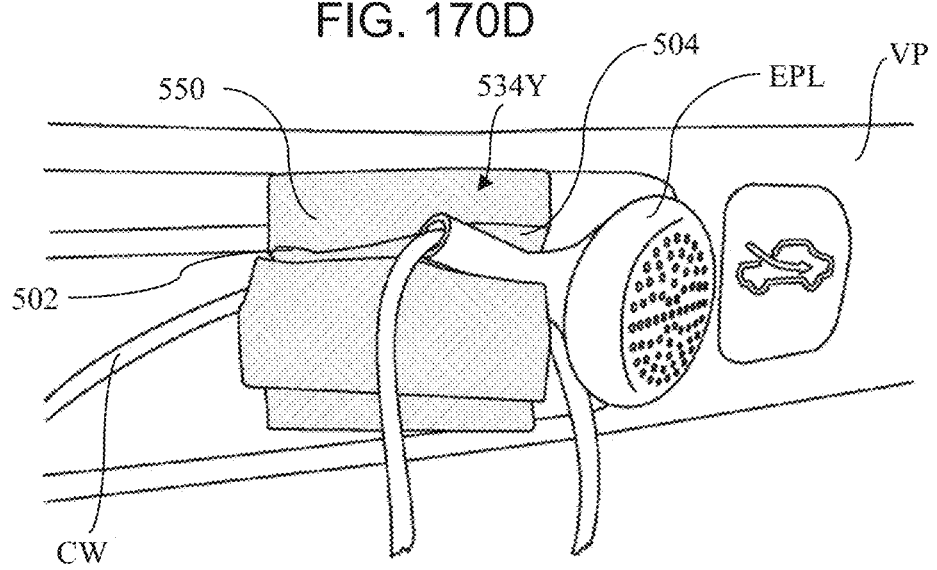

FIG. 170D shows also the collar of FIG. 170 received in a capture passageway as may be provided in the interior housing molding of a vehicle and with a different received instrument (ear phone plug or ear bud) releasably retained within the collar (and which can represent the sole collar in the capture cavity or one of a multi-set of two or more (e.g., three) collars of, for example, a common design but different orientation within the one or more receiving cavities (as in the illustrated vehicle interior housing cavity environment).

Figure 171:
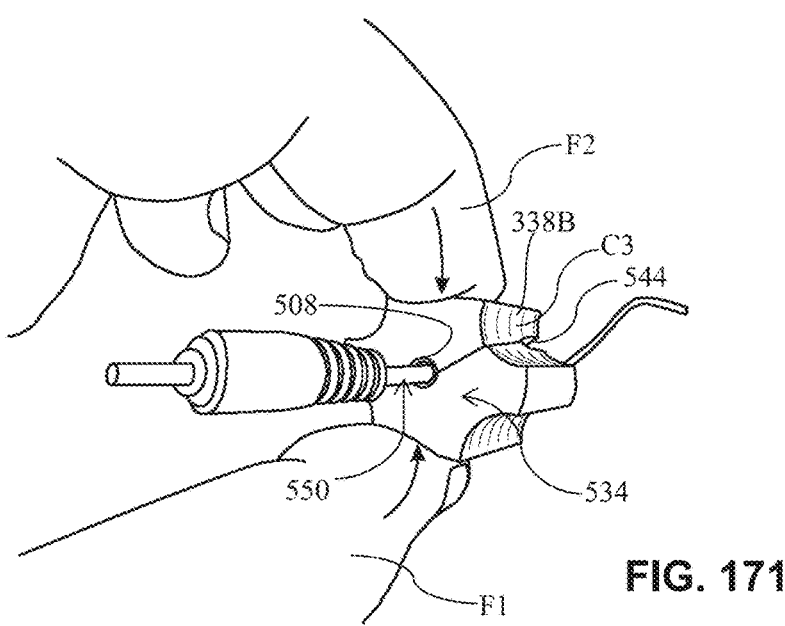

FIG. 171 shows the collar of FIG. 170 in a finger compression "two finger pinch" state.

Figure 86:
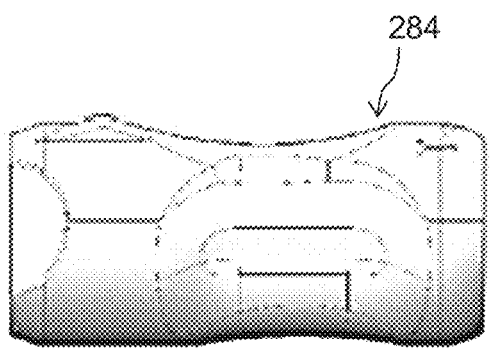
FIG. 86 shows a collar or sleeve similar to that attached to the needle hub of the syringe in FIG. 61, but with a modified haptic promotion cavity which is well suited for, for example, catheter equipment manipulation.
Figures 91, 92, 93, 94:
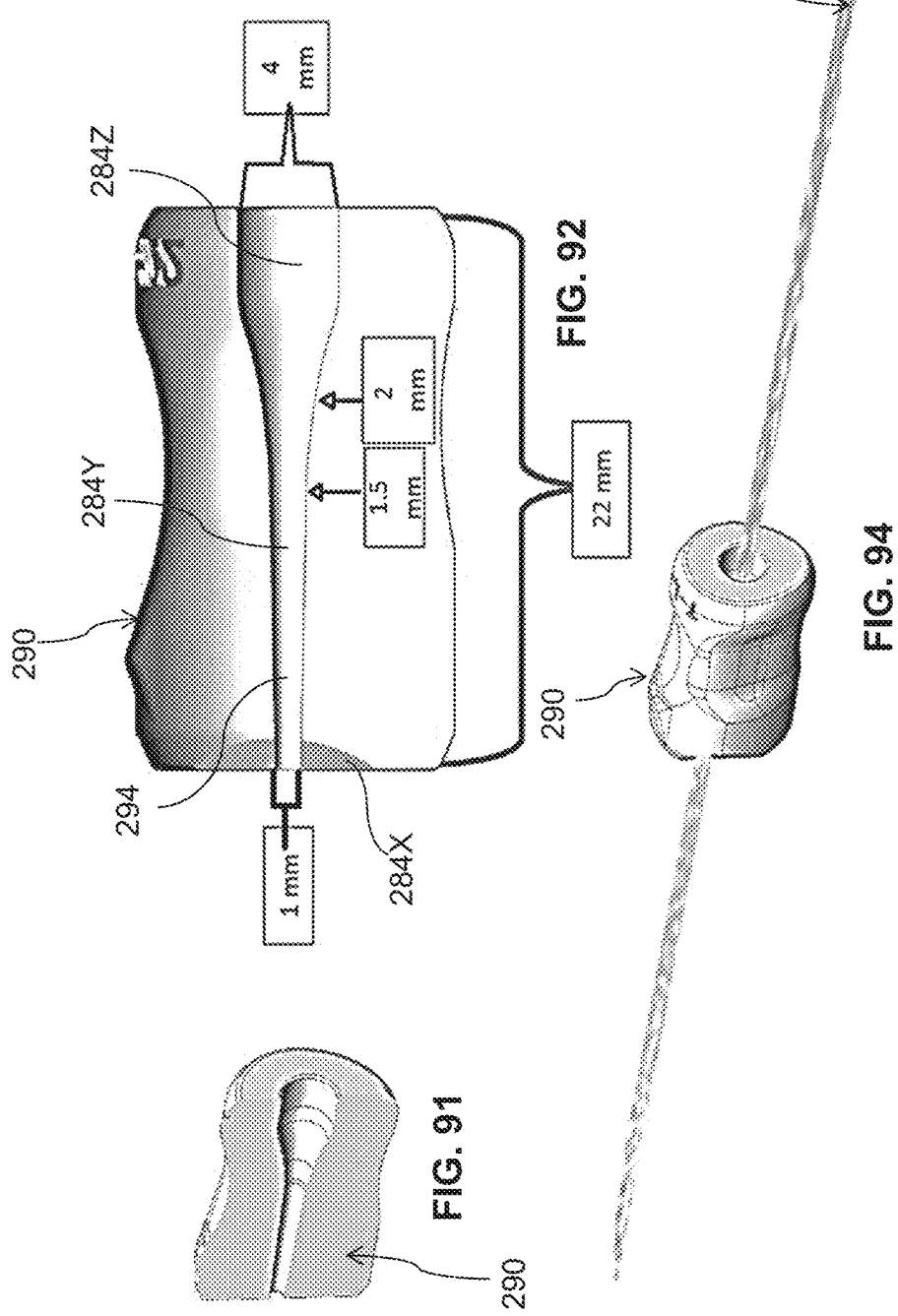
FIG. 91 shows an alternate embodiment of a catheter line grasping collar or sleeve with its central haptic cavity shown in cross-section.
FIG. 92 shows the cross-sectional view of FIG. 91 with some non-limiting, illustrative haptic cavity diameter values relative to the varying diametrical nature of the cavity along its length.
FIG. 93 shows a front elevation of the exterior contoured surface of the collar of FIG. 91.
FIG. 94 shows the collar of FIG. 91 in position on a catheter line.
Figure 172:
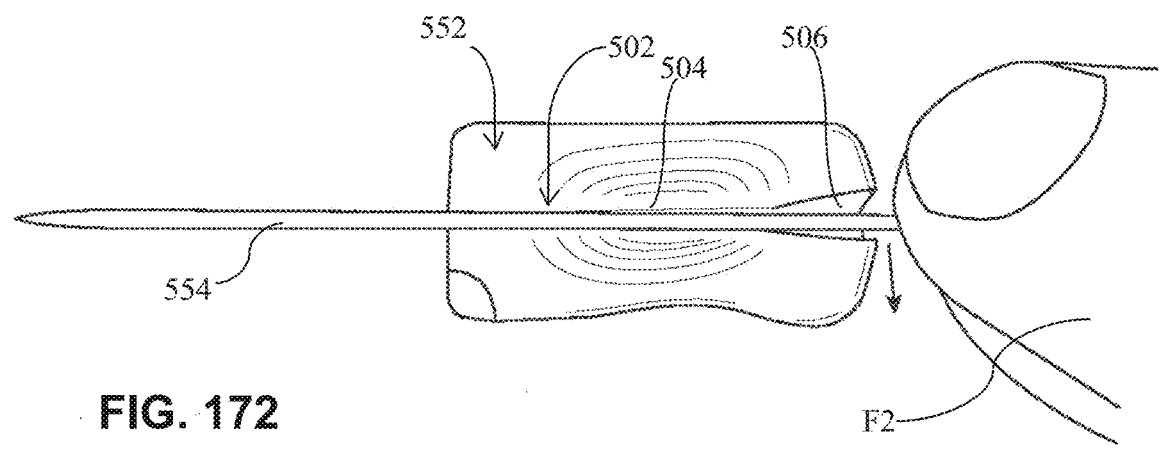

FIG. 172 shows a top plan view of a modified, "split" embodiment of the collar such as that shown in FIGS. 86 and 93 (with or without a varying diameter central aperture), with the instrument in an initial stage of insertion, wherein the instrument's underlying surface is in contact with the collar and forcing at least the narrow slit farther open.

Figure 173:
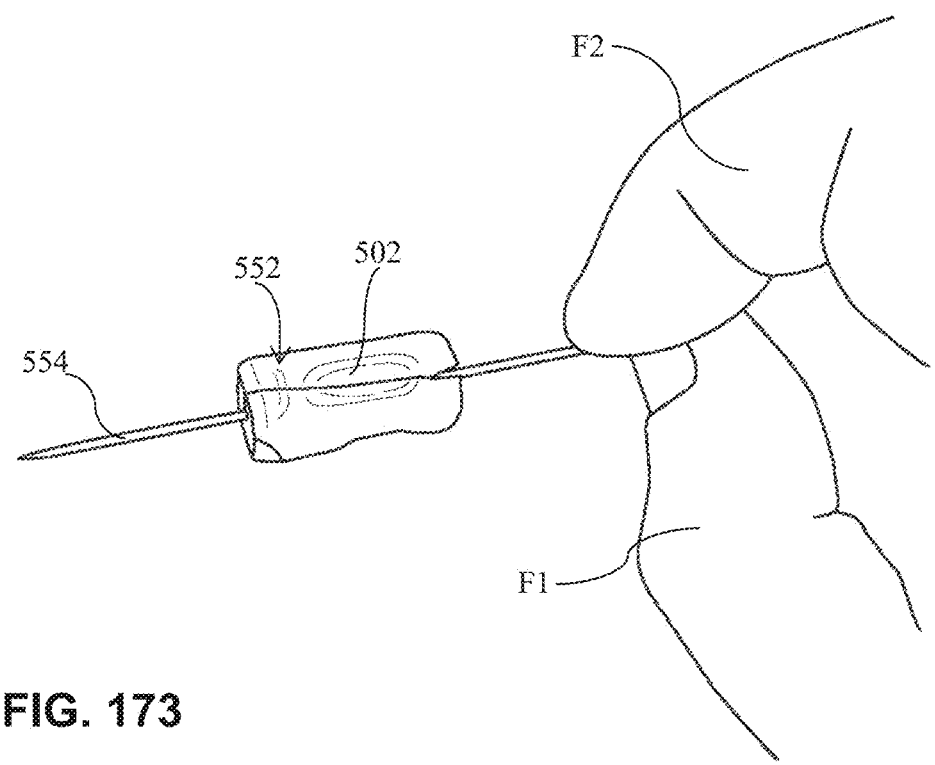

FIG. 173 shows that which is shown in FIG. 172 but in a final stage of insertion.

Figure 174:
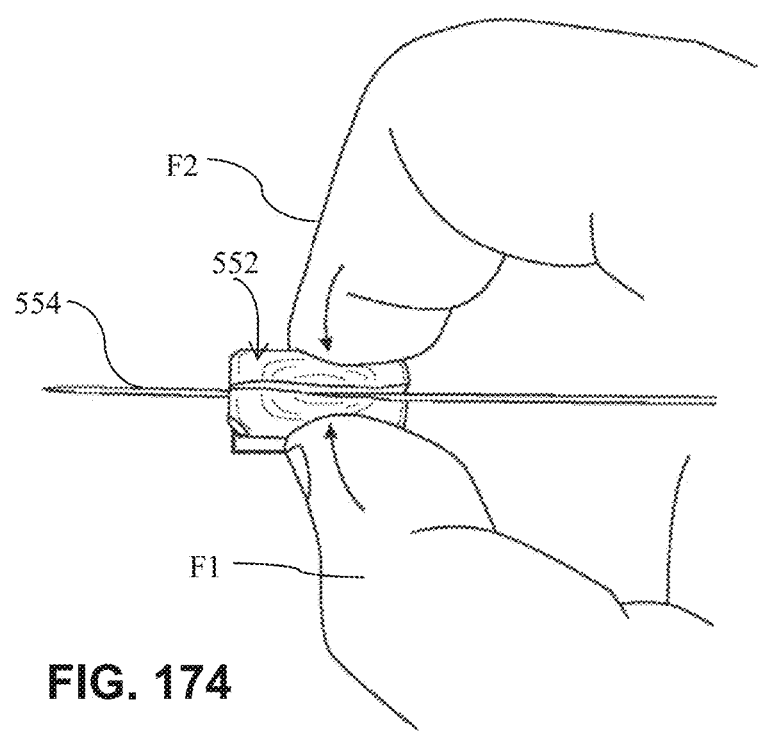

FIG. 174 shows that which is shown in FIG. 173 but in a user two finger pinch mode.

Figure 175:
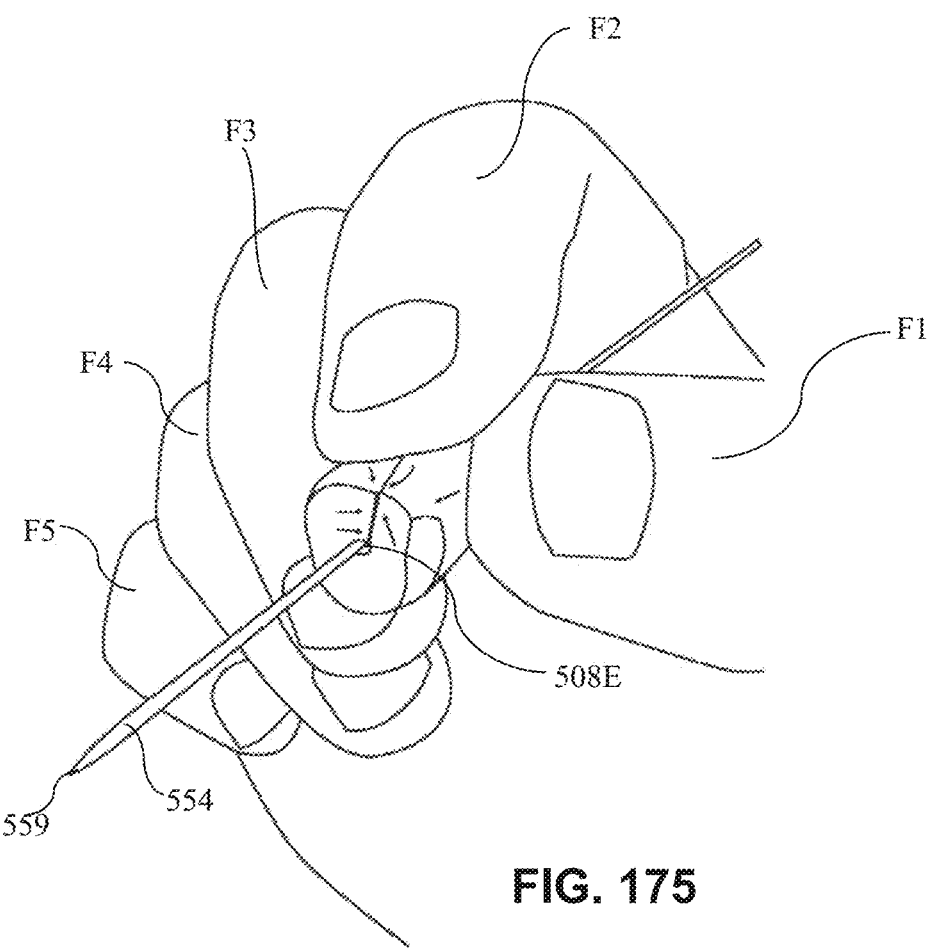

FIG. 175 shows that which is shown in FIG. 173 but in a three finger "pencil hold" mode.

Figure 176:
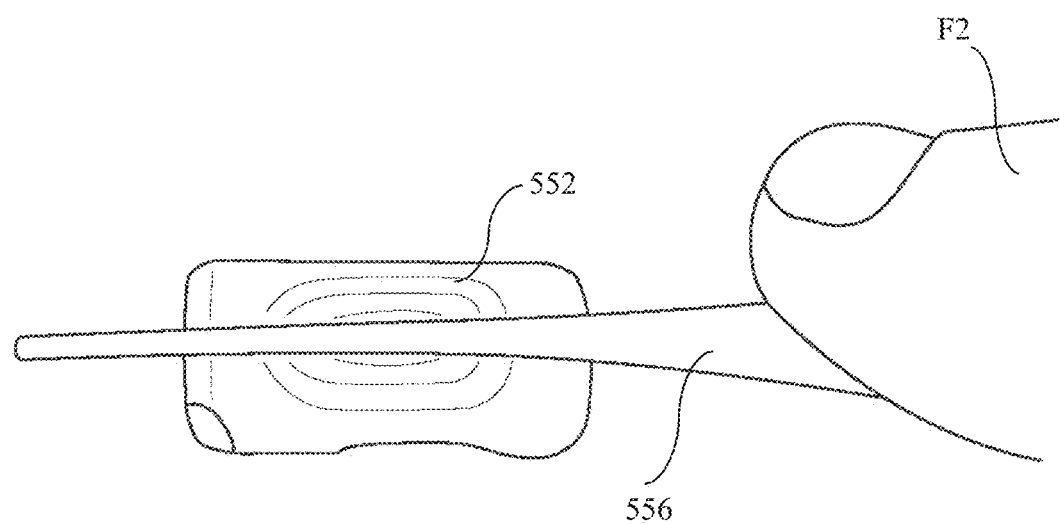
Figure 177:
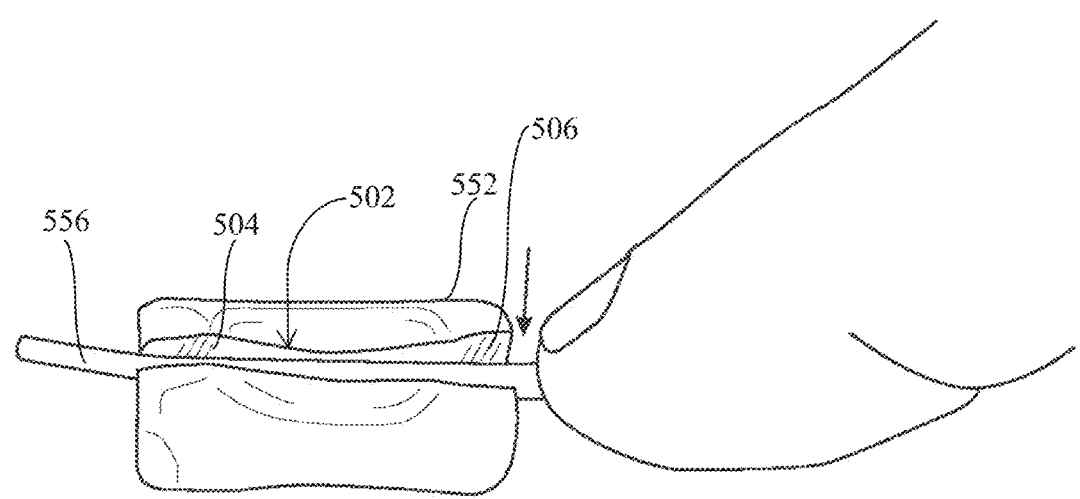
Figure 178:
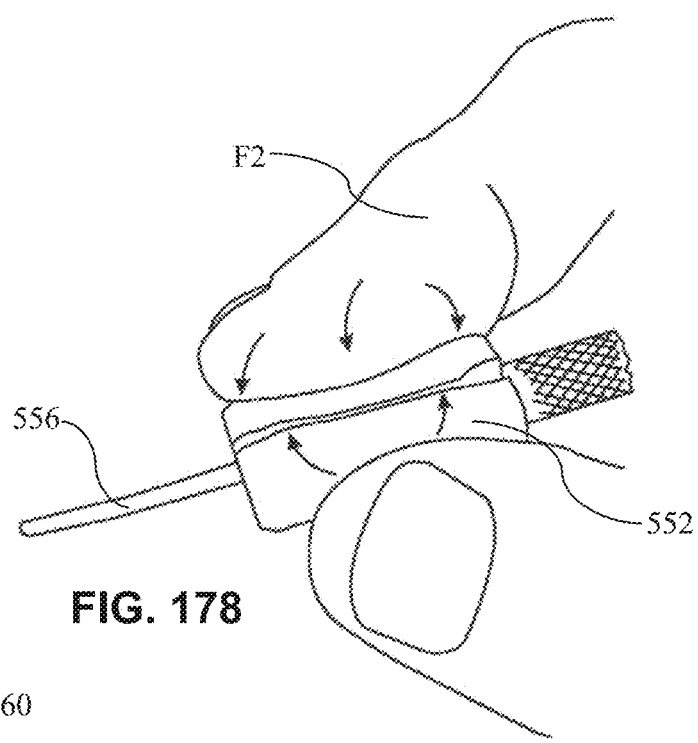

FIGS. 176 to 178 show a split collar embodiment similar to that of FIG. 172, with FIG. 176 showing an initial contact state of insertion of a hand held instrument, FIG. 177 showing a nearly fully inserted state (the instrument within the confines of the periphery of the collar but not quite in its final resting state) of that instrument, and FIG. 178 showing a user two finger pinch mode with the instrument supported in its final reception state.

Figure 179:
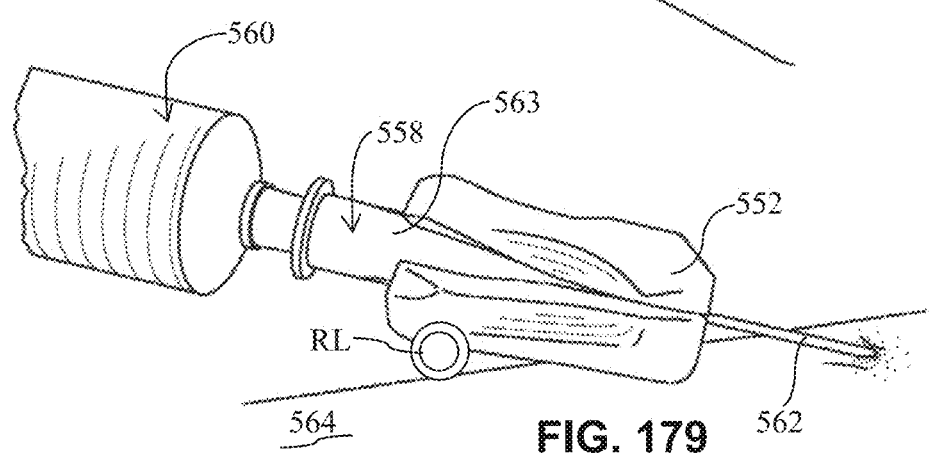

FIG. 179 shows the split collar shown in FIG. 172, but with the needle assembly of a syringe received by the collar in a fully inserted state but with the gap still open at least partially as to improve instrument visibility.

Figure 180:
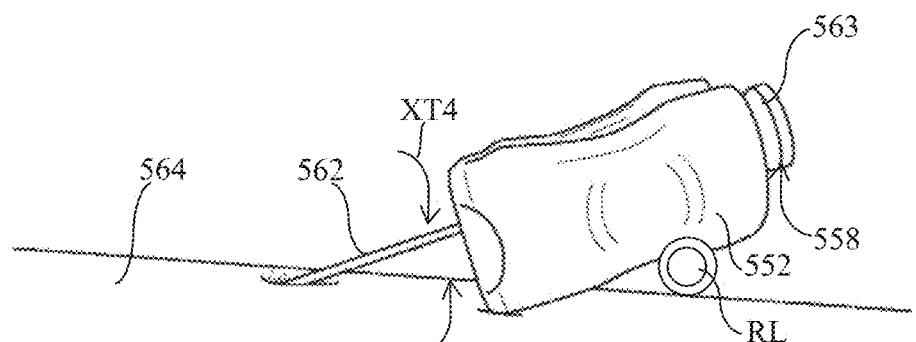

FIG. 180 shows the split collar shown in FIG. 179, but from a different view point wherein there can be seen the needle assembly relationship with respect to the punctured skin and the receiving, flexed out collar receiving the needle assembly.

Figure 181:
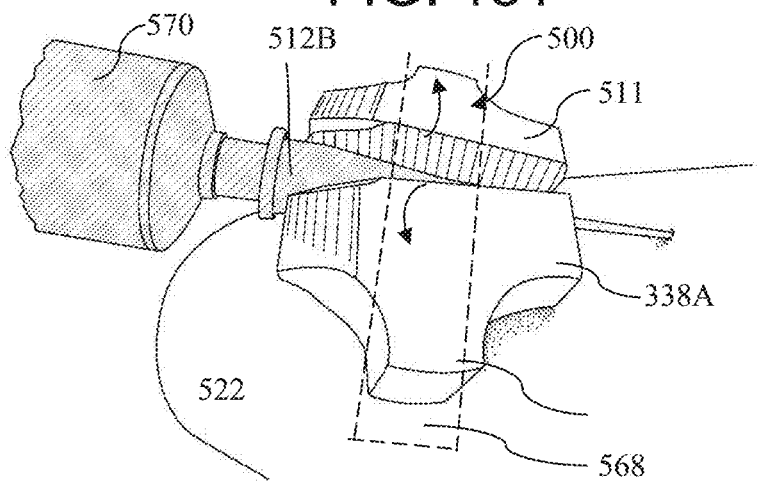

FIG. 181 shows a view of the split wing collar shown in FIG. 155 but from a different viewpoint and with optional hold down means illustrated in dashed lines.

Figure 182:
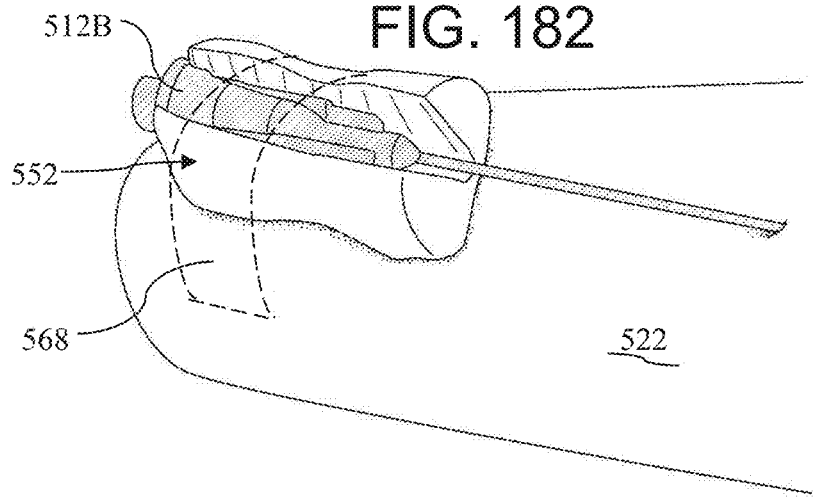

FIG. 182 shows a top perspective view of the split collar shown in FIG. 179 with a fully received needle hub configuration and with optional hold down means illustrated in dashed lines.

Figure 183:
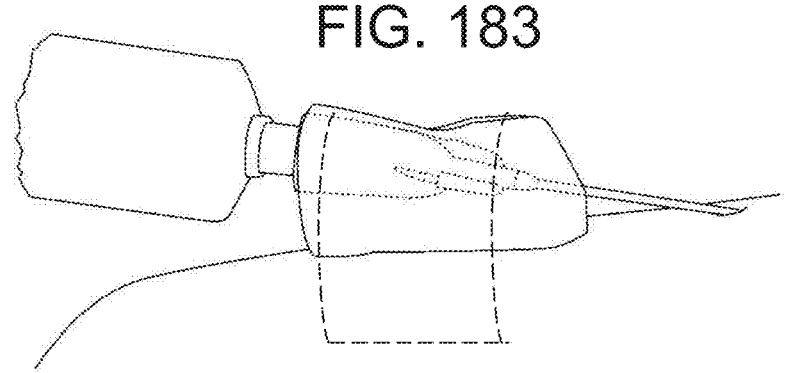

FIG. 183 shows a side view of the split collar shown in FIG. 182 with received needle hub and optional hold down means.

Figure 184A:
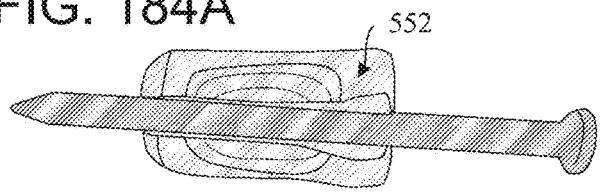

FIG. 184A shows the collar shown in FIG. 179 but with a fastener (nail) received therein.

Figure 184B:
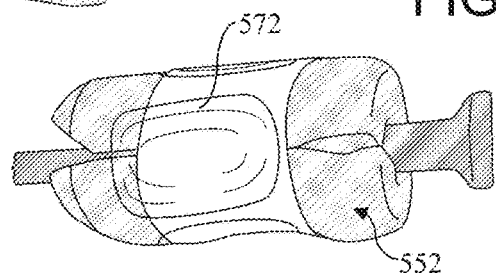

FIG. 184B shows the same collar shown in FIG. 184A but with a wrap extending around the periphery of the collar.

Figure 185A:
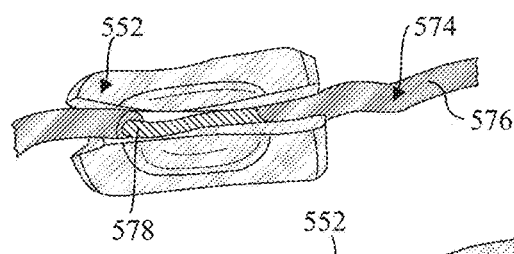

FIG. 185A shows the collar shown in FIG. 179 but with an exposed wire initially received therein (before natural collapse).

Figure 185B:
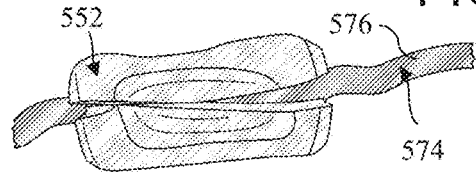

FIG. 185B shows the collar shown in FIG. 185A with an exposed wire received therein and after the natural collapse of the material.

Figure 185C:
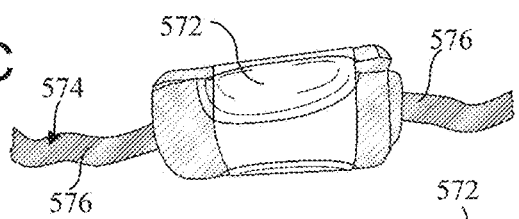

FIG. 185C shows the collar shown in FIG. 185A but with a wrap around the collapsed collar.

Figure 185D:
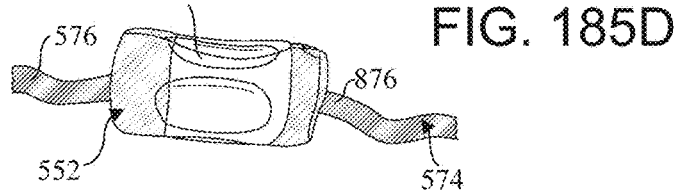

FIG. 185D shows the collar shown in FIG. 185C from a different rotated viewpoint.

Figure 185E:
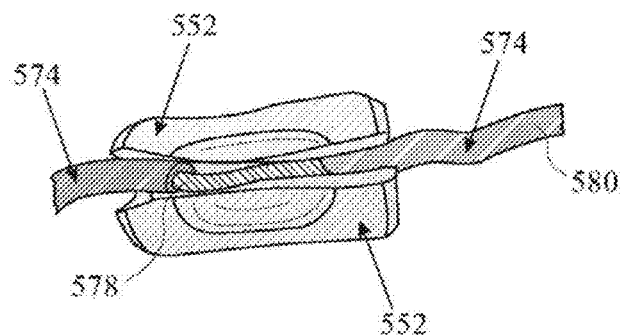

FIG. 185E shows the collar shown in FIG. 185C but receiving the twisted end region of two connected wires.

Figure 185F:
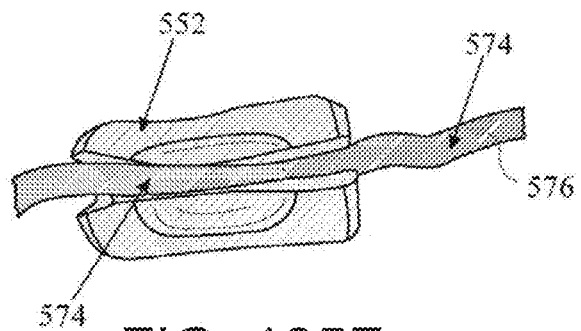

FIG. 185F shows the collar shown in FIG. 185C but receiving a fully insulated wire as a preventive measure against subsequent fraying due to positioning and potential abrasion with another surface.

Figure 185G:
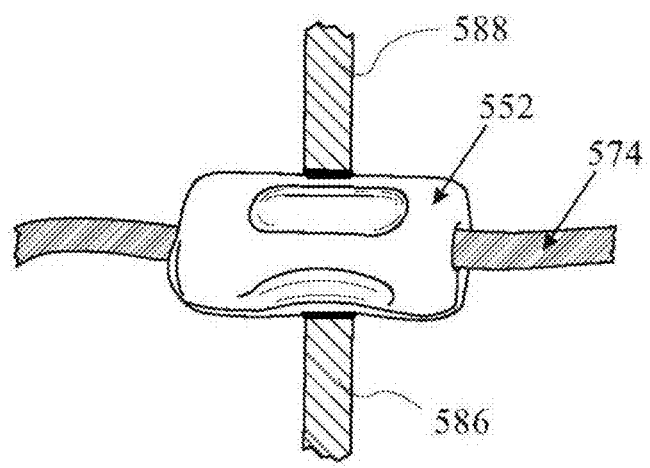

FIG. 185G shows the collar shown in FIG. 185C put in a compressive retention position relative to a hole in a plate or wall (etc.) and surrounding and protecting any of the various exposed or non-exposed wire regions featured in FIG. 185A, 185E or 185F.

Figure 186A:
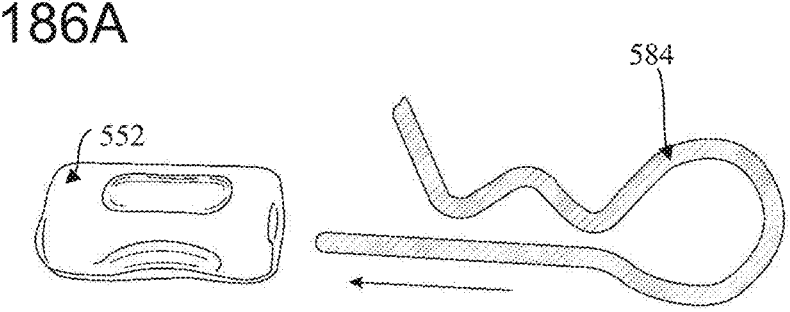

FIG. 186A shows the same collar as shown in FIG. 179 prior to formation of an insulating assembly with a cotter pin.

Figure 186B:
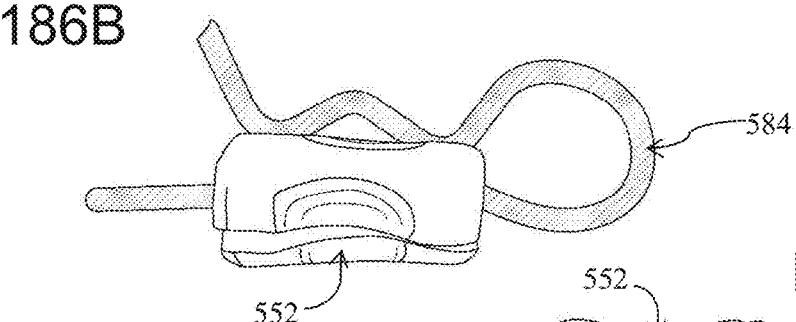

FIG. 186B shows the collar shown in FIG. 186A following insertion and retention of the cotter pin within the collar.

Figure 186C:
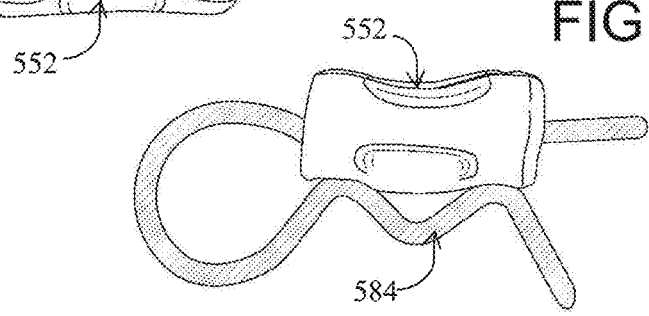

FIG. 186C shows the collar shown in FIG. 186B but from a different viewpoint.

Figure 186D:
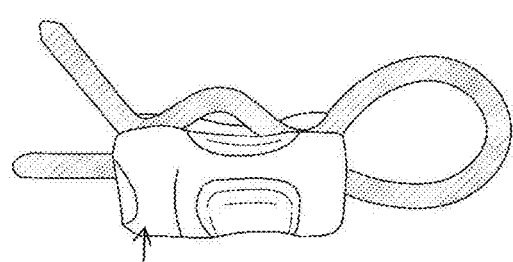

FIG. 186D shows the collar shown in FIG. 179 in a non-insulating, direct contact relationship with a cotter pin.

Figure 186E:
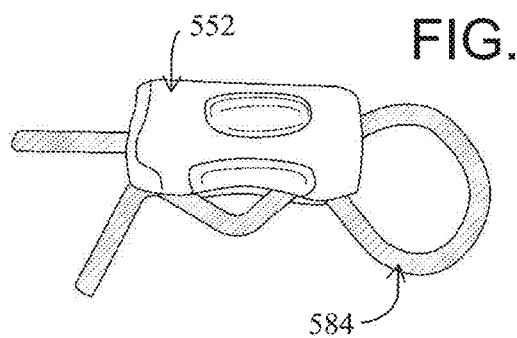

FIG. 186E shows the same collar as shown in FIG. 186D but from a different viewpoint.

Figure 187A:
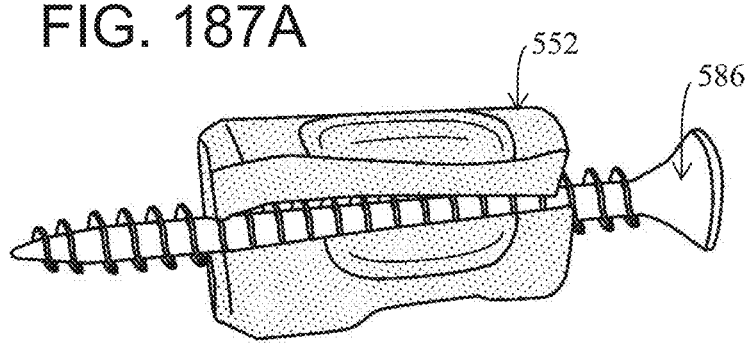

FIG. 187A shows a fastener receiving slit or split collar embodiment similar to that shown in FIG. 184A, but receiving a fastener in the form of a screw instead of a nail.

Figure 187B:
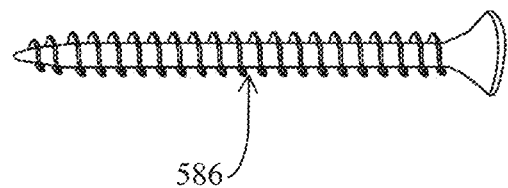

FIG. 187B shows the screw fastener that is received by the collar in FIG. 187A.

Figure 188A:
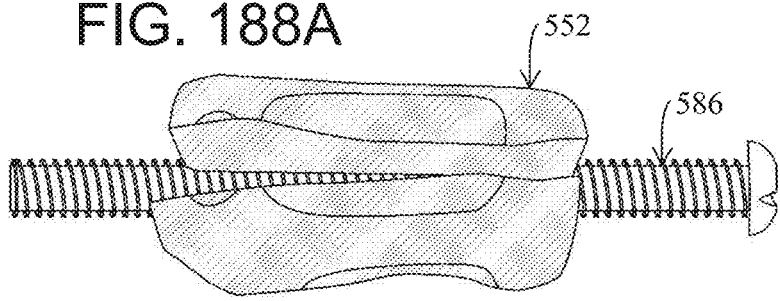

FIG. 188A shows a fastener receiving slit or split collar embodiment similar to that shown in FIG. 184A, but receiving a non-tapered free end machine screw instead of a nail.

Figure 188B:
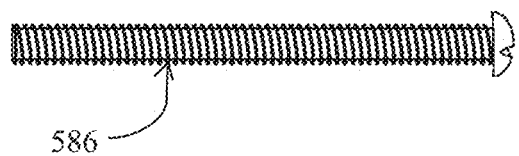

FIG. 188B shows the non-tapered screw fastener that is received by the collar in FIG. 188A.

Figure 189:
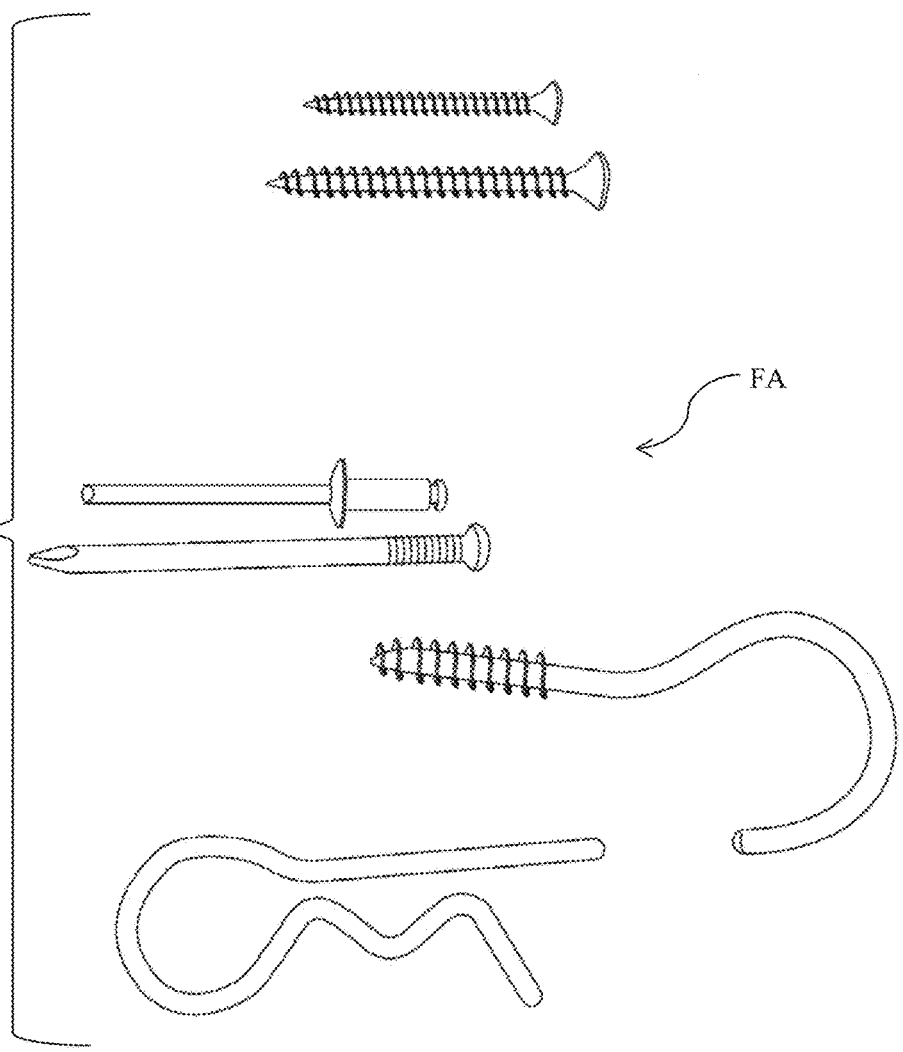

FIG. 189 shows a group of fasteners (including the aforementioned cotter pin suitable for receipt within the same split collar shown in FIG. 184A).

Figure 190A:
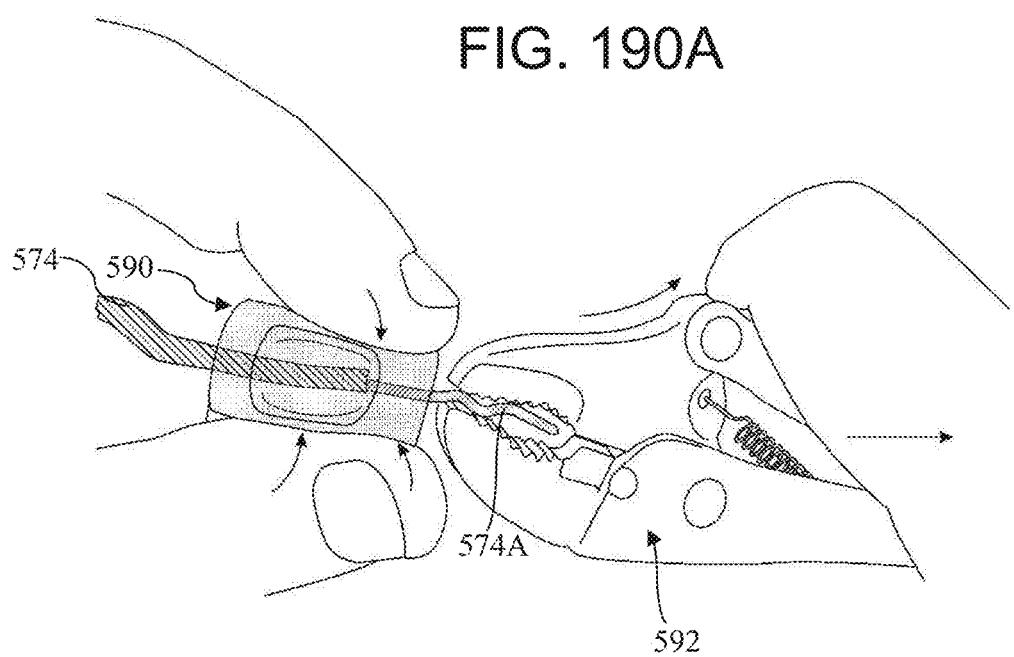

FIG. 190A shows a non-split collar embodiment similar to that shown in FIG. 86 but receiving a wire with exposed, non-insulated free end that is being manipulated with a tool.

Figure 190B:
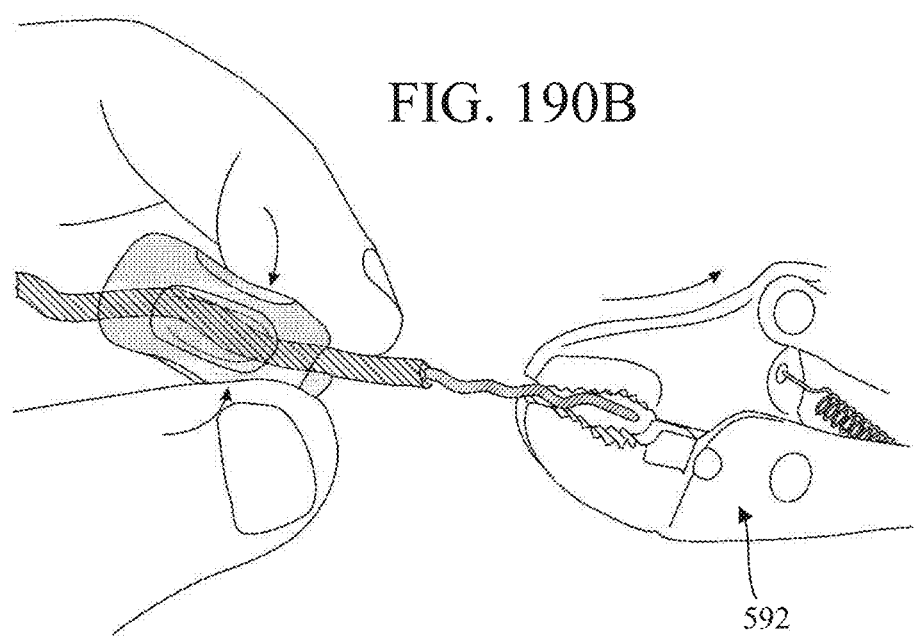

FIG. 190B shows the same collar as shown in FIG. 190A with further manipulation being carried out and with the collar adjusted as to be on only the insulated portion of the wire.

Figure 191A:
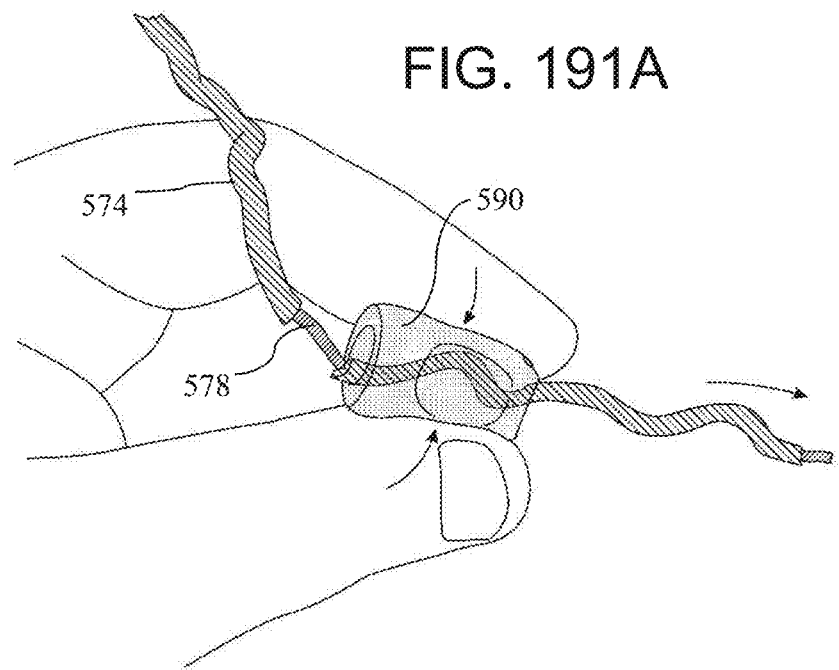

FIG. 191A shows a non-split collar embodiment similar to that shown in FIG. 86 but receiving a wire with an exposed, non-insulated intermediate section.

Figure 191B:
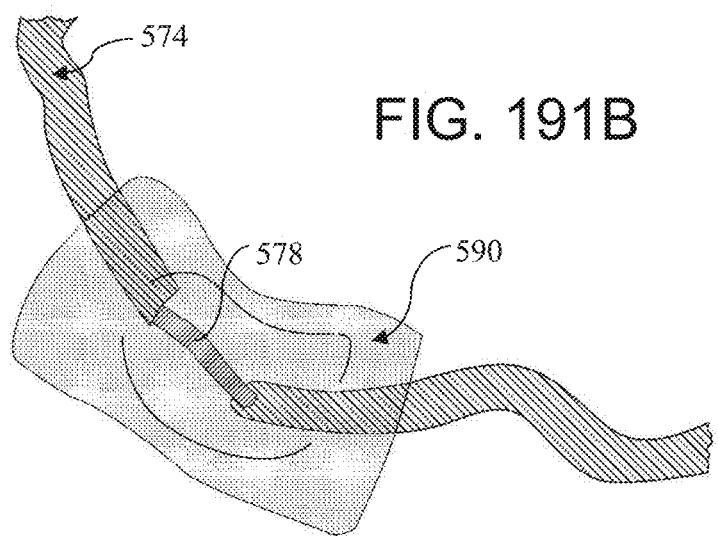

FIG. 191B shows the same collar as shown in FIG. 191A with the collar fully covering over the exposed intermediate section.

Figure 192A:
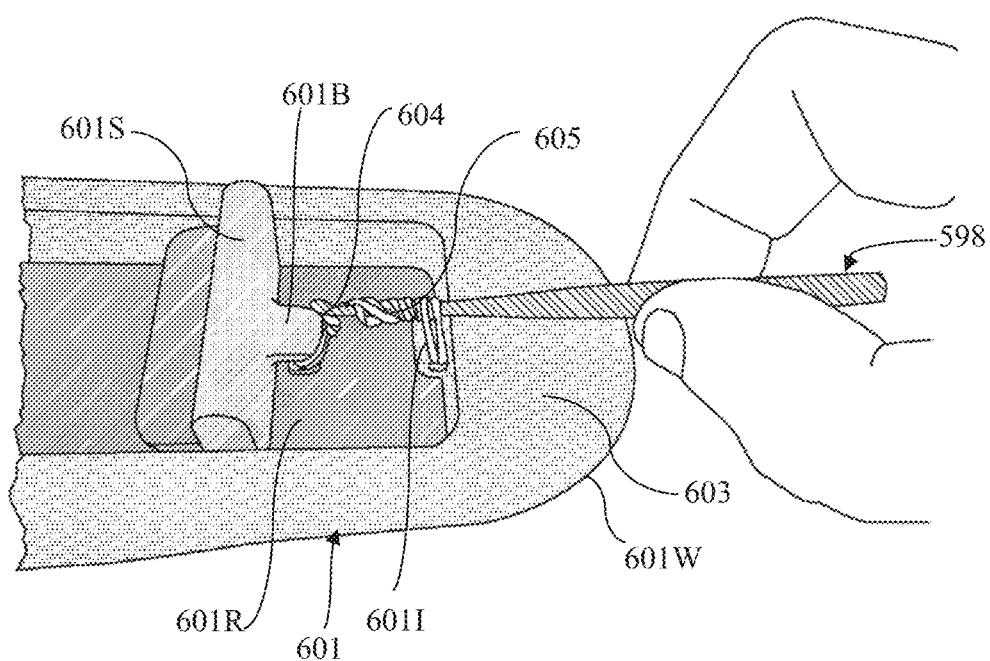
Figure 192B:
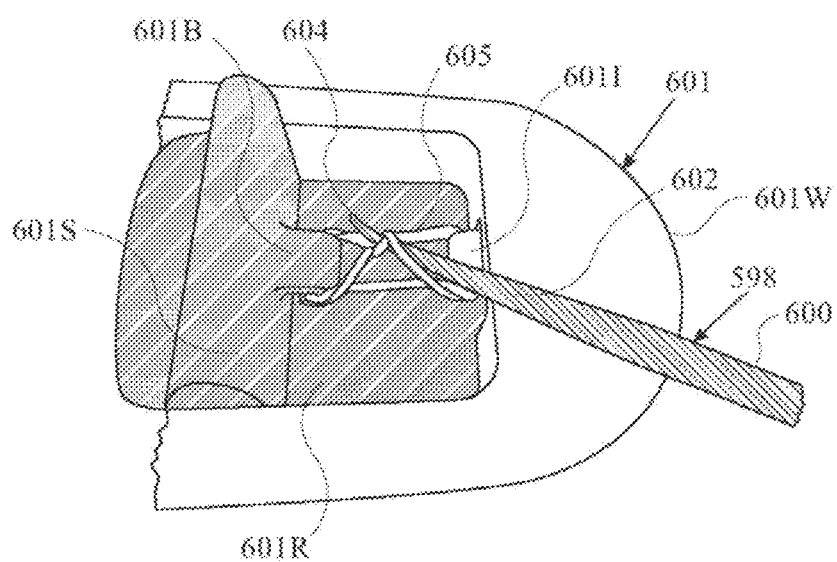

FIGS. 192A and 192B show a tool that is mounted on a worksite component (in this case a tray having a torsion generating elastic band for collar position retention capability illustration purposes) in a finger hold down state and a finger release state, respectively.

Figure 192C:
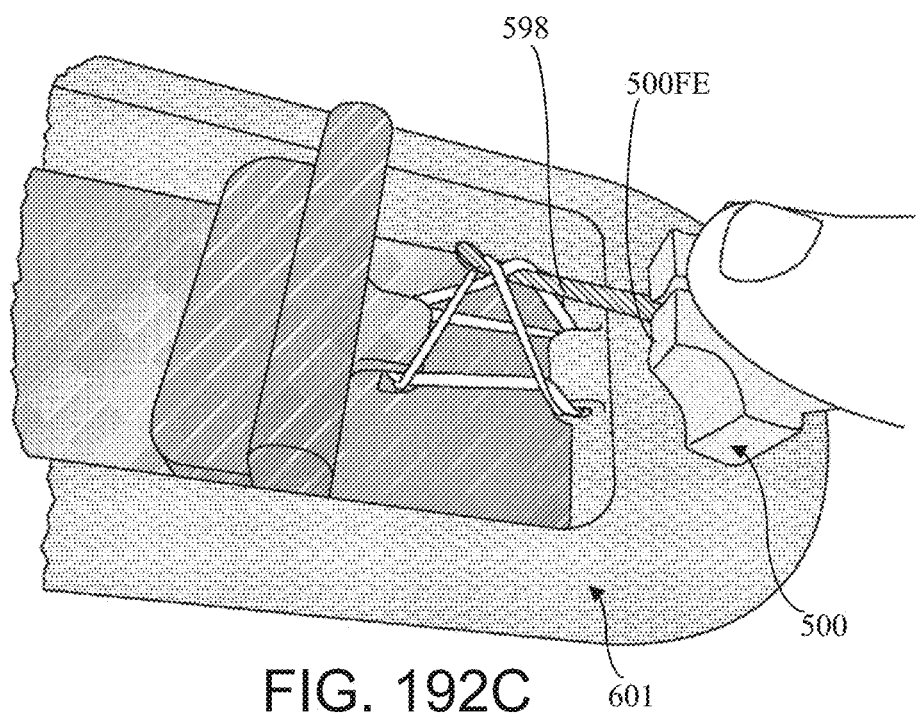

FIG. 192C shows hand "retention" of a tool in its relative holding position with respect to a split collar which is in surface contact with a periphery portion of a receiving tray.

Figure 192D:
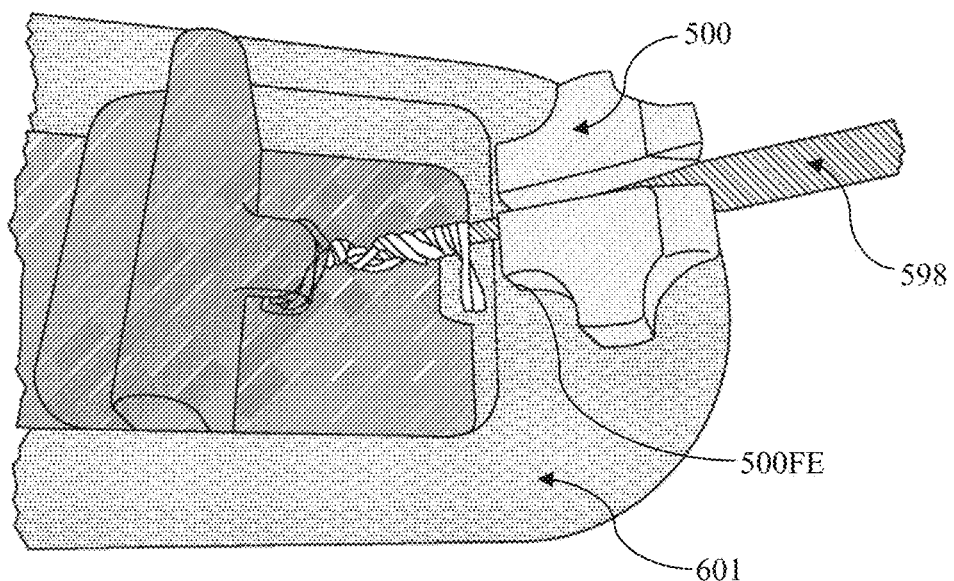

FIG. 192D shows the same view as that in FIG. 192C, but for the fingers of the user no longer in a "retention" state with respect to the collar and received tool with the collar and tool combination shown as staying in the same state and location despite finger release.

Figure 192E:
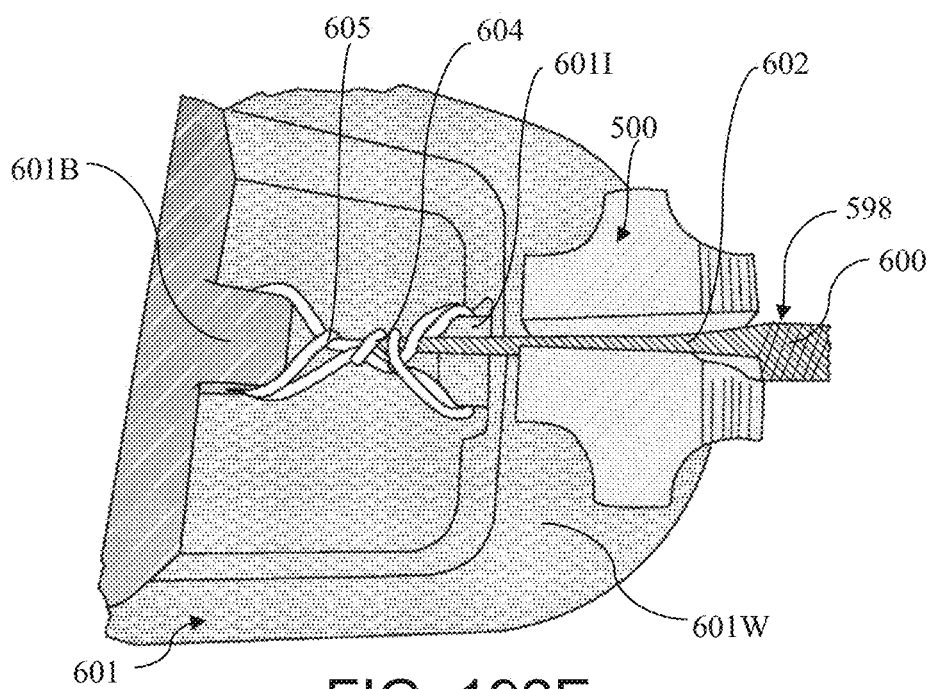

FIG. 192E provides a closer view of the retained collar status as shown in FIG. 192D but with a closer view of the tool and collar interrelationship.

Figure 192F:
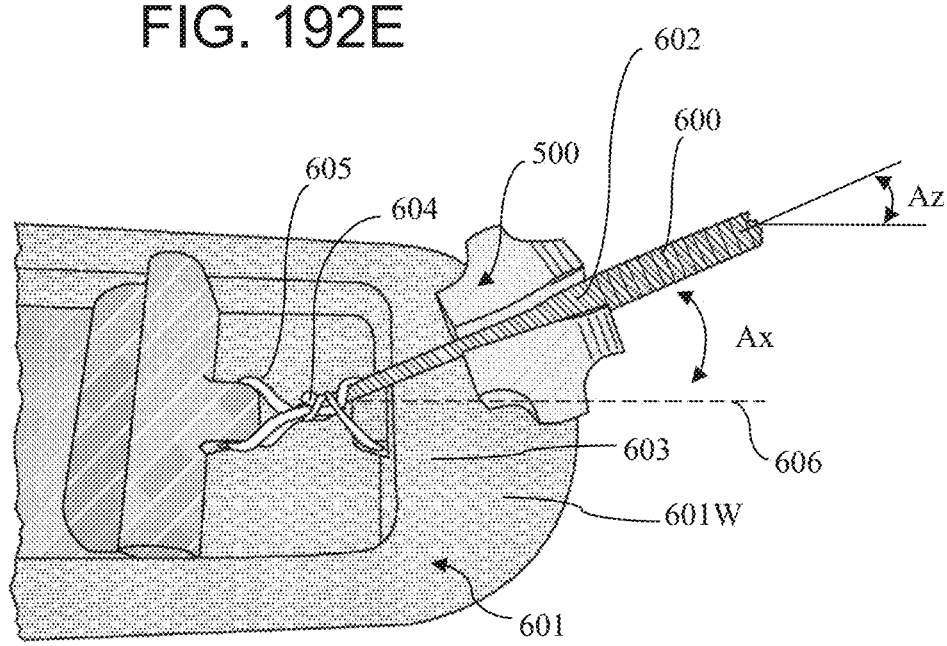

FIG. 192F shows a further, different positioning of a collar with received tool on the periphery of a worksite tray (at about a 30 degree alignment away from the longitudinal).

Figure 192G:
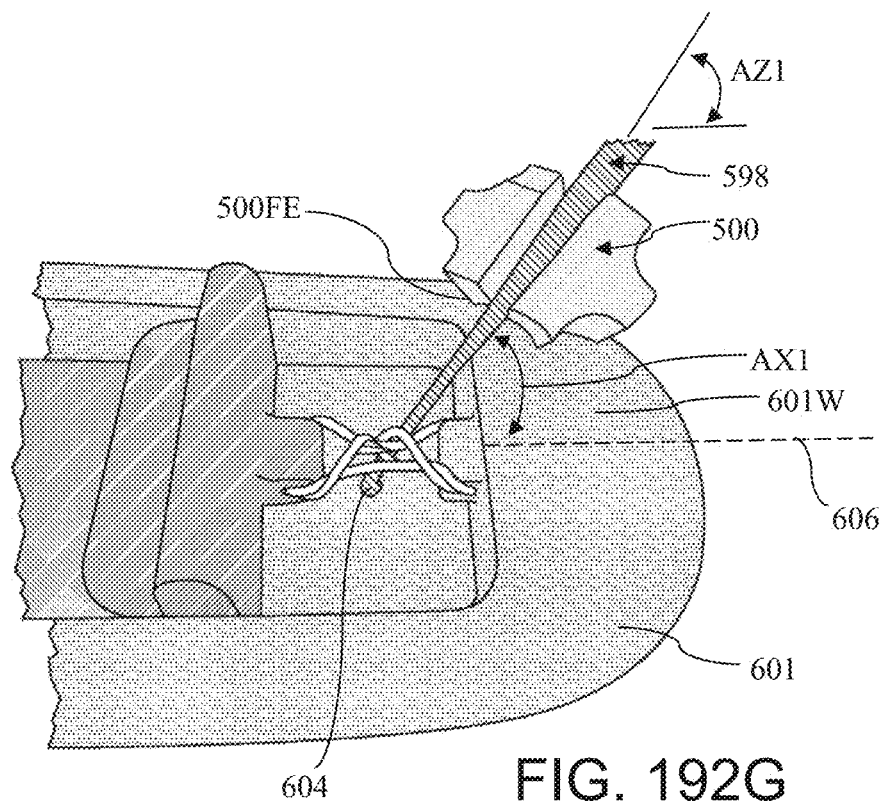

FIG. 192G shows a still further, different positioning of the split collar with received tool on the periphery of a worksite tray (at about a 45 degree alignment away from the longitudinal).

Figure 192H:
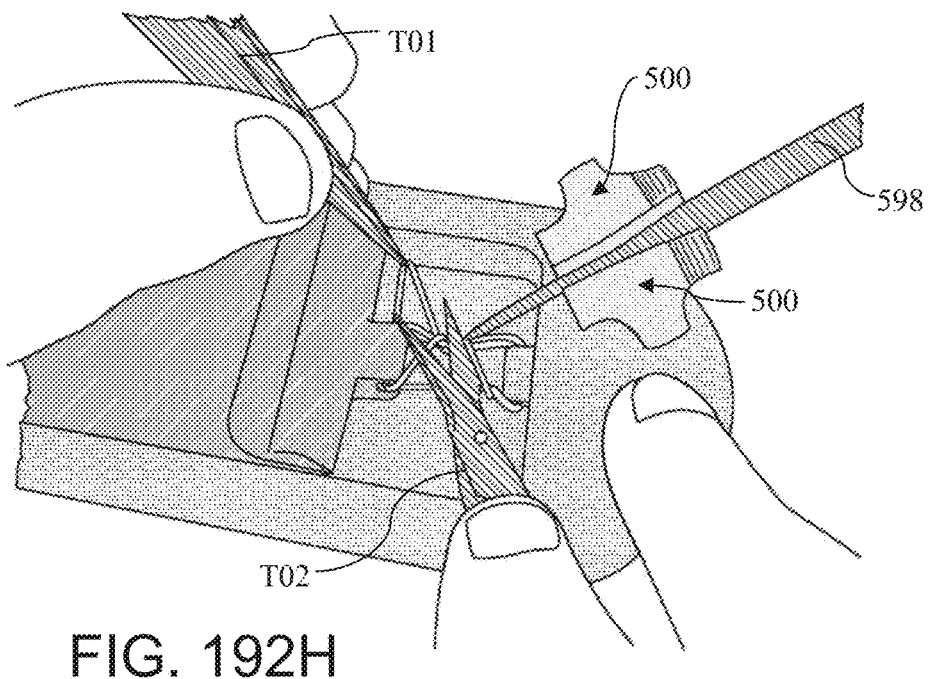

FIG. 192H shows the same non-hand contact collar holding tool in a similar adjusted location as shown in FIG. 192G, but with added hand held instruments in the region of the worksite.

Figure 192I:
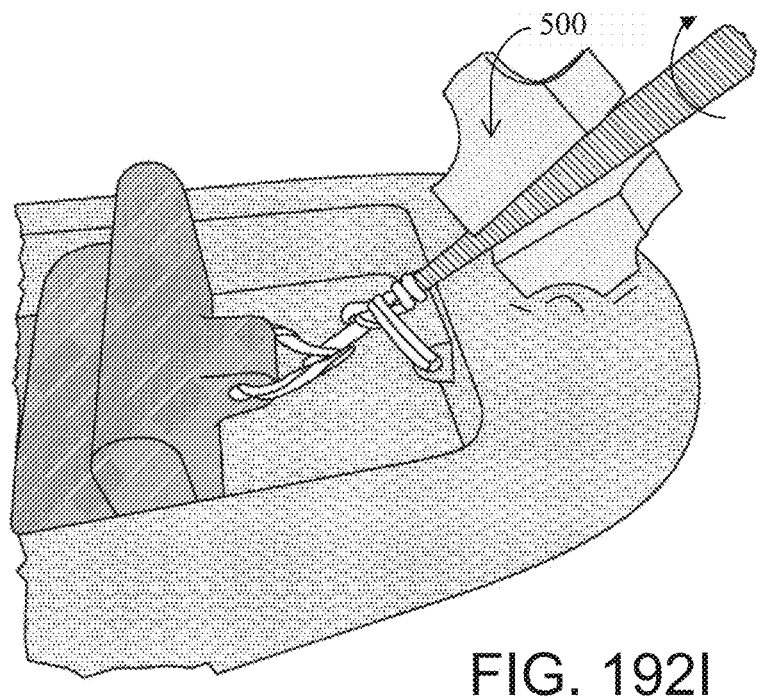

FIG. 192I shows an alternate collar orientation relative to the tray, wherein the corner edges of one of the corner cut-outs is that which is in contact with the underlying tray.

Figure 192J:
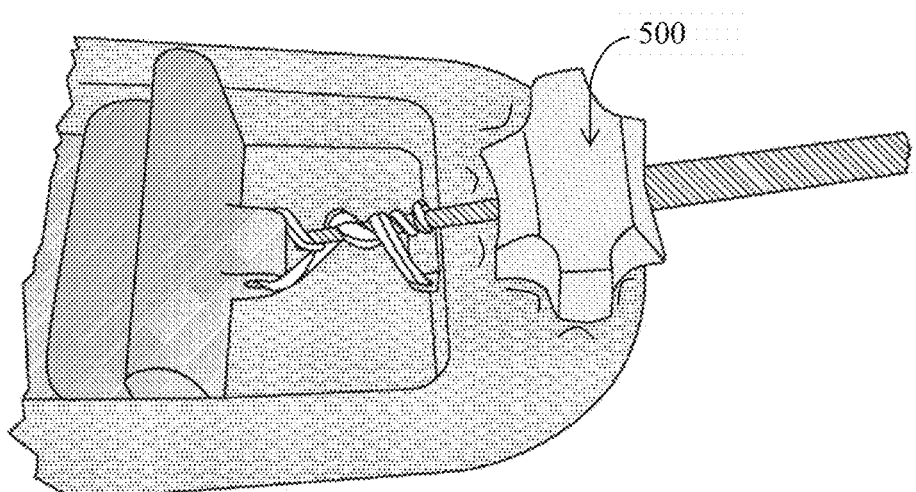

FIG. 192J shows an arrangement where the grasping collar has its split face down such that the non-slit opposite planer surface of collar is face up relative to the contacted tray surface.

Figure 193A:
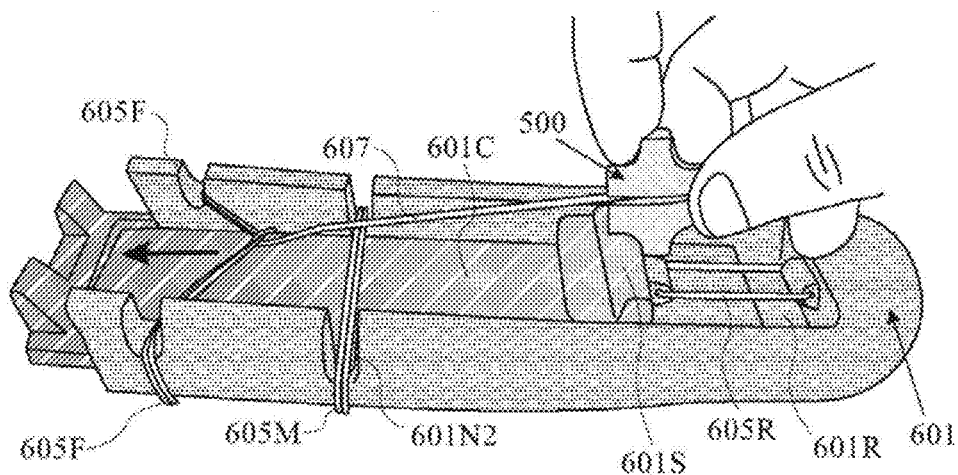

FIG. 193A shows a state where there is not yet mounted an instrument grasping collar relative to the tray working site and with the instrument retained despite pull back on collar only.

Figure 193B:
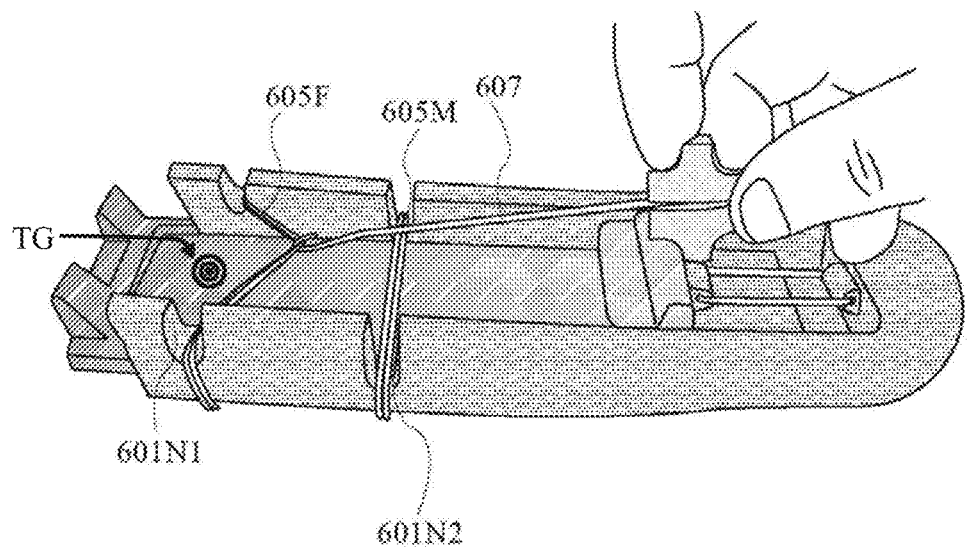

FIG. 193B provides an enlarged view of the working end region of the instrument featured in FIG. 193A with hooking end engaged with the elastic band wrapped into slots formed into the tray illustrating a high level of retention capability along the axis of elongation of the held tool.

Figure 193C:
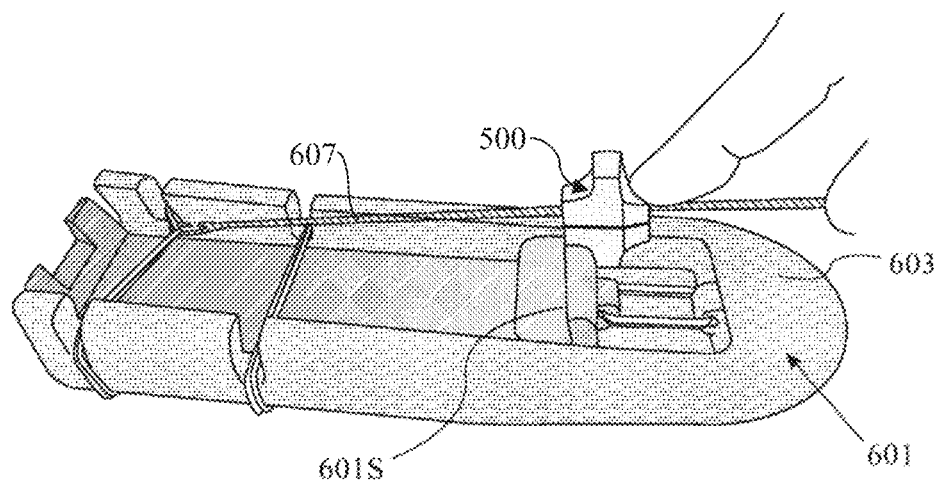

FIG. 193C shows the resting position of the collar with fully grasped tool relative to the tray.

Figure 193D:
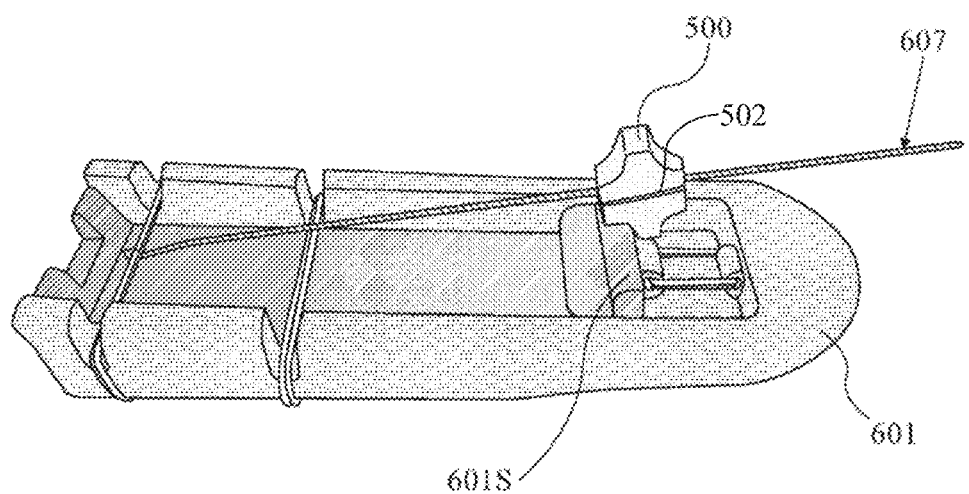

FIG. 193D shows the hand released collar once engaged as shown in FIG. 193C with the corner cut out maintaining position on wall of the carrier tray.

Figure 193E:
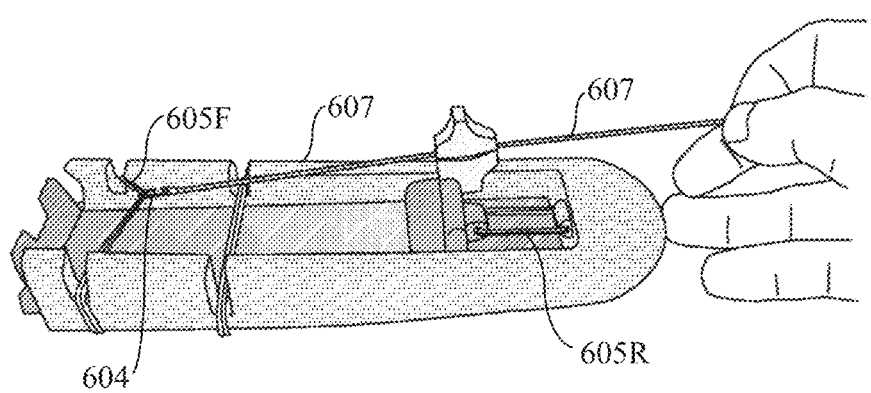

FIG. 193E shows the hand released collar once engaged as shown in FIG. 193C with the corner cut out maintaining position on wall of the carrier tray and with the wire alone being grasped for adjust the level of pull back or tension increase in the grasped band.

FIG. 194A shows a user grasping a fork with a three finger contact arrangement that is rendered relatively unstable in light of the thin edge contact requirement.

Figure 2A:
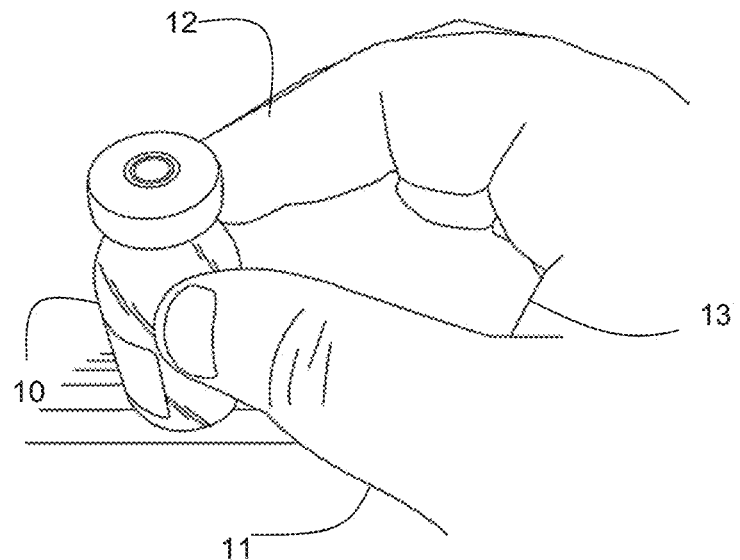
FIGS. 2A and 2B show the tendency of a cylindrical bottle to slip when gripped non-diametrically.
Figure 2B:
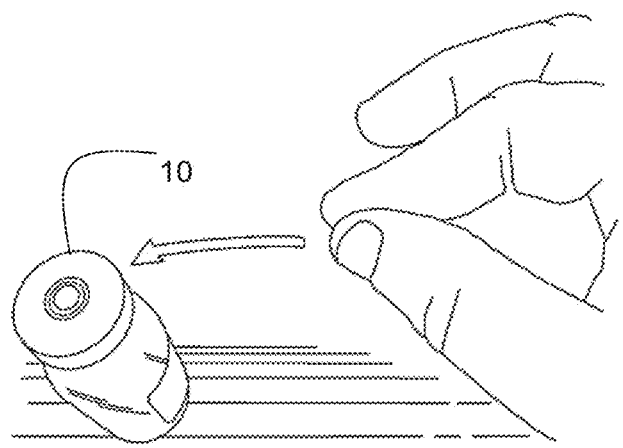
Figure 2C:
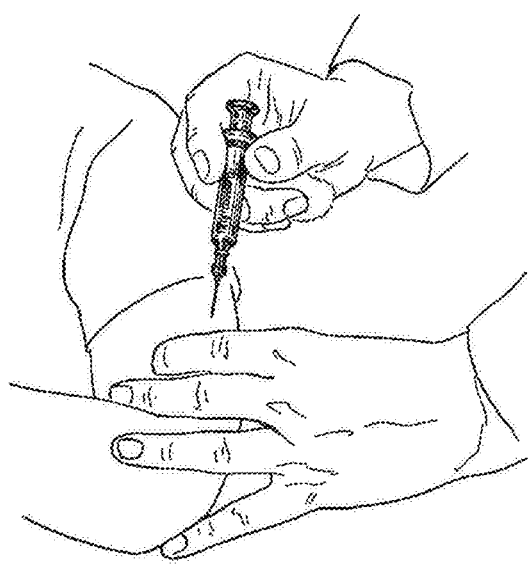
FIG. 2C shows pictorially conventional two-handed use of a hypodermic syringe.

FIGS. 194B1 and 194B2 show a split collar like that of FIG. 172, but in a modified form inclusive of an enlarged interior reception cavity area for receipt of a larger instrument (in this case a flattened region of a fork shown in position to be inserted).

Figure 194C:
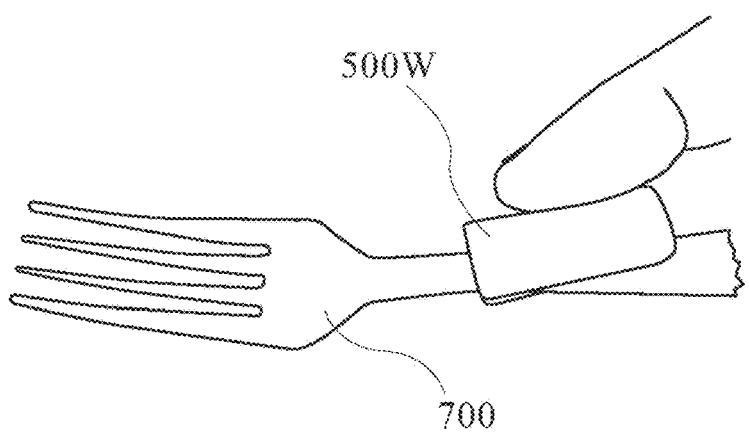

FIG. 194C shows the split collar of FIG. 194B1, but in a partially received stage of insertion of the collar on the instrument.

Figure 194D:
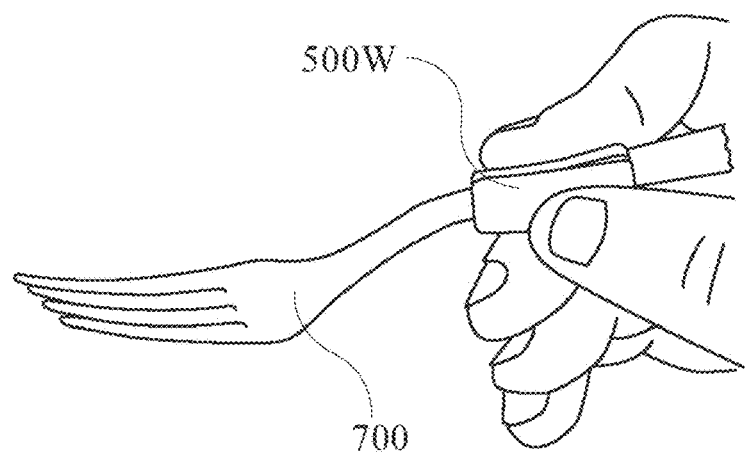

FIG. 194D shows the split collar of FIG. 194B1 in a fully received stage of insertion and with the collar being held in a firm and highly stable three-point "pencil grip" grasp arrangement.

Figure 194E:
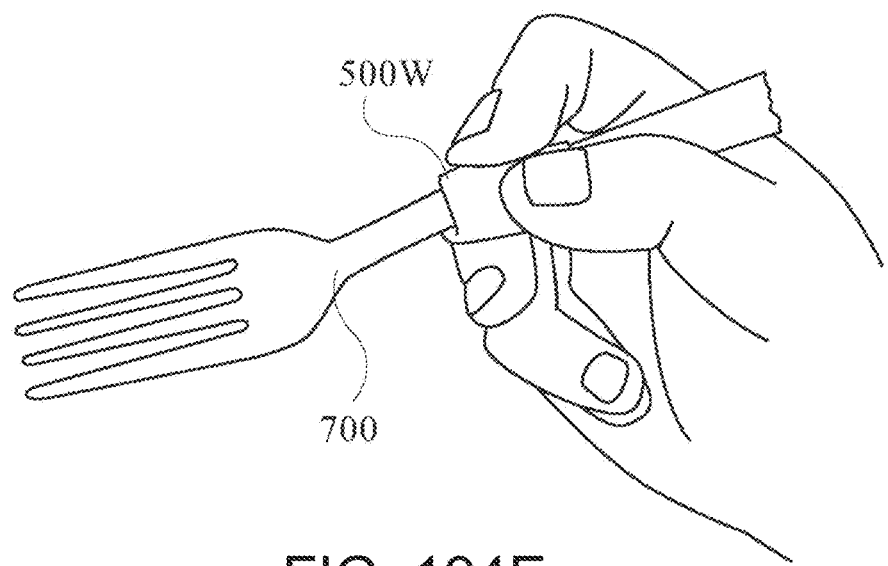

FIG. 194E shows a similar view as in FIG. 194D but in with a different viewpoint of the three-point "pencil grip" grasp arrangement.

Figure 195:
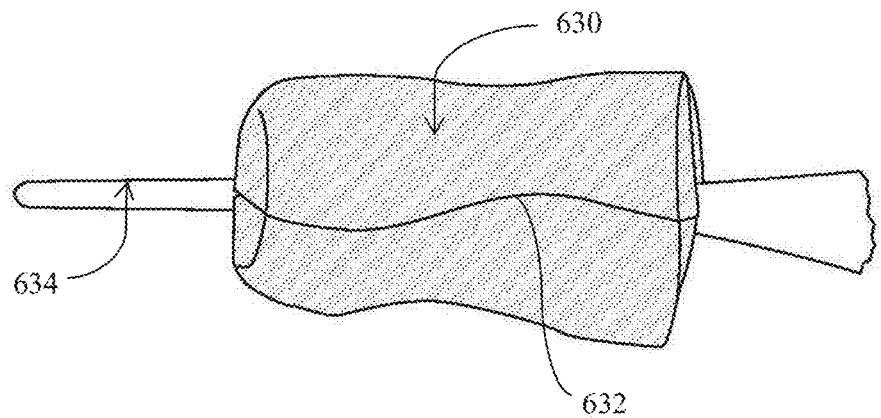

FIG. 195 shows an alternate embodiment of a collar having an axial through-hole with a slit extending down into it which follows a non-linear path as in the sinusoidal patterned slit shown.

Figure 196:
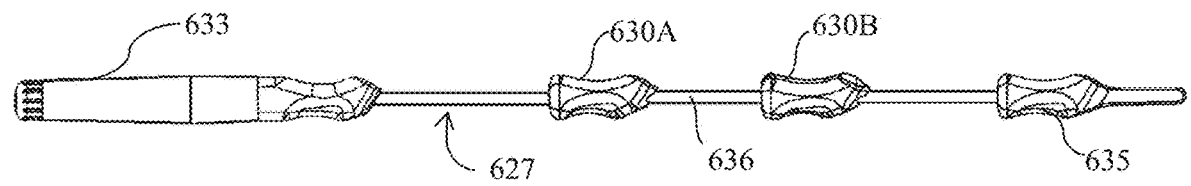

FIG. 196 shows a deep surgery medical instrument having at least one split collar for sliding along a rod extension of the instrument.

Figure 197A:
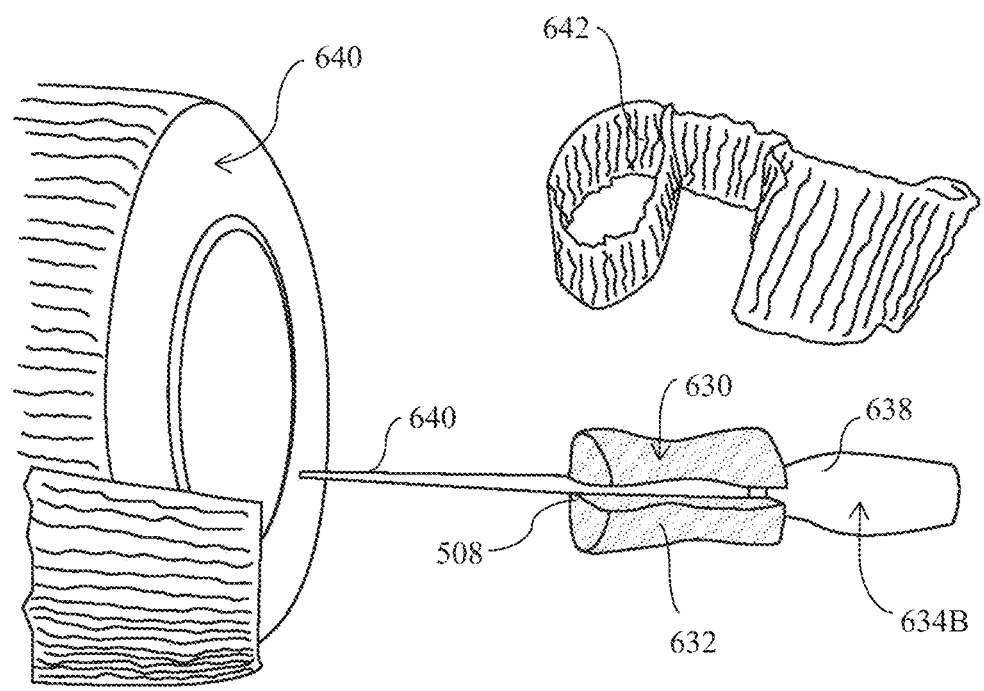
Figure 197B:
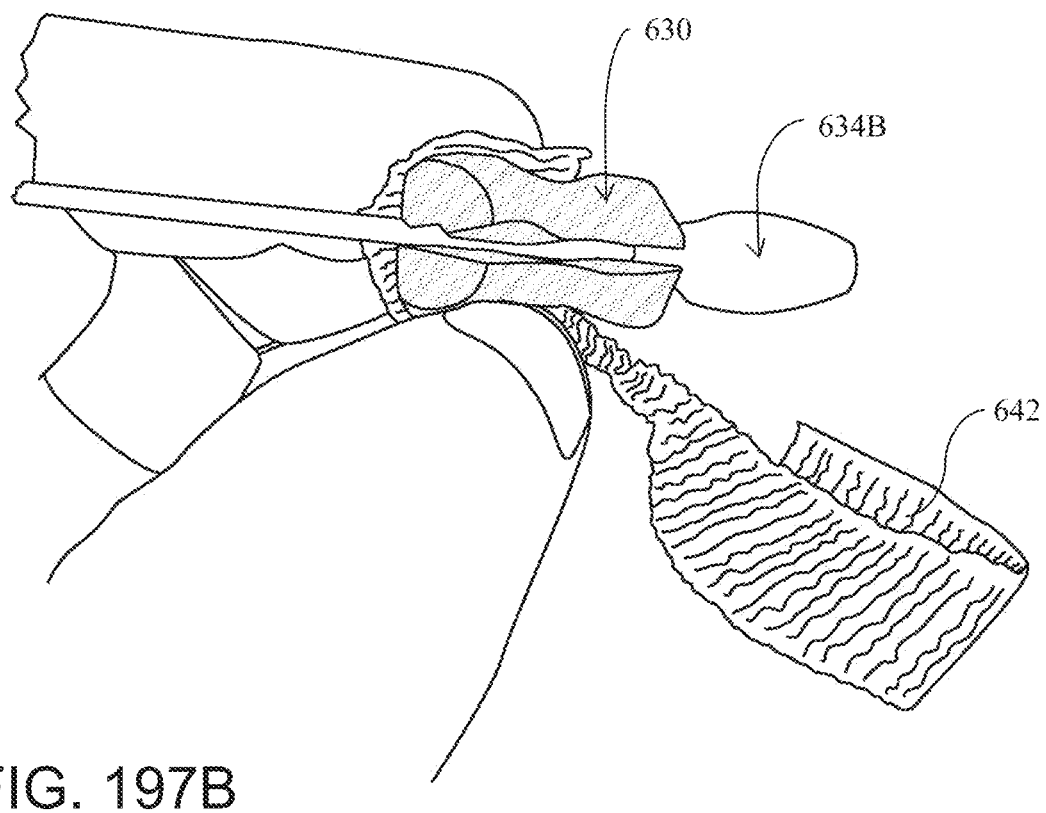
Figure 197C:
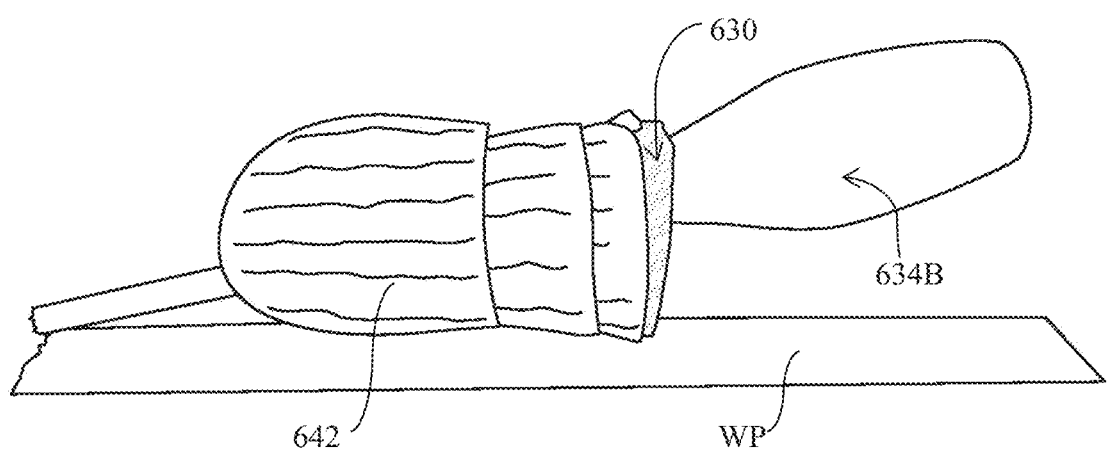

FIGS. 197A to 197C illustrate the collar of FIG. 195 together with a received instrument and wrapping provided around the collar exterior.

Figure 198A:
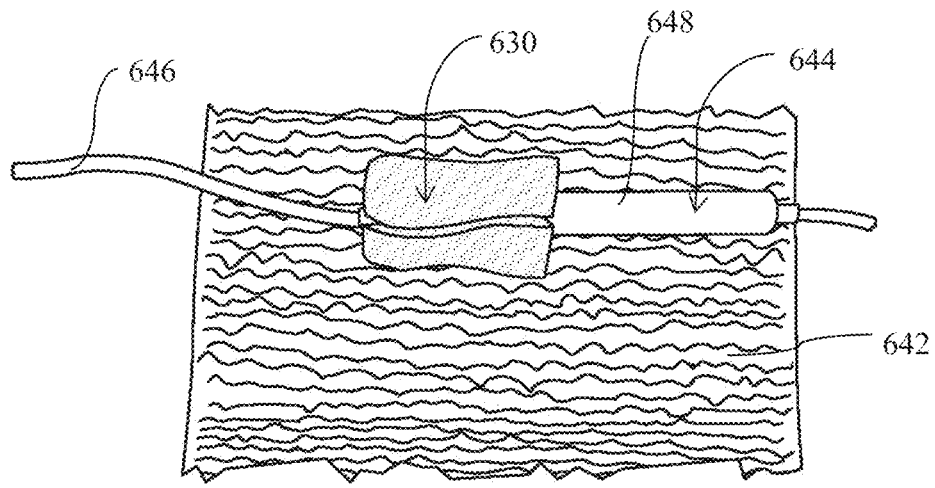
Figure 198B:
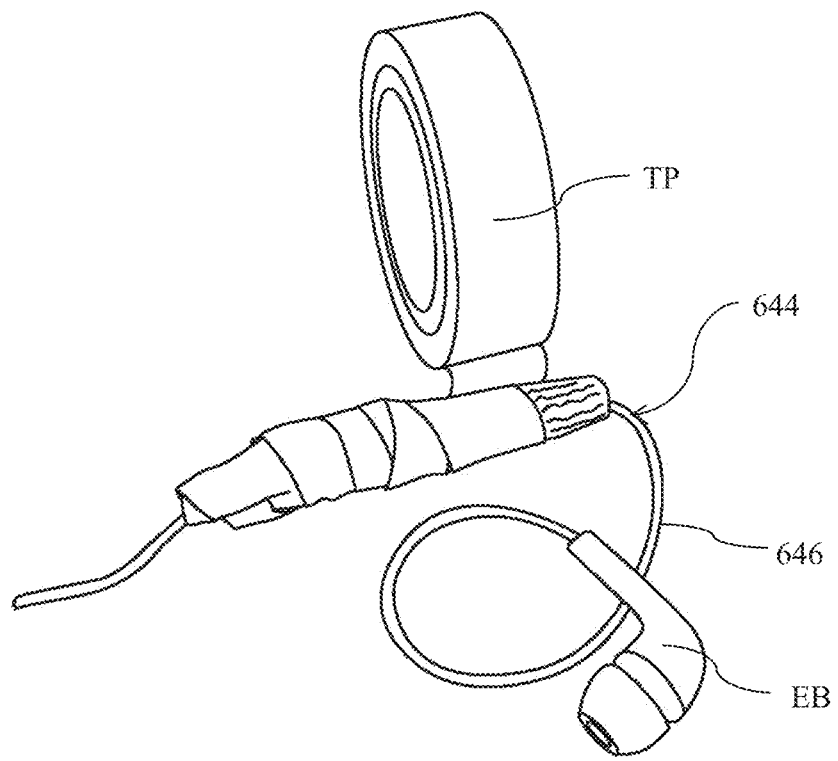
Figure 198C:
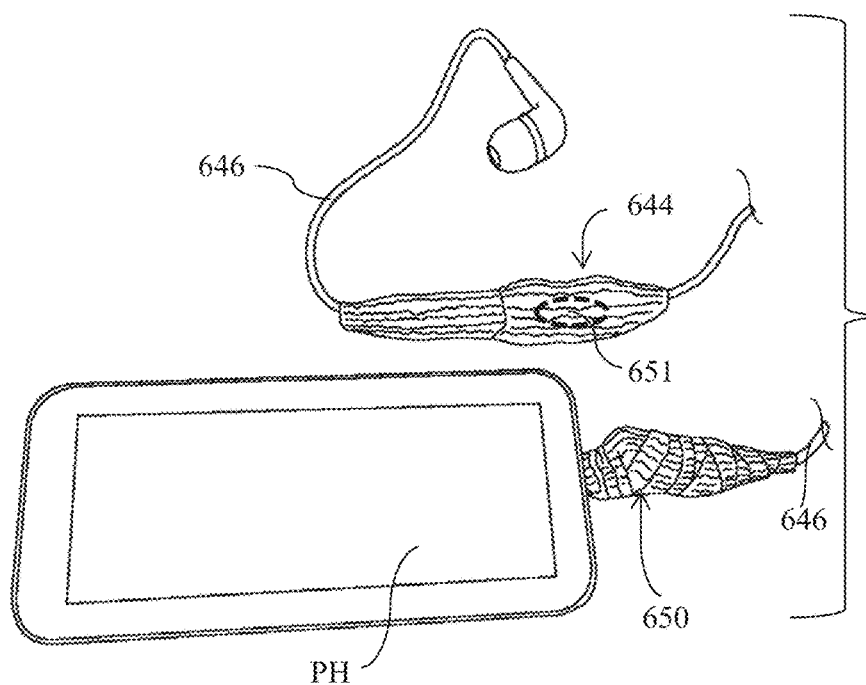
Figure 198D:
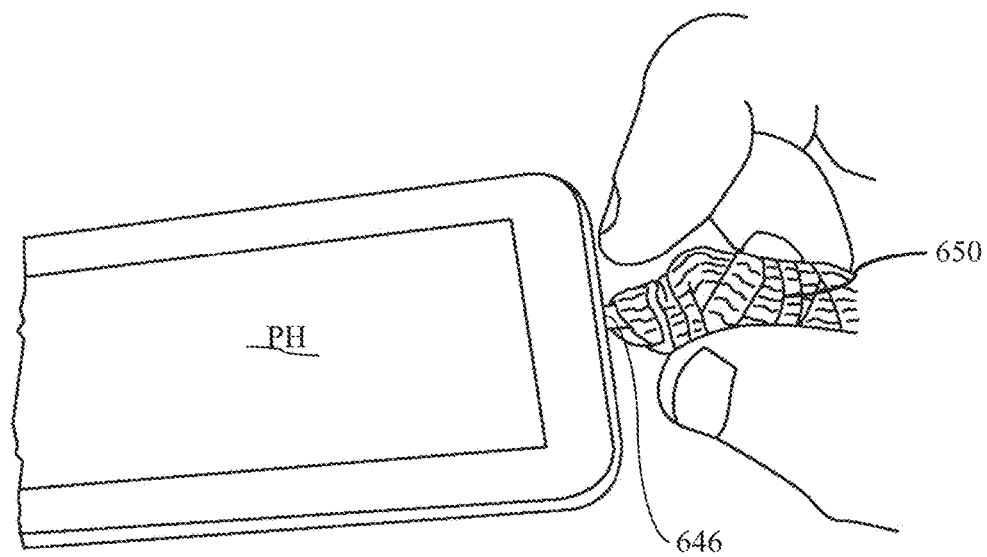

FIGS. 198A to 198D show the collar of FIG. 195 in use on a multi-dimensioned wire assembly (single or multi ear-bud, ear-phone assembly) received within the collar and a wrap extending around both the collar and the wire assembly. FIGS. 198C and 198D further show a phone connected with the wire assembly.

Figure 199:
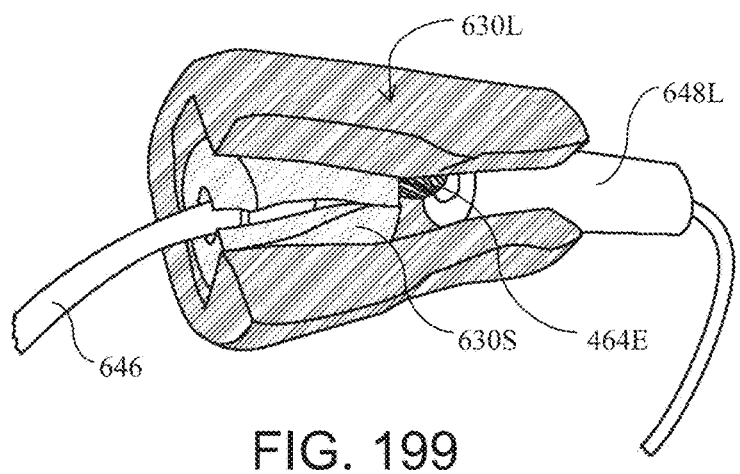

FIG. 199 shows a larger/smaller double nested collar set which also receives an instrument as in a wire assembly such as the one shown in FIGS. 198A to 198D.

Figure 78:
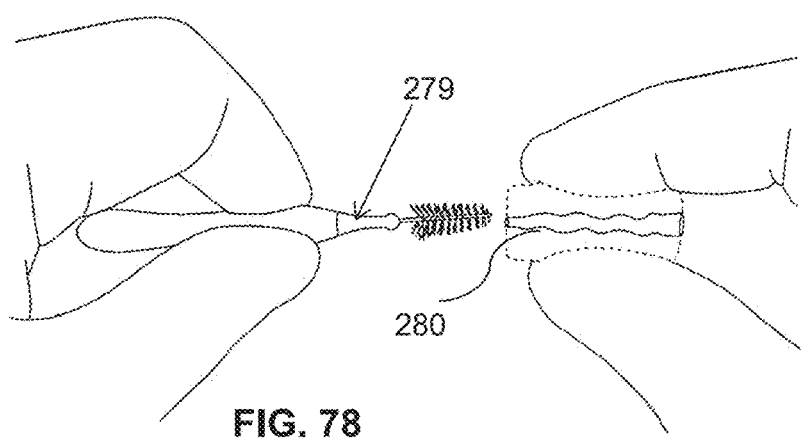
FIG. 78 shows an alternate embodiment of the present invention with a haptic promoting cavity provided in a grasping device that is suited for an instrument support and transfer, which in this case is a bristle cleaning instrument, with the haptic feel including the sensitivity of being able to feel when each bristle ring set moves forward or back once asserted.

FIGS. 200A to 200F show a system and technique using, to start, a non-slit collar (such as that of FIG. 78 (as an example of collar choice) which is then slit open to receive a wire assembly, with the combination being porous material wrapped and then stiffened/waterproofed with an adhesive or adsorbed coating material.

FIGS. 201A to 201D show a system and technique for tourniquet (or cast, as when wrapped) immobilization and position retention relative to a broken or fractured body part (with leg and arm depictions presented).

DETAILED DESCRIPTION OF EMBODIMENTS

In the following description of some embodiments, identical components that appear in more than one figure or that share similar functionality are referenced in some instances by identical reference symbols or by new reference symbols with references back in the description.

Figure 3B:
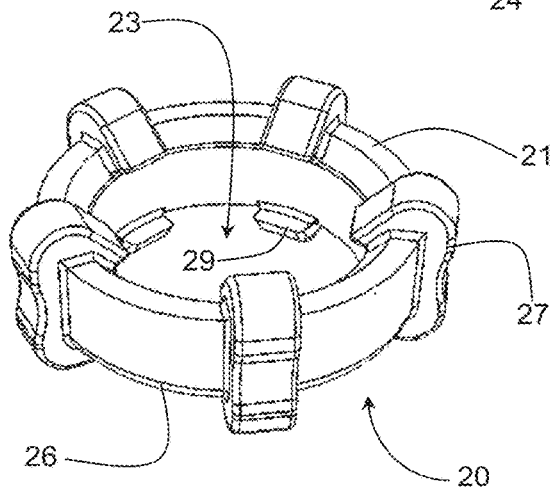
Figure 3C:
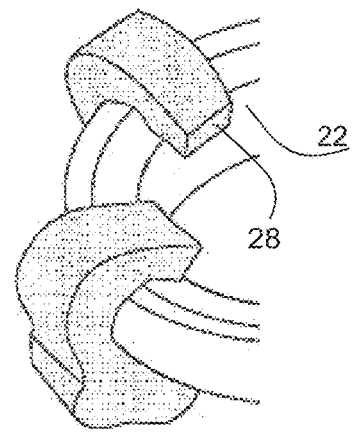

FIGS. 3A, 3B and 3C show a bottle support or mount 20 for supporting an object such as a cylindrical utensil, most typically having axial symmetry such as a cylindrical bottle. It should be noted that the bottle does not need to have a circular cross-section and the term cylindrical is used herein in its strict mathematical sense, namely a surface generated by a straight line intersecting and moving along a closed plane curve, the directrix, while remaining parallel to a fixed straight line that is not on or parallel to the plane of the directrix.

The bottle support 20 includes an annular core 21 having an inner side surface 22 defining a hollow opening 23, an outer side surface 24, a top surface 25 and a base surface 26. A plurality of pliable ribs 27 at least partially encircle the annular core 21 so as to overlap the outer side surface 24, the top surface 25 and the base surface 26 such that at least an upper end 28 of each rib where it overlaps the top surface extends into the hollow opening 23. In some embodiments the lower ends 29 of at least some of the ribs where they overlap the base surface 26 also extend into the hollow opening 23. The annular core 21 may be formed of rigid material or it may be pliable. If it is rigid and circular, then the shape of a bottle than can be conveniently inserted is largely dictated by the extent to which the ribs can deform. Typically, this will restrict use of the device to bottles of regular cross-section, most typically circular. But if the core is also formed of pliable material, then there is virtually no limit to the shape of the bottle, or any other artifact, that can be securely retained therein.

The annular core 21 and the ribs 27 may be formed of a composite molding (e.g., a one shot molding of both the ribs and annular core together) of pliable material. Alternatively, the ribs may be a composite C-shaped molding of pliable material and may be attached to an also molded annular core 21 using friction retention alone, adhesive or plastic welding. In this case, there is no requirement for the annular core 21 and the ribs 27 to be formed of the same material.

Before describing applications of the mount, briefly explained is the manner in which its construction is distinguished over known bottle supports. First, the pliability of the ribs 27 where they overhang the top surface 25 and extend into the hollow opening 23 allow the ribs to deform and grip the side surface of an object. Secondly, because the ribs are parallel to the axis of the core they are compressed transversely rather than deflected and no less importantly any two ribs may be deformed at different times and to different extents. This avoids the need to insert an object axially symmetrically and allows it to be inserted at an angle to axis. Thirdly, because the ribs overlap the outer side surface 24 of the core they increase the effective base area of the mount and lend added stability. Fourthly, since the ribs overlap the base surface 26, they serve to raise the base surface and insulate it from an external surface on which it is placed. Furthermore, where the lower ends of the ribs extend into the hollow opening 23, they support the base of an object supported therein and insulate it from the external surface. This helps to prevent the object, which may be a medicine bottle or vial, from becoming contaminated. Finally, because the ribs 27 extend outwardly from the generally smooth surface of the core they provide additional support surfaces that serve as ledges that are more easily grasped or pinched between thumb and forefinger or other fingers. This makes it much easier to grasp the mount securely even with wet or slippery hands and significantly reduces the tendency of the mount to roll away as shown in FIG. 2B. This functionality will now be described with reference to the drawings.

Figure 4A:
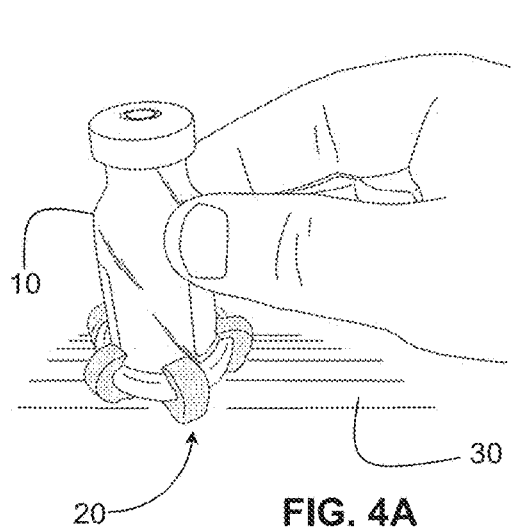
FIGS. 4A and 4B show a cylindrical bottle supported within the bottle support of FIG. 3A.
Figure 4B:
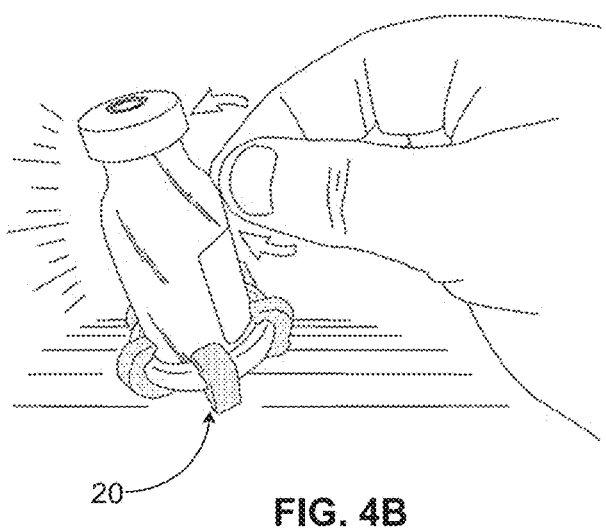

FIGS. 4A and 4B show a cylindrical bottle 10 supported by the bottle support 20. When the side surfaces of the bottle are grasped between forefinger and thumb particularly with the intention of lifting the bottle 10 from an external support surface 30, there is still a tendency for the bottle to slip away from the user's grasp. But this tendency is reduced owing to the friction between the lower surfaces of the ribs and the support surface 30 and the low center of gravity of support 20.

Figure 5A:
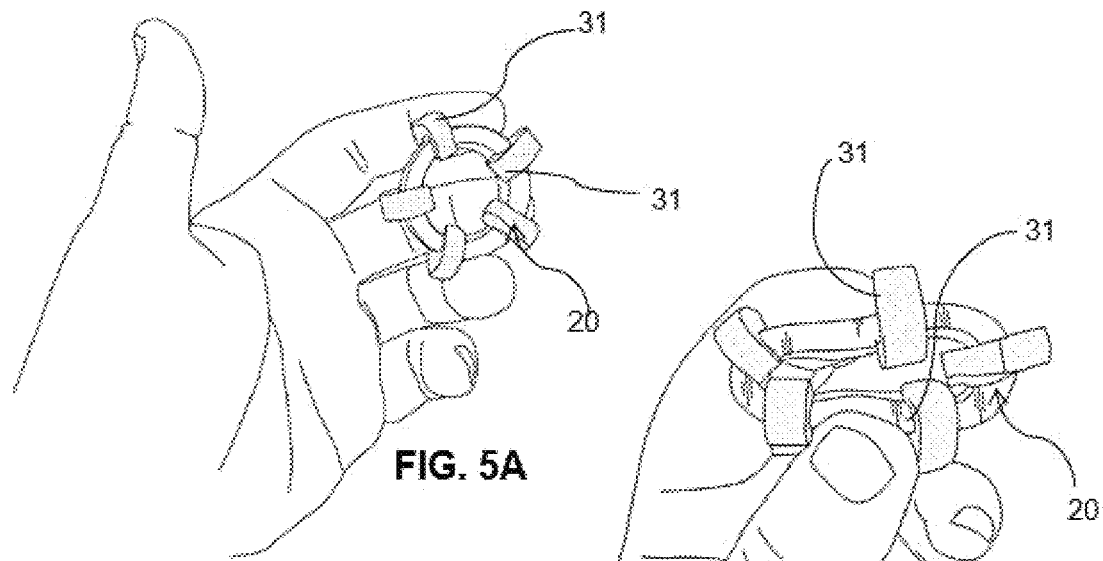
FIGS. 5A, 5B and 5C show the bottle support securely held between thumb and forefinger.
Figure 5B:
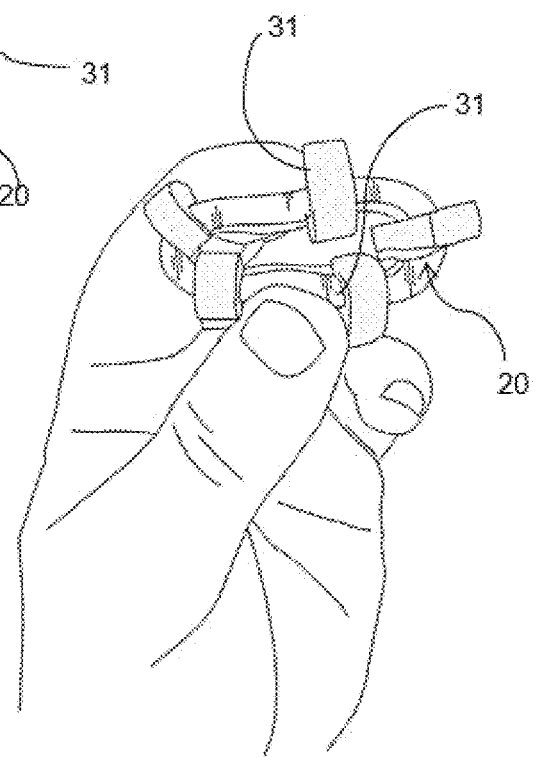
Figure 5C:
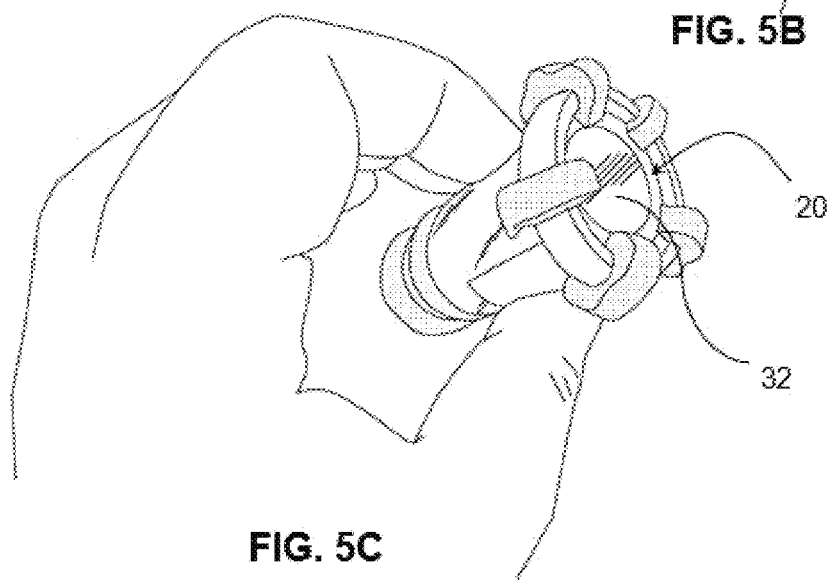

FIGS. 5A and 5B show the bottle support securely held between the tips of two fingers or between thumb and forefinger by pinching protruding outer side surfaces 31 of the ribs that serve as ledges that are more easily grasped or pinched between the fingertips. In FIG. 5C, rather than lifting the bottle by holding the bottle support 20, the bottle is grasped but with the tips of the forefinger and thumb pressing against the tops of the ribs, which likewise serve as ledges that facilitate grasping or pinching activity between the fingertips. It is also seen that the lower surface of the bottle does not protrude out of the lower surface of the base of the bottle holder, thus forming a recess 32 into which a user may insert his thumb or finger when grasping the bottle support from below. Applications that exploit this functionality are described below. FIG. 5B shows the flexible quality in the mount 20. Further, its "open" design makes for visibility not being obstructed in use, as in being able to view for liquid content in the bottom when the bottle is clear as well as side labeling.

FIG. 6A shows the bottle support 20 preventing rolling of a bottle 10 placed on an inclined support surface 30, with the pertinent parts of the bottle still visible. FIG. 6B shows that the bottle support 20 is less prone to tipping even when partially tilted owing to its being placed, possibly inadvertently, on a tool 34 lying on a level surface 30 as is easily done in stressful working conditions such as operating theaters and the like. FIG. 6C shows a bottle 10 supported within the bottle support 20 while stably retained at a significant incline on a spherical object 35. FIG. 6D shows how medical staff may otherwise try to prevent a bottle 10 on an inclined surface 30 from rolling when no bottle support is available by retaining the bottle with the needle of a hypodermic syringe. FIGS. 6A to 6C also show that in all positions the open nature of the mounts avoids obstructing view points as in vial labels.

Figure 7:
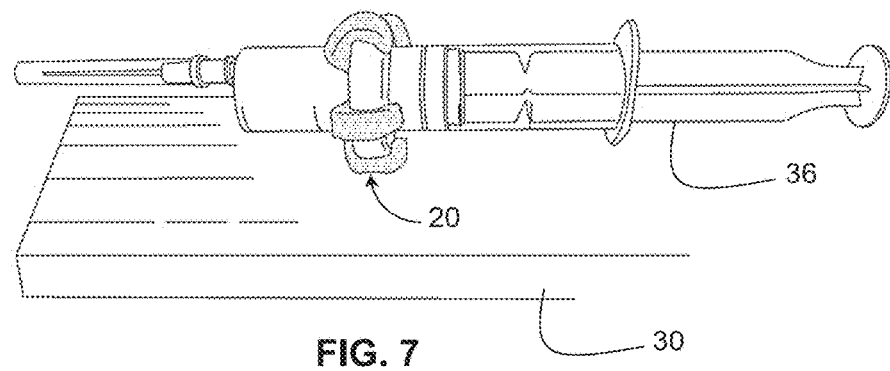
FIG. 7 shows use of the bottle support to avoid rolling of a hypodermic syringe.
Figure 8:
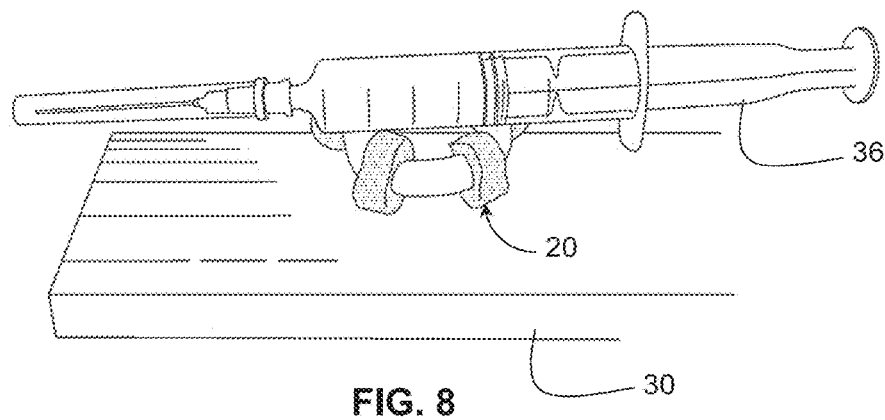
FIG. 8 shows use of the bottle support to isolate a hypodermic syringe from a working surface.

FIG. 7 shows pictorially use of the bottle support 20 to avoid rolling of a hypodermic syringe 36 by securing the bottle support 20 around the body of the syringe. Such use can include an arrangement where that the lower ends of the ribs of the bottle support 20 do not extend into the hollow or extend to a lesser extent, thus allowing the bottle support to be slid up and down the body of the syringe. FIG. 8 shows use of the bottle support 20 to isolate a hypodermic syringe 36 from a working surface 30 to thus prevent cross-contamination and at the same time prevent rolling of the syringe 36 (e.g., it has a suspended horizontal state relative to a potentially contaminated undersurface). Obviously, the same principles can be applied to other utensils. Also, FIG. 7 shows that the syringe is supported in a manner that both avoids contamination and allows ready finger insertion below the syringe for easy pick up.

We now describe another aspect of the invention that relates to grasping a bottle not by its base but rather from its neck.

Figures 9A, 9B:
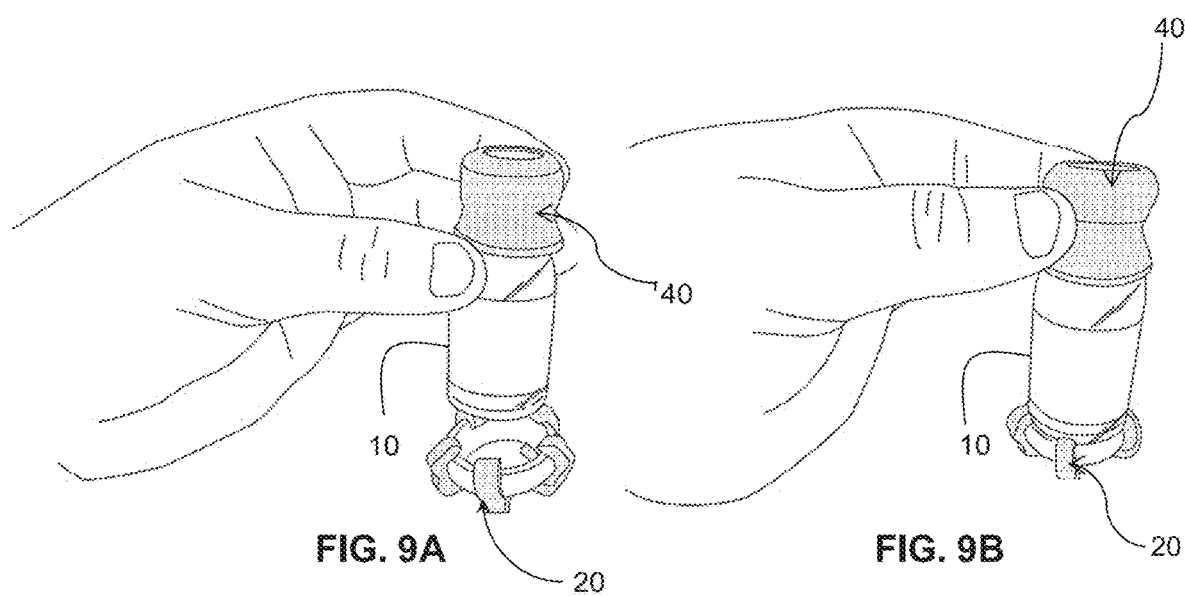
FIGS. 9A and 9B show an assembly or kit according to a second embodiment of the invention comprising a bottle support and a collar.

Thus, referring to FIGS. 9A and 9B, there is shown bottle 10 having attached to its neck collar 40 for facilitating non-slip gripping of the bottle.

Figure 10B:
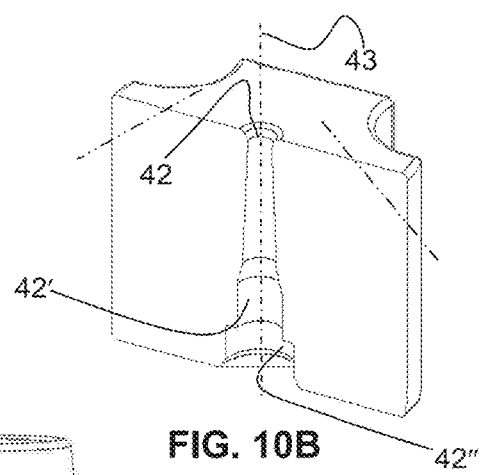

FIGS. 10A and 10B show a first embodiment of the collar 40 comprising a body portion 41 having an axial bore 42 for surrounding the neck of a utensil such as a bottle, and defining along at least a portion of an axis 43 thereof a substantially quadrilateral cross-section having in each corner thereof a respective arcuate recess 44, each for accommodating a user's thumb or finger. The axial bore 42 may be configured to accommodate an end of a hypodermic syringe and, to this end, may include at least two mutually contiguous sections 42' and 42" of different cross-sectional areas so that the internal shape of the bore 42 is complementary to the external surface of the hypodermic syringe 36. The collar 40 may be formed of deformable material and dimensioned for axial compression or displacement of a predetermined distance that is adjusted to define a known protrusion of a hypodermic needle. This allows the collar 40 to be located at the end of the hypodermic needle, while concealing the tip of the needle, such that pushing the body of the syringe into the patient's skin causes the collar to compress and the needle to enter the skin. In an alternate embodiment collar 40 is formed of a non-compressible plastic material that, in use, ensures the exposed end of a needle shaft extending away from the collar reaches the same depth of penetration upon collar-to-skin contact.

In the embodiment of FIG. 10A the body portion 41 is of rectangular cross-section and defines opposing pairs of first and second ridge side surfaces of different widths. In other embodiments, the body portion may be of square cross-section all of whose surfaces are of equal width. At least one of the side surfaces may have an indent or depression 45 for accommodating the user's finger. By way of example, the indent may be elongated with a major axis normal to an axis of the body portion. In some embodiments the top corners of the collar may be slanted as shown schematically by chain-dotted lines in FIG. 10B so that, when the collar 40 is fitted to the operative end of a hypodermic syringe (or some other object) as described in more detail below, the resulting slanted edges may serve to guide the insertion of the needle at an angle determined by the degree of slant.

As a few non-limiting but illustrative dimensions for collar 40 embodiments, such as those in the examples described herein, a width (space between opposing longer length ridge walls representing peripheral, generally straight longer sides of the collar's periphery) of 18 mm is featured, while a length range (between opposing short length opposing ridge walls) of 25 mm is featured. As described in greater detail below, the height can vary greatly as in 2 mm heights up to 60 mm or more. As with all ranges discussed herein (unless otherwise indicated) all end points and points between the end points at the same unit dimension are intended for coverage herein. Additional non-limiting, but illustrative values for collar 40 of FIG. 10A form includes a thickness height of 21 mm, a peripheral length of 6.5 mm in the short ridge sides, and a 13 mm peripheral length for the long ridge sides. The overall long length of collar 40 (from short ridge surface to short ridge surface) of 30 mm is illustrative. Some additional non-limiting, illustrative dimensions are provided below relative to FIGS. 110A to 123B.

FIG. 11 shows a second embodiment of a collar 40, having a body portion 41, an outer surface of which has a tapered portion 42 that projects axially upward opposite a base portion of the collar. The body portion includes a lower portion of substantially quadrilateral cross-section, typically square or rectangular. The tapered portion 42 may be of smaller cross-sectional area than the base portion as shown in the figures so it that it tapers upward. Alternatively, it may be of larger cross-sectional area than the base portion so that it tapers downward. As in the first embodiment shown in FIG. 10A, in each corner of the body portion 41 there is formed a respective arcuate recess 44 for accommodating a user's thumb or finger. In some uses, it may be advantageous for the collar to be closed at one end to form a cap, or at the bottom to form a reception collar.

Figure 12:
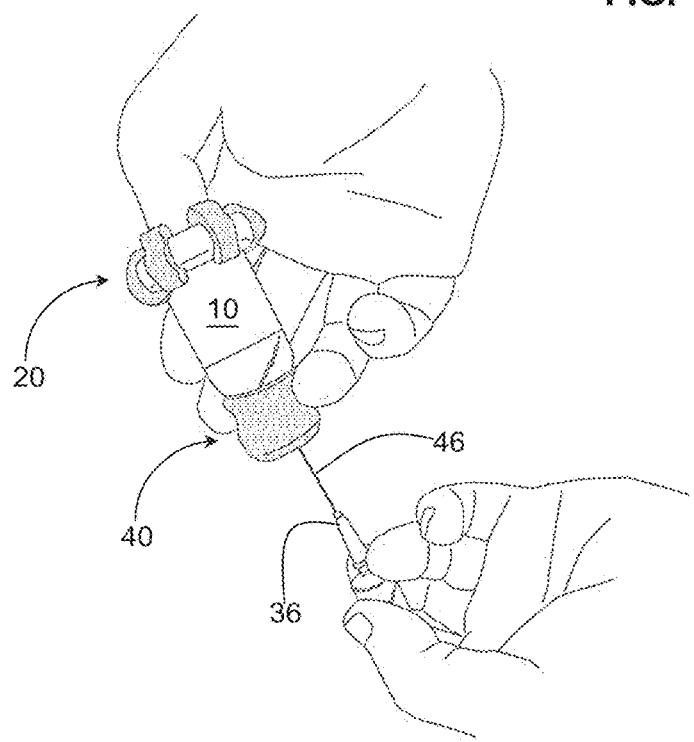
FIG. 12 shows use of the collar when transferring liquid between the bottle and a hypodermic syringe.
Figure 13:
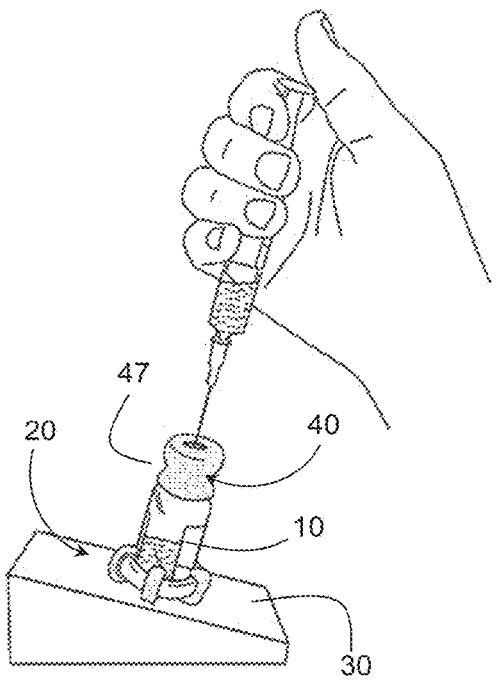
FIGS. 13 and 14 show different uses of the bottle support to reduce the risk of self-injection or damage when transferring liquid between the bottle and a hypodermic syringe.

FIG. 12 shows use of the collar 40 when transferring liquid between the bottle 10 and a hypodermic syringe 36. Thus, the neck of the collar 40 defines a ribbed surface that is gripped between two fingers of one hand while the thumb of the same hand is held within the recess 32 of the ring base described above and shown in FIG. 5C. To this end, the collar may have a beveled indent 47 for better accommodating the fingers as best shown in FIG. 13. The users' other hand holds the hypodermic syringe 36 and aligns the needle 46 into the opening of the bottle. The ribbed surface of the collar 40 provides some measure of shielding that reduces the risk of self-injection.

FIG. 13 shows one use of the bottle support 20 to reduce the risk of self-injury by supporting the bottle or vial 10 in the bottle support 20 on a support surface 30 so as to obviate the need for the user to touch or hold the vial while aligning the hypodermic syringe therewith.

Figure 14:
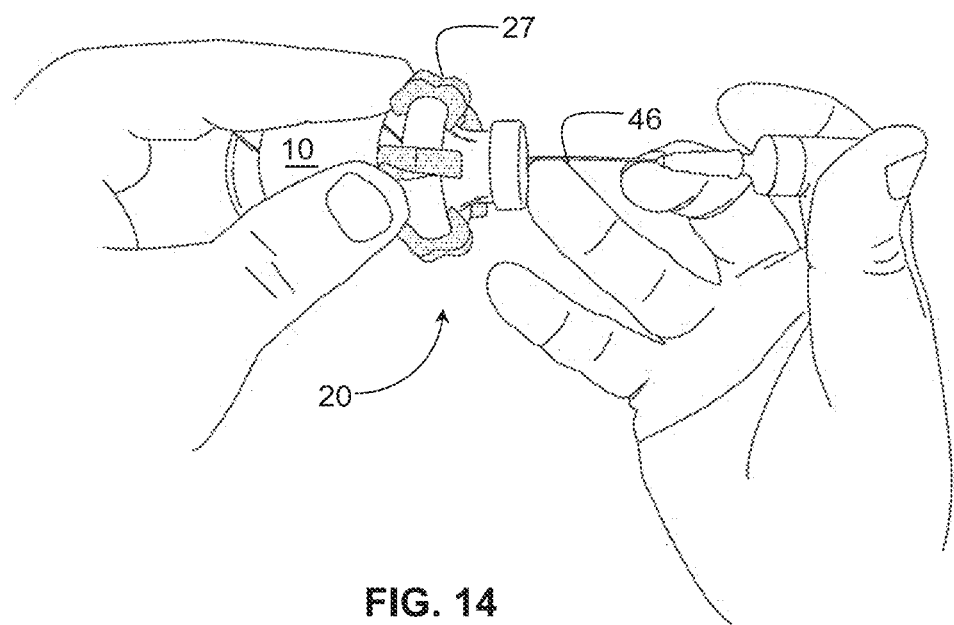

FIG. 14 shows another use of the bottle support 20 to reduce the risk of self-injury by displacing the support 20 from the base of the bottle 10 toward the neck and grasping the bottle behind the ribs 27, which completely shield the fingers from the needle 46. In FIG. 14, the ribs are arranged in reverse orientation as when used as a base bottle support. That is, the ribs 27 have their planar surface extensions 29 oriented in a down direction (the opposite arrangement to that when extensions 29 are oriented to support the underside of the supported vial when the collar is a base support mount) so as to push down and contact the upper neck part of the bottle where the neck extends into the larger circumference main body of the bottle. In this way the mount retains a steady position while the user grasps the collar in a protective pull-down behind mount arrangement.

Figure 15:
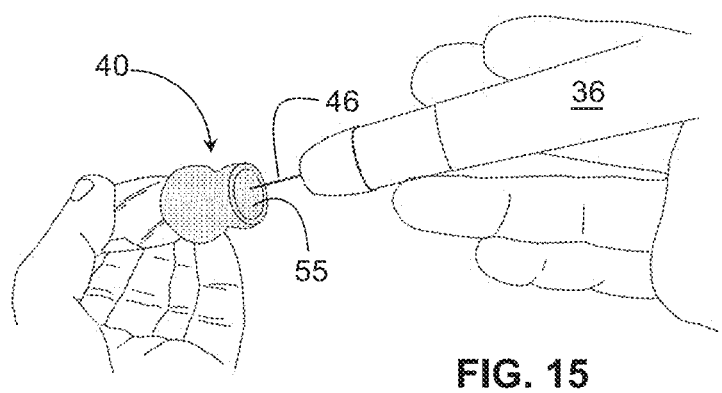
FIGS. 15 and 16 show use of the collar to avoid the risk of self-injection or damage when transferring liquid between the bottle and a hypodermic syringe and also to provide the possibility of a one handed suspended retention after connection.
Figure 16:
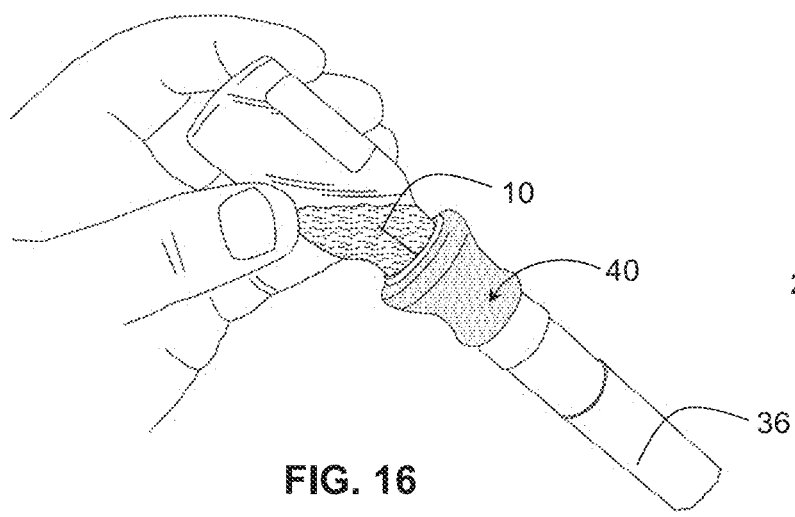

FIG. 15 shows another embodiment where this risk is avoided altogether by elongating the collar 40 and providing at its end an internal axial bore 55 configured to accommodate an end of the hypodermic syringe 36, thus allowing the neck of the bottle 10 to be coupled to the hypodermic syringe 36 as shown in FIG. 16. By such means the collar 40 serves both as a grip and a sleeve or coupler for coupling to the mouth of another utensil as shown in FIG. 16.

Figure 17:
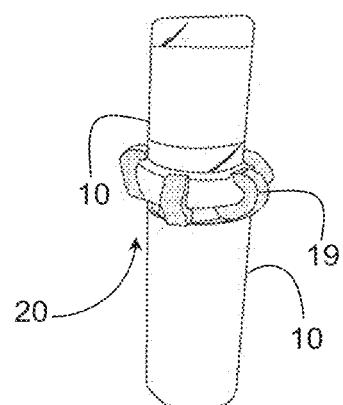
FIG. 17 shows use of the bottle support to effect limited coupling between the bottle and another utensil.

FIG. 17 shows use of the bottle support 20 to affect limited coupling between the bottle 10 and another utensil 10. Thus, when the bottle 10 is inserted into the bottle support 20, the depth of the ribs 19 at their lower ends creates a recess 32 shown in FIG. 5C. It will be appreciated that the depth of the recess depends on the dimensions and geometry of the ribs, specifically how far they extend beneath the base of the bottle support. But it also may be a function of their overall length and thickness and even their resilience since these factors will determine how far the bottle 10 needs to be pushed down into the bottle support to be firmly supported thereby. If the ribs are sufficiently stiff to support the bottle without the need to push the bottle down fully, this allows the effective depth of the recess 32 to be increased.

We have described so far multiple uses of the bottle support and the collar, both independently and in combination. We now describe further optional features of the collar which have particular application to its use with hypodermic syringes and other utensils and are intended to ameliorate one or more of the drawbacks discussed above.

Figure 18:
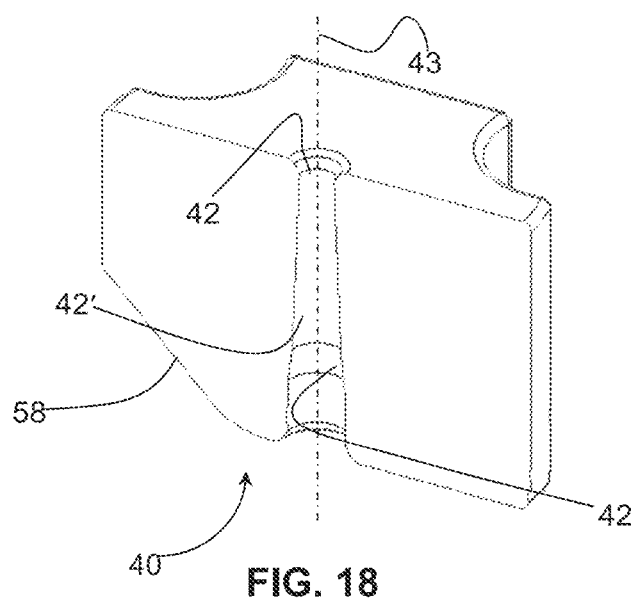
FIG. 18 shows in cross-section a collar having a slanted surface for guiding a hypodermic syringe or fitting over a narrow vial at the bottom while a hypodermic needle syringe enters from the top.

FIG. 18 shows in cross-section a collar 40 having a bore 42 shaped for accommodating the end of a hypodermic syringe (not shown) as described above with reference to FIG. 10B. One side face 58 of the collar is at least partially beveled or slanted at an angle of, for example, 15° (or one of the other angles described above for (e.g., 15°, 20°, 40°, 60°) so that, in use, when this surface is guided along (or retained relative to) the surface of a patient's skin, the needle (not shown) will be maintained at an appropriate angle for venous injection without the need for manual support by the operator's finger. It should be noted that the drawing is schematic and in practice the slanted edge can be positioned toward the front of the collar, as shown by the chain-dotted lines in FIG. 10B, or at both ends.

Figure 19:
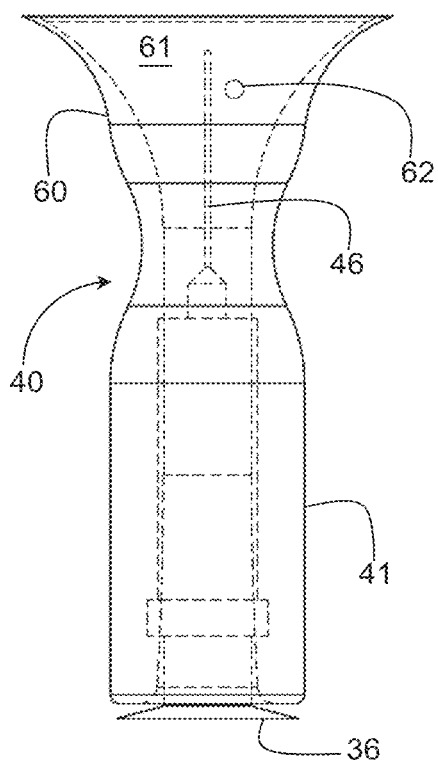
FIG. 19 shows in cross-section a collar fitted over the operative end of a hypodermic syringe for shielding the needle.

FIG. 19 shows in cross-section a collar 40 whose body 41 has an axial bore shaped to accommodate the operative end of a hypodermic syringe 36 and having a horn shaped front end 60 for shielding the needle 46. The horn shaped front end 60 is flared to provide a peripheral flexible skirt 61 that is formed of thin elastic material (e.g., 1.0 mm to 2.0 mm thickness at the skin contact end of the skirt) that is dimensioned such that in the initial state prior to use it completely covers and conceals the needle, but axially deforms when pushed against the surface of a patient's skin so as to retreat as the needle is injected. In order to prevent the flexible skirt 61 sticking to the patient's skin, one or more breathing apertures 62 are provided around the periphery of the skirt that admit air and hinder suction. Alternatively, the flexible skirt 61 may be dimensioned so that that in the initial state prior to use the needle protrudes a predetermined length.

Figure 20:
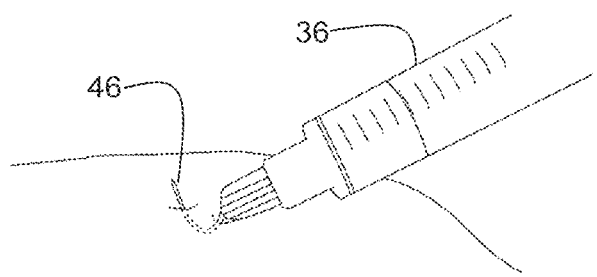
FIG. 20 shows bending of a hypodermic needle that may occur with conventional syringes resulting in extension under the skin in fish hook type fashion.

The extent to which the needle 46 protrudes in the default state directly impacts on its tendency to bend. Some hypodermic needles are very thin and easily deformed. If they are injected at the wrong angle and/or the patient moves, the needle can bend as shown in FIG. 20 and puncture the patient's skin in two locations. This is both painful and ineffective because the contents of the syringe are wasted and thus requires a further injection.

Figure 21:
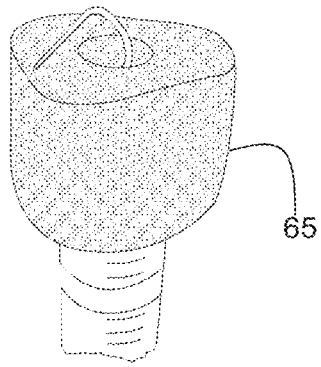
FIG. 21 shows a resilient collar that reduces the malfunction shown in FIG. 20.
Figure 22:
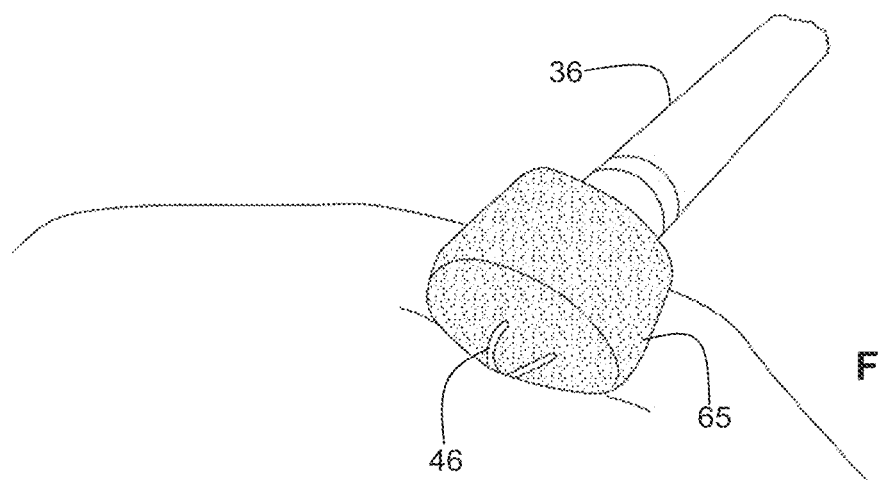
FIG. 22 shows how the collar of FIG. 21 cushions the needle and prevents it from bending inside the patient's skin.
Figure 23A:
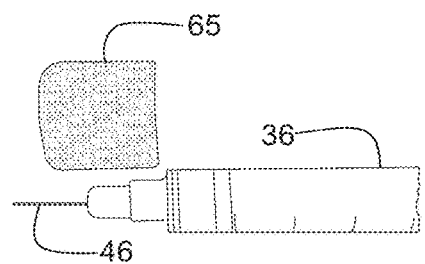
FIGS. 23A and 23B show respectively details of a hypodermic syringe before and after the collar of FIG. 21 is fitted over the needle.
Figure 23B:
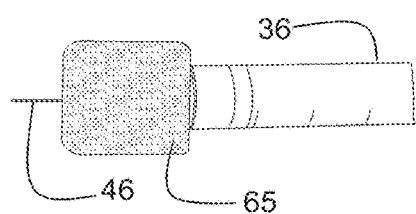
Figure 24A:
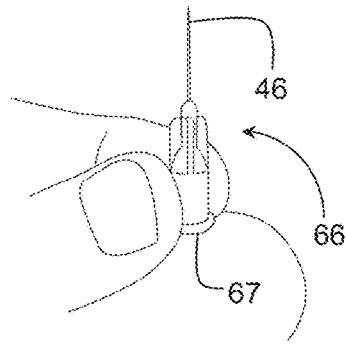
FIG. 24A shows a detail of a prior art needle assembly.
Figure 25:
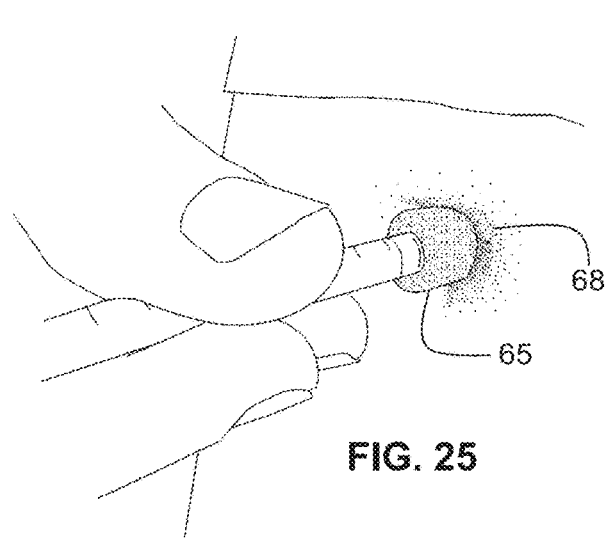
FIG. 25 shows the effect of using the collar to spread the pressure over a wider area.
Figure 24B:
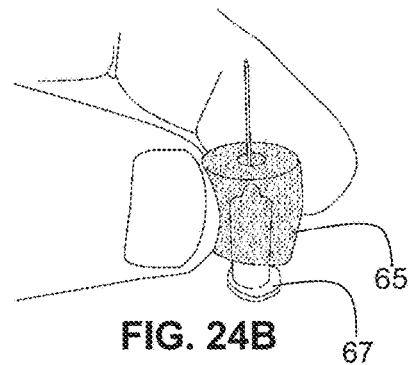
FIG. 24B shows how the collar of FIG. 21 is fitted on to such a needle assembly.
Figure 26A:
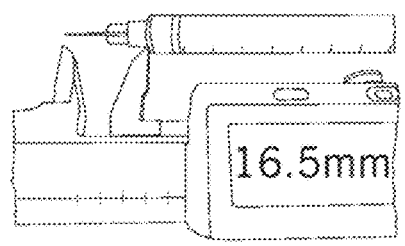
FIGS. 26A, 26B and 26C show typical dimensions associated with the needle assembly with and without the collar in situ.
Figure 26B:
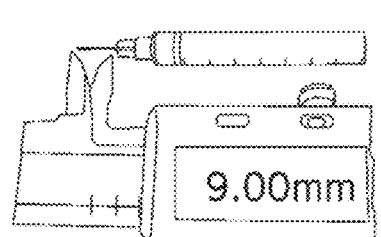
Figure 26C:
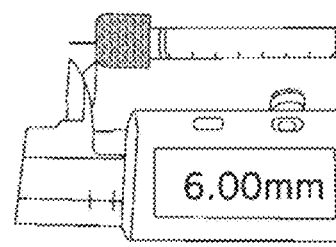

FIG. 21 shows how this malfunction can at least be mitigated by use of a collar 65 formed of deformable material such as foam and dimensioned for axial compression or displacement of a predetermined distance that is adjusted to define a known protrusion of a hypodermic needle. In this embodiment, the collar has a solid base portion that serves as a cap. FIG. 22 shows use of the collar 65, which abuts the skin as the needle 46 is injected. Should the needle bend owing to slight misalignment, it is cushioned by the collar and will bend back on itself without penetrating the patient's skin. FIGS. 23A and 23B show respectively details of the hypodermic syringe before and after the collar 65 is fitted over the needle. FIG. 24A shows a detail of a needle assembly 66 having a base 67 supporting the needle 46. FIG. 24B shows the collar 65 as it is fitted on to the needle assembly 66 so as to be supported by a peripheral flange of the base with the needle protruding through the opposite end of the collar. FIG. 25 shows the effect of using the collar 65, which pushes against the surface of the patient's skin over an extended area 68 thereof, which spreads the pressure over a wider area thereby reducing pain and assists in distributing the contents of the syringe more quickly through the surrounding tissue. FIGS. 26A, 26B and 26C show respectively typical dimensions of the needle assembly 66 (16.5 mm), and the length of the protruding end of the needle 46 without (9 mm) and with (6 mm) the collar in situ. In an alternate embodiment the collar is designed to not be compressible upon skin contact but to keep a fixed length needle extension below the skin contact.

In all embodiments, the collar may be integral with the object or utensil to which it is coupled. So, for example, it may be integral with the bottle allowing easy coupling to the hypodermic syringe, or vice versa.

FIGS. 27A, 27B and 27C show comparisons of prior art syringes with a syringe fitted with the collar of FIG. 21. Thus as best seen in FIGS. 27B and 27C the operative end of the hypodermic syringe has two intersecting ridges that press into the skin if pushed too deeply, causing significant pain to the patient. In contrast thereto, the resilient collar 65 cushions the impact and helps to distribute pressure and thereby reduces pain. Alternatively, the collar can be made rigid enough not to compress in use against skin contact as to control the puncture depth, while still helping to disperse (increase) the area of instrument to skin contact.

FIG. 28 shows pictorially multiple bottle supports 20 of different diameters stacked for easy display and packing. Preferably, the annular core 21 of each bottle support is dimensioned so that when stacked on top of an immediately adjacent bottle support of larger diameter, the annular core 21 of the upper bottle support is supported by the ribs 19 of the lower bottle support, while the ribs of the upper bottle support are supported by the annular core of the lower bottle support. Even more preferably, the annular cores 21 are dimensioned so that any two alternate bottle supports can be stacked flat. In other words, the outer edges of the ribs 19 of the smaller bottle support fit snugly within the inner edges of the ribs 19 of the lower bottle support. In this case, multiple bottle supports can either be stacked into a tower as shown in FIG. 28 or they be dismantled and reassembled to form two sets of concentric rings.

FIG. 29A shows pictorially a tray 70 for mounting multiple bottle supports 20. The tray 70 has a plurality of upraised protuberances each dimensioned for accommodating a bottle support of appropriate diameter as shown in FIG. 29B.

Figure 30:
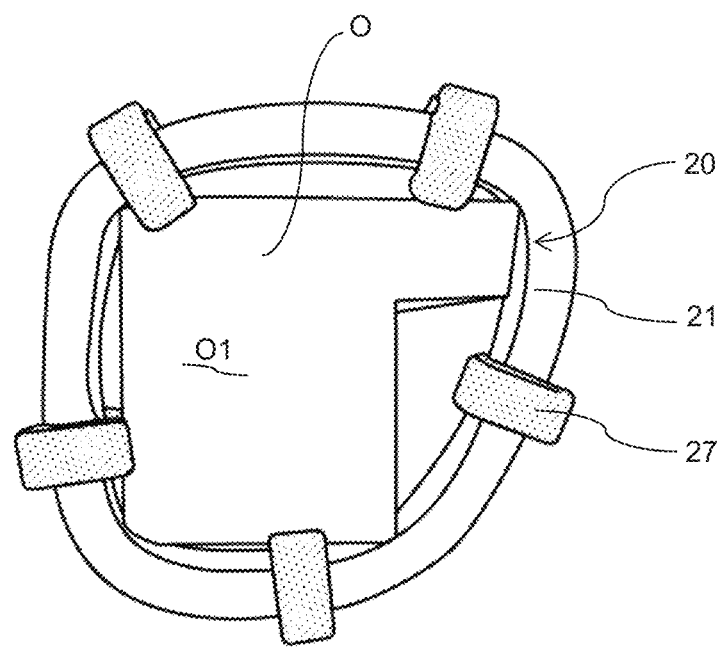
FIG. 30 shows a bottom plan view of a pliable annular core mount providing mounting support to a multi-linear sided utensil.

FIG. 30 shows a bottom plan view of pliable annular core mount 20 providing mounting support to a multi-linear side utensil O. FIG. 30 illustrates the versatility of mount 20 with a pliable annular core 21. As seen in the support interrelationship between pliable mount 20 and the multi-sided utensil O, mount 20 is adaptable to a wide variety of objects inclusive of those having non-curved peripheries and inclusive of those having deep notches or concave sections. FIG. 30 further shows pliable ribs 27 conforming as well to the non-curved, convex periphery of object or utensil O.

In the illustrated FIG. 30 embodiment there are five ribs 27 equally spaced about the length of annular core 21 (e.g., an annular core of an internal (hollow defining) diameter of, for example, a non-limiting but illustrative range of 3 mm to 7.5 cm), although greater or less than five ribs 27 are featured under the present invention, as in 2 or more and 10 or less ribs 27 for the noted annular core range (although, for larger diameter annular cores, as in those falling in the upper half of the interior diameter range noted or above, more than 10 and less than 20 ribs may be applicable). FIG. 30 further illustrates that, depending on the shape of object O, one or a multiple (e.g., less than half of the total ribs 27 mounted on the annular core 21) may be suspended away from the object O's periphery and not in contact with the utensil or object O's surface.

FIG. 30 also shows that for some object O configurations, annular core 21 may directly contact one or more points of the object O's periphery. In this case, there are three points or more of contact between an edge of the object O and annular core 21, and four ribs in direct contact locations, and one free rib 27. Again, this shows the versatility of the mount 20 in both accommodating a wide variety of peripheral object shapes, while still providing a stable support at the base of the object, which base support can avoid planar slipping along a supporting surface such that a user can free up a hand for other uses rather than holding the object O in place. Providing the ribs 27 of a high friction material such as silicone enhances the non-slip relationship with the support surface. That is, as explained above, ribs 27 can be formed of a variety of material with a preference toward high friction and pliable or flexible materials as in silicon rubber compounds; Thermoplastic elastomers (TPE), Thermoplastic Rubber (TPR), Polyvinyl chloride (PVC), or any combination of the above either blended before formation or a physical combination as in a laminate arrangement.

As also explained above, the ribs 27 and annular core 21 can be formed of the same or different material, inclusive of different materials, but with each being flexible.

For example, an embodiment features each of ribs 27 and annular core 21 being pliable or flexible as in when formed of one material in a common molding. Other embodiments feature, ribs being more flexible than the annular core, with additional alternate embodiments featuring less pliable ribs mounted on a more pliable annular core, or equally pliable levels in the ribs and core (e.g., each rib and the core formed of medical grade silicone and/or one of the other TPE, TPR, or PVC plastics described above). Medical grade silicone comes in a variety of hardness values and for the purposes of mount 20 the hardness values are preferably about 20 to 80 shore D hardness, as in 30 to 50 shore D hardness, with 40 shore D hardness being well suited for many embodiments (the shore ranges being suitable for each of core 21 and ribs 27). Also, although object O is shown to be of equal height above its base, the present invention is also suited for supporting the base of non-common height bodies. Further, although ribs 27 are shown each of common height and configuration, variations to achieve ribs in a mount of different height and/or configuration are featured.

Figure 31:
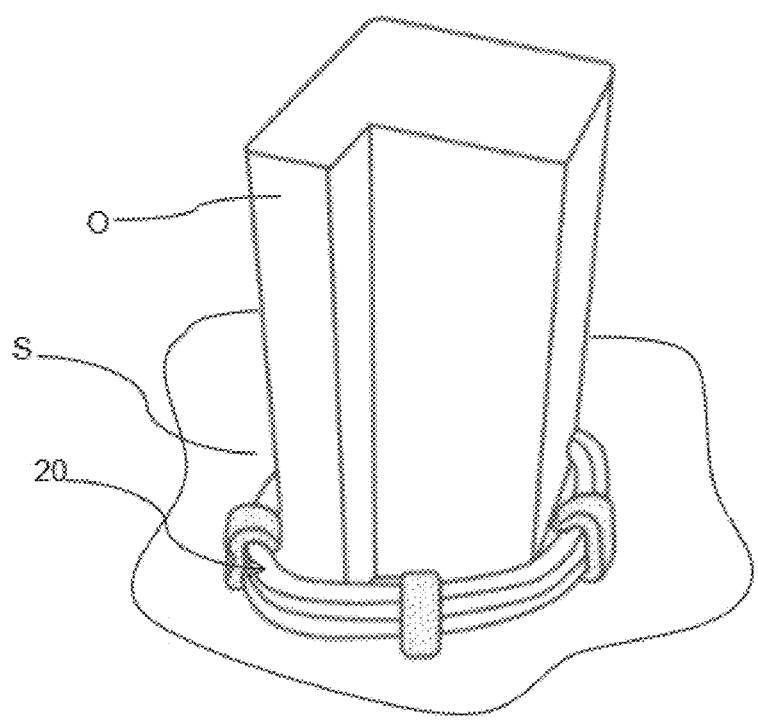
FIG. 31 shows the mount and utensil combination of FIG. 30 in a front elevational view.

FIG. 31 shows the mount 20 and utensil O combination of FIG. 30 in a front elevational view and the manner in which the ribs 27 suspend object O off of support surface S while still providing high friction contact with that surface S. FIG. 31 further shows a perspective view of that which is shown in FIG. 30 with mount 20 being engaged with the base end of object O as to lift the bottom surface O1 off from contact with the underlying surface S. This suspension of object O above surface S is achieved by way of the ribs 27 extension below the lower most surface of annular core and the engagement of the ribs such that they extend to opposite sides of a plane resting on bottom surface O1. For example, some non-limiting, but illustrative numerical values for mount 20 (e.g., see FIG. 3B) are as follows: the top surface of annular core 21 has a 2.5 mm width, the radial thickness of the annular core at its middle is 4 mm, and the height of the core is 8 mm. As some non-limiting examples of suitable rib dimensions for some uses under the present invention there is noted: a rib width of 5 mm (along the circumference of the annular core). Also, the radial extension into the hollow of 1.5 mm at the top free end of the rib, with a longer (e.g., 3.5 mm radial extension into the hollow at the bottom of the rib (this extension having a height thickness of 2 mm, for example)). The ribs minimum thickness at the center of the annular core height and preferably is 2 mm with thicker curved rib sections extending above and below. The overall height of the ribs is about 14 mm. Thus, for this embodiment a suspension height between the bottom of the supported object and the support surface of about 2 mm is present. As further described herein various other dimensions for mount 20 are featured and thus the suspension height can be varied as well.

Figures 32A, 32B:
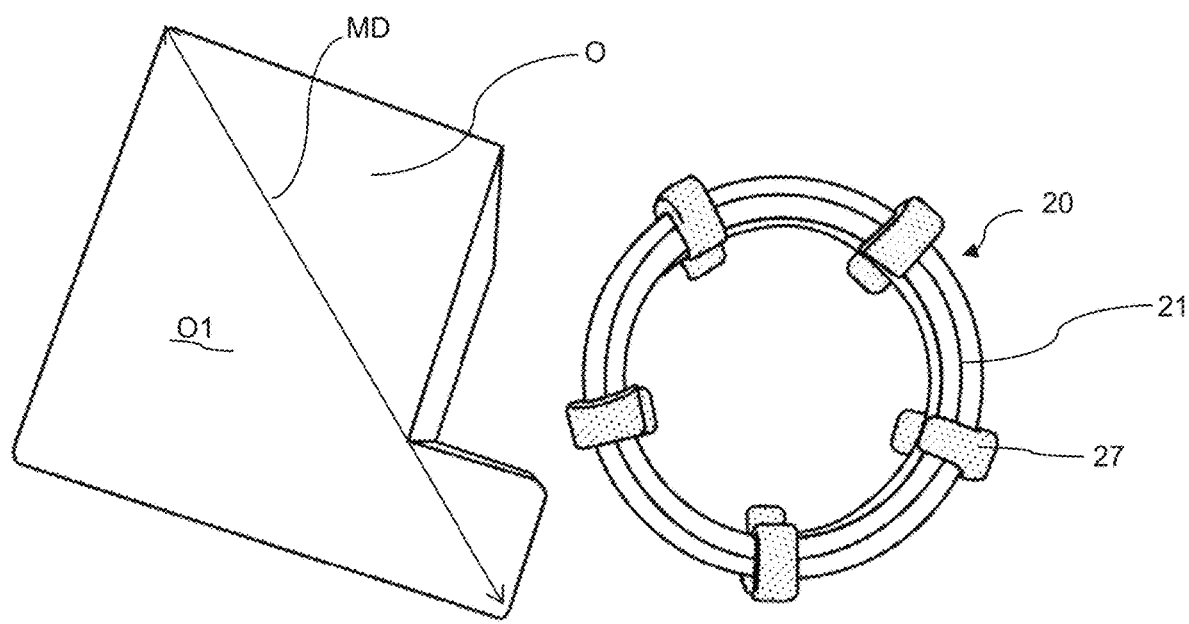
FIGS. 32A and 32B show a top plan view of the components of FIG. 31 separated.

FIGS. 32A and 32B show a top plan view of the components of FIG. 31 separated apart. In other words, FIGS. 32A and 32B show the removal or separation of mount 20 from object O, with contraction of the previously expanded annular core 21 (e.g., annular core stretch value at the time of utensil support is sufficient to extend the core diameter from its natural contraction state to one that can accommodate the maximum peripheral distance value MD shown in FIG. 32A). Upon separation of mount 20 from object O, core 21 contracts back down from its stretched mount state to its contracted non-stretched/non-use state of, for example, 3 mm to 7.5 cm to reflect the natural hollow diameter of core 21. The initial non-contraction annular core dimension suited for the object will also be dependent upon the stretch % in the material used, as in typically a lower shore hardness value will have a greater stretch percentage potential and vice versa. For example, a stretch percentage of 5-25% of the original contracted diameter is illustrative; with a lower shore D value of say shore D20 will typically be at the higher 25% end of the stretch range, while a shore D80 material will typically be more toward the 5% end of the elasticity range. In other words, a shore D80 elastomeric material typically has the advantage of strength and rigidity, while lower shore value (e.g., 20 shore D) have the disadvantages of potential tearing and excess elasticity. The decision will be in the force of the function one is achieving relative to particular embodiments described herein. Also, there is the possibility of combining multiple surrounding mount ring assemblies, with a shore D20 mount ring combined in nested fashion and with a shore D of about 40 or 60 surrounding it, either based on physical nesting or based on a secured together laminate arrangement.

Figure 33:
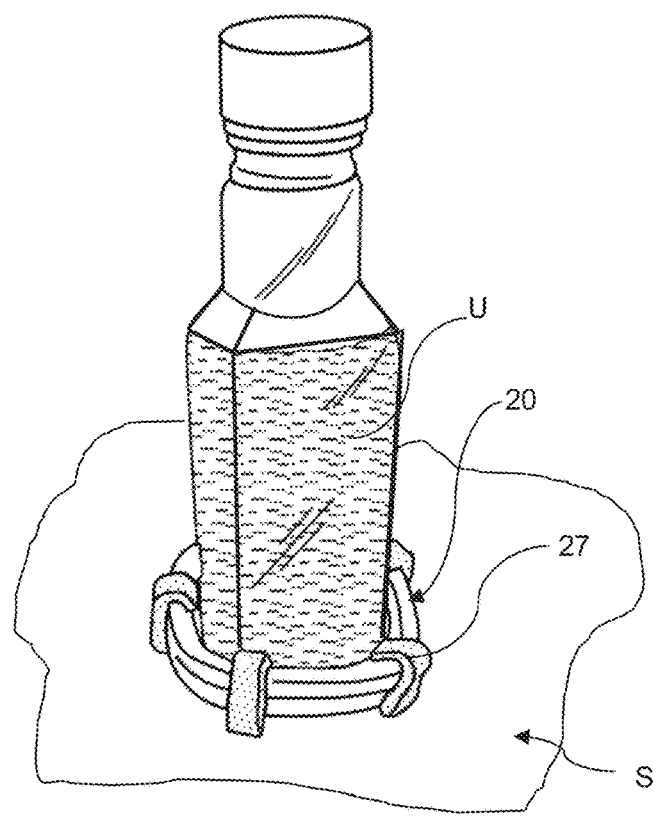
FIG. 33 shows the pliable annular core mount in supporting fashion at the base of a different utensil in the form of a bottle with a quadrilateral periphery.

FIG. 33 shows the pliable annular core mount in supporting fashion at the base of a different utensil U, in the form of a bottle with a quadrilateral periphery (e.g., a square periphery). That is, FIG. 33 provides an additional perspective view of a suspended bottle U (different than the above described vial bottles with rubber seal tops and crimping metal ring covers). Bottle U in FIG. 33 is also shown as being suspended above support surface S in similar fashion to the suspension of object O described for FIG. 31. Suspended bottle U is shown as having a polygonal (e.g., square) periphery with the five ribs 27 contacting multiple flat side surfaces thereof.

Figure 34:
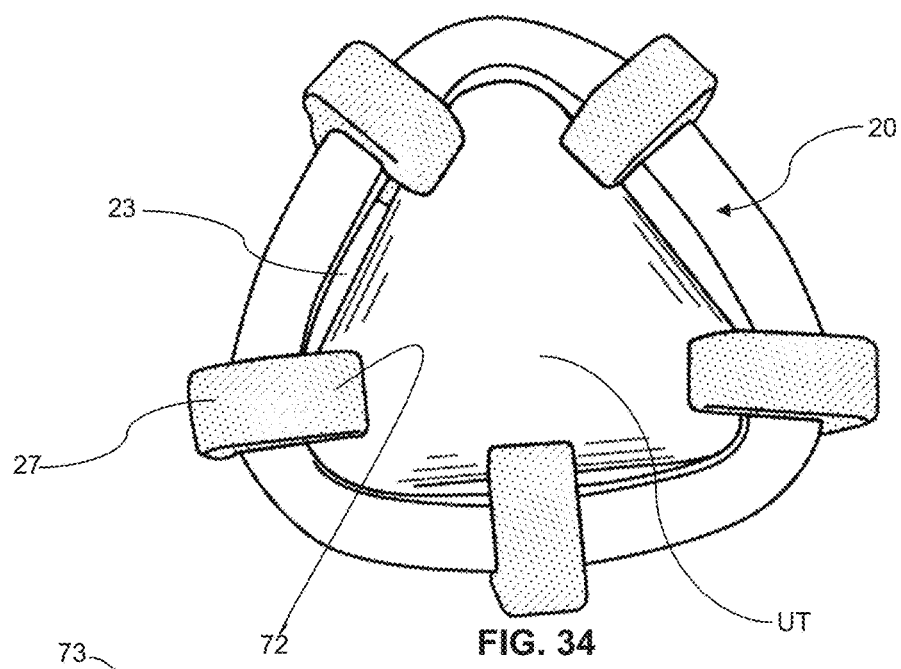
FIG. 34 shows a bottom plan view of the pliable annular core mount providing base support to a triangular cross-sectioned utensil.

FIG. 34 shows a bottom plan view of the pliable annular core mount or ring 20 providing base support to a triangular cross-sectioned utensil UT (e.g., an open top container for temporary fluid retention). That is, FIG. 34 shows an additional depiction of mount 20 provided as a high friction retention base mount to object UT, which in this case is a triangular shaped object with three sides, all of which are in contact with ribs 27. FIG. 34 further illustrates the lower extensions 72 of ribs 27 extending out into hollow 23 (e.g., for a length of 3.5 mm and a thickness of 2 mm, and with a horizontal, planar utensil support surface in that extension) as to contact an outer peripheral undersurface portion of object UT. In this way, there is provided a desired degree of object suspension above any supporting surface (from the upper planar surface of extensions 72 to the bottom (high friction) contact surface portion of ribs 27).

Figure 35:
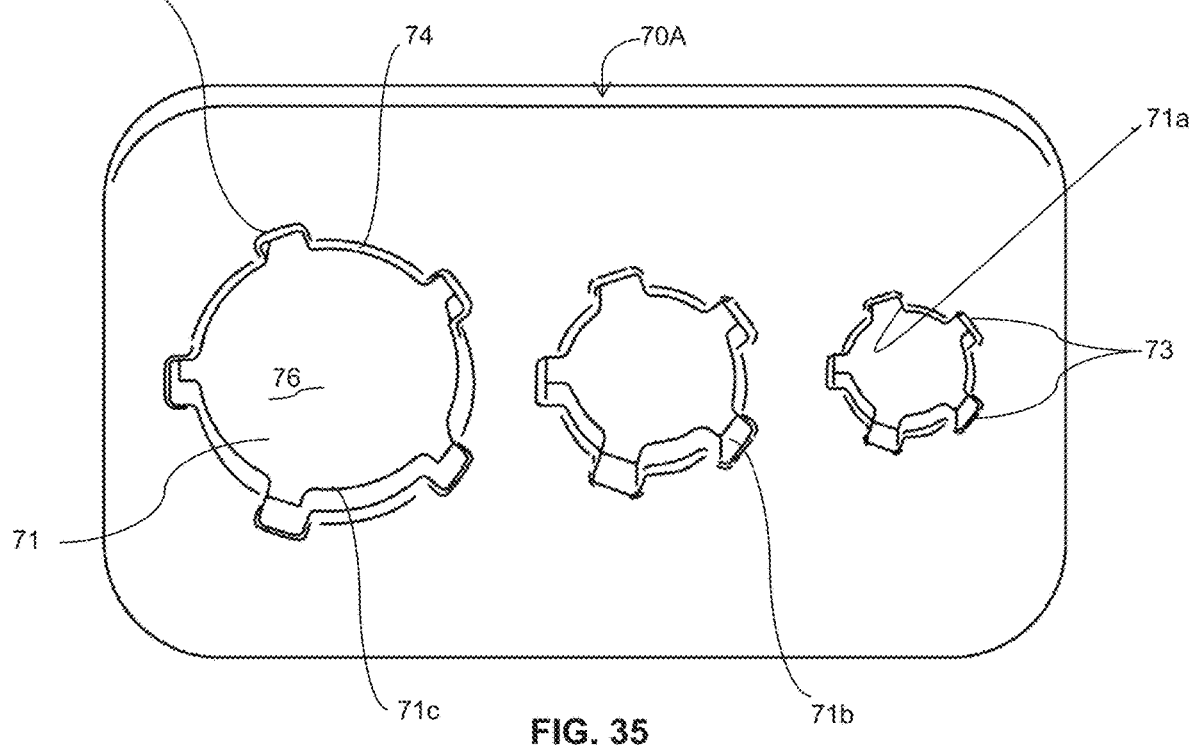
FIG. 35 shows a top perspective view of an alternate embodiment of a mounting tray which in this embodiment features three sequential sized apertures configured to frictionally receive respectively sized mounts and/or respective utensils directly.

FIG. 35 shows a top perspective view of an alternate embodiment of mounting tray 70A which is similar to that featured in FIG. 29A, but in this embodiment features three sequential sized apertures 71, with aperture 71a representing a reception aperture that is the smallest; 71b (medium sized), and 71c (largest sized). The apertures 71 in tray 70A thus extend inward into the tray's body, rather than having mount support projections extending up off the tray as in FIG. 29A. In both situations (tray 70 and tray 70A), however, the tray accommodation regions are designed to retain a corresponding sized mount 20 in position until intended for use either remotely off the tray or in a holding or transfer mode on the tray itself. Moreover, trays of the present invention are also configurable to frictionally receive respectively sized mounts and/or respective utensils directly, with the apertured embodiment tray 70A being particularly well suited for such direct utensil or utensil with collar tray reception as there is a nesting region provided in the body of the tray itself. Further, the tray reception is designed for single hand removal of components.

As further seen in FIG. 35, tray 70A is designed to support less mounts (three vs. ten mounts as featured in tray 70), which makes it well suited as a transfer tray for use in surgical operations and the like. The apertures in tray 70A, such as aperture 71a, feature peripheral wall extension recesses 73 that are designed with circumferential spacing in common with the circumferential spacing of ribs 27 about the annular core 21, such that upon resting a mount 20 in a corresponding aperture in tray 70A, the mount is held from rotation due to the ribs retention in the corresponding wall extension recesses 73. The wall extension recesses 73 can also be sized to provide the same means for preventing rotation upon receipt of, for example, a corner portion of a peripheral wall surface in a collar (e.g., collar of FIG. 10B) of the present invention, when placed in an aperture such as 71a. Further, between wall extension recesses 73, each aperture has a plurality of circle segments 74 (five segments adjacent the five wall extensions) that represent the inner most region of tray material relative to the formed apertures, and are preferably designed to come into friction contact with the annular core 21 of each mount placed in a corresponding aperture. Also, tray 70A features bottom floor 76 in each of the apertures that is an integral part of the tray body and thus is indicative that apertures 71 are not throughholes relative to the tray body in the embodiment of FIG. 35, although other embodiments are inclusive of the providing of through-holes with reliance being placed on the frictional retention between the tray and mounts for retention relative to a vertical axis extending perpendicular to the tray and centered in each respective aperture 71.

Trays 70 and 70A are preferably formed of a sufficiently rigid plastic as to enable non-deflecting (non-sagging) transfer from one person to another, and thus are typically formed of a different material than mounts 20 or collars of the present invention, although alternate embodiments of the invention are inclusive of a common material in the tray relative to the noted collar and/or mounts (with an annular core 21 having common material as the tray 70A being one example). In embodiments of the present invention the tray is formed of, for example, PVC plastic material.

Figure 36:
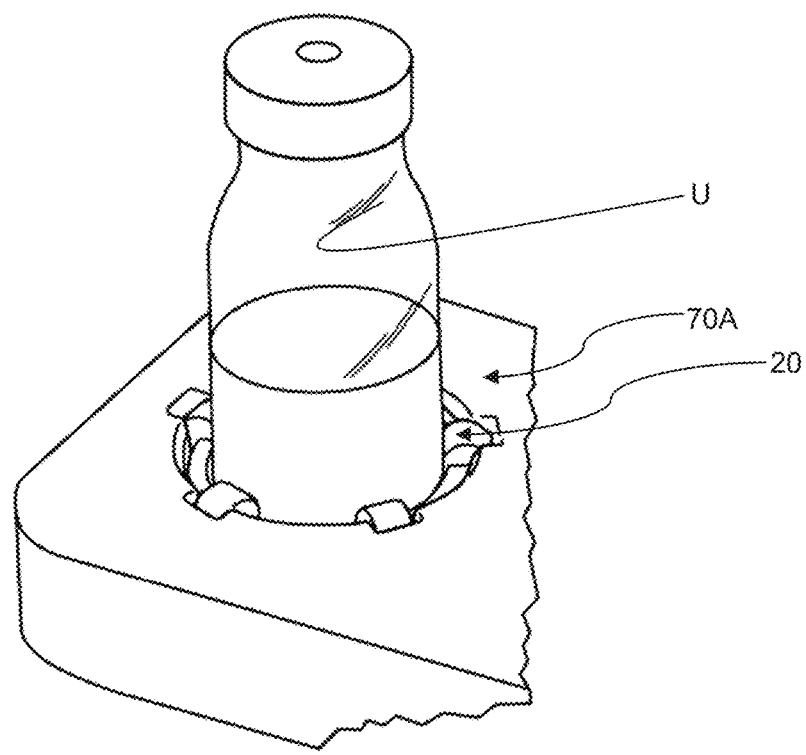
FIG. 36 shows a cut away portion of the tray of FIG. 35 showing the tray holding a combination of a mount and supported vial, with the combination being held in a snug, fixed from moving state (at least until the combination is pulled out, as the combination is removed as a unit due to the higher friction level between the mount and vial as compared to the friction level between the mount and conforming tray aperture).

FIG. 36 shows a cut away portion of tray 70A showing the tray holding a combination of a mount 20 and supported vial (utensil) U, with the combination being held in a snug, fixed from moving state (at least until the combination is pulled out, as the combination of the mount and vial is removed as a unit due to the higher friction level between the mount and vial as compared to the friction level between the mount and conforming tray aperture).

Figure 37:
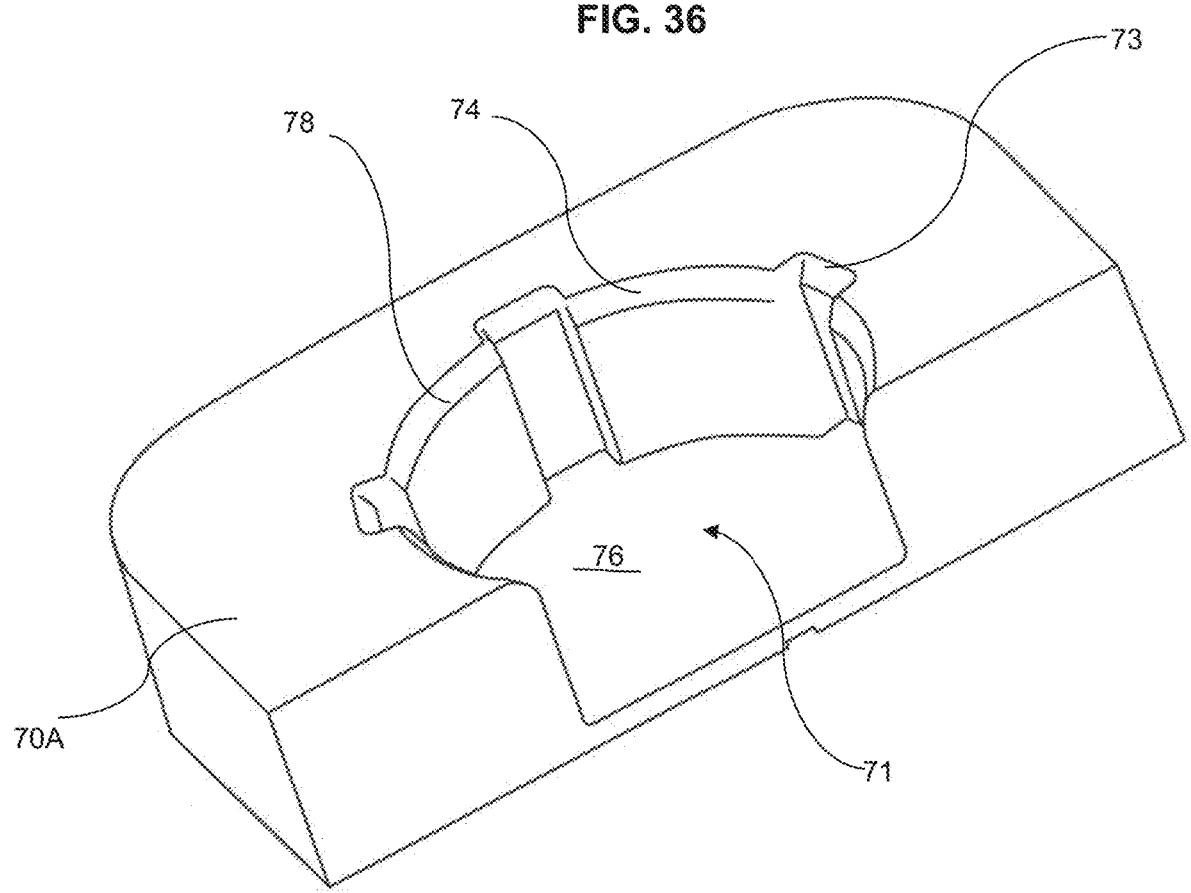
FIG. 37 shows a cut-away view of the tray of FIG. 35 showing the conforming apertures in the tray that are configured to receive internally a corresponding sized mount.

FIG. 37 shows a cut-away view of the tray of 70A showing the conforming apertures 71 with circular segments 74 between which are the radially outward extending ridge reception recesses 73, as well as bottom floor 76. FIG. 37 also illustrates the conical insertion edge or rim 78 which has its greatest diameter at the top of the tray and extends in oblique fashion downward and inward until reaching the interior most circle segment walls 74 of the tray. The upper conical rim 78 facilitates the slide-in insertion and centralization of the mount and associated utensil support (or collar and associated utensil support). As such, it only extends for a minor percentage of the depth of the aperture, as in 10 percent or less.

Figure 38:
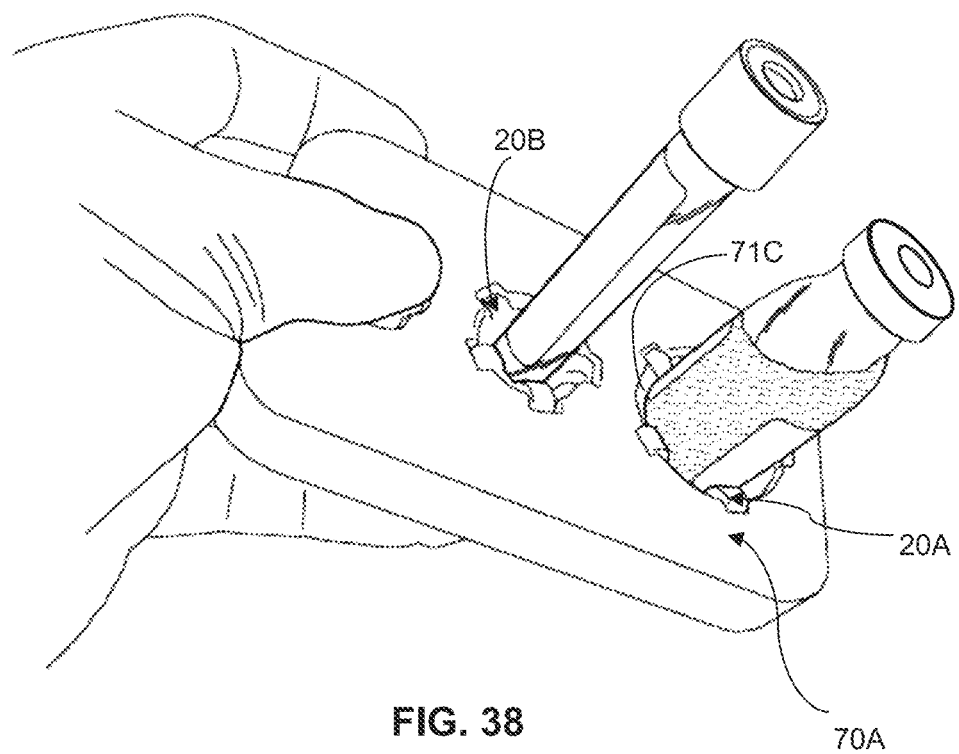
FIG. 38 shows the mounting tray supporting the vial of FIG. 35 plus the smaller (non-capped) end of a specimen tube, with the remaining aperture providing a convenient finger (thumb) grasping location.

FIG. 38 shows the mounting tray 70A supporting the vial and mount 20A combination of FIG. 36 in aperture 71c, plus the smaller (non-capped) end of a specimen tube ST and mount 20B in aperture 71b, with the remaining aperture 71a, providing a convenient finger (thumb) grasping depression location to facilitate single hand tray transfer.

Figure 39:
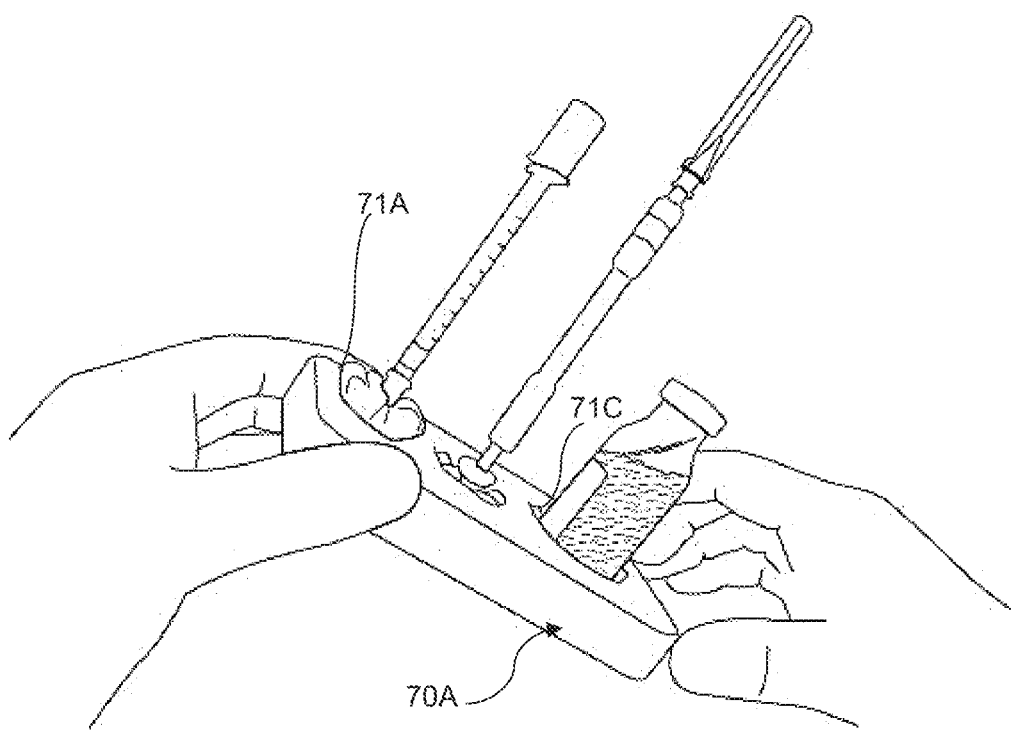
FIG. 39 shows a view similar to FIG. 38, but with each of the three apertures of the tray occupied, and a user having a side periphery of tray passing grip.

FIG. 39 shows a view similar to FIG. 38, but with each of the three apertures of the tray occupied, and a user having a side periphery of tray passing grip. While three apertures 71 are shown in FIG. 39, less or more of such apertures are possible, inclusive of multiples of common sized apertures on a common tray base 70A rather than the earlier described different sized apertures 71a to 71c. In FIG. 39 tray 70A is shown functioning as a mount holder and utensil retentioner as well as a passing tray when so desired. That is, tray 70A has its aperture 71c with a mount hold on a vial in similar fashion as shown in FIG. 36. However, its middle positioned aperture has an aperture configuration designed to receive (and preferably preclude rotation) of a syringe with grasping collar (e.g., collar 40 or 65) attachment, such as that shown in FIG. 23B (with less or no exposed needle length to ensure no needle tip contact with the tray) or the collar 230 shown in the upper portion of the vial in the below described FIG.

60. As such, the size of middle aperture 71*b* may be smaller or equal to that of aperture 71*a* (rather than larger than 71*a* as described above) in an effort to have an aperture well suited to receive the desired collar embodiment, with the type of utensil received by tray 70A being designed, for example, to match with a planned usage sequence of medical utensils, as in use of the syringe shown in the middle position, and then a follow up medical step involving drawing medicament from the bottle in aperture 71*c* using the utensil provided in aperture 71*a* and then using that syringe.

In FIG. 39, the above noted different medicament syringe is shown received within the end aperture 71*a*, and the aperture 71*a* is shown configured for reception of a collar provided at the end of the syringe as, for example, collar 40 of FIG. 18, which is shown in the below described FIG. 42 as being mounted to the needle assembly end of a syringe. Thus, the aperture 71*a* can be designed as a universal collar and mount aperture having the five rib reception extensions 73 that are also sized to frictionally receive and retain (both vertically and rotationally) a collar. Alternatively, one or more of the apertures can be dimensioned, not to match the configuration of a mount, but for specific accommodation of a collar configuration, as in an aperture having a side wall with extensions that are designed to match the corner concavities of the collar such as that shown in FIG. 10A, with an otherwise general four sided recess tray recess designed to frictionally retain and conform in length with each generally straight segment wall shown in FIG. 10A, between the corner concave recesses.

Figure 40:
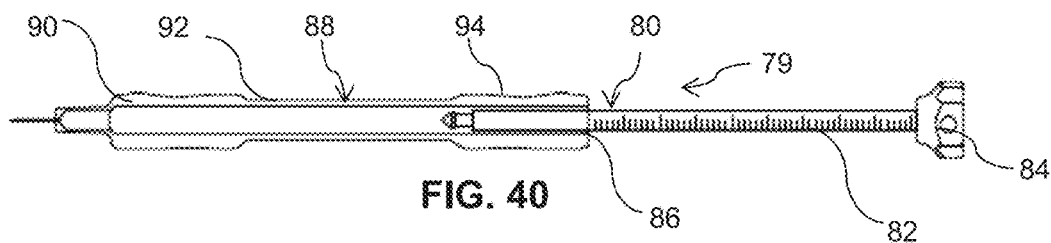
FIG. 40 shows a syringe with a modified plunger base featuring an added or one piece gripping collar of the present invention as well as a dumbbell shaped grasping device for the syringe cylinder.

FIG. 40 shows syringe assembly 79 featuring syringe 80 with a modified plunger 82 featuring, at one end, an added grasping collar 84, which can represent a snap-on collar featuring a collar of, for example, FIG. 11 configuration with open top rimmed end that is flexible enough to receive an inserted plunger flange (such as the circular flange located to the far right of the syringe of the below described FIG. 45). In an alternate embodiment, a one piece gripping collar forming a monolithic unit with the plunger 82 itself can be utilized (in similar fashion to the integrated plunger end shown in FIG. 48 as described below). FIG. 40 also shows, extending over the syringe cylinder 86, a grasping collar 88 in the form of an elongated dumbbell elastomeric shaped sleeve comprised of a needle end enlarged portion 90, an intermediate extension portion 92, and an opposite enlarged portion 94 similar in configuration to that of the needle end enlarged portion 90. Collar 88 is provided with a central through-hole designed to receive in slide-on gripping fashion the cylinder 86 of syringe or collar 88 can be molded over cylinder 86 or formed as a monolithic unit with the plunger cylinder.

Each enlarged portion 90, 94 represents an adaptation of the gripping sleeve device for precision instruments described in U.S. Pat. No. 8,745,825 issued on Jun. 10, 2014 (US '825), and which patent is hereby incorporated by reference in its entirety for background purposes. That is, each enlarged portion has an outer surface with the finger contact regions described in US '825 that provides for enhanced finger manipulation, both with respect to longitudinal advancement or retraction in the direction of needle insertion, but as well as rotation of the syringe. The elongated dumbbell shape also facilitates handing off the utensil from one person to the next or one hand to the other, as the length of extension portion 92 is sufficient for finger grasping without contacting the two, opposite end enlarged portions 90 and 94 and also in a fashion that avoids interfering with extended plunges. In addition, the enlarged dumbbell ends 90 and 94 provides for lifting the needle away from a contaminated surface and ready pinch pick up due to the lifted off surface arrangement provided by enlargements 90 and 94. Further, the inclusion of the dumbbell sleeve with enlarged sleeve portion 94 provides a grasping location that avoids the need for a syringe cylinder end flange. Also the inclusion of grasping collar 84 removes the requirement for a free end plunger flange.

Figure 41:
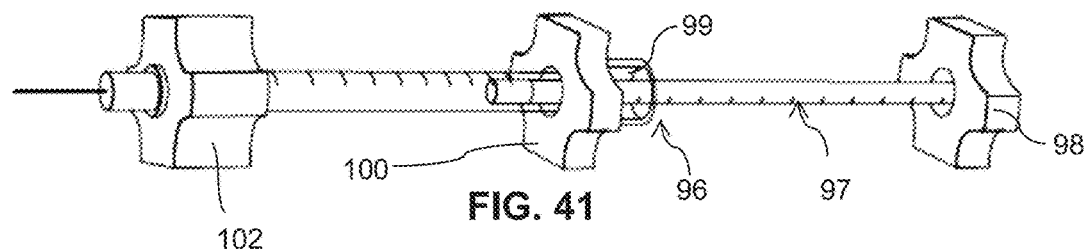
FIG. 41 shows another embodiment of the present invention featuring a set of different collars inclusive of a first smaller thickness grasping collar at the plunger base, a second, similar smaller thickness collar at the syringe's cylinder base, and a third, larger thickness collar at the needle support end of the syringe cylinder.

FIG. 41 shows another syringe assembly 96 embodiment of the present invention featuring a syringe 97 with a set of different collars inclusive of a first, smaller thickness grasping collar 98 at the plunger base, a second, similar smaller thickness collar 100 at the syringe's cylinder base, and a third, larger thickness collar 102 at the needle support end of the syringe cylinder. The smaller collars have interior apertures (through-holes) suited for stretch over (e.g., snap-on or just slide over) retention to their respective syringe sights (as in a sufficiently flexible material collar with an aperture that snaps over and engages the circular flange located to the far right of the syringe of the below described FIG. 45 including expansion over a plunger's flanged end or simply slides over a flange less plunger end). In addition, the same collar (collar 100) with its flexibility and suitably sized aperture can slide over and engage with the base of the cylinder of the syringe 97 of needle assembly 96.

As seen, each of the flexible grasping collars 98, 100 and 102 feature a peripheral configuration similar to that of FIGS. 10A and 10B, inclusive of four concave recesses at corners of the grasping collar, two opposing longer length generally straight or slightly curving (e.g., a radius larger than that of a circumference contacting the outermost points of collar 98, 100 or 102), and two opposing also generally straight or slightly curving (see above) shorter length sides. Collars 98 and 100 can be of the same configuration. Also the thickness of the thinner collars 98 and 100 can be, for example, ½ of that of the thicker collar 102 (e.g., a thickness value of, for instance, 6 to 9 mm for the thinner collars 98 and 100 which is suitable for the small volume (e.g., a cylinder volume of, for example, 0.5 ml (or cc) to 10 ml) syringe 96 shown). Also, the concave recessed corners and adjacent projections resulting in the noted shorter and longer generally straight or slightly curved ridge sides provide for ready finger pinching external to the cylinder of the syringe and multiple finger grasp locations for a transfer (e.g., one person pinching and holding one of collars 98, 100 and 102 and the other person receiving the syringe with the needle in a safe location by grasping one of the remaining two collars not already grasped). The collars also are well suited to maintain the needle of the syringe suspended above an underlying potentially contaminated surface.

Figure 42:
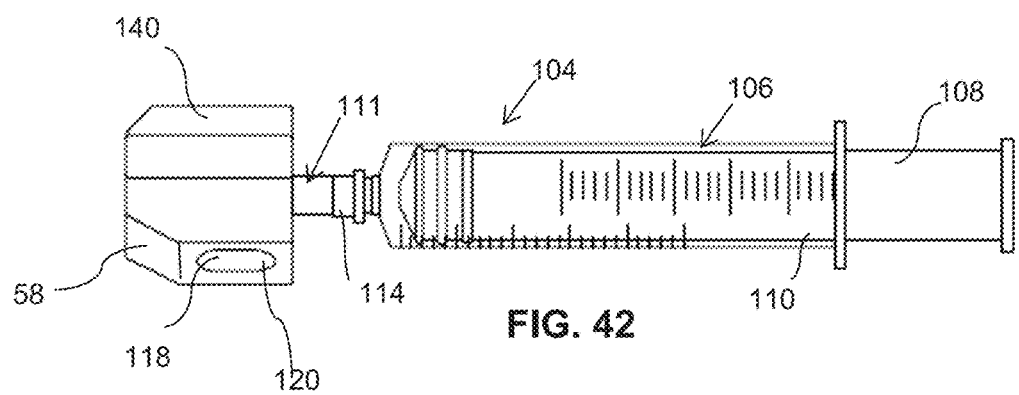
FIG. 42 shows the collar of FIG. 18 (but with the taper on the distal end rather than the proximal end shown in FIG. 18) in an initial slide on position relative to the needle assembly of a syringe.
Figure 43:
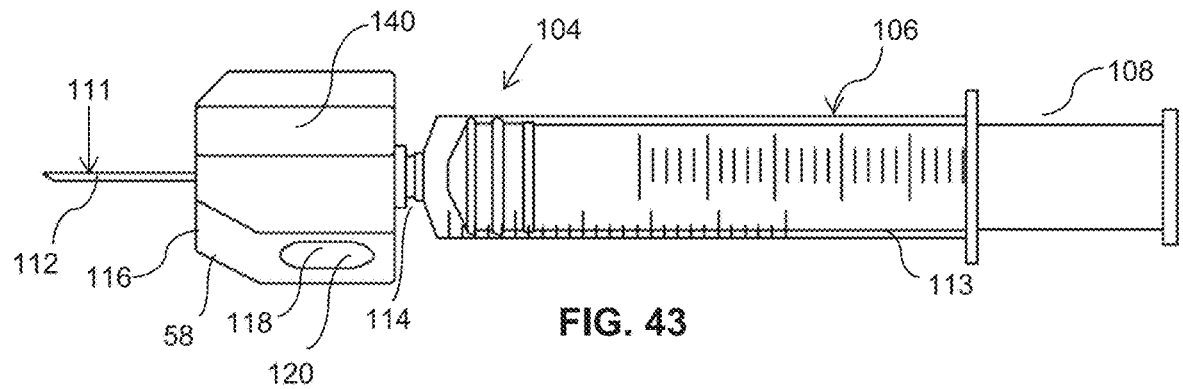
FIG. 43 shows the collar of FIG. 42 in a final resting position over the base of the needle assembly and with a predetermined length of needle extending outward away from the free end of the collar with slanted exterior surface.

FIG. 42 shows an additional syringe assembly 104 under the present invention featuring a syringe 106 comprised of a plunger portion 108, a cylinder portion 110 (e.g., a higher volume cylinder as in, for example, >10 ml to 400 ml), and a needle assembly 111, with the latter having a needle 112 and needle base hub 114. In FIG. 43, syringe assembly 104 is shown further comprising collar 140 (see FIG. 18) having its aperture set (42, 42' and 42" in FIG. 18) in position for a slide on connection with the above described components of needle assembly 111 as in the needle associated with a 20 ml to 50 ml syringe. As seen, collar 40 in FIG. 42 has a similar external periphery as that of the above described collar 102 with its four corner positioned concave recesses and short and long sides extending between the corner concave recessed and in common opposing fashion (i.e., short-to-short generally straight ridge sides opposing, and long-to-long generally straight sides opposing). Collar 140 in FIG. 42 is also shown with the above described sloped surface 58 which facilitates needle tip and needle orientation relative to the skin surface to receive the needle (this being in addition to the offset finger pinch grasping potential when holding, passing or receiving the needle assembly 104).

FIG. 43 shows the collar 146 of FIG. 42 in a final resting position over the base of the needle assembly 111 and with a predetermined length of needle 112 extending outward away from the free end 116 of the collar 40 with slanted exterior surface 58. FIG. 43 further shows the tapered surface 58 being formed on the longer opposing generally straight side which further includes a finger depression recess 118 (same as the oval recess depression 45 in FIG. 10A) along the non-slanted portion 120 that extends from an end of tapered surface 58. As also seen in FIG. 43, the outer circumference of the collar 40 has a larger diameter as that of the syringe cylinder (even the larger volume syringe cylinder) as to provide for offset grasping away from the needle, etc.

Figure 44:
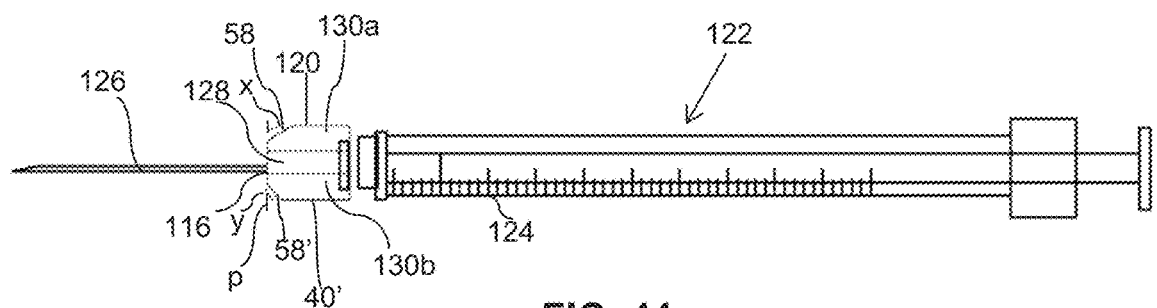
FIG. 44 shows a similar view as FIG. 43 but with a different, smaller volume cylinder syringe and with a longer needle extension out from the collar secured to the syringe's needle assembly.

FIG. 44 shows a similar view as FIG. 43 but with needle assembly 122 featuring a different, smaller volume cylinder 124 and with a longer needle extension 126 out from the collar 40' secured to the syringe's needle assembly. FIG. 44 also provides a different viewpoint wherein there can be seen the short side ridge 128 of the opposing short sides ridges. Also, in this embodiment, collar 40' is similar to that of FIG. 18, but features a second, shorter length oblique surface 58' on the one side opposite the long or wider width ridge side in which oblique surface 58 extends. For example, concave recesses 130a and 130b extend in longitudinal fashion for the full entire length of collar (longitudinal is perpendicular to plane P that extends flush on free end 116 of collar 40'). Suitable angle ranges for angles X and Y defined by plane P and the respective oblique side (58, 58') range from 10° to 80° with X preferably being equal to or greater than angle Y shown in FIG. 44.

Figure 45:
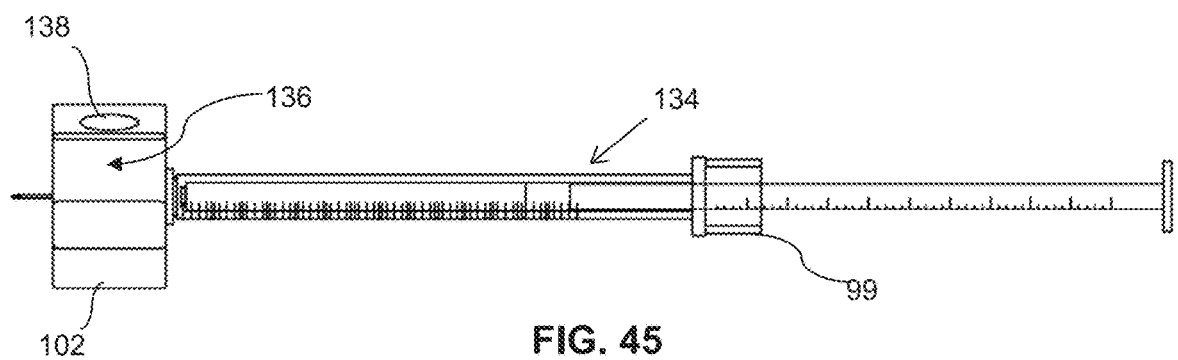
FIG. 45 shows an alternate arrangement featuring a similar volume cylinder syringe as in FIG. 44, but with a collar having the configuration shown in FIG. 10B.

FIG. 45 shows an alternate needle assembly 134 arrangement featuring a similar volume cylinder syringe as in FIG. 44, but with a collar 136 having the configuration shown in FIG. 10B. As further shown in FIG. 45, collar 136 comprises a finger depression recess 138 (in common with depression 45 shown in FIG. 10A and with an illustrative depression level of 0.5 mm). This finger recess can help a user control the desired tilt for insertion of the only partially visible needle shaft extending out from the collar.

Figure 46:
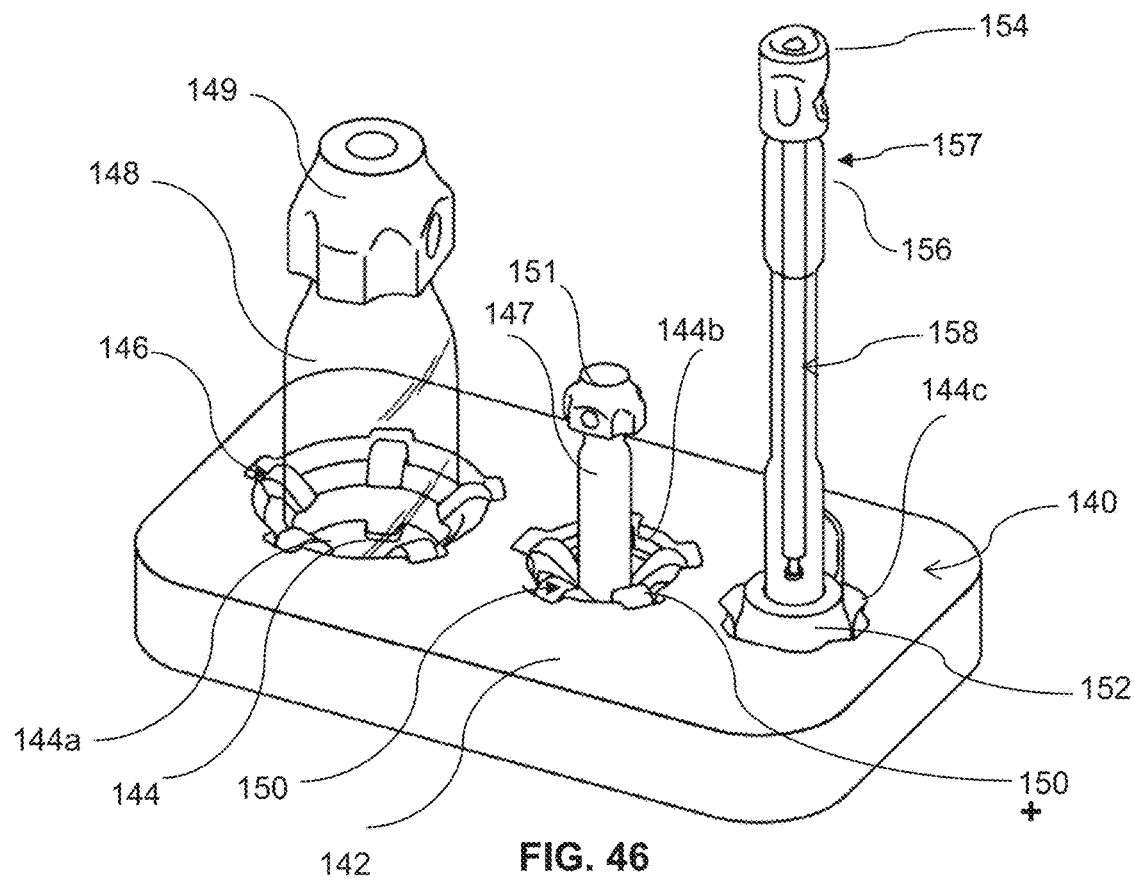
FIG. 46 shows a tray similar to that of FIG. 35 with the base mounts of two of the three utensils secured in the corresponding tray mount reception apertures, as well as an additional needle capping and crushing collar base component received in a corresponding collar tray reception aperture; and a grasping collar provided at the top of each utensil, including an open top collar for the far left utensil, a closed top cap configured collar for the interior utensil, and a grasping collar at the top end of the syringe shown received in the far right tray reception aperture.

FIG. 46 shows tray 140 (similar to that of FIG. 35) comprising base body 142, having apertures 144, with a largest diameter aperture 144a, an intermediate aperture 144b, and a third, smallest aperture 144c. Apertures 144b and 144a are similar to the above described counterpart apertures 71c and 71b, but aperture 144c represents an aperture configured for specific friction retention of the below described capping needle and crush collar (150 in FIGS. 52 and 53 and hereafter referenced just as "crush collar"), which crush collar generally has a FIG. 11 configuration. Aperture 144c thus has a unique shape designed to conform to the exterior periphery of collar 150 with its long and short ridge sides and in between cavities.

FIG. 46 further shows a kit combination embodiment under the present invention involving tray 140 plus one or more additional components. While a kit combination is described for that which is shown in FIG. 46, the present invention described components can be provided in a variety of kit forms including combinations involving some or all of the component categories described herein; such as i) mounts (annular collar and ribs combination), ii) container collars (as in vial or bottle collar, with closed top or open top of various aperture sizes and configurations), iii) syringe collars (collars on a syringe plunger, syringe cylinder, and/or needle assembly) and iv) haptic collar(s) such as for catheter use, split grasping collars as a few examples. In the FIG. 46 embodiment, the additional components include a larger sized base mount 146 (having the above described mount 20 configuration) supporting the base of a larger sized bottle 148, with the mount and bottle nestled within conforming aperture 144a. In addition to base mount 146, the kit includes a FIG. 11 configured collar 149, which is shown as a cap to bottle 148 and as having an open top (suitable for syringe insertion as described below).

The middle positioned aperture 144b also is configured to receive a corresponding sized base mount 150, which is supporting the base of a sample vial 147 having a smaller version FIG. 11 collar 151 which in this case has a closed top. Thus, the two larger apertures 144a and 144b have apertures designed specifically for receiving the mount ribs 27 in extension recesses, while the smallest aperture 144c is configured differently, with an aperture configured to accommodate needle support-and-crush collar 152 received in the friction fit collar tray reception aperture 144c.

Additional components associated with the kit involving tray 140 include syringe assembly 157 comprising syringe 158 as well as plunger end grasping collar 154 and dumbbell sleeve 156 provided along the cylinder of syringe 158 (provided by a slide fit over the cylinder or an overmolding integrated combination). The kit associated with tray 140 can be one that is functionally coordinated, as in a liquid bottle medicament supply 148, for drawing liquid medicament solvent therefrom, with syringe 158 (after pulling the syringe from collar 152 (in a not yet needle crush state) and inserting it into the open top of collar 149) and then passing the drawn liquid medicament to the powder storing vial supported in aperture 144b by puncturing the top seal of collar 151 whereupon the powder and medicament solvent can be mixed and drawn up for patient insertion and then, upon patient treatment completion, the syringe 158 is returned to collar 152 whereupon the enlarged lower end of the dumbbell sleeve (with associated enlarged "saddle horn" projection (described in US '825)) is rotated so as to avoid an interior projection in collar 152, whereupon a downward force is applied to move the syringe so as to crush the needle. The entire syringe collar and crush collar can then be discarded with a covered and crushed needle.

Figure 47:
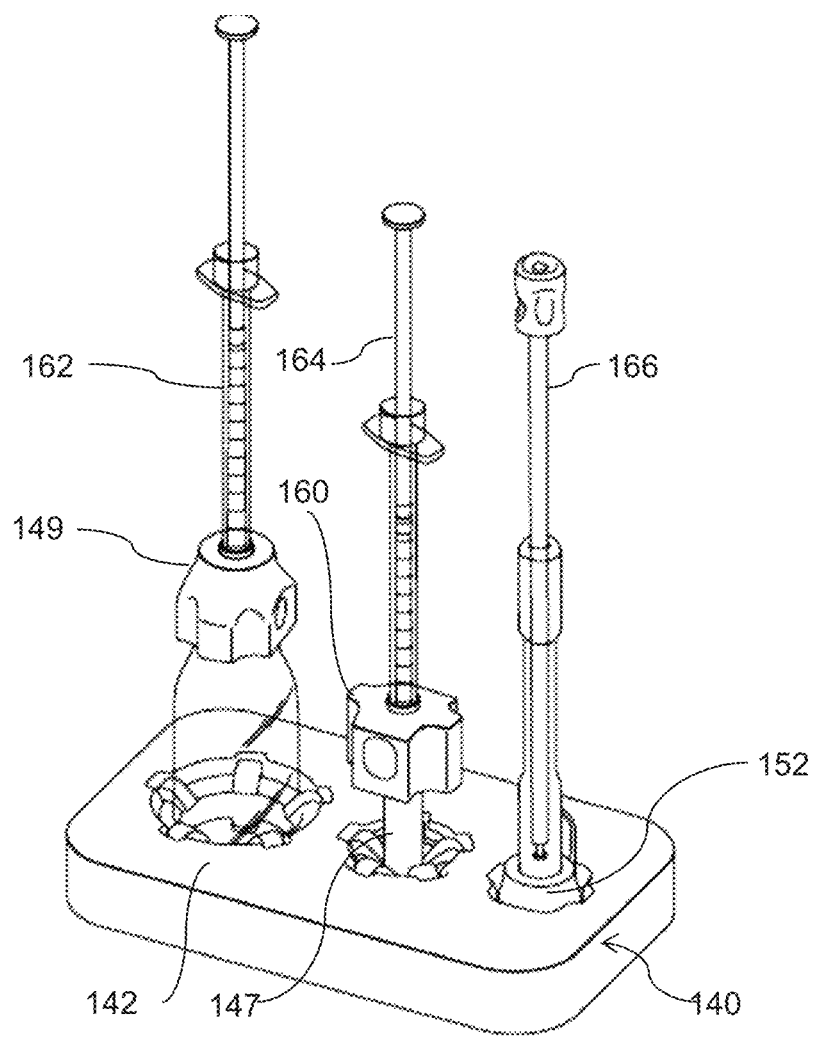
FIG. 47 shows a similar view as FIG. 36, but with a FIG. 10A collar embodiment for the intermediate utensil, and the added feature of the far left and intermediate collars showing syringe needle reception with the needle in each passing through and being supported by the receiving collar mounted on the utensil below.
Figure 48:
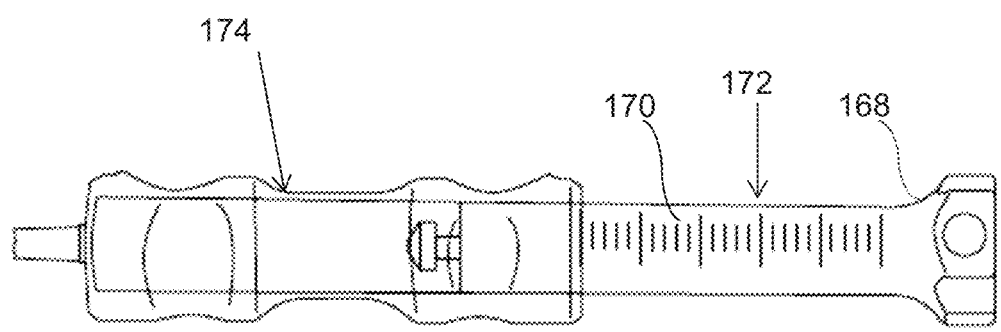
FIG. 48 shows an alternate embodiment of the invention featuring an integrated (unitary or monolithic) grasping body formed integrally with a plunger of a syringe and of a common material as well as a non-monolithic grasping collar in a dumbbell shape provide over the cylinder of the syringe shown, and with volume demarcation provided on the plunger body rather than the dumbbell sleeve covered syringe cylinder.

FIG. 47 shows a similar view as FIG. 46, but in different kit form as it comprises, instead of collar 151, a FIG. 10A collar (160) embodiment is attached to the top of vial 147 as the intermediate utensil. There is also shown in FIG. 47, the added feature of the far left and intermediate syringes 162 and 164 with the needle of each of syringe 162 and 164 shown passing through and being supported by the receiving collar mounted on the utensil below. As above, the kit associated with FIG. 47 can be a functionally coordinated kit, with, for example, a pre-filled syringe 166, and the other two syringes (once liquid medicament is drawn from the associated utensil), being used in a desired sequence of application on a patient, as in a plurality of different type medicine injections required for a common medical treatment. Further, each component supported on the tray is designed for single hand removal or insertion FIG. 48 shows an alternate embodiment of the invention featuring an integrated (unitary or monolithic) grasping body 168 formed integrally with a plunger 170 of the illustrated syringe 172. That is, FIG. 48 shows a grasping collar 168 that is formed as a monolithic component of the base end of a syringe plunger and preferably of a common material (e.g., a one polymer plastic molding of collar 168 and plunger body). Additionally, syringe 172 features a cylinder with a dumbbell grasping sleeve 174 which is a non-monolithic grasping collar in a dumbbell shape (and having the characteristics described above for grasping collar 88 in FIG. 40) provided over the cylinder of the syringe shown. Also, rather than demarcations on the covering dumbbell collar, volume demarcations are provided on the plunger itself. This arrangement is particularly suited for high viscosity liquids requiring a high plunger draw force.

Figures 52, 53:
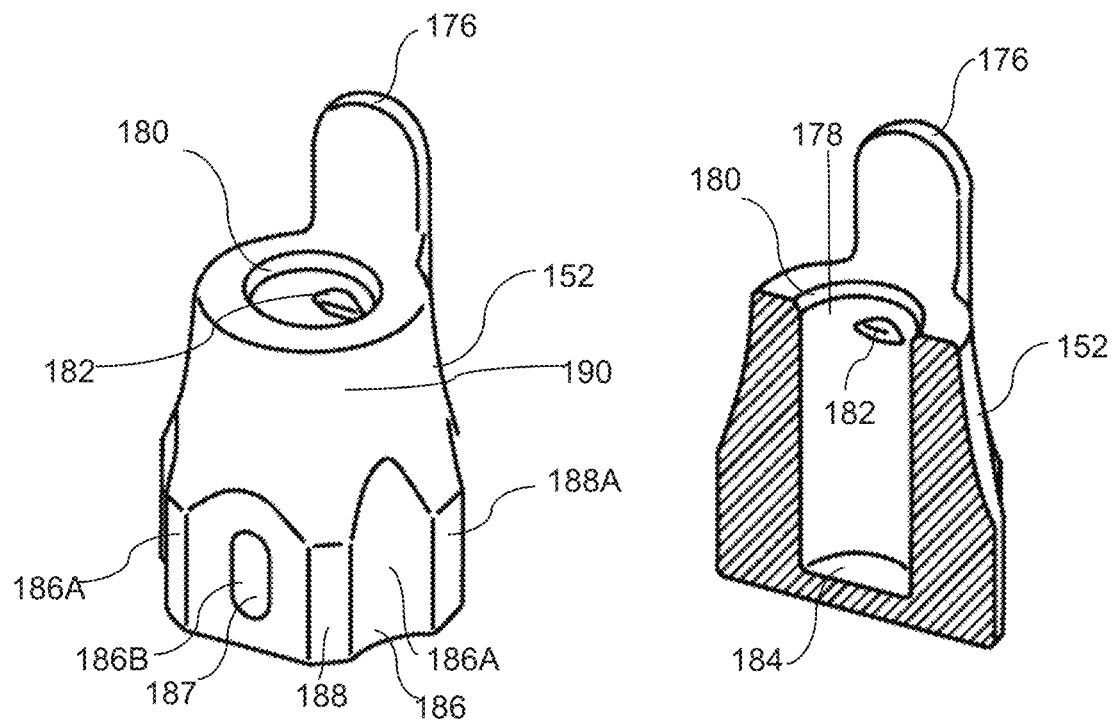
FIG. 52 shows a front perspective view of the crush collar shown in FIG. 51.
FIG. 53 shows a cross-sectional view of that which is shown in FIG. 52.

With reference to FIGS. 49 to 53 there is described the syringe support/needle crush collar 152 briefly described above. With reference to FIGS. 52 and 53 there is shown collar 152 alone with FIG. 52 showing a perspective view of collar 152 and FIG. 53 showing a cross-sectional view with the collar half removed being positioned away from tab extension or clip 176.

As seen from FIG. 52, collar 152 has the FIG. 11 configuration, but for the added tab extension or clip 176, as well as preferably added revisions with respect to providing a needle blockage base for facilitating needle crushing when so desired and an added interior projection 182. FIG. 52 further shows crush collar 152 with an open top 178 preferably having a slight conical alignment ledge 180 which tapers inward and downward from the top face of collar 152. In the interior cavity 181 shown in FIG. 53, there can be seen inward projection 182 that extends inwardly into cavity 181 away from tab extension 176 as to provide for pre-crush axial resistance during syringe support in collar 152. Floor 184 is preferable formed of a sufficiently hard plastic or is supplemented with a metal disc or the like that is supported by the circular face associated with floor 184. The harder plastic can be representative of the entire collar 152, but since having a flexible collar 152 that can be pliable to facilitate positioning of utensils in a support relationship is desirable, a dual plastic molding relationship can be implemented such that the floor is of a different, harder plastic or the aforementioned metal disc insert can be utilized (i.e., insertion of a thin metal, circular disc to conform to and cover floor 184). The collar 152 configuration and dimensions is suited for receiving collar 192 and thus is preferably similar to those featuring a "large mouth" reception aperture such as featured in FIG. 59 and FIGS. 128A and 128B described below.

FIG. 52 further illustrates in common fashion with FIG. 11 that the exterior side wall periphery of collar 152 is comprised of a series of concave depressions 186 separated by wall projections 188. As seen in FIGS. 11 and 52, the concave depressions can come in different length and width sizes, with a plurality of narrower and higher extending depressions 186A (higher extension up into the conical top region 190 of collar 152), separated by shallower height concave depression 186B, with the latter also having finger depression recess 187 (on the side opposite the tab extension 176). The ridge line projections 188 include a similar shaped series of such ridge lines (188A, 188*b* . . . ) that provide for offset finger grasping with any two of such projections with finger nesting in the adjacent concave depressions.

Figure 49:
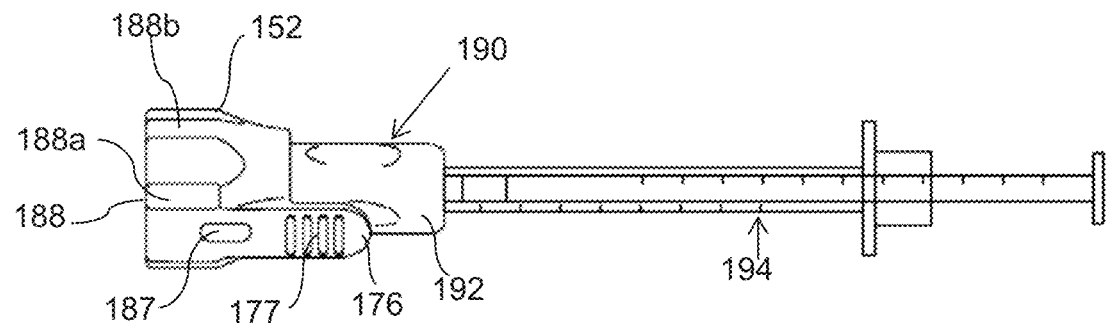
FIG. 49 shows an additional embodiment of the present invention featuring a capping and needle crush collar base component, noted in FIG. 46 above, working in combination with a needle assembly reception collar that is received by the capping and crush collar ("crush collar" for shorthand reference).

FIG. 49 shows an additional embodiment of the present invention featuring needle crush collar 152 providing support to syringe assembly 190. As shown, syringe assembly 190 has grasping collar 192 formed at the needle assembly end of syringe 194 (of syringe assembly 190) working in combination with the receiving crush collar. Grasping collar 192 represents an adaptation of the gripping sleeve device for precision instruments described in the earlier noted U.S. Pat. No. 8,745,825 issued on Jun. 10, 2014. The adaptation in this case includes having the interior through-hole having a diameter or diameters to conform to the diameter(s) associated with the needle assembly of syringe 194. Due to the non-symmetrical configuration of collar 192 (e.g., the saddle horn projection 191 in FIG. 50), the plateau of the sleeve or handle will engage inward projection 182 protrusion(s), which will block further penetration into the cap. When returning after use the syringe with the sleeve may be rotated such that protrusion 182 will meet a smooth surface of syringe assembly 190 and therefore be able to be depressed deeper into the crush collar and, after needle crushing, disposed, safely, as a unit (syringe and cap connected) into a disposal bin. Thus, a single hand needle decapacitating safety system is provided.

Figure 50:
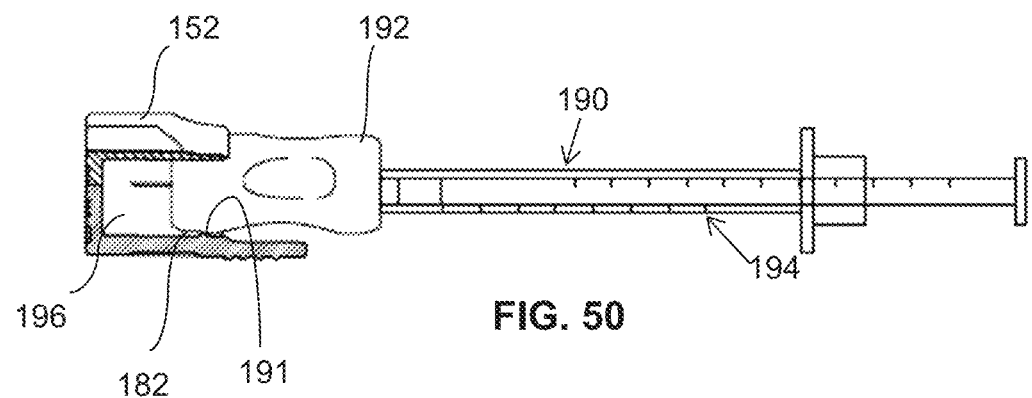
FIG. 50 shows a partially cut away view of that which is shown in FIG. 49 with the crush collar receiving the grasping collar at the distal end of the syringe and in a pre-needle crush state, due to abutting projection alignment for projections found on the crush collar interior and syringe grasping sleeve exterior.
Figure 51:
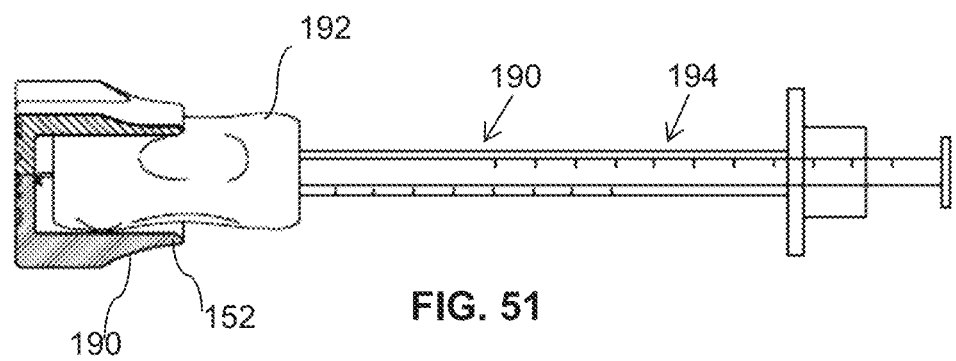
FIG. 51 shows the same view as FIG. 50 but with the syringe assembly and collar having been compressed together fully leading to the bending of the free portion of the needle extending out of the grasping collar on the syringe; in this state the entire assembly is suited for discarding in a needle collapsed, safe state.

With reference to FIGS. 49 and 50 (with FIG. 50 providing a cut-away view of syringe assembly 190 in a support (non-needle-crush) mode), there is shown needle 196 in a suspended state above floor 184 of collar 152. There can further be seen the syringe support function provided by collar 152. As further seen from FIG. 49, tab extension 176 includes finger enhanced friction ridges 177 formed in the body of tab extension on the exterior side and above finger depression recess 187. This finger friction enhancement facilitates the ability to grasp collar 152 and the supported syringe either for movement to or from a support surface or for pulling out (or placement in) of collar 152 in a conforming tray aperture such as 144*c* in FIG. 46, or the final discard step described above. The needle crush conversion can be seen by a comparison of FIGS. 50 and 51 wherein the latter shows the crush state of the needle, and with floor 84 showing a partially harder material section via different cross-sectioning.

Figure 54:
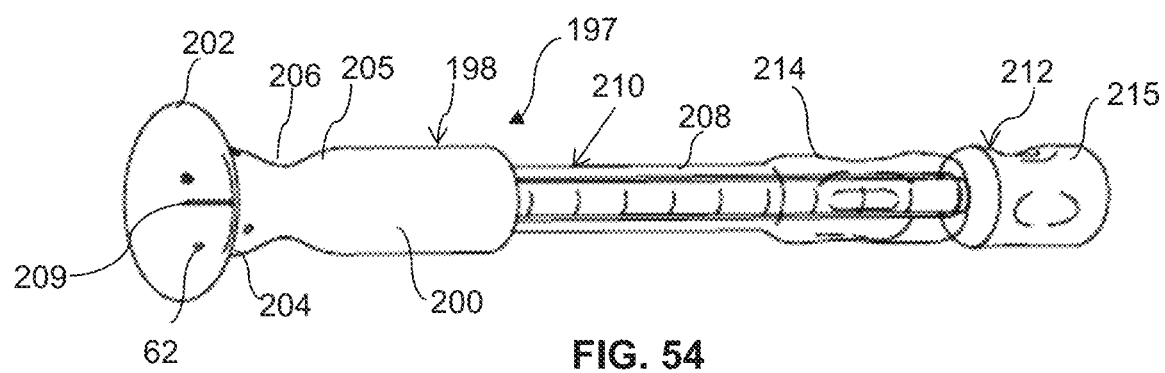
FIG. 54 shows a perspective view of the horn ended collar shown in FIG. 19 with additional grasping collar enlarged portions provided on the syringe's cylinder and the plunger base, respectively.

FIG. 54 shows a perspective view of a combination horn collar and syringe assembly 197 comprising syringe 210 and a horn ended collar 198 of the type shown in FIG. 19. Collar 198 is shown as comprising a syringe cylinder engagement portion 200 which has an axial bore of a diameter suited for engagement with the cylinder portion 208 of the supporting syringe 210 (or an enlarged end of a dumbbell shaped collar). As seen from a comparison of FIG. 19 and FIG. 54, collar 198 can extend for the full sleeve length or a portion of it, with the FIG. 54 embodiment showing coverage of only the needle end portion of cylinder portion 208. The collar's cylinder engagement portion 200 is of an outer diameter smaller than the outer periphery of the free edge 202 of horn portion 204, which horn shields the needle 209 both circumferentially and axially (when the horn is in an uncompressed state). Also, collar 198 extends longitudinally (or axially) along the length of the syringe into an intermediate, hour-glass shaped portion 205 (having the minimum diameter portion 206) which covers the interface region between the syringe's cylinder and the base region of the needle assembly supporting needle 209. Horn portion 204 extends distally away from the intermediate region 205, and has a rapid diametrical expansion from its interface with the intermediate region. For example, an outer peripheral edge 202 diameter of 6.0 mm to 2.5 cm is suitable for some intended uses of the present invention. In addition, edge 202 is preferably of a skin contact thickness of 1.0 mm to 2.0 mm, and the diameter can be relied upon as a demarcation means, as in a border region demarcation means for skin removal out from an area of highest concern (e.g., as by a physical marking along the edge of edge 202). Further, this demarcation can be used as a boundary region to gauge mole growth or the like over a period of time by photo comparison example. FIG. 54 also shows suction apertures 62, which are optional in some instances in the sense that suction breakage generated when apertures 62 are not present can be achieved by a suitable tilting for some configurations of horn collar 198, but not as easily.

As further shown in FIG. 54, syringe assembly 212 includes the aforementioned syringe 210 plus proximal grasping collar or sleeve 214 representing, again, an adaptation of the sleeve of a U.S. Pat. No. 8,745,825 grasping sleeve. In addition, to the dumbbell shaped sleeve 214, there is provided on syringe 210 plunger end collar 215, also representing an adaptation of the above referenced US '825 patent's sleeve. As with other embodiments of the invention, the dumbbell collar and plunger collar avoid having to have the complexity associated with having flanging on the cylindrical end and plunger end as found on prior art syringes.

Figure 55:
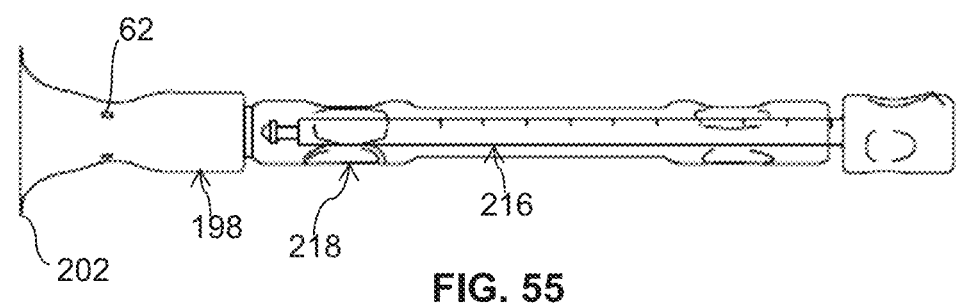
FIG. 55 shows a side view of an alternate horn collar embodiment to that which is shown in FIG. 54.

FIG. 55 shows a view similar to FIG. 54 but with the syringe 216 having an entirely exposed dumbbell syringe grasping collar 218 (similar to that described for FIG. 40). Thus, both enlarged ends are exposed instead of the less exposed collar 214 in FIG. 54.

Figure 56:
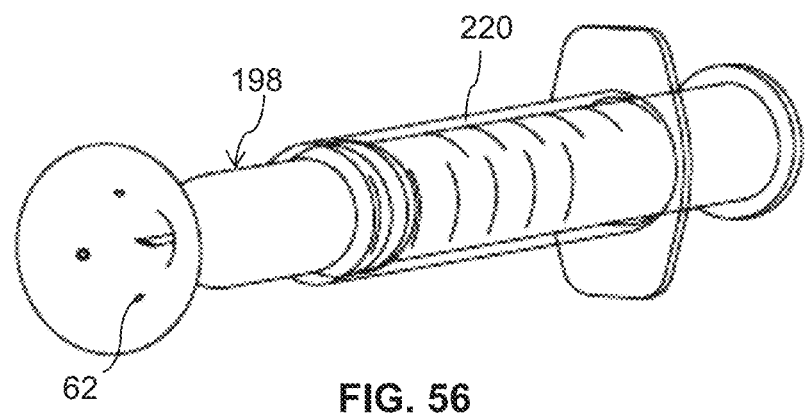
FIG. 56 shows another view of the horn shaped collar of FIG. 19 and FIG. 54 mounted on the needle assembly at the distal end of a large volume cylindrical syringe.

FIG. 56 shows another view of the horn shaped collar 198 of FIG. 54 (and FIG. 19) and mounted on the needle assembly at the distal end of a large volume cylindrical syringe 220.

Figure 57:
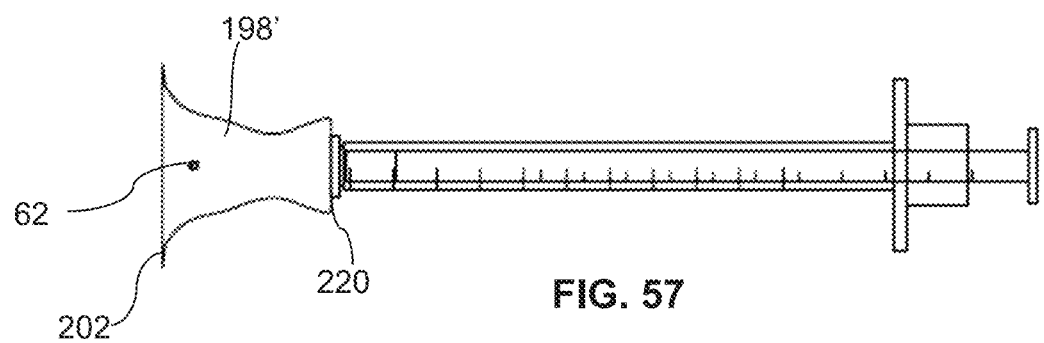
FIG. 57 shows a similar view as that in FIG. 56, but with the horn collar of FIG. 19 mounted on an intermediate volume syringe, and with the horn collar having a lower base strength.

FIG. 57 shows a similar view as that in FIG. 56 but with the horn collar 198' being of a modified design having a shorter length cylinder engagement portion 220 as compared to the longer cylinder engagement portion 200 in FIG. 54.

Figure 58:
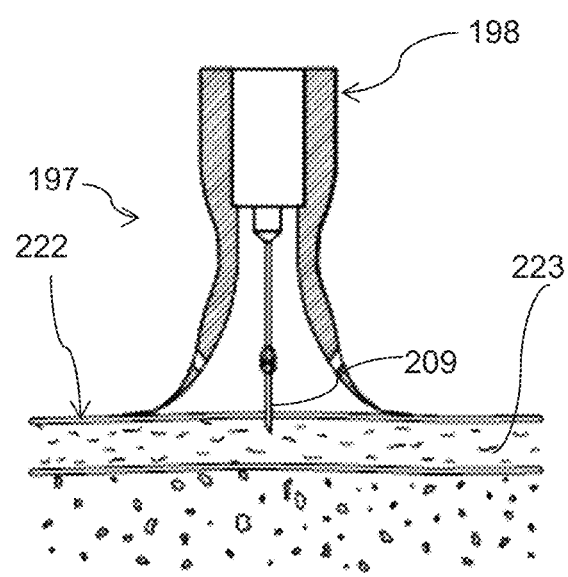
FIG. 58 shows the horn collar with just the needle assembly portion of a syringe and the needle in a perpendicular puncture state below the outer stratum corneum of the recipient's epidermis.

FIG. 58 shows a cut-away view (only the needle portion of the syringe shown) of the combination syringe and horn collar 197, with the needle 209 in a perpendicular initial puncture state below the outer stratum corneum 222 of the recipient's epidermis, with the level of needle puncture below the stratum corneum into the lower layered area 223 being based on needle length, diameter and horn collar configuration. As seen the horn collar 198 provides for both positioning and a spring back tension that helps return the needle after a user compresses the horn collar to a desired extent. Horn collars can be provided with different compression levels by pre-designed based on thickness adjustment in the horn walls. As also shown in FIG. 58 the horn walls have a thicker higher section that leads to a lower thinner, flared section intended for skin contact.

FIG. 59 shows a kit combination 227 of the present invention components, inclusive of a base support mount 221 of FIG. 3A configuration, which supports fluid containing sealed vial 224, and collar 225 of FIG. 11 configuration, (just prior to vial top attachment), with the FIG. 11 collar 225 in this embodiment having a rimmed open top 226 for receipt of a syringe assembly or other interconnecting component. As seen from FIG. 59, collar 225 has the attributes earlier described for the FIG. 11 and FIG. 52 embodiments, but is absent the tab extension of FIG. 52. Thus, collar 225 has axially extending peripheral concave recesses 186 extending up to the conical top 190 as well as the circumferentially spaced ridges 188 and the finger depression recess 187 (e.g., one recess on each opposite side of the collar 225 to facilitate fingertip pinch control).

Figure 60A:
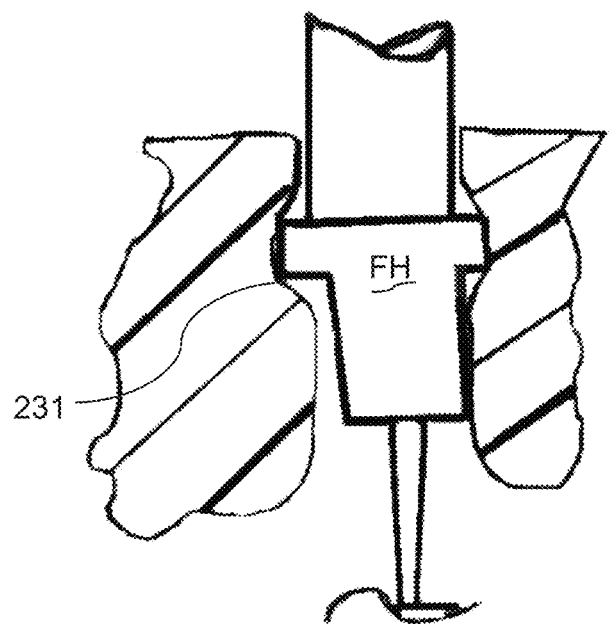
FIGS. 60A and 60B show a first embodiment deeper positioning of a flange of a needle, and 60B showing added radial groves in the collar cavity providing added snap-in positional needle length capability; this relationship also provides for improved syringe-to-bottle flexing as when trying to get access to the last amount of medicament in the bottle.
Figure 60B:
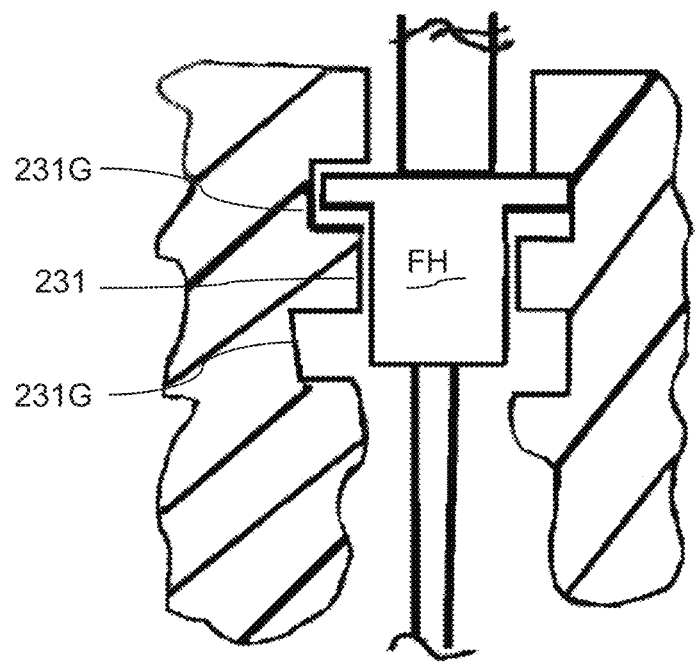

FIG. 60 shows a schematic line drawing showing a similar combination of vial 224 and a top collar such as shown in FIG. 59. As seen from a comparison of FIGS. 59 and 60, collar 230 has the same peripheral exterior as collar 225 in FIG. 59, but has a modified top region and interior cavity set up. That is, collar 230 has an upper smaller top aperture designed to receive directly syringe 232, which small top cavity 231 opens out in stepped fashion with enlarged diameter aperture 233 designed to provide a flex attachment (preferably non-threaded) to the vial top 228 (see FIG. 59). The combination of vial top collar and base mount shown in FIGS. 59 and 60 are representative of kit combinations within the above described potential kits based on the present invention described components (such kits can also include associated syringes, vials etc. in addition to the above described present invention component categories). Also, the combination of vial and syringe assembly in FIG. 60 can represent, for example, an insulin injection situation wherein after syringe 232 is engaged with collar 230, the syringe and vial may be single handedly tilted to receive the medicine. Also, as seen by a comparison of FIGS. 60, 60A and 60B, flanged needle hub FH can have its upper flange sit on the top border of cavity 231 in collar 225 (FIG. 60). However, if there is desired to have the needle tip deeper in the bottle the flexible cavity wall can be expanded out to receive in a tighter squeeze fashion needle hub FH (FIG. 60A). This relationship also provides for controlled flexing and tilting of the needle within the bottle as when attempting to get remnants at the bottom of the bottle. Alternatively, as shown in FIG. 60B, cavity 231 can be provided with one or more radial grooves 231G, which provides for staged control of needle hub adjustment and needle tip extension in the bottle. The groove 231G and needle hub FH relationship also provides a good fulcrum location for needle tilting in the vial.

FIGS. 61 and 62 show the combination of top vial collar 225 of FIG. 59 and the receipt of an associated syringe assembly. In this embodiment, the syringe assembly is similar to that described above in FIG. 46. In other words, the syringe assembly of FIG. 61 that is being inserted into the open end of collar 225 features syringe assembly 157 comprising syringe 158 as well as plunger end grasping collar 154 and dumbbell sleeve 156 provided along the cylinder of syringe 158 (provided by a slide fit over the cylinder or an overmolding integrated combination and because of this volume measurements can be on the plunger). In addition, there is provided needle hub sleeve 192 like that described in FIG. 50. However, rather than needle hub sleeve 192 being inserted into a crush collar like in FIG. 50, in this case it is being inserted into the open topped collar 225 which provides for stable puncturing of (e.g., the top membrane of) vial 224 and removal of medicament therefrom. This stable puncture relationship between syringe assembly 157, collar 225 and vial 224 is illustrated in FIG. 62 wherein the syringe is in puncture mode with vial 224.

Figure 63:
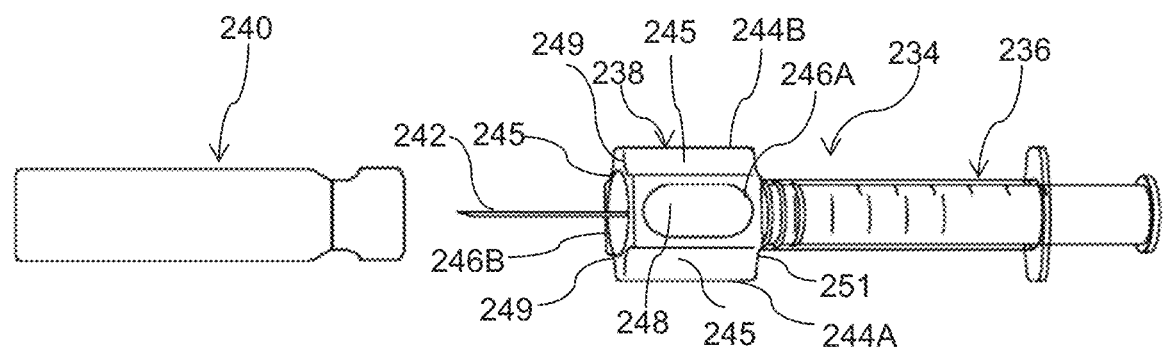
FIG. 63 shows a syringe having attached to it the collar of FIG. 10A just prior to supply vial puncturing with the needle of the syringe.

FIG. 63 shows syringe assembly 234 comprising syringe 236 as well as grasping collar 238 of FIG. 10A configuration. Syringe assembly 234 is shown just prior to supply vial 240 puncturing with the needle 242 of syringe 236. Collar 238 is shown as having elongation in the direction of needle extension and partially covering a portion of that needle. Further, as in the FIG. 10A embodiment, collar 238 is formed from a monolithic block of material that is preferably an elastomeric plastic and flexible as in medical grade silicone rubber. Further, collar 238 has a quadrilateral cross-section periphery that includes two opposing longer ridge walls (246A, 246B) that are circumferentially straight or only slightly curved about their periphery surface, two opposite opposing shorter ridge walls (244A, 244B), and finger depression recess 248. These walls are separated by concave recesses 245 at locations that would otherwise have represented corners of the quadrilateral block. The side walls form gripping projections that are separated by the concave recesses that extend the full elongation length between forward surface 249 and rearward planar surface 251. The general range of height or thickness for collars having the FIG. 10A general configuration includes 2 mm to 60 mm with the embodiment of FIG. 63 being preferably about 20 mm to 50 mm, as in 40 mm long. The length can vary depending on the circumstances as in the length of the needle, the length of needle desired for exposure, the length of the needle hub assembly, the nature of the utensil involved at the collar engagement site at the cavity in the forward end 249 of collar 238.

Figure 64:
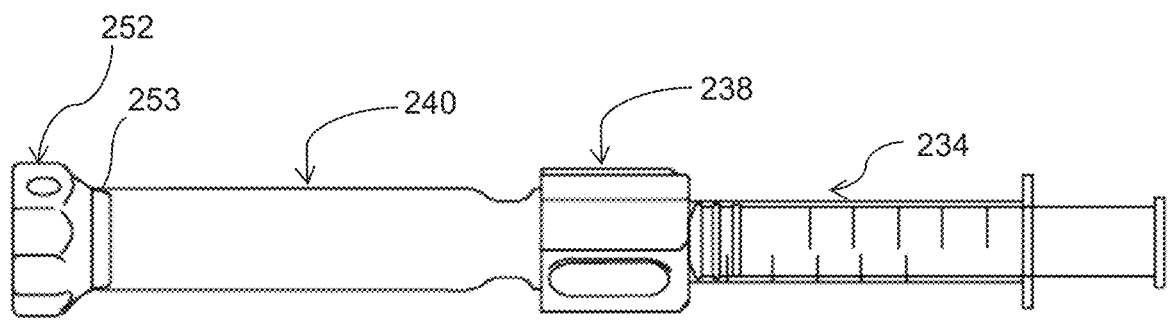
FIG. 64 shows a similar combination as FIG. 63 but with the combination of the FIG. 10A collar (with non-tapered or a tapered hole as show in FIG. 10B) and syringe fully attached together, and with the supply (e.g., specimen or medicine source) vial having the collar of FIG. 11 as a means to better grasp the supply or specimen vial's base end; the sequence of collar attachment and utensil-syringe combination can be either collar first attached to syringe or collar first attached to vial before mutual connection.
Figure 65:
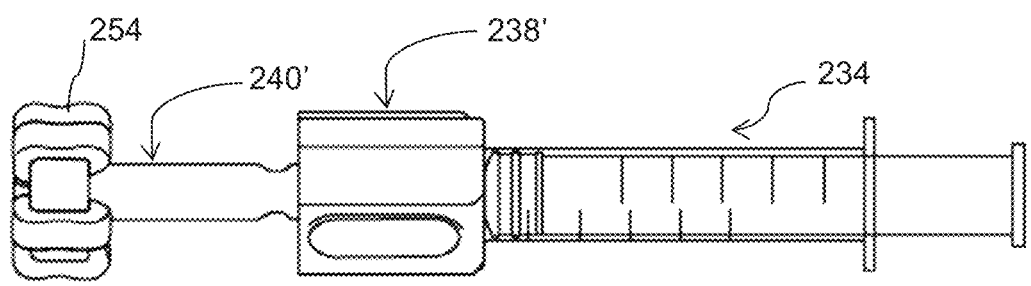
FIG. 65 shows a similar combination as that of FIG. 64, but with the vial having a base mount of FIG. 3A rather than the collar of FIG. 11, and with a diameter size suited for horizontal orientation of the syringe assembly (in similar fashion to FIG. 64).

FIG. 64 shows a similar combination as FIG. 63 but with collar 238 of syringe assembly 234 being fully attached to the sealed end of vial 240 in a puncture relationship, and with the supply (e.g., specimen or medicine source) vial 240 having collar 252 (of FIG. 11 configuration) mounted by flexure (or in an overmolding relationship) on the vial's base 253 as a means to facilitate better grasping of the vial as when separating the vial from the collar 238 following medicament draw from the vial or medicament insertion into the vial. Collar 252 also provides for a more stable base for plunger push down or just for support surface stand up. As noted, collar 252 can be supplied to the vial base by an overmolding plastic injection technique. Further, rather than attaching collar 238 to syringe before vial puncturing, collar 238 can be first mounted on the vial and the syringe then inserted FIG. 65 shows a similar combination as that of FIG. 64, but with a small diameter vial 240' having a base mount 254 of FIG. 3A configuration rather than the collar of FIG. 11 shown in FIG. 64. The smaller vial 240' is received in a corresponding smaller capture recess in the forward end of collar 238' (as compared to the larger capture recess in collar 238). The base mount also provides stable support during plunger down movement and while in stand-up state in general or may be rested horizontally.

Figure 66:
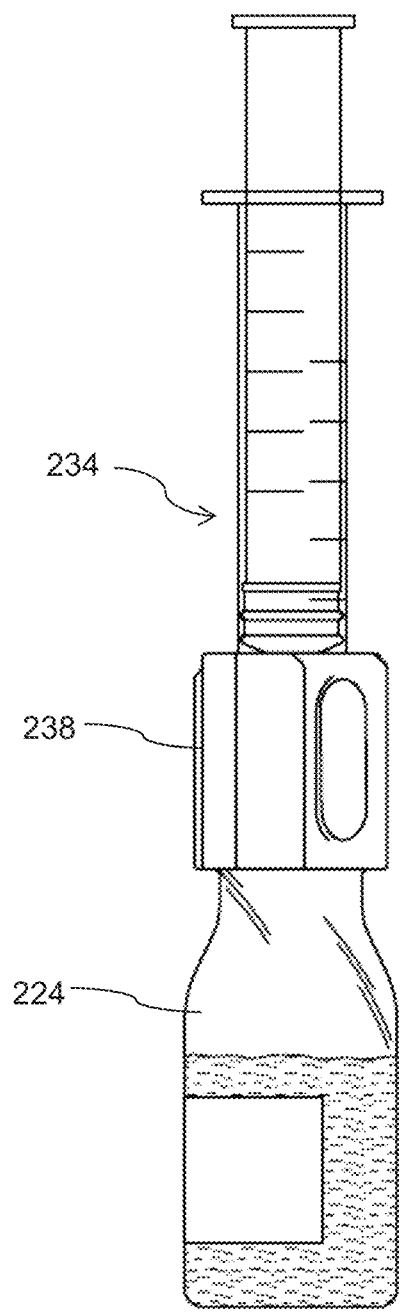
FIG. 66 shows the collar of FIG. 10A (elongated or thicker in height version) attached to the syringe's needle assembly with the needle assembly's needle inserted in a medicine bottle.

FIG. 66 shows the same type collar 238 mounted on syringe assembly 234 in engagement with the upper rim of bottle 224. Again, the flexible nature of collar 238 and suitably dimensioned cavity at that end provides for a sealed engagement during needle puncturing or placement into the bottle. Alternatively, the collar 238 may be placed first over the vial (rather than first on the syringe) and the syringe inserted into the vial, allowing one handed fluid withdrawal procedures.

Figure 67:
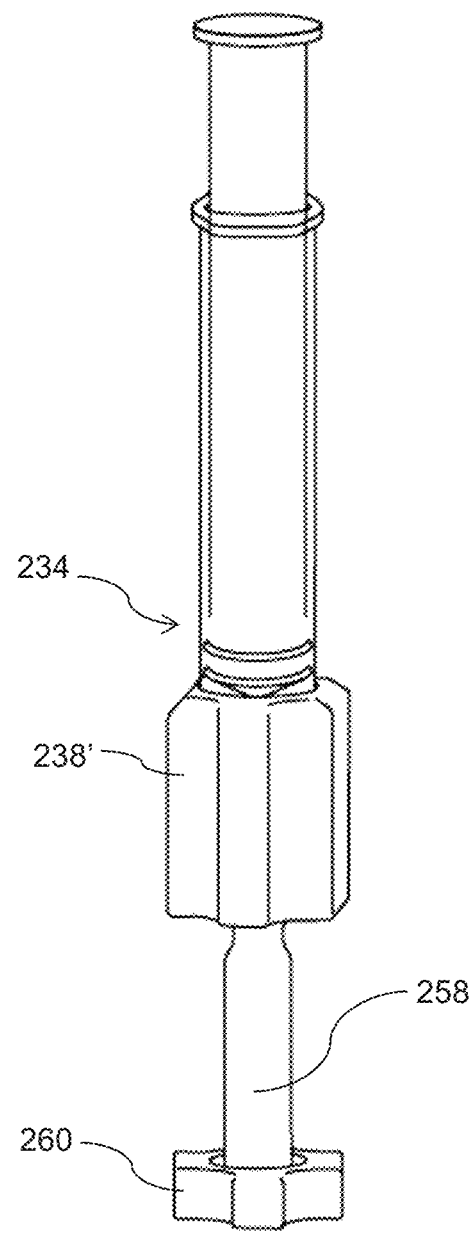
FIG. 67 shows the collar and syringe combination of FIG. 66 in fluid communication with a vial having at its base a FIG. 10A collar (short or thinner in height version).

FIG. 67 shows the same type collar 238' mounted on syringe assembly 234 in sealed off engagement with the upper end of canister 258 having at its base collar 260 of FIG. 10A configuration (short or thinner version depicted). As depicted, the aperture in collar 260 is in friction engagement. The friction level can be increased upon a squeeze compression action on collar 238, such as when removing collar 238' from its engagement with canister 258. Collar 238' would have its vial capture end of a smaller diameter than collar 238 when the top rim of the bottle 224 has a significantly greater diameter than that of the vial 258.

Figure 68:
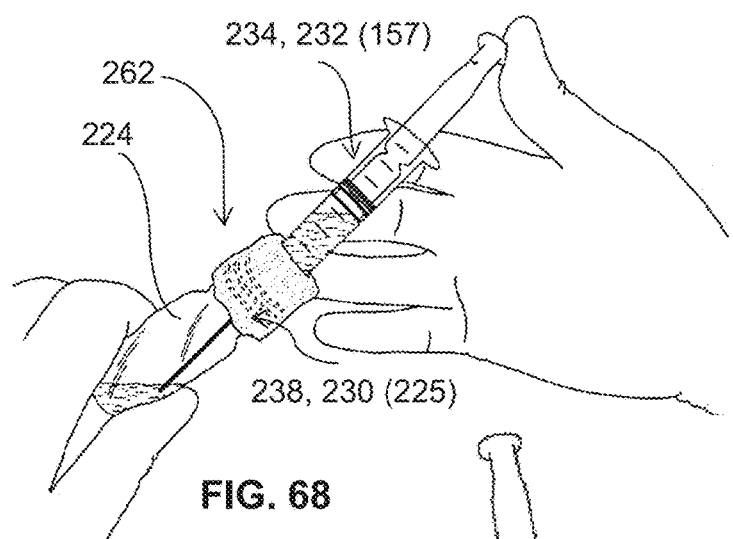
FIG. 68 shows a flexible collar of the present invention with opposite, different sized apertures, with the larger aperture opening out at a first end of the collar and being configured for releasable and flexible attachment with the threaded top opening of the bottle (with a flex over such as a snap over relationship, and not a threading requirement relationship in this embodiment, although in other embodiments a threaded relationship is featured between the collar and the threads of the container (bottle)); and the other collar aperture being smaller and opening out at the opposite end of the collar and being configured for a releasable and flexible engagement with the cylinder portion of a syringe at the needle end; the flexibility of the collar allowing for needle repositioning which is useful in efforts to draw out the last part of liquid in a bottle.

FIG. 68 shows combination 262 comprised of a flexible collar of the present invention supported on a syringe in combination with a bottle with liquid. Thus, FIG. 68 is illustrative of a relationship such as that described having a collar 230, syringe 232, and bottle 224 combination (shown in FIG. 60); or collar 225, bottle 224, and syringe assembly 157 of FIG. 62; or collar 238, bottle 224, and syringe assembly 234 of FIG. 63. As in FIG. 60, the collar design is typically one with opposite, different sized apertures, with the larger aperture opening out at a first end of the collar and being configured for releasable and flexible attachment with the threaded top opening of the bottle (with a flex over relationship and preferably not a threading requirement relationship between the lower end of the collar and the bottle received); and the other collar aperture being smaller and opening out at the opposite end of the collar and being configured for a releasable and flexible engagement with the cylinder portion of a syringe at the needle end (or a sleeved end of the syringe assembly as in sleeve 192 in FIG. 62). As seen in FIG. 68, the flexible nature of the collar of the present invention, provides for a degree of relative adjustment between the needle and the vial such that the needle end can be repositioned in the bottle for drawing up the final amount of liquid.

Figure 69:
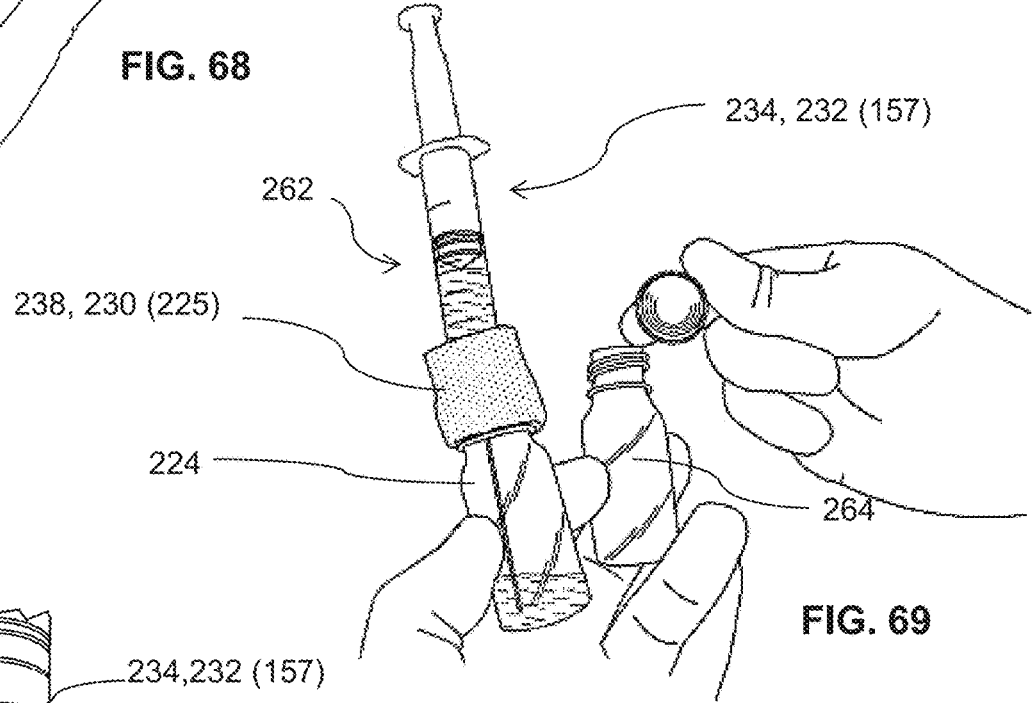
FIG. 69 shows the FIG. 68 combination under the present invention with a view of the ability for a user as, in a surgeon or the like, to multi-task, (thread cap back on a second bottle) due to the ability to hold the entire combination plus the second bottle with one hand.

FIG. 69 shows the FIG. 68 combination 262 under the present invention with a view of the ability for a user, as in a surgeon or the like, to readily multi-task (thread cap back on a second bottle 264) due to the ability to hold the entire combination plus the second bottle with one hand.

Figure 70:
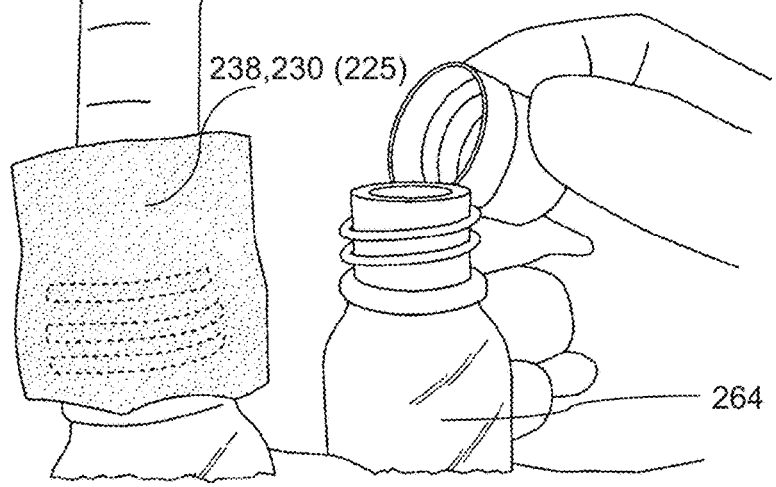
FIG. 70 shows a closer view of the combination and second bottle in one hand, leaving free a second hand for threading a cap on the second bottle.

FIG. 70 shows a closer view of the combination 262 and second bottle 264 in one hand, leaving free a second hand for threading a cap on the second bottle.

Figure 71:
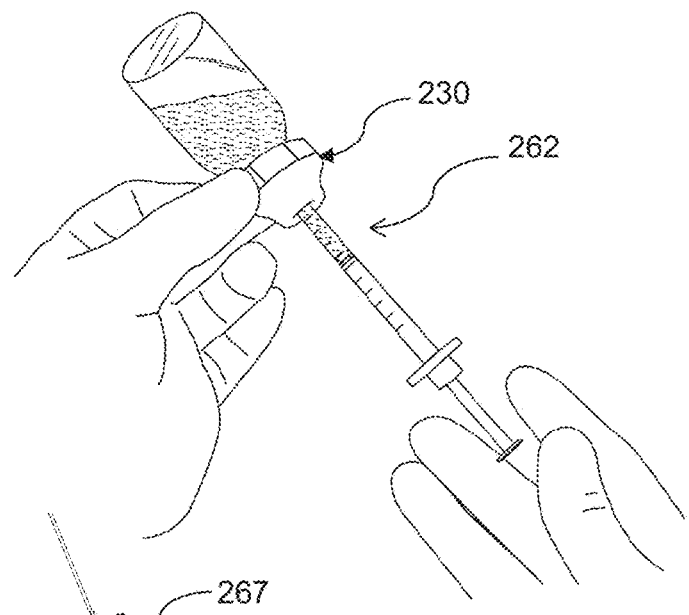
FIG. 71 shows a bottle and FIG. 11 collar combination, but with the collar having a smaller aperture opening out at the smaller diameter collar end that is opposite to the larger diameter collar end in engagement with the threaded opening of the bottle (or a rimmed end); as in the prior embodiment, needle placement relative to the bottle is adjustable and there is also provided the ability to securely grasp and hold the bottle with a two finger off-center pinching operation, which is fixed enough for plunger activation.

FIG. 71 shows combination 262 as represented by the FIG. 60 configuration. As further seen in FIG. 71, the projections of the FIG. 11 type collar 230 (only schematically shown in FIG. 71, but understood to have the periphery as shown in FIG. 11) has a plurality of projections that provides the ability in a user to securely grasp and hold the bottle with a two finger off-center pinching operation, which is fixed enough for a draw plunger activation with the opposite hand.

Figure 72:
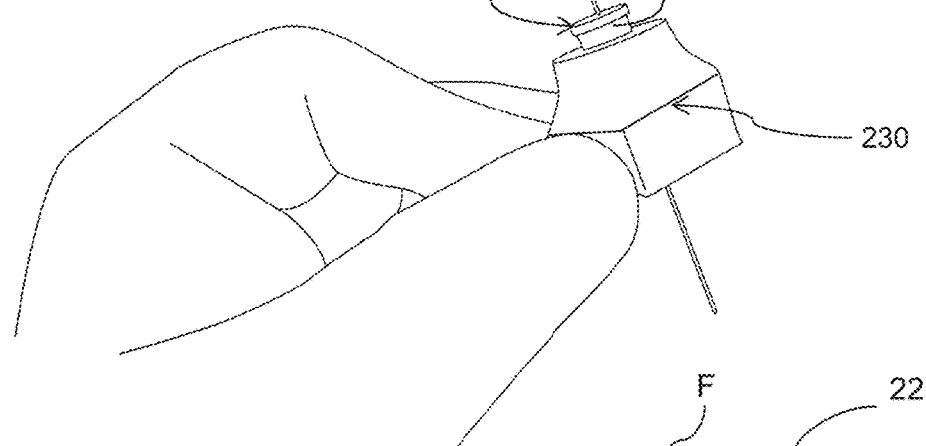
FIG. 72 shows the same off-set two finger pinching relationship with a FIG. 11 collar but with the through hole in the collar supporting a double-ended transfer needle with the user's pinching fingers well away from the needle.

FIG. 72 shows the same off-set two finger pinching relationship with a FIG. 11 collar 230, but with the two stage through hole in the collar supporting hub 267 of the double-ended transfer needle assembly 268, with the user's pinching fingers well away from the needle. Further, with collar 230 in position, the combination may be rested on a surface using the middle collar 230, which will distance the two sided needle from being contaminated due to surface touching.

Figure 73:
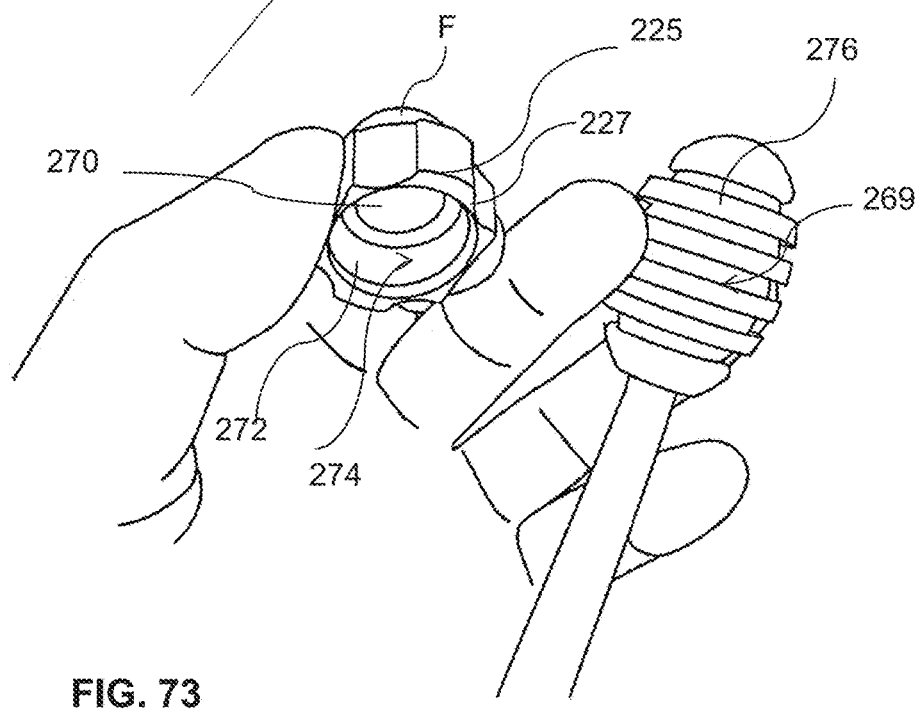
FIG. 73 shows a single hand grasping of a FIG. 11 collar (open top version, with larger base aperture opening out at the bottom of the collar) and a grooved bulb head utensil.

FIG. 73 shows a single hand grasping of a FIG. 11 type collar (open top version, with larger base aperture opening out than the upper open top aperture such as collar 225 of FIG. 59) and a grooved bulb head utensil 269. FIG. 73 also shows the interior of collar 225 as having an upper diameter opening 270 for receipt (and relative flexible support and sealing) of, for example, a syringe assembly. The lower opening 272 in collar 225 is defined by the enlarged (smooth in this embodiment) diameter wall surface 274 designed to engage a bottle top as in FIG. 61, as well as different configured shaped utensils such as the bulbous head 276 of utensil 269, made possible by the flexibility and thinner relative nature of wall 227 defining wall surface 274. FIG. 73 also shows the freedom to hold collar 225 with two fingers, one on the periphery, and the other finger (F) extending to (e.g., into) the top opening of collar 225 (or in some embodiments the top is closed off with a depressed recession).

FIG. 74 shows the components of FIG. 73 in an engaged state and with the same offset, two finger grasping described above. Also, FIG. 74 illustrates that collar of FIG. 11 configuration also preferably, like the FIG. 10A general peripheral configuration, has opposing ling ridge sides PRL (one shown) and opposing short ridge sides PRS (one shown) separated by concavities CV as to provide for enhanced grasping as by two finger pinching.

FIG. 75 shows the combined components of FIG. 74 and the ability for a pinch support to hold the combination in a suspended state with one hand.

FIG. 76 shows modified tray embodiment 276 which is shown in cut-away but the remaining portion is in one embodiment represented by tray 140 in FIG. 46. In this embodiment, however, tray 276 has an end aperture 278 that has a configuration not designed specifically for a base mount such as shown in FIG. 3A, but has a generally quadrilateral outer periphery with inwardly extending convex walls, That is, as shown in FIG. 76, reception aperture 278 has a pair of opposing long sides 280A, 280B, a pair of opposing shorter sides 282A and 282B, and four corner projections 277 with curved exposed surfaces. Aperture 278 is designed to snugly receive a collar such as shown in FIG. 11, wherein there are long and short ridge sides opposing each other and recesses at the corners between the formed projections along the sides. Thus, tray 276 has aperture 278 that is well suited for support of components of the invention such as grasping body 168 formed integrally with plunger 170 of the illustrated syringe 172 in FIG. 48.

FIG. 77 shows the snug interrelationship or integrated collar and plunger support relationship shown in FIG. 48. As seen in FIG. 77 the collar 168 end of plunger 170 is inserted into the conforming aperture 278c in a snug reception state relative to supporting/transfer tray 167.

FIG. 77A shows plunger 170 (with rubber seal piston for mounting on the top plunger end not shown), having a main body 171 (with graduations for liquid content) and the attached collar 168 of FIG. 11 general configuration (e.g., a flex attachment, overmolding or bonded relationship for securement if not molded as a monolithic unit). Also, as shown in FIGS. 77B and 77C, collar 168 has opposing ridges with long (circumferential) sides PRL, opposing ridges with shorter (circumferential) sides PRS, and concavities CV separating the adjacent short and long ridges (PRL-PRS). FIGS. 77B and 77C also illustrate the underlying depression UD formed at the base undersurface of collar 168 which features upwardly and inwardly extending wall sections WS that form the boundary for the interior depression area ID, which is centralized on the undersurface. In this way, the rim edging defined by wall surfaces WS and the outer periphery of the collar provide for a degree of compression flexure along the collar edging. Also, the interior depression depth is preferably less than the depth of the concavities CV on the periphery of the collar.

FIGS. 77D and 77E illustrate plunger 170 in a lying down state (rather than an upward or vertical support state shown in FIG. 77A). As seen, the interior edging of the adjacent projections PRS and PRL can contact with the support surface, and since they are separated by bottom positioned concavity CVB, collar 168 acts to preclude rotation of plunger 170 once set on its side, which is helpful in a working environment where undesirable utensil roll offs can occur.

FIG. 78 shows an alternate embodiment of the present invention with a haptic promoting cavity provided in a grasping collar device 280 that is suited for instrument support and transfer, which in this case is a bristle cleaning instrument 279. As shown in FIG. 78, grasping collar 280 has a solid main body of elastomeric material (preferably relatively soft as in 20 to 50 shore D, more preferably 20 to 40 shore D) with a central through-hole that is a wavering cavity with varying diameter dimensions along the length. The nature of grasping collar 280 is such that there is retained a "feel" component of the inserted instrument through the elastomeric sleeve thickness. For example, a user can feel the stepped progress of the bristles within the non-smooth cavity and also still be able to evaluate the relative level of compression on the received instrument.

Figure 79:
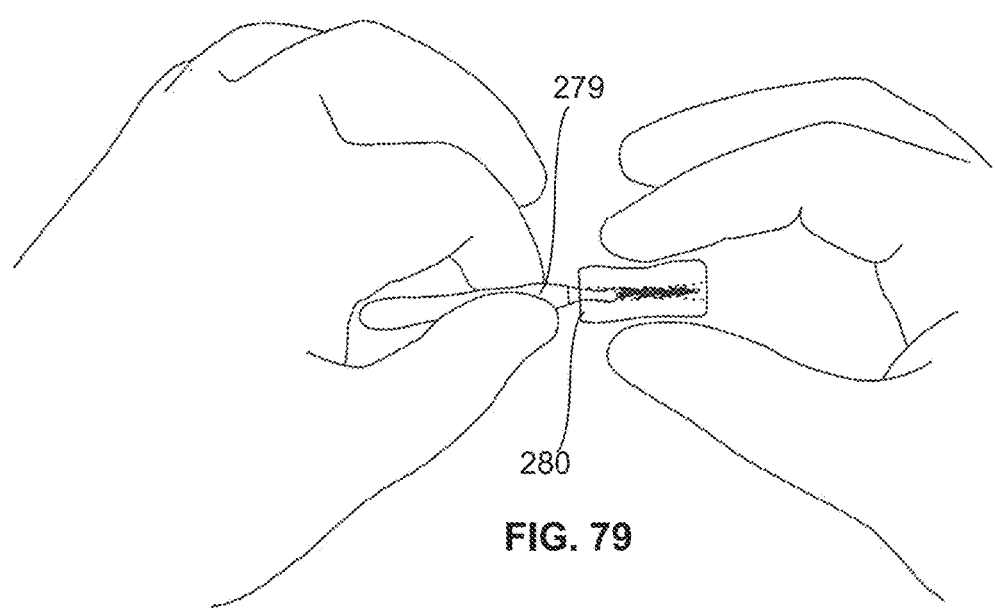
FIG. 79 shows the cleaning instrument with bristle brush having been inserted into the sterile cavity of the grasping device which provides, for example, transfer from a one person to another without finger contamination and also without inadvertent bristle crushing due to over pinching of bristles directly.

FIG. 79 shows the cleaning instrument with bristle brush 279 having been inserted into the sterile cavity of the grasping collar 280, which provides, for example, transfer from one person to another without finger contamination, and also without inadvertent bristle crushing due to over pinching of bristles directly (based on the retained "feel" provided by the cavity and collar haptic combination).

Figure 80:
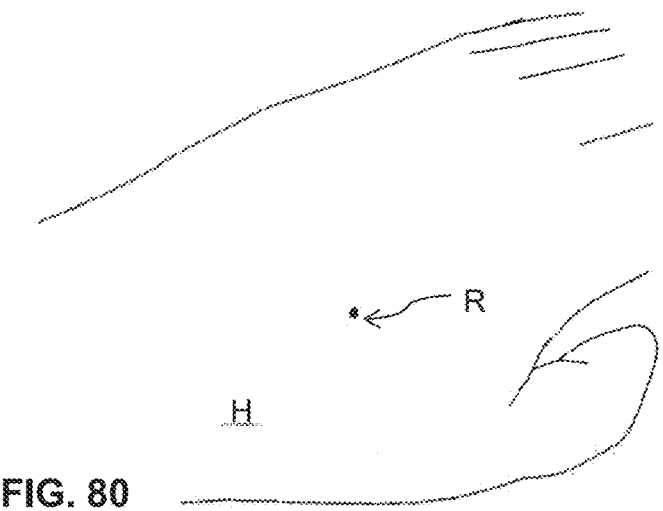
FIG. 80 shows a hand with a region intended for treatment.
Figure 81:
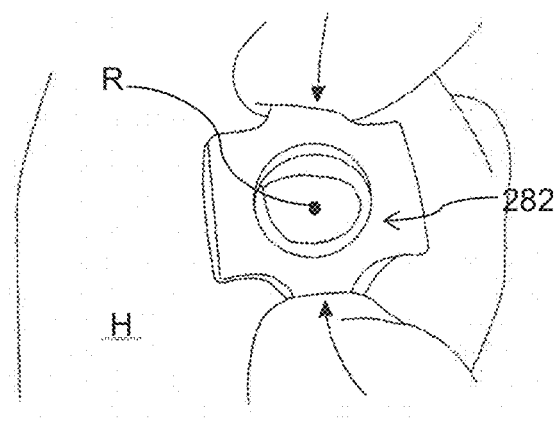
FIG. 81 shows the versatility of the collar, which is shown as a base mount in FIG. 67, but as a skin collector and positioner of the region intended for treatment in the present Figure, with this Figure showing initial placement of the collar around the region intended for treatment.

With reference to FIGS. 80 to 84, there is described a treatment procedure using grasping collar 282 of the FIG. 10A configuration, and of a thinner mode (e.g., 1.5 mm to 6 mm, and more preferably 2 mm to 4 mm). FIG. 80 shows hand H with region R intended for treatment, while FIG. 81 shows the versatility of collar 282, which is shown as a base mount in FIG. 67, but as a skin collector and positioner of the region intended for treatment in the present FIG. 81, with FIG. 81 showing initial placement of the collar around the region R intended for treatment. Also, FIG. 81 shows the beneficial short ridge to short ridge compression orientation.

Figure 82:
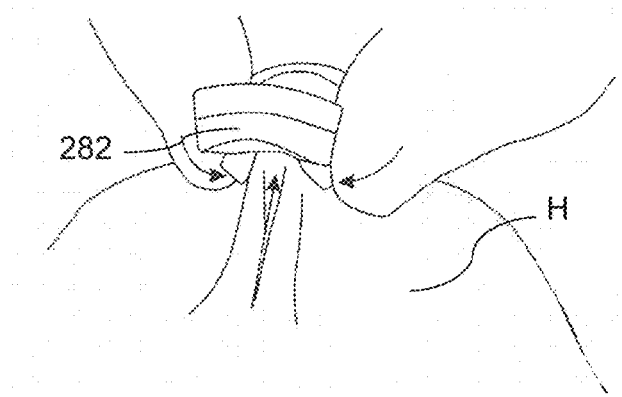
FIG. 82 shows the collar of FIG. 81 in a compression state (pressing together of two opposing shorter ridge side surfaces) that causes a simultaneous capture and lifting of skin such the region intended for treatment is presented within an intermediate, upper region, (or above) the aperture of the collar with the skin assuming a mushroom configuration due to the lower edging of the collars recess bending upward.

FIG. 82 shows collar 282 in the peripheral compression state that causes a simultaneous capture and lifting of skin such the region R intended for treatment is presented within an intermediate, upper region, or above the aperture of the collar 282 and the underlying skin is compressed by the collar there below. Further, as seen from FIG. 82 the lift up is achieved by having the collar flex in a bowed up state that results in the lower interior cavity edging achieving an automatic skin pile lift up while compression is ongoing which helps isolate the region R without pain in the patient, and with the lower edging of the collars cavity being closest together to form a mushroom configuration in the skin pile.

Figure 83:
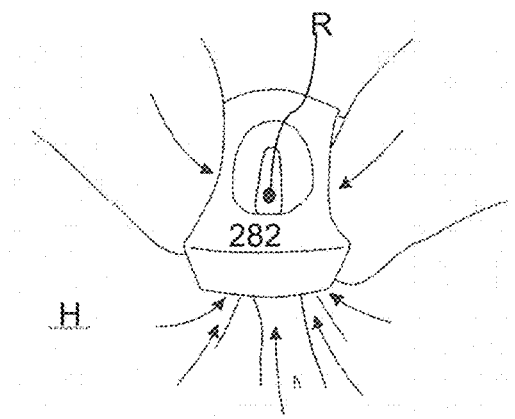
FIG. 83 shows another view of the relationship shown in FIG. 82.

FIG. 83 shows a more top oriented view of the pinched pile of skin.

Figure 84:
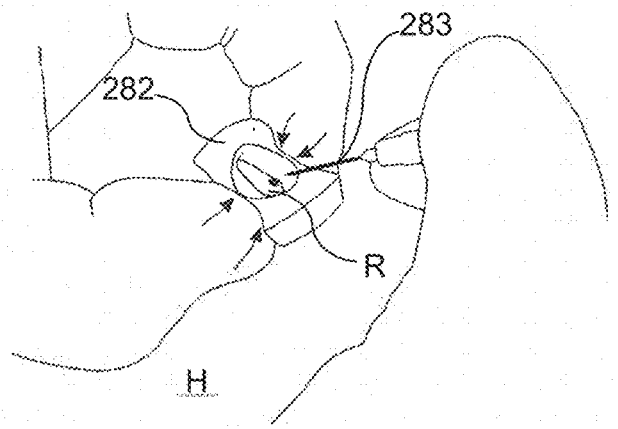
FIG. 84 shows the insertion of a needle in the exposed, desired area in the region intended for treatment.

FIG. 84 shows the insertion of a needle 283 in the exposed, desired area in the region R intended for treatment.

Figure 85:
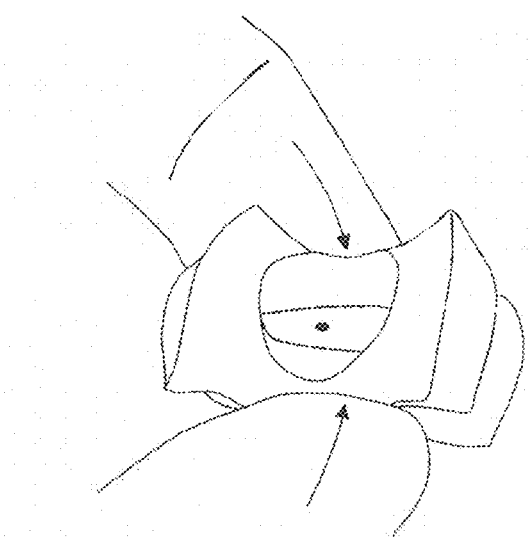
FIG. 85 shows the collar of FIG. 81 in a similar compression, lift state relative to a different object, and how the lower edging of the collar moves inward and upward simultaneously.

FIG. 85 shows collar 282 of FIG. 81 in a similar compression, lift state, but relative to an object O other than skin.

FIG. 86 shows an alternate embodiment collar 284 similar to that of FIG. 78 but with a modified haptic promotion cavity which is well suited for catheter equipment CE manipulation. FIGS. 87 and 88 show cross-sectional views of collar 284 as well as the central cavity 286. Central cavity 286 includes concavities and convex depressions that form a meandering pattern, with FIG. 90 showing some illustrative (non-limiting) values for the concavities and convex valleys that are off-set in longitudinal length. This meandering cavity with different projection and cavity regions along the length of the cavity facilitate the feel of an inserted instruments movement (e.g., stepped advancement in collar), while also providing for the option of different compression level locations in the collar. In this embodiment, the central cavity 286 includes an enlarged end 286E having a horn shape shown with an increasing diameter to the opening (right side in FIG. 90). The enlarged end facilitation initial insertion of a catheter sleeve or other thin instrument.

FIG. 88 shows a perspective view of the collar shown in FIG. 87. Collar 284 functions to avoid having a surgeon directly grasp a thin catheter line for an extended period of time which can lead to hand, muscle lock up, while it, due to its haptic nature, also avoids unintended crushing of an outer catheter sleeve which can be <3 mm (as in 2.5 mm) in diameter for some catheters and thus can be fragile in nature.

FIG. 89 shows the grasping collar 284 in three different positions (time sequenced as only one collar featured in the embodiment) on catheter line 288 of catheter equipment CE and with the middle (time position relative to either a catheter sleeve feed relative to a stationary collar, a clamped movement of both, or a collar movement relative to a fixed in position catheter sleeve). FIG. 89 shows collar 284 in cut away in similar fashion as in FIG. 90 to illustrate the haptic generally sinusoidal wave pattern of the through-hole cavity 286 featured for the sleeve which has different clearance widths along the length as well as different outlet opening diameters in this embodiment. In this way, the user can feel the relationship between the catheter object and collar 284 for proper manipulation, with a higher compression squeeze providing for a more secure locking of collar 284 and received catheter line 288 (or some other object that is threadable through cavity 286). A lower compression state provides for a haptic feel that provides for a gradual slide relationship that is more resistant than a non-compression slight resistance between the central cavity meandering walls and catheter line object 288. A slight resistance without compression relationship is also useful for better control over a feed adjustment FIG. 90 shows the intermediate positioned grasping collar presented in FIG. 89 in an expanded view such that the haptic promoting cavity configuration can be better seen together with some illustrative cavity thickness values of the length of the collar for the catheter equipment embodiment featured. FIG. 90 illustrates a relatively larger grasping collar having a longitudinal length of 27 mm, a first end opening 286D of 2.5 mm, and an outer opening at end 286E of 3.5 mm, thus making it well suited for precision procedures involving catheter embodiments as in catheter 289 shown (e.g., a colonoscopy catheter). The haptic central cavity design makes the collar well suited for finger controlled (external; pressing of sleeve 286) fine adjustments in the catheter CE relative to the collar 284 or vice versa, while the exterior contouring on collar 284 further enhances the control and ease of finger manipulation (e.g., catheter sleeve retention with sliding interior wire or the like still possible due to non-crushing compression). In some embodiments, the collar 284 can be provided with a simple circular cylinder exterior configuration with reliance on the haptic central cavity for improved catheter manipulation. However, having both the exterior surface and interior cavity 286 designed with surface contouring provides a synergistic combination of haptic and controlled manipulation with low strain on the fingers. This feel also helps avoid over compression which can lead to undesirable sleeve crimping.

FIGS. 91 to 94 show a similar haptic collar arrangement for a catheter such as that for FIGS. set 86 to 90, but with collar 290 being, at one end 286X, a finer grade grasping collar well suited for a finer grade catheter 292. The larger end provides for easy catheter insertion (e.g., 2 to 2.5 mm catheter sleeve) while the smaller diameter section providing friction resistance (while still allowing free sliding) to improve the relative feeding of the catheter sleeve. As seen in FIGS. 91 to 94, collar 290 has a non-meandering through-hole or central cavity 294; featuring, along its 22 mm longitudinal length, a small diameter first end 284X (e.g., 1 mm is shown as an example) with a slight gradient of diameter expansion such that the intermediate area 284Y of cavity 294 has, for example, a 1.5 mm diameter that more quickly expands to 2.0 mm in the intermediate area, which in turn is followed by an even greater and non-graduate expansion that opens out at the other end and in this embodiment has a 4.0 mm diameter. Thus, this sleeve has a first end that can retain a finer diameter catheter in sliding friction contact, but an intermediate area with a gradual need for compression to place the cavity surface in contact with the catheter and a still greater clearance end for facilitating initial threading.

FIG. 95 shows a similar haptic collar arrangement for a catheter as that for FIGS. set 86 to 90, but with collar 296 being of a shorter length of 17 mm and having a venturi shaped central cavity 297 featuring a straight initial section 297X of 1.0 mm diameter, a narrower diameter venturi throat section 297Y in an intermediate section (shown with a 0.6 mm constriction diameter in FIG. 97), at the other end, a flaring out section 297Z that goes, in expansion sequence, from, 0.8 mm at the throat section interface, to 1.5 mm which leads to the conical outlet having a 2.5 mm (insertion) opening as shown.

Thus, it is the intermediate area or throat region of the central cavity in this embodiment that is in initial contact with the catheter sleeve and it's the outer ends that can be compressed to increase the degree of contact or released to provide for more ease in relative adjustments between the sleeve and received catheter as shown in FIGS. 98, 99 and 99A. Again, having the illustrated outer contouring on the exterior surface of grasping collar 296 is preferable in combination with the central cavity haptic catheter contact capability, but the central cavity haptic catheter contact capability is beneficial in and of itself and thus can be advantageously used with non-contoured (collars with circular cylinder without diameter adjustment along its length) outer collar surface.

Along the lines of the aforementioned figure set of FIGS. 98, 99 and 99A there is featured a variety of embodiment options, inclusive of those shown in FIGS. 99B and 99C. In FIGS. 99B and 99C there is shown haptic collar 296 but in a modified form "296T" featuring two, parallel through-holes with a more central one being similar to that shown above in FIG. 99A as having a varied profile in its through-hole (e.g., a pair of different diameter conical converging portions at the ends and a narrower passageway region in the central region). While FIGS. 99B and 99C are presented as different, individual figures of the same device, the two figures can also represent two grasping devices in an assembly as in where the linear elements represent different sections of a pulley configuration.

That is, FIGS. 99B and 99C show haptic collar 296T as having a common exterior configuration as collar 296 described above and can also have a common interior central passageway 297A and/or 297B, inclusive of a varying diameter passageway having at least one smaller and larger diameter passageway differential as in an hourglass configuration (and more preferably multiple differentiating regions as in the embodiment described above (e.g., embodiments of FIGS. 90, 92 and 97) and designed for the preferred haptic feedback in the intended use environment). In addition to the central through-hole passageway 297A, there is provided an additional through-hole passageway 297B extending preferably generally parallel to, and radially eccentric to, the central axis of the collar (shown as generally being coincident with the central passageway 297A).

Extending within passageways 297A and 297B, respectively, are linear elements 296FA and 296FB which can represent elongated elements of the same or different constitution as in linear elements represented by wires, elongated conduits, threading, cording, or other tension means, elongated rods, and other extended body means (preferably flexible but also can be more rigid as in the rod reference). Also, the described linear elements 296FA and 296FB can be representative of medical device components as in the catheter discussion described above (e.g., an optical fiber as one linear element and a probe wire as the other), although alternate embodiment feature non-medical usage as in grasping collars for window shade lift cords and other non-medical assemblies where haptic collar usage is desired. The above medical and non-medical embodiment description is also applicable to the other haptic collars described herein. For instance, linear elements 296FA and 296FB can be catheter elements as in gastronomical catheter lines as in one of 1.0 mm received in the passageway such as shown in FIG. 97 featuring passageway sections of 1.0 mm (first end)/0.6 mm intermediate area/1.5 mm (second end). Thus line 296FA is in a high friction arrangement with its 1.0 mm diameter line held tightly by the constricted 0.6 mm intermediate area. The inherent flexibility of collar 296T does still however allow for a controlled pushing and/or pulling of the element 296FA to a desired location as in a treatment site. The other passageway can be of a less restrictive size relative to its received element 296FB as in a 1.0 mm element and 1.0 mm non varying diameter passageway at 297B as to provide for less restricted sliding (e.g., for an instrument or element 296FB for which precision is not of the level of element 296FA such as a light catheter optical fiber or spray conduit, etc., versus a cutting knife, balloon, electrical heater line, etc., for 296FA)

The haptic collars such as featured in FIGS. 99A and 99B are shown in the preferred finger compression sizing (e.g., as in having a maximum exterior collar diameter of 15 mm to 30 mm and a length of 15 mm to 30 mm), although variations are also featured under the present invention as in smaller or larger versions intended to better suit the environment of intended usage. Thus, an advantageous characteristic in collar 296T brought about by the usage of a non-varying and varying diameter wall through-hole configuration for passageways 297A and 297B is that there can be provided varying friction levels between the two passageways which facilitates switching between free slide mode for both linear elements, one locked and one readily slideable linear element mode, and both relatively locked or in high friction (not easily slid within passageway) mode. Also, while two passageways are shown in FIG. 99B there may be instances where even more passageways are desired that are preferably parallel and with the different friction contact characteristics with the element extending therein described above.

While FIGS. 99B and 99C are shown with exterior contouring designed for finger compression, larger embodiment sizes are contemplated as in full hand manipulation such as the aforementioned mechanical pulley discussion above as where there can be adjusted one linear element (larger cord) upon full hand haptic compression, while the other passageway provides stabilizing guidance to another line.

Figure 100A:
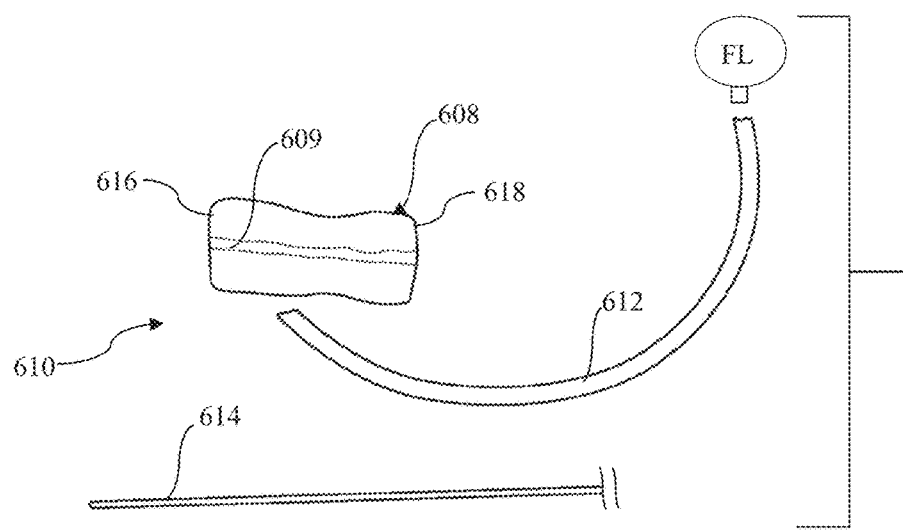
FIG. 100A shows a kit assembly featuring a grasping collar or sleeve kit having a haptic collar, such as those described above, together with an a flexible fluid conduit, optional fluid source, and an optional (flexible or rigid) tool designed for receipt within the fluid conduit while providing for fluid flow between the exterior of the tool and the interior of the tool during non-crimped valve flow states.
Figure 100B:
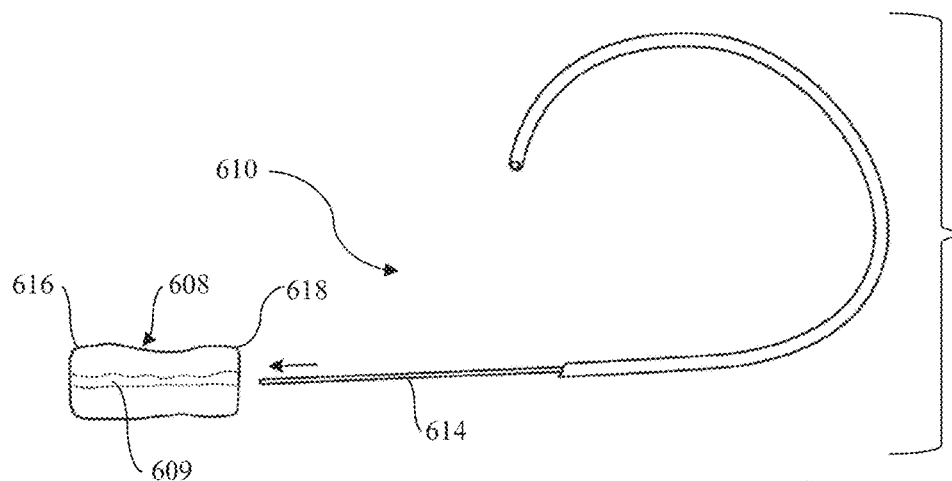
FIG. 100B shows the kit assembly shown in FIG. 100A (with fluid source as in a pump and tank combination removed) in a partially assembled state and without fluid flow shown.
Figure 100C:
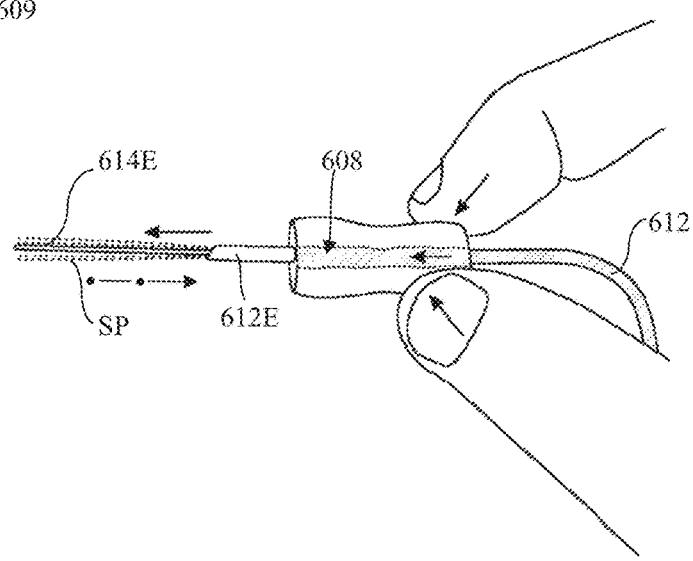
FIG. 100C shows the completion of assembly of the kit components shown in FIG. 100B, with fluid flow with that flow shown exiting the free end of the conduit along the exposed surface of the tool and with the finger grasp in a state of conduit grasping without sufficient compression for fluid flow valving into a shut off or reduced flow state.
Figure 100D:
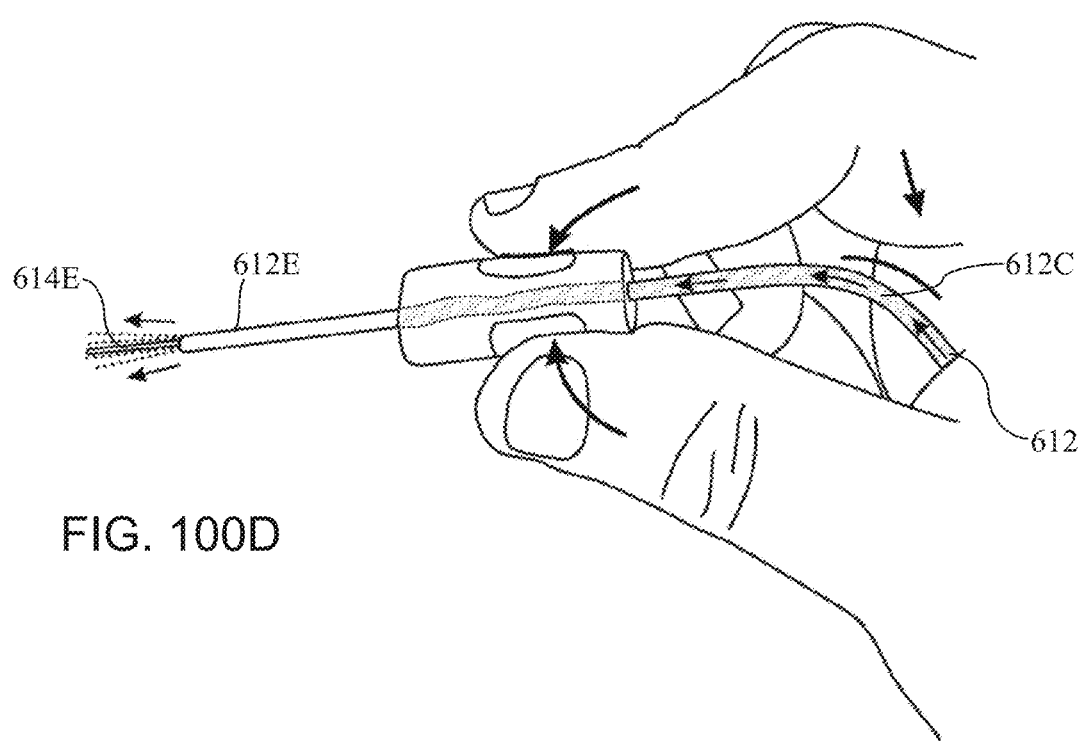
FIG. 100D shows the assembled kit shown in FIG. 100C with greater detail in the non-crimped, curved flow (valve fully open) configuration of the flow conduit extending within the upper palm region of the grasper's hand (providing the illustrated three point contact arrangement), with fluid flow shown exiting the end of the flow conduit and with an adjustment in the relative telescopic relationship between the tool and fluid conduit (the tool being positioned farther internally within the free end of the flow conduit and not facilitating a significant blocking state due to the slight curvature extending past the received, free end of the tool).
Figure 100E:
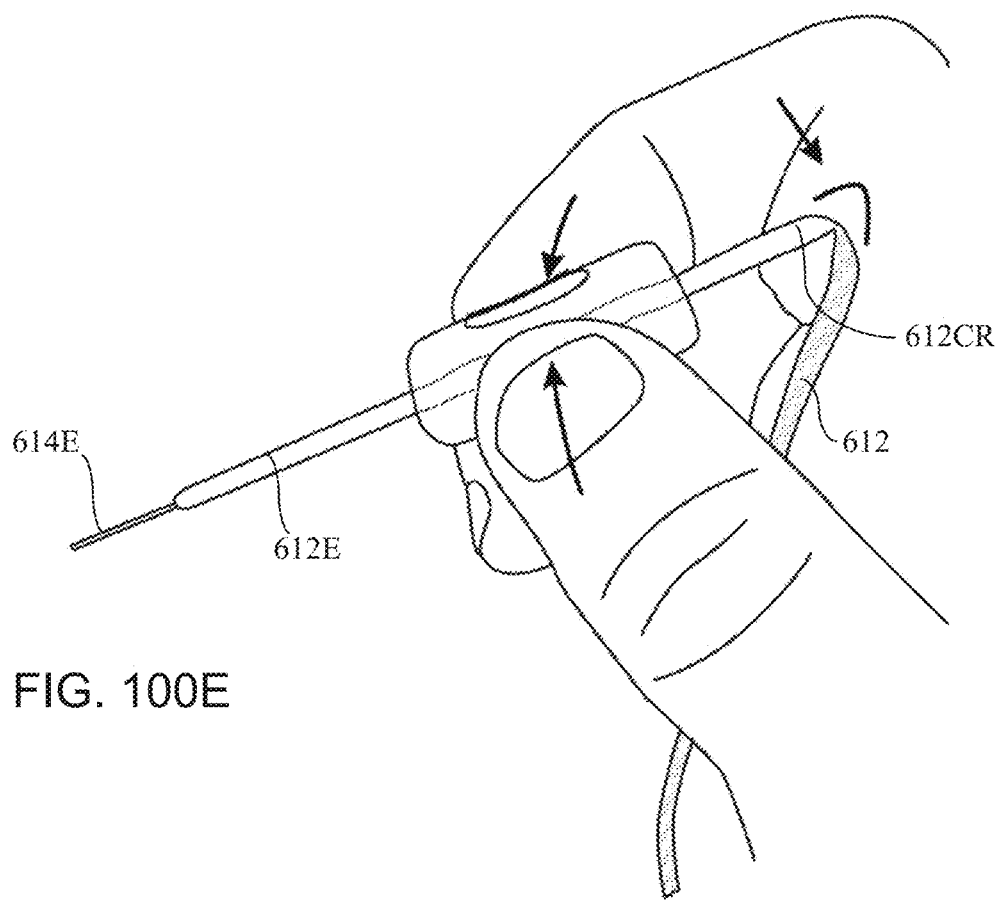
FIG. 100E shows the assembled kit shown in FIG. 100D with the non-crimped, curved flow configuration of the flow conduit having been modified such that the contact relationship between the grasper (the grasper's finger undersurface in this embodiment) and the formerly curved section of the flow conduit has a fully crimped, shut off valve, no flow state (with the tool and flow conduit retaining the same telescopic relationship as shown in FIG. 100D).
Figure 100F:
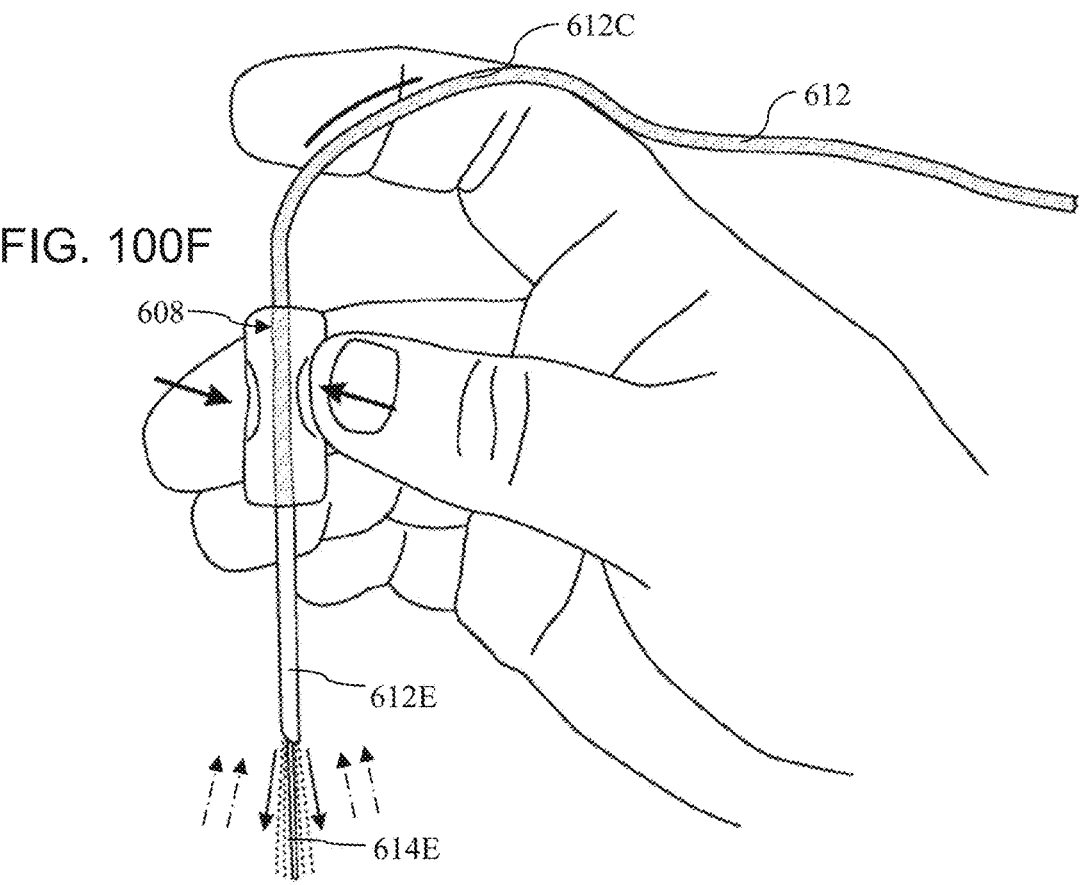
FIG. 100F shows the assembled kit shown in FIG. 100C, but rather than having the index finger and thumb pinch relationship shown in FIG. 100C.
Figure 100G:
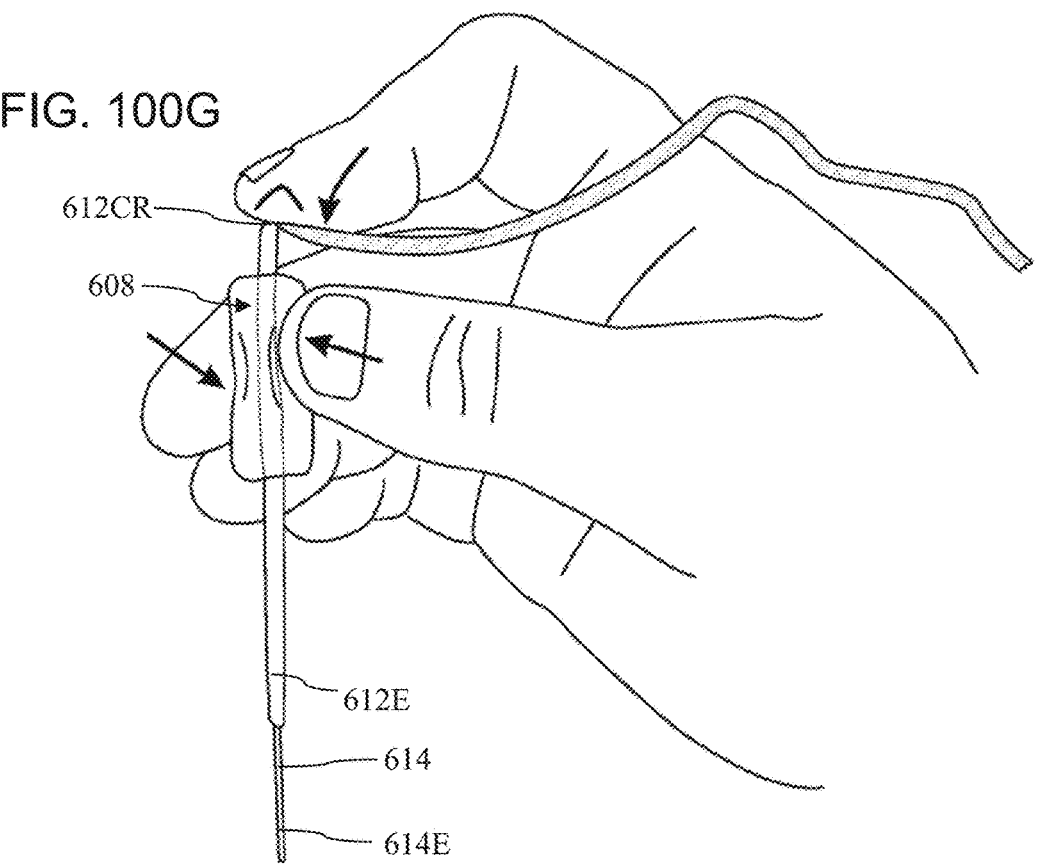
FIG. 100G shows the same grasping arrangement as featured in FIG. 100F, but with a full crimping or full flow shut down valve arrangement brought about by the index finger pressing down on the conduit as to achieve a "tri-pod" crimping relationship.
Figure 100H:
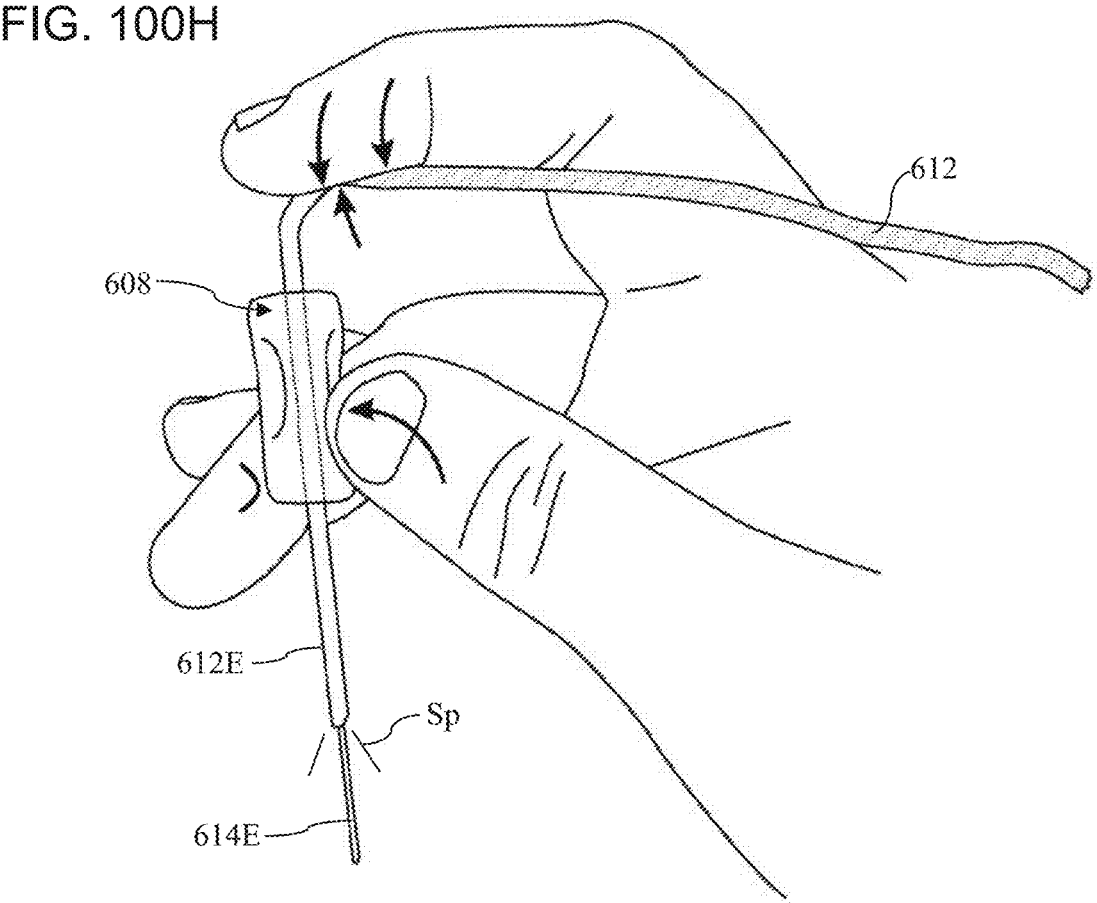
FIG. 100H shows the same grasping arrangement as featured in FIG. 100G, but with a partial crimping or partial flow valve arrangement brought about by the index finger pressing down on the conduit as to achieve a "tri-pod" crimping relationship that has the index finger contacting a region of the conduit.
Figure 100I:
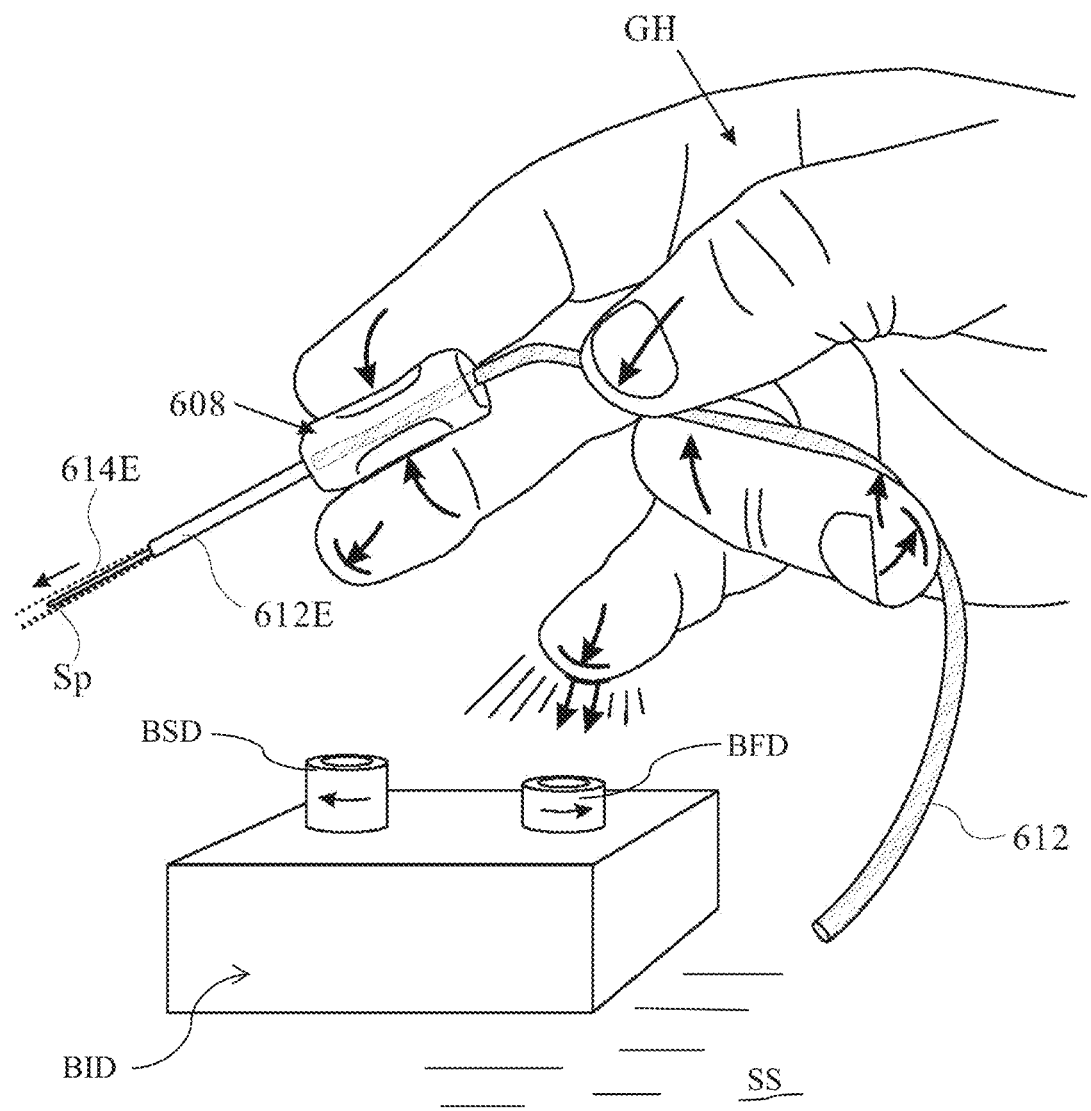
FIG. 100I shows another grasping arrangement that features the index finger and middle finger as the two fingers handling the collar while the thumb is free to contact the fluid conduit as to either place it in a flow valve state, as shown, or in a crimped partial or full shut down state (not shown) with this relationship also providing for optional finger support surface balance points as in pinky and/or middle finger contact with the supporting surface or with switches of a bi-directional flow controller; also, the ring finger provides added fluid conduit contact guidance and/or flow control.
Figure 100J:
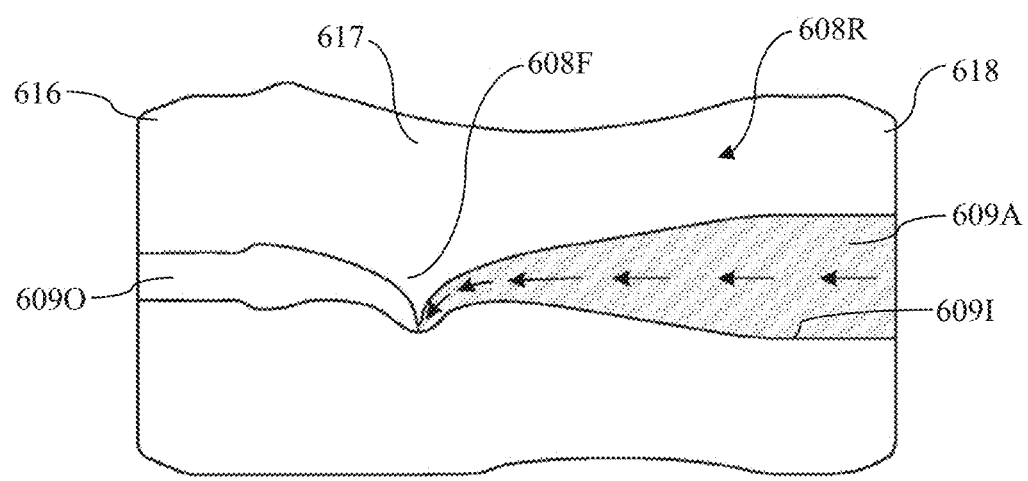
FIG. 100J shows a reverse valve flow arrangement haptic collar wherein in its natural state there is flow blockage due to an internal flexible region in the through passage formed in the collar.
Figure 100K:
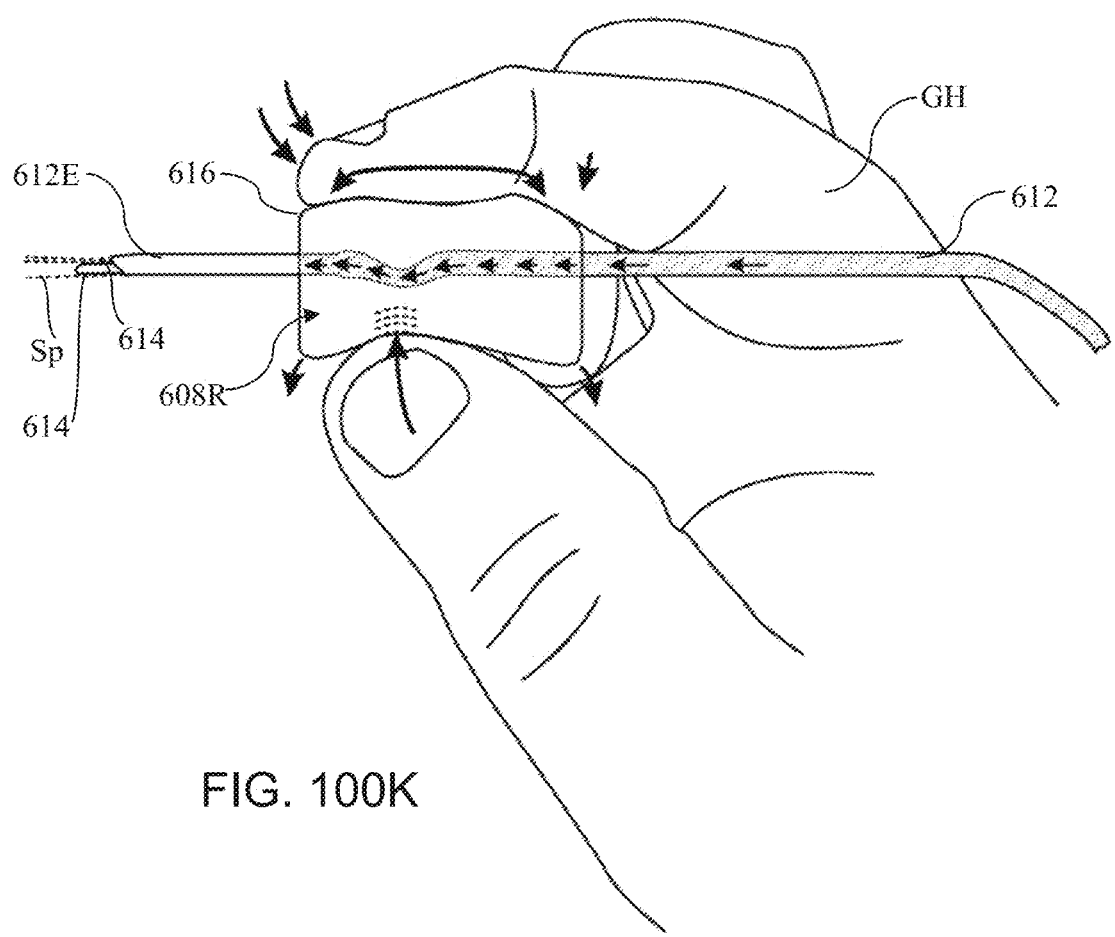
FIG. 100K shows the reverse valve flow arrangement haptic collar shown in FIG. 100J but in a flow or valve open state brought about by finger compression on the exterior of the collar, which in this embodiment features a two finger convex collar development compression arrangement as to cause the internal blockage region to adjust into a flow through state in the valve collar (e.g., an upper convex surface formation provides for the intermediate positioned valve extension to rise up into a flow opening state).
Figure 100L:
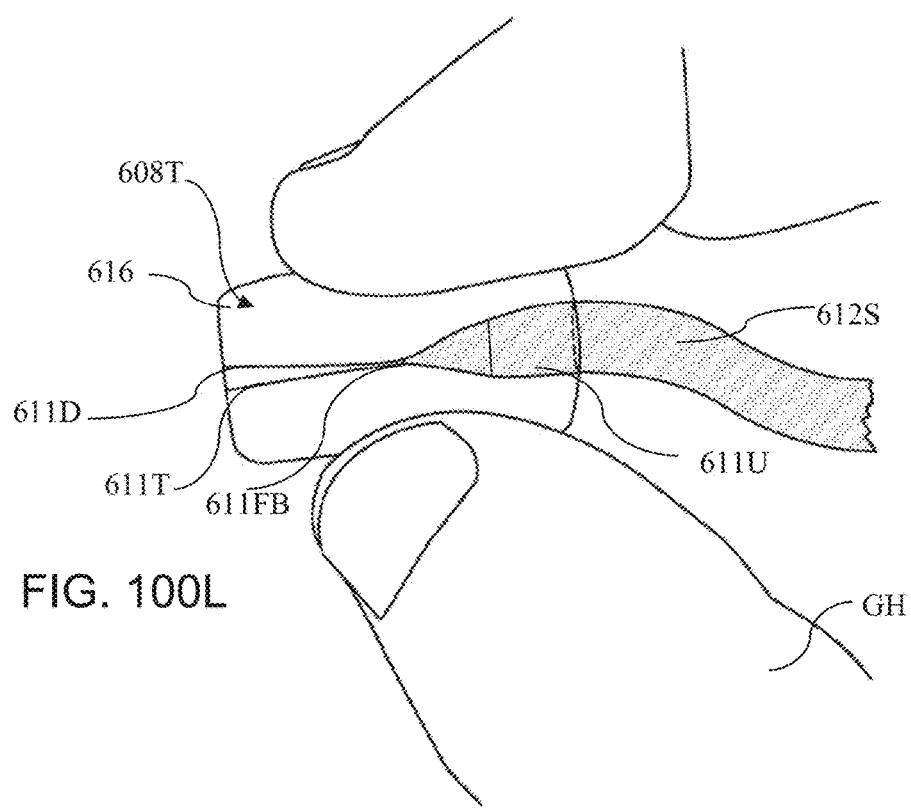
Figure 100M:
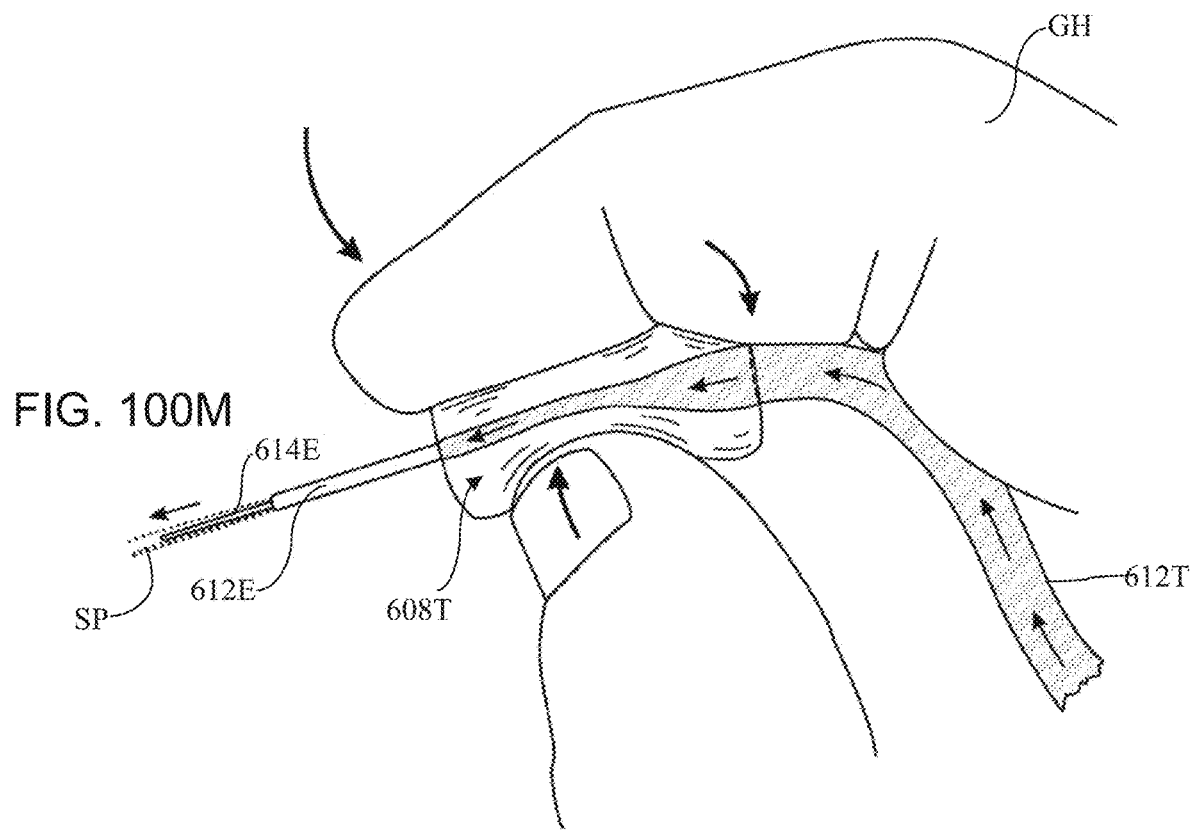
Figure 100N:
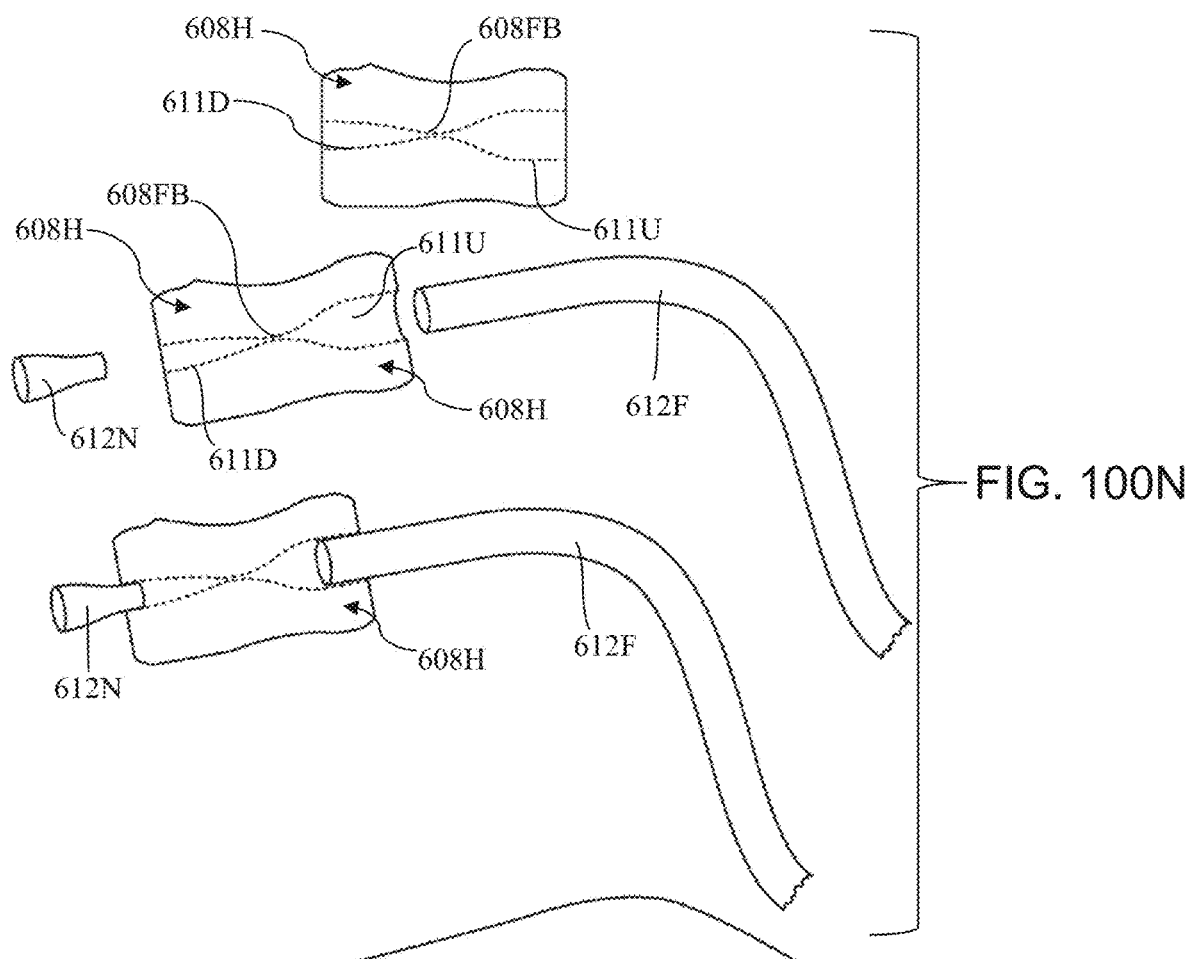
Figure 100O:
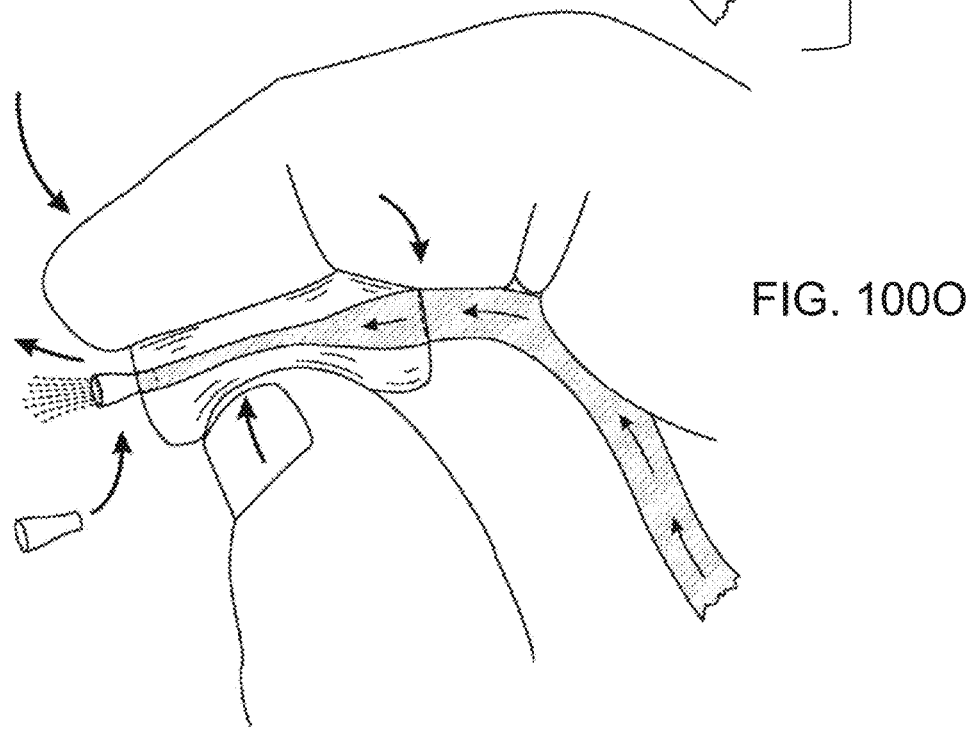

FIGS. 100A to 100O show a haptic collar 608, sharing similarities with the collars above described above relative to, for example, FIGS. 87, 93 and 98, but with a flow control function inclusive of valving operation. That is, flow control collar, in addition to providing the above described grasping function like that for the common configured collars, such as collar 284 in FIG. 87, collar 290 in FIG. 93, or collar 296 in FIG. 98, functions as well as a means for controlling and regulating through-flow therethough. For example, flow control means 608 provides a sleeve (non-slit) geometry that can be used alone or in conjunction with a mechanical assembly such as that described below in kit assembly 610. As such, collar 608 can operate in a variety of valving categories such as a safety valve (e.g., thermal expansion and contraction based, or a safety relieve valve based on pressure increases), as well as in other valve categories. The interior through-hole is referenced in FIG. 100A as throughhole 609 extending through from one end 616 to the opposite end 618 and has an interior contour that is preferably varying at one or more points along its longitudinal length inclusive of the below described blockage extension provided along the longitudinal length of the through-hole 609.

In this regard, FIG. 100A shows a kit assembly featuring a grasping collar or sleeve kit 610 having haptic collar 608, together with flexible fluid conduit 612, optional fluid source FL, and an optional working tool 614 designed for receipt within the fluid conduit while providing for fluid flow between the exterior of the tool and the interior of the tool during non-crimped valve flow states. Fluid source FL is shown in fluid flow communication with conduit 612 and one that preferably provides flow power in either direction (e.g., a pump for feeding from flow source FL toward the end 618 of collar 608 and out the opposite end 616, or a vacuum pump for drawing fluid flow toward the nonconnected end 616 of collar 608 and out the opposite end 618 toward source FL—at which location a variety of different attachments such as an addition flow conduit including spray nozzles such as described above or a suction conduit. Tool 614 can take on a variety of forms suited for the intended usage and can be a flexible tool member (in which case it can extend along way within the conduit 612, or a solid tool at least at its end region intended for exposure or a combination (a solid end as well as a flexible wire or the like leading through the conduit). The flexible nature of the tool or a portion of the tool provides for the below described crimping based fluid flow control (either as a suction flow or as a feed flow). Examples of tool 614 include, but are not limited to, cutting, piercing, visual display, laser, or other electrical based tool such as a cauterization tool. Further the fluid that is intended for passage between the tool and the conduit 612 can also take on a variety of forms suited for the intended usage such as a highly viscous lubricant flow out, a cooling or heating liquid or gas, or an air suction back through tube as when there is a desired to clear out a region of interest of fluid or gas, as well as combinations of the same as in cooling fluid during a portion of usage and a suction of air and external pooled cooling fluid, etc.

FIG. 100B shows the kit assembly 610 shown in FIG. 100A (with fluid source FL as in a pump and tank combination removed) in a partially assembled state and without fluid flow shown.

FIG. 100C shows the completion of assembly of the kit 610 components shown in FIG. 100B with fluid flow. As shown in FIG. 100C the conduit 612 is flexible and extends entirely through collar 608 as to have an exposed conduit end portion 612E. Tool 614, which is less flexible than conduit 612 in some embodiments or can be flexible together with conduit 612 in other embodiments, is shown as being received within conduit 612 and is also shown as having an exposed end region 614E extending out farther away from the free end of exposed conduit end portion 612E. The fluid flow is shown by flow direction arrows in FIG. 100C as passing within the portion of conduit received within the collar 608 and a long exposed end region 614E (i.e., within collar 608 fluid flows along the exterior of tool 614 and the interior surface of the through-hole 609 of collar 608, whereupon reaching the free end of conduit 612 the fluid passes out in a general (e.g., slight conical spray) flow along the exposed region 614E of tool 614. Thus in FIG. 100C there is shown a two finger pinch grasp that is of a level of compression that enables fluid flow along the conduit 612 and out the free end of collar 612 in a full (relative) valve fully open flow state. Thus, in the embodiment shown in FIG. 100C, the tool 614 can be representative of a metal probe as in a scaling teeth probe or teeth cleaning pick or a metal probe for craftsman work, with the fluid flow being designed for such use as in an air or water spray for cleaning off removed teeth particles or removing smoke or debris in a medical or craftsman setting or a lubricant or coolant, also for use, for instance, in a craftsman or medical setting. Also, as represented by the dash-dot flow direction lines in FIG. 100C, there can be a suction draw of fluid within the same passageway between the tool exterior and the conduit interior (or some alternative passageway arrangement providing within conduit 612). For example, smoke (as an example of a fluid) can be removed by appropriate suction following cutting, cauterization or some other smoke generating technique by tool 614, with the fluid passing along the exterior of tool 614 and the interior of conduit 612, for instance.

FIG. 100D shows the assembled kit shown in FIG. 100C but with an additional view of the grasping relationship as well as an adjusted relationship between conduit 612, collar 608 and tool 614. As shown the 612 collar is slid farther toward the operator as to expose a greater portion of conduit 612 while there is covered up more of tool 614 (as seen by a comparison of the respective exposed portions 612E and 614E in FIGS. 100C and 100D). In addition there is seen more detail in the non-crimped, curved flow (valve fully open) portion 612C of the flow conduit extending within the upper palm region of the grasper's hand (providing the illustrated three point contact arrangement), with fluid flow shown exiting the end of the flow conduit; and with the tool 614 being positioned farther internally within the free end of the flow conduit 612, but not representing a significant blocking state at the covered tool end (not shown) and covering section of the conduit due to either having a tool length that provides a freed end within the conduit (preferably upstream of any crimping location if a solid, non-flexible tool as in a steel or the like solid probe or, if sufficiently flexible can extend through the intended crimping location of the conduit 612). There is thus shown a slight curvature in the portion 612C of conduit 612 in a region of the grasping hand that can provide for easy crimping force application by that hand.

FIG. 100E shows the assembled kit shown in FIG. 100D with the non-crimped, curved flow configuration 612C of the flow conduit 612 having been modified such that the contact relationship between the grasper (the grasper's finger undersurface in this embodiment) and the formerly curved section of the flow conduit has a fully crimped region 612CR. As further represented by the lack of flow passage arrows, the crimping of conduit 612 achieves a stoppage of flow such that the collar valve 608 is a shut off valve with a "no flow" state (with the tool and flow conduit in this embodiment retaining the same general telescopic relationship as shown in FIG. 100D). In addition, a comparison between FIG. 100D (full flow) and FIG. 100E (blocked flow), shows an adjustment in the gripping arrangement from a two finger collar grasp (index pad and thumb pad) while the middle finger and palm region of the grasping hand contact the curved region of conduit 612, to one featuring a three finger (thumb pad/index pad/side middle) contact arrangement with the crimp formed by the region between the index finger base and palm region of the grasping hand in FIG. 100E. Also, while there is featured in FIG. 100E a full valve shut down mode, through a lessening of the crimping forces provided on the conduit (e.g., an adjustment of the index finger so there is less downward compression on crimped conduit region 612R) there can be achieved a partial flow arrangement between the two above noted, illustrated extremes of full flow and non-flow (with flow in either direction depending on whether there is a suction or outward flow mode, with embodiments featuring a switching unit to achieve either mode depending on hand or finger contact with that switching unit inclusive of the same hand being used to hold the tool 614).

A comparison of FIGS. 100F (full flow) and 100G (non-flow) show an alternate grasping relationship for the valve assembly 610 (with reference to the above discussion of the benefit of enabling the same or similar functioning to be achieved with a variety of finger grasp positions to avoid overwork of the grasping hand due to a lengthy or repetitive single grasp mode being used, as in a pipette (on/off) technician's repetitive usage). FIG. 100F shows the assembled kit shown in FIG. 100C, but rather than having the index finger and thumb pinch relationship shown in FIG. 100C. FIG. 100F shows a different grasping relationship wherein the middle finger and thumb are compressed upon the haptic collar or sleeve and the index finger is free (while also providing for a fluid conduit guidance flow curve along the underside of the index finger), with the compression level on the haptic collar allowing for maximum or intermediate flow levels in the fluid passing out (or in with suction) the free end of the conduit about the exterior of the tool positioned within the conduit). As seen in FIG. 100F, collar 608 is grasped with a two (thumb/index) finger pinch or with a three (thumb/index/middle) finger collar only grasp, while the index finger undersurface provides a curved conduit 612C guidance surface as to enable the curved flow though valve arrangement like that described above which enables fluid flow out along the exterior of the section of exposed tool 614E (again with a minor angled conical spray shown).

FIG. 100G shows the same grasping arrangement as featured in FIG. 100F but with a full crimping or full flow shut down valve arrangement brought about by the index finger pressing down on the conduit as to achieve a "tri-pod" crimping relationship (or a four finger grasping relationship if the middle finger is added in contact with collar 508 for added stability). Further, the non-seen free end of tool 614 that is provided within the interior of conduit 612 (when a solid, non-flexible tool) can be utilized to help in achieving a secure valve stop relationship by providing a support surface upon which the conduit can crimp tightly while at the same time the close off index finger can press the conduit back against itself with the tool as an intermediary (although in alternate embodiments reliance on crimping alone can be utilized as when the tool is differently positioned or non-present).

Also, with a lessening of the imposed crimping force by the index finger pad there can be achieved a partial flow provided the conduit has sufficient internal stability as to avoid full crimping upon initial bending. FIG. 100H shows just such an arrangement featuring the same grasping arrangement as featured in FIG. 100F, but with a partial crimping or partial flow valve arrangement brought about by the index finger pressing down on the conduit 612 as to achieve a less compressive "tri-pod" semi-crimping relationship. Thus, in FIG. 100H there is featured a partial fluid flow exit spray Sp that exits the free end of exposed conduit section 612E and exposed tool section 614E (or there can be implemented an intermediate suction force level going back into the free end of the conduit 612). By varying the relative level of compression in the index finger and curved region 612C of conduit 612 there can be provided a corresponding varying in the degree of fluid flow out (or in) from the free end of the conduit, all while having a firm and comfortable finger grasp of collar 608.

FIG. 100I shows another grasping arrangement that features the index finger and middle finger of grasping hand GH as the two fingers handling the collar 608 while the thumb is free to contact the fluid conduit 612 upstream of the free (covered) end of tool 614 as to place it in a flow valve state with full spray SP coming out of the free end of conduit 612 and along the exposed tool end 614E. In addition, in this embodiment grasping hand GH has a pinky that can be positioned to contact one of the bi-directional flow switches (in communication with flow source FL of the system) BSD (suction mode switch) and BFD (out flow mode switch of bi-directional flow controller unit BID supported on an underlying support surface SS (e.g., a table or body surface SS with the control unit BID providing for a liquid (e.g., an air or water spray irrigation activity on going in a treated area or in the suction mode the drawing in of liquid as in fluids or smoke, etc.). Rather than (or in addition to controller unit BID), a foot pedal flow switching direction control unit is provided as another aspect of the present invention.

Further, as shown, with the index finger and middle finger collar grasp contact there is provided the thumb and ring finger as potential conduit 612 contact points to provide a smooth curvature and also a way to avoid conduit movement into a sight area or the like during a fluid flow procedure. Accordingly, as with the other embodiments there can be adjusted from the full flow valve setting shown to one that is in a crimped partial or full shut down state (not shown) with this relationship also providing for optional finger support surface balance points as in pinky and/or middle finger contact with the supporting surface or a curved side of the palm on support surface SS (if such exists). Also, while the above embodiments show hand grasping, a non-human device can also be used to provide the noted collar support with mechanical (e.g., pressure) conduit valving adjusters FIG. 100J shows an alternative embodiment of collar 608 shown above, which is referenced as collar 608R in view of it being a reverse valve flow arrangement that is free of tool 614 and can be utilized with a fluid conduit only leading to an inlet engagement with that collar 608R. Under one embodiment of haptic valving collar 608R, its natural state is a state where there is flow blockage due to an internal flexible blockage portion 608F positioned in the adjustable through-passage 609A provided in the collar. As shown, collar 608R is of a flexible material (such as those flexible materials described elsewhere in the present application) and features a fluid flow side section 609I of adjustable fluid through-passage 609A leading up to blockage portion 608F of common material preferably as the remainder of the collar 608R. As shown in FIG. 100J fluid can be supplied into either end of collar 608R (either end 616 and 618 before being blocked by blockage portion 608F), but in the illustrated FIG. 100J embodiment collar end 618 is shown as being the inlet end for fluid per the shading and flow arrows shown (or the suction flow out end). Accordingly, collar end 616 represents the non-fluid flow end due to fluid blockage developed by the natural bias and configuration of blockage portion 608F (as in an hourglass shape with a narrow flexing blockage/release section in the narrowest region of the hourglass shape). As seen from the discussion below, however, upon suitable bias force application as by grasping hand GH (or some alternative, similarly functioning bias adjustment mechanical means) the flow blockage provided by blockage portion 608F can be removed as to allow through flow entirely through the collar 608R.

FIG. 100K shows an example of this compression against bias application in collar 608R shown in FIG. 100J as to achieve a valve open state brought about by finger compression on the exterior of the collar. As in the above embodiments the collar 608R has contouring in its exterior surface including raised or relatively enlarged radius areas (as compared to the intermediate recessed regions) at its opposite ends 616 and 618 as compared to the intermediate region 617. For instance, in this embodiment there is featured a two finger convex collar development compression arrangement as to cause the internal blockage region to adjust into a flow through state in the valve collar upon suitable finger compression. A similar compression imposition as illustrated in FIG. 100K, if applied to the conduit-less embodiment in FIG. 100J, can achieve a similar blocked-to-open flow transition. However, in the FIG. 100K embodiment, there is provided the earlier described conduit 612, tool 614, wherein the flow blockage section 608F in collar 608R provides sufficient enough crimping pressure on the fluid channel provided between the interior of conduit 612 and the exterior of tool 614 (e.g., flow blockage portion 608F configuration is inclusive of a fully circular projection defining a smaller circular passageway in its natural unbiased state (similar to the below described collar 608T of FIG. 100L) or, as in FIG. 100J, there is featured a top-to-down wall flange. While one blockage portion 608F is shown as the blocking means in the conduit in FIG. 100J, there can be a plurality (e.g., 2 to 4) of such valves blockage that cooperate to provide an overall blockage means for a same or extended in length valve body.

FIGS. 100L and 100M show a different valve grasping collar embodiment 608T, again with FIG. 100L illustrating a situation free of tool 614 and with a modified shortened conduit 612S extending only to the narrowest diameter blockage region 611FB in through passageway 611T. Further, through passageway 611T is comprised of an upstream tapering (converging inward) section 611U in which a corresponding tapered or corresponding collapsed end of conduit 612S is inserted up to blockage region 611FB. Through passageway 611T is further comprised of a downstream tapering section 611D (diverging from blockage region 611FB to the outlet end 616 of collar 608T). This internal conical diverging portion 611D thus provides an inherent nozzle outlet cone in the interior of collar 608T (or a suction passageway inlet going in the reverse direction). In this embodiment, and in any of the aforementioned suction embodiments, there is provided a sufficient enough suction force to achieve the desired result of, for instance, removal of one or more of smoke, liquid and debris.

FIG. 100M shows collar 608T but in a situation wherein there is received flow conduit 612T that extends all the way through collar 608T and has a conforming tapered (converging end) that tapers down to the exposed region 612E of conduit 612T. There is also featured in this embodiment tool 614 such that there is an exposed tool section 614E extending out away from the free end of section 612E of conduit 612T such that there is a fluid flow exiting as shown in flow spray SP.

In FIG. 100L the grasping hand GH is grasping collar 608T in a central pinching mode only such that the natural closed valve bias of flow blockage section 611B is retained. On the other hand, FIG. 100M shows an index finger applying an overall collar bend force by forming a more convex configuration in collar 608T due to the upper index finger applying force to both ends 616 and 618. Accordingly, there is a natural state valve shut off configuration in FIG. 100L with FIG. 100M showing the multi-finger bending of collar ends about a central fulcrum to form a convex shape that places the collar valve in a flow through state (which in FIG. 100M is represented by a lessening of central compression levels in the flow block region 611FB so that flow can travel within the confines of conduit 612T FIG. 100N shows an assembly sequence for a different embodiment of the present invention wherein the kit features a valve collar 608H (a natural state closed haptic collar valve in this embodiment) together with a feed supply conduit 612F and an exit conduit 612N in the shape of a flow dispersion nozzle in this embodiment. In similar fashion to the collar 608T, collar 608H has an interior hourglass shaped through-hole which is sufficiently narrow in the flow blockage region 608FB as to preclude flow through in its natural bias state. Further, there can be seen in FIG. 100N that the inlet diameter of upstream tapered section 611U for receiving a free end of conduit 612F is larger than the outlet diameter of downstream tapered section 611D in which is shown inserted conduit 612N. The nozzle shaped conduit 612N can take on a variety of configurations inclusive of more elongated out away from valve collar 608H, have a curving central axis of be tapered differently or be multi-ported as in a plurality of outlet holes such as a shower head. Further conduit 612N can be formed of a flexible material or a non-flexible material with the valve body being preferably more flexible than the conduit 612N when the conduit is non-flexible.

FIG. 100O shows the completed assembly shown in FIG. 100N in use wherein the convex compression forces provided by the fingers shown on the exterior of collar 608H result in an opening of the valve collar (removal of the closure bias at flow blockage collar region 608FB) for achieving fluid supply from the supply conduit to the outlet conduit 612N (nozzle shown with a diverging spray output in this embodiment—although can also represent a diverging suction inlet when flow goes in the opposite direction).

Figure 101A:
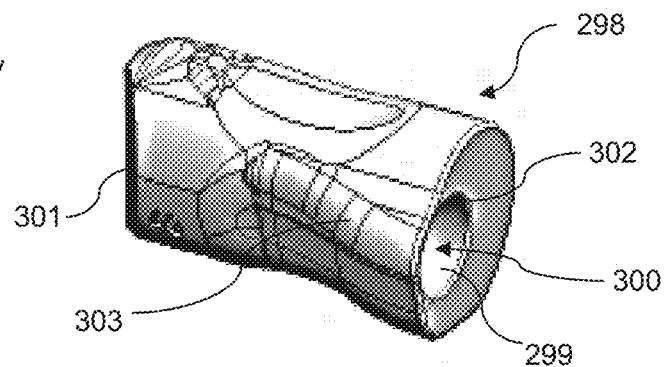
Figure 101B:
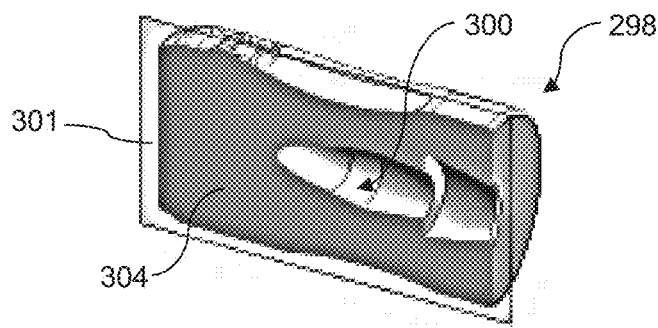
Figure 101C:
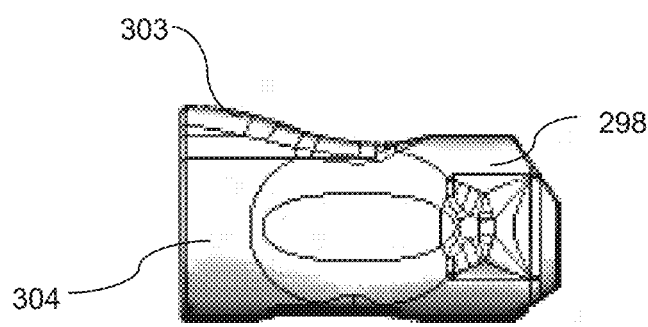

FIGS. 101A to 101D illustrate an alternate needle assembly collar 298 which, like the above described collar 40 (with through-hole 42), collar 298 is mountable on the hub of the needle assembly or some other instrument (preferably by way of an elastomeric compression fit) such that the desired amount of needle extends out away from a free end of the collar. Also, enlarged exterior segment 303 preferably is placed at the top when collar 298 is pressed against a skin surface (with a single finger for instance) such that the needle shaft extending out of end 301 will be at a desired (fixed and preset angle) despite different finger sizes. FIG. 101C thus shows an example of the orientation that collar 298 would have when placed in skin contact under one embodiment of use.

Collar 298 has an arrangement that is well suited as a needle assembly collar as it provides, among other features, an ergonomic, gripping sleeve device for needle placement, insertion and dispensing of liquid through the needle as by syringe operation. This collar represents an adaptation of the gripping sleeve device for precision instruments described in U.S. Pat. No. 8,745,825 issued on Jun. 10, 2014, and which patent is hereby incorporated by reference in its entirety for background purposes.

FIG. 101A shows a perspective top view of collar 298 (not a top orientation in use, but an orientation that shows the saddle recess, and there can be seen that the angled interior cavity 300 is non-centralized at the time it opens out at end 302 of collar 298 (the needle insertion end). The opening shown at end 302 of collar 298 represents the needle assembly initial insertion end, as the needle tip extends out from the opposite end 301 of collar 298. Thus, collar 298 comprises a solid main body 304 or elastomeric material that is open at opposite ends thereof and attachable as a sleeve close to a needle hub region of a syringe, said sleeve device being designed to facilitate the positioning of the user's hand grip, said sleeve device comprising a longitudinally extended solid body of elastomeric material with beneficial exterior contouring used in conjunction with the syringe internal cavity configuration.

FIG. 101C shows a top plan view of collar 298 with the needle assembly initial insertion opening 299 to the left and the needle extension end 301 of collar 298 to the right. FIG. 101C also shows a preferred in use orientation wherein 303 slopes down on the top exterior surface which is also the direction of needle assembly slope in the sleeve at least in one embodiment of use.

Figure 101D:
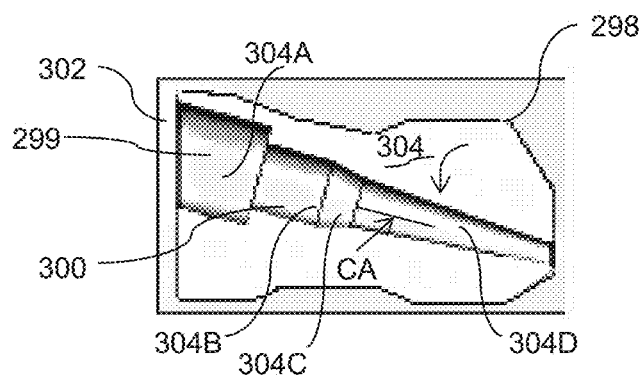

FIG. 101D shows the arrangement of the interior cavity 300 with its multi-diameter through-hole formed at an angle in the interior of the solid main body. Through-hole 300 comprises a first, largest diameter cylindrical section 304A, a second, intermediate diameter cylindrical section 304B, and a third section 304C represented by a first frustoconical section, followed by a narrower diameter and longer length second frustoconical section 304D. The larger frustoconical section is sized as to, for example, abut the end of a needle holder hub (e.g., see the star shaped hub shown in FIG. 27C) at its border region with section 304D so as to block forward movement of the needle assembly such that the needle extends out through the next, narrower diameter section 304D to a desired extent (while still being easily inserted due to the tapering of each frustoconical section). The first through-hole section 304A opens out at proximal end 299 of the collar, whereas the minimum diameter section 304D opens out at distal end 301 of collar (e.g., the end of the collar closest to the needle tip when present).

As particularly shown in FIG. 101A to 101D, collar 298 is a monolithic solid body but for the through-hole 300 which extends at an incline relative to the central axis CA of extension of collar 298 shown in FIG. 101D. Illustrative embodiments of the invention feature inclines like that described above, inclusive of an inclination that places the needle axis at a 15° relationship with the skin surface in a planar state. Additional incline angles A1 include a range of 15° to 60° and more preferably 40° to 60° inclusive of and each angle point in the noted range and sub-range and at the end points of each range.

With reference back to FIGS. 24A, 27A and 27B and current FIGS. set 101A to 101D, there can be seen that aperture 304A has a diameter that conforms to the other diameter portion of needle assembly 66 (FIG. 24A) such that, upon insertion, there is a slide contact or a stretch and retraction action on the surface of aperture 304A for a snug (compressed, friction contact) retention on the cylindrical base 67 of the needle assembly 66. Furthermore, the intermediate diameter region is designed to frictional/snugly retain the hub portion of a needle (which can take on a variety of shapes in the art with the star pattern ridges like that described above being one example) extending up from the cylindrical base 67 (e.g., the circumferentially spaced ridges extending up from base 67 of needle assembly 66). In so doing, the conical hub is snugly received in the most internal portion of aperture 304C, while the needle shaft is also closely retained. Various other collar cavity designs are featured under the present invention with the goal to provide a good working fit with the needle assembly components as in the hub and needle shaft.

With the arrangement of FIGS. 101A to 101D, featuring collar 298 of an illustrative length of 22 mm (a more suited design for other than fine needles such as the smaller shaft "IV" needles), the user can readily arrange the needle shaft at a desired angle of entry as in a 40° to 60° angle. The user can be, for example, medical personnel or the recipient himself when self-inserting, with the collar 298 and its improved grasping function providing for those with poor finger compression capability or handling dexterity (e.g., arthritis in hands) being better able to manipulate the needle. A scaling up or down in sizes can be implemented if the needle assembly dictates. Collar 298 can be sized to best accommodate the intended instrument received as in having a shorter 7 or 8 mm length which is more appropriate for receipt of very fine needles such as the aforementioned IV needles (e.g., like that shown in FIG. 23A).

FIGS. 102A to 102D illustrate an alternate needle assembly collar 306 which, like the above described collar 298 (with through-hole 42), collar 306 is mountable on the hub of a needle assembly. Collar 306 is particularly suited for use with finer needles such as IV needles and has a different configured cavity 308 that is narrower than the above described through-hole 300, as to better conform to the finer grade needle assembly being inserted therein (there is less distinct shoulder regions from one diameter to the next and more of a conical adjustment in collar 306 as compared to 298). The entry angle for through-hole 308 in collar 306 is, however, similar as that of collar 298 (an entry angle of 60° to 40°). The overall length of collar 306 (e.g., a length of 18 mm) is shorter than its collar 298 counterpart for this embodiment.

FIGS. 103A to 103D illustrates an alternate needle assembly collar 310 that features a non-offset or coincident central axis CA through-hole 312 extending through the main body of collar 310. As with the above described collar embodiments, the collar is formed of a soft to touch elastomeric material such as the aforementioned material such as silicone rubber, TPE, and TPR.

FIGS. 104A to 104D illustrate an alternate needle assembly collar 314 that features a non-offset but altering in diameter central cavity 316. Central cavity 316 shares a common central axis of elongation with collar 314 with the central axis of through-hole 316 extending through the main body of collar 314. Collar 314 is, in this embodiment, a relatively short collar with an illustrative length of 17 mm. Also central cavity 316 has from left to right in FIG. 104B, initial circular cylinder cavity section 318 of the least diameter (suitable as a needle shaft receiving region and visibility covering section of the collar), a first diverging frusto-conical cavity portion 320, a first converging frusto-conical cavity portion 322 with common maximum radius at the interface with cavity portion 320, and a second diverging frusto-conical cavity portion 324 with common minimum radius interfacing with the minimum radius end of cavity portion 322. Second diverging frusto-conical cavity portion 324 also opens out as the end of collar 314 opposite the end from which cavity section 318. Thus, cavity portion 324 provides a sloped inlet for centering the needle hub upon initial insertion and the symmetric frusto-conical combination of cavity portions 320 and 322 provide a nesting region for the hub base of the needle. The central coincident axis of elongation provides for 90° insertions, although through grasping manipulation of the collar the other insertion angles can also be achieved.

FIGS. 105A to 105D illustrates a short (e.g., 11 mm) versatile grasping collar 328 that is suited for syringe cylinder attachment in that it has a smooth central bore dimensioned to slide over and frictionally retain a position on the syringe cylinder as to provide a means for syringe manipulation via the collar's retention on the syringe.

Collar 328 is also suited for other object grasping such as a "pushed puncture" tool (e.g., dental and other medical and non-medical uses) instrument, and as part of a kit associated with such tool or instrument manipulation. As seen in FIGS. 106A, 106B and 107A to 107E, collar 328 forms part of a two component kit suited for single hand securement of such an instrument 329 and desired no-rotation or rotation states, through single handed manipulation. Instrument 329 in this embodiment has a narrow shafted end 330 (two stage 330A, 330B) extending from a (e.g., knurled) handle 332. Although shown as a straight shafted end 330, the shafted end can take on a variety of configuration and functions such as a curved or looping end.

The second part of the kit is shown as base collar 334 of the FIG. 18 configuration that includes one or more slanted long sided projections as best shown in FIGS. 106B and 107B. The kit combination 327, comprised of base collar 334 and distal end collar 328, provides for a secure but readily adjustable grasping arrangement on the object (tool or instrument) shown. That is, the combination provides for smooth rotation of the instrument within the one common holding hand by twisting fingers pinching collar 328 while discontinuing compression at the palm and collar 334 interface. Also since the slanted projection of collar 334 sets against the thicker part of the palm (extending out and to the thumb of a hand) upon compression of the instrument thereagainst such that sleeve portion can be locked into place on the noted palm region with minimum effort, until a rotation of the instrument or forward projection is desired. Also, the FIG. 107D grasping configuration with the projections separated by elongated concavities enables the holder to push the fingers holding collar 328 forward (or retract the fingers back in the opposite direction), while base collar 334 is sufficiently released from compression and allowed to slide along the palm in controlled manner due to the "sliding runners" associated with the projection edges of the collar periphery (FIG. 18 configuration) resting in the palm of the hand. The central cavity of each of the collars can be a straight smooth circular cylindrical cavity that holds on to the body of the instrument (or any desired object for the present combination kit) with sufficient friction retention or can be a different diameter stepped portion matching 330A and 330B diameters in collar 328. The materials for this kit can be similar to those described above for other collars.

FIG. 107E shows a modified kit arrangement with added interface or adapter component 336 that facilitates the connection between the base end of instrument 329 and base collar 334. This adapter 336 can be relied upon to bridge the gap when the cavity of the collar 334 is too large for the instrument intended. Also, the central cavity of collar 328 is preferably designed to preclude passage of the base of the instrument out through the non-receiving end of collar 334. A central cavity such as that shown in FIG. 104D is an illustration of a suitable type cavity in this regard. As for finger holding collar 328, a sufficiently retaining smooth circular cylinder cavity can be utilized or a stepped arrangement that coordinates with a step down (330A and 330B) in the instrument's body as represented by the step down 336 shown in FIG. 107E (noting the collar when formed of an elastomeric material can have high friction contact that might not be desirable where easy relative rotation is desired). If the adapter 336 has a non-circular interior that matches that of the tool shaft's base there can be provided an arrangement designed not to have relative spinning between the tool base and adapter/collar combination. On the other hand the adapter 336 can provide a free spin hub, with the fingertip collar 328 providing spin control. For instance, the adapter can be of a smooth non-compressible material that, when collar 334 is compressed in the hand, there is retained a non-compressed and non-inhibited smooth surface relationship between the interior of adapter 336 and the conforming (narrower) free end section of base 329 of the instrument received therein. If, instead, a rotation lock arrangement is desired a conforming multi-side wall relationship can be utilized as in square projection/square reception (male/female) interrelationship.

With reference to FIGS. 108A to 108D an illustration of the versatility and benefits of the kit combination 227 shown in FIG. 59 is provided. That is, the combination of base mount 221 and collar 225 provides for one handed removal as well as the ability for a person to take a variety of grasping approaches including approaches made available to a person with arthritis that would otherwise be unable to open the bottle.

Figure 108A:
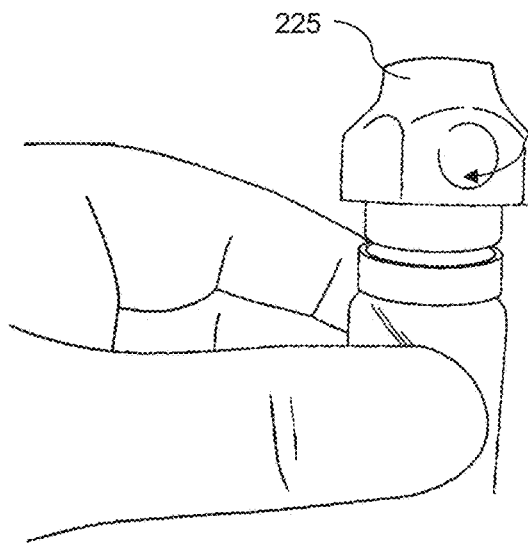

For example, FIG. 108A shows a grasp that a person with two free hands could take as with one hand holding the bottle and pushing down into the mount 221 (not shown in FIG. 108A), while the other hand (not shown) can readily grasp and compress collar 225 (e.g., fingers within the recesses to compress against the underlying threaded cap) and then rotate off. There is an enhanced torque capability here with two components spaced apart (collar and mount) and each able to provide friction resistance in appropriate direction. Depending on the relative surfaces (support surface and bottle surface for example), collar 225 can be utilized without ring band 221 (such as upon a downward pressure on collar 225 followed by a rotation such as any of the below described rotation techniques on collar 225) inclusive of those described below. Collar 225 is also well suited for a two handed approach with one hand holding the bottle or container while the collar is rotated with the other hand.

Figure 108B:
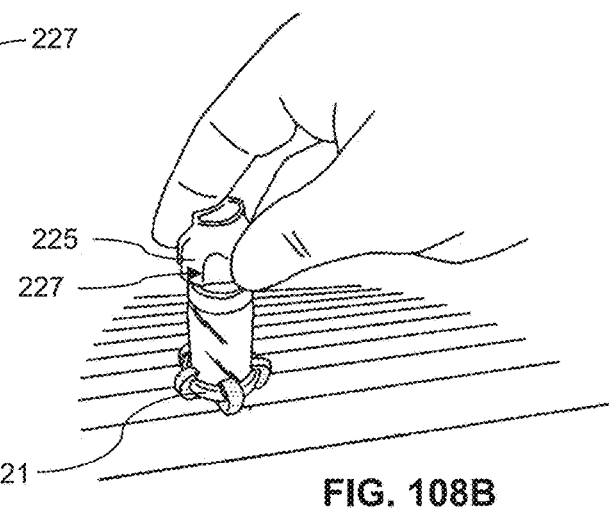
Figure 108C:
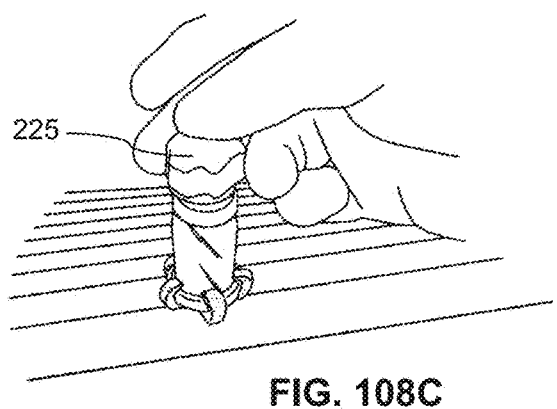
Figure 108D:
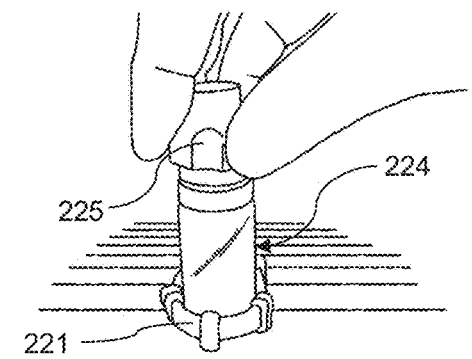

For situations or for personnel not having a second hand free, the present combination 227 allows for one hand cap removal. For example, each of FIGS. 108B, 108C and 108D illustrate single hand bottle removal capability (either relative to a pre-set up combination kit or one where a single hand free user carries out both collar and mount installation before cap removal). In the situation where the person does all stages in entirety, a suitable sized mount is set on a surface whereupon the bottle is slipped into the ribs 27 for friction retention. Once the bottle is mounted, the collar 225 can be readily flexed and inserted onto the bottle cover (in similar fashion to collar attachment to the bulbous head in FIG. 74). Following collar 225 attachment, the bottle cap can be readily removed due to the added grasping power provided by collar 225. That is, as shown in FIG. 108B the user can place one finger (e.g., the thumb) within one of the elongated grooves while a pair of fingers (e.g., the index finger and adjacent long finger) is placed upon the cone portion 190 with at least one finger compressing the free rim defining the open top or extending into the open top. In this way, there is sufficient friction retention as to initiate cap removal of the bottle while the bottle base is pressed down on mount 221 which frictionally precludes bottle rotation in favor of cap rotation.

FIG. 108C shows an alternate gripping approach that a person with arthritis might favor. As seen, the thumb is placed on the top opening with top rim contact and the two interior long fingers form a V-compression relationship on collar 225 with the combination being suitable for vertical press down and circumferential spin off without the need for thumb and adjacent most long finger pinching which can be difficult for some.

FIG. 108D shows yet another approach, where there is a three finger general vertical extension combination (thumb and adjacent most two long fingers) around collar 225, with each of the three fingers nested within a respective one of the concave recesses so that they are abutting a respective adjacent ridge. With the nestled fingers (and their abutment with a ridge that is ahead in the direction of spin off) coupled with an inward radial compression of the three fingers as well as a vertical mount compression force, the cap can be readily spun off.

Figure 108E:
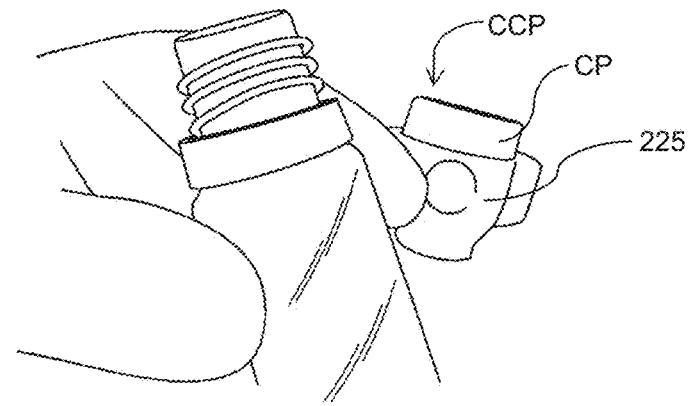

FIG. 108E shows cap and/or collar 225 following removal from the bottle and which can be readily held with the non-bottle holding fingers. FIG. 108E further shows the collar 225 and cap CP in combination (combination CCP) either due to the above described insertion over and flexed retention, or the collar and cap can be a preassembled combination as in an adhered or overmolded relationship, which combination CCP is well suited for a variety of cap usages in addition to medical containers as in solid or fluid retention containers (as in soda bottles (e.g., pressurized or non-pressurized liquid capped containers)).

Figures 108F, 108G:
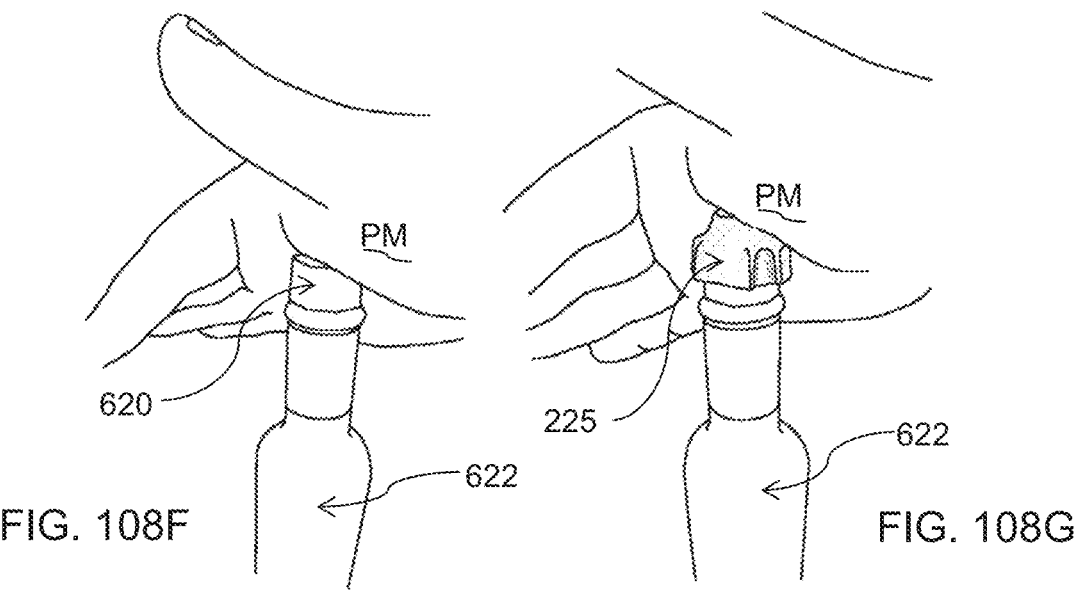
Figure 108H:
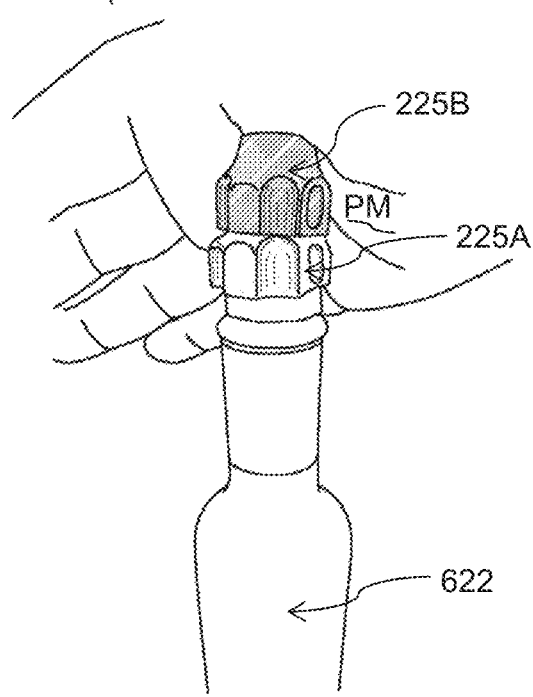

With reference to FIGS. 108F, 108G and 108H, there is illustrated an additional benefit provided by collar 225, in its ability to provide for "fingerless" removal as by one with severe arthritis or one with fingers preoccupied with holding something else or one with liquid covering the cap as with something greasy. This "fingerless" cap removal can be achieved through use of only the inner palm region of one hand as by placing the inner palm region over the multi-faceted exterior surface of the FIG. 10A collar shown in FIG. 108A.

For instance, as shown in FIG. 108F, there can be great difficulty (or an inability) to remove a cap 620 with just the palm of one hand, even with a large surface friction relationship between the base of the container (e.g., bottle, vial, etc.) and the supporting surface. For example even with the high friction benefit of ring support 20 shown in FIG. 3A (not shown in FIG. 108F) at the base of the container 622 in FIG. 108F, the removal of cap 620 can be difficult, if not impossible, to remove due to a variety of potential reasons (e.g., smaller diameter, less configuration contact with flesh of palm, oils on cap, less torque moment, etc.).

As seen by FIG. 108G, however, the collar 225 of the present invention provides for removal in the noted "fingerless" manner through use of the palm PM of one hand with a combination downward and rotative torqueing force application technique. Again, the more friction provided at the base, as in the noted support ring 20, the easier it is to remove the cap (less downward compression required with the palm). Nonetheless, the collar configuration alone can facilitate cap removal as seen in the FIG. 108G relationship between collar 225, the palm of the hand and cap 620 of container 622 wherein there is increased the surface area contact relative to the palm both though an increased diameter contact, added edge and recess contact combinations relative to the recesses and edging of collar 225 in the fleshy portion of the compressing palm, as well as torque enhancement edges that extend further out and provide for better tangential rotational force application with the palm of the hand.

In the cap/collar relationship featured in FIG. 108G, the collar 225 has a lower cavity (e.g., see collars 400 and 404 in FIGS. 127A and 129A as representative examples of collar 225 having a base receiving cavity for the inserted cap) that receives therein, at least a portion (if not all) of cap 620, in a snug reception relationship (friction contact at least upon collar compression). Also, as a cap often is provided with surface ridging, collar 225 preferably has a sufficiently elastomeric material body as to also extend into such ridging at least partially upon compression relationship being established between cap and collar.

In the cap/collar/collar combination 624 in FIG. 108H there is shown another arrangement which features a first collar 225A which receives the cap as in FIG. 108G as well as a second collar 225B which receives with its base cavity the conical top of collar 225A. As further seen in FIG. 108H this combination provides even a greater enlargement of the amount of palm flesh capturing contact within edges and recesses of the respective collar and high torque surface area contact as compared to FIG. 108G. The high torque relationship is retained as the upper collar 225B receives the multi-curved and edges base region of the lower collar 225A as the conical top end of the collar 225A extends deeper into the upper collar 225B (upon palm compression down) and the elastomeric material of the upper collar 225B is received within the recesses of the lower collar 225A as to provide for dual collar torque transfer to the cap 620 received in the lower collar 225A.

Again, while this "fingerless" removal system and technique is preferably carried out with ring support 20 at the base of the container (as also true with the other above described embodiments, featured in FIGS. 108A to 108E) it (they) can also be carried out without a ring if the relative container to support friction relationship allows for sufficient based capture (with a reasonable amount of compression by the user).

FIG. 109 provides a schematic depiction of the collar configuration of FIG. 10A and shows a top plan view of a collar of FIG. 10A configuration with a long length L1 and a width length L2, together with corner "cut outs" (actually preferably molded-in concavities) C1 to C4 each being concave with a general radius value R1. The corner concavity open areas C1 to C4 result in projection surfaces PCS on each of the long length projections (having surfaces 338A and 338B each of peripheral length $L_L$), as well as short length projections (having surfaces 339A and 339B each of peripheral length $L_S$). Also, a slight curvature can also be provided in each of the long and short sides as demarcated with dashed lines in FIG. 109 with the dot-dash lines reflecting the concavities where no material is present. For some of the intended uses of the present invention, as in the FIG. 10A configured collar, the length L1 ranges from, for example, 20 to 40 mm (e.g., 30 mm), the length L2 ranges from 10 mm to 30 mm (e.g., 18 mm), resulting in $L_L$ ranges from 8 mm to 18 mm (e.g., 13 mm), $L_S$ ranges from 4 mm to 10 mm (e.g., 6.5 mm) and radius R1 sufficient to enable finger reception with sufficient ridge interior wall friction contact, with suitable concave edge-to-edge distancing of 5 to 15 mm as in 8 mm (sufficient for enough insertion in most finger sizes), coupled with a radius of 8 mm to 12 mm as in 10.5 mm.

FIGS. set 109A to 109N illustrates a variety of examples of the collar configuration of FIG. 10A, with some of the features of this set being generally thin "height" lengths from forward to rearward planar ends 335, 337 (in which planes the central cavity intersects). For example, the "thinner" versions of the FIG. 10A collar feature lengths of, for example 2 to 13 mm, and more preferably about 6 mm to about 13 mm (the invention includes each value within this range and the end points; with the FIGS. set of 109A to 109N including examples of thickness values of 6, 9 and 11 mm).

Also, examples of different apertures are shown in the figure set of FIGS. 109A to 109N with some of the apertures being through-holes and others being partial thickness apertures (extending for greater than a majority of the thickness). For example, FIGS. 109A and 109B show embodiments where there is a solid region at the top (341 and 343) with the underlying region not shown can include an aperture extending vertically part of the way through the solid body (e.g., a cap type arrangement), or alternatively (or in addition) there is featured a more horizontally oriented hole as in a through hole such as represented by 350H in FIG. 109A (illustrative of, for example, an instrument through hole for a more horizontally oriented instrument which is combined with a more vertical aperture with such a combination shown and described in greater detail below for FIG. 139). FIG. 109B, with its sloped end wall SL is preferably an example of a more horizontal through-hole only 350H embodiment, with the body being otherwise solid. Thus, FIGS. 109A and 109B illustrate side to side cavities as in a horizontal aperture (350H opening with opposite hole end on the other side not shown), with the horizontal aperture having, for example, the above described needle reception cavity configuration with larger inlet opening (not shown). A tapered orientation in the central cavity is also featured. FIG. 109B also shows the sloped surface SL that is well suited for fixed needle insertion incline purposes (e.g., 20°, 40°, 60° angle insertion).

The apertures AP, directly shown in FIGS. 109C to 109N, are shown as being formed at the boundary region with the above and/or below surfaces of the collars or sleeves. Apertures AP preferably have downwardly sloping reception rims 339 to facilitate attachment to an object when so utilized.

The remainder of collars shown includes ones with smaller diameter apertures AP (e.g., 3.8 mm), medium diameter apertures AP (e.g., 6.2 mm to 10 mm) and larger relative diameter apertures AP (>10 to 13 mm and beyond) relative to the peripheral overall sizes featured in FIGS. 109C to 109N.

Figure 109C:
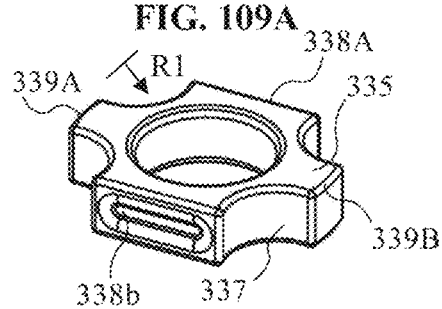
Figure 109D:
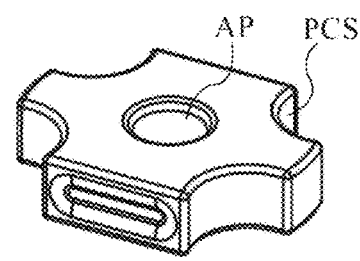
Figure 109E:
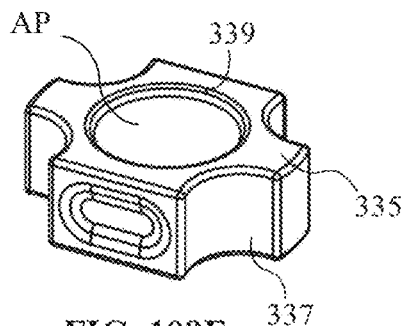
Figure 109F:
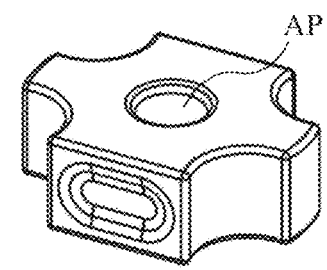
Figure 109G:
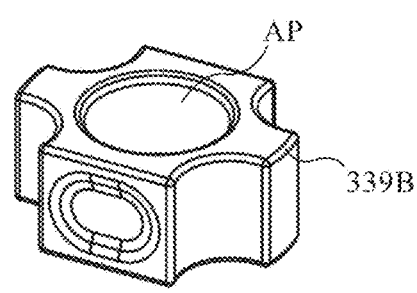
Figure 109H:
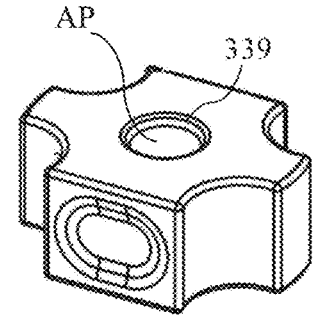

As shown in FIG. 109C, the radius R1 of each concavity, which is generally in the form of a semi-circle, is set at, for example, 8 mm to 15 mm for the collars shown in FIGS. 109A to 109N. In alternate embodiments different radius concavities can be featured, with an object being to provide suitable grasping surfaces PCS wherein fingers can be inserted in the concavities and compression forces applied to the ridges having PCS surfaces to each side. Further, the collar embodiments shown in FIGS. 109A to 109N of the thinner height type, feature apertures of one diameter through the thickness, although alternate embodiments feature varying diameter values along the length of an aperture AP, such as the different stepped and sloped configurations described below for the FIG. 10A type collars of, for example, the longer height mode.

FIGS. sets 110A and 110B; 111A and 111B; 112A and 112B; 113A and 113B; 114A and 114B; 115A and 115B; 116A and 116B; 117A and 117B; 118A and 118B; 119A and 119B; and 120A and 120B show examples of the FIG. 10A collar configuration with thicker or long heights as well as a variety of aperture AP variations. The plan view for collars of FIG. 10A type configuration and associated lengths and widths provided in FIG. 109 are applicable for the above thicker embodiments referenced in this paragraph as well as the earlier referenced medium and thinner versions. The "thicker" embodiments of the present invention are generally greater than 13 mm, as in 14 mm to 50 mm in thickness, with examples presented in the figure set of this paragraph including values of 14 mm, 14.5 mm, 17 mm, 22 mm, 27 mm, 31 mm, 40 mm and 48 mm.

In FIGS. set 110A and 110B collar 362 represents a collar well suited as a connecting collar between a vial and a syringe, with a collar thickness or height of 27 mm. As shown in the cross-section view of FIG. 110B, aperture AP1 has a frusto-conical shape that features a diverging top to bottom shape having an uppermost diameter of 13 mm and a lowermost diameter of 16.5 mm, which makes the top well suited for syringe insertion, and the bottom well suited for vial attachment. FIG. 110A also shows sloping shelf 364 at the top end of each of the long length ridges 366A and 366B.

In FIGS. set 111A and 111B collar 368 represents a collar well suited as a connecting collar between a vial and a syringe, with a collar thickness or height of 27 mm. As shown in the cross-section view of FIG. 111B, aperture AP2 has a frusto-conical shape that features a converging top to bottom shape having an uppermost diameter of 13 mm and a lowermost diameter of 10 mm, which makes the top well suited for syringe insertion, and the bottom well suited for a smaller sized vial attachment.

In FIGS. set 112A and 112B presents two different views of collar 370. Collar 370 represents a collar well suited as a connecting collar between a vial and a syringe, with a collar thickness or height of 48 mm. As shown in the cross-section views of FIGS. 112A and 112B, aperture AP3 has a frusto-conical shape that features a converging top to bottom shape having an uppermost diameter of 17 mm and a lowermost diameter of 9.5 mm which makes the top well suited for syringe insertion, and the bottom well suited for smaller vial attachment.

In FIGS. set 113A and 113B collar 372 represents a collar well suited as a connecting collar between a vial and a smaller diameter syringe, with a collar thickness or height of 17 mm. As shown in the cross-section view of FIG. 113B, aperture AP4 has a frusto-conical shape that features a diverging top to bottom shape having an uppermost diameter of 6 mm and a lowermost diameter of 14.5 mm which makes the top well suited for small diameter syringe insertion, and the bottom well suited for vial attachment.

In FIGS. set 114A and 114B collar 374 represents a collar well suited as a connecting collar between a vial and a smaller diameter syringe, with a collar thickness or height of 17 mm. As shown in the cross-section view of FIG. 114B, aperture AP5 has a frusto-conical shape that features a diverging top to bottom shape having an uppermost diameter of 6 mm and a lowermost diameter of 9 mm, which makes the top well suited for small diameter syringe insertion, and the bottom well suited for smaller vial attachment.

In FIGS. set 115A and 115B collar 376 represents a collar well suited as a connecting collar between a vial and a smaller diameter syringe, with a collar thickness or height of 48 mm. As shown in the cross-section view of FIG. 115B, aperture AP6 has a cylindrical configuration as in one with a constant diameter of 15.5 mm rendering it well suited for medium range syringes and vials or containers having a top head suited for securement within the interior of the cylindrical cavity. In an alternate embodiment the same exterior shaped collar has a frusto-conical shape bore that features a diverging top to bottom shape having an uppermost diameter of 9.5 mm and a lowermost diameter of 15.5 mm which makes the top well suited for an intermediate diameter syringe insertion, and the bottom well suited for vial attachment.

In FIGS. set 116A and 116B collar 378 represents a collar well suited as a connecting collar between a vial and a syringe, with a collar thickness or height of 40 mm. As shown in the cross-section view of FIG. 116B, aperture AP7 is made up of a smaller diameter circular cylindrical bore AP7A that opens out into a larger diameter circular cylindrical bore AP7B. Upper bore AP7A has a 10 mm diameter in the illustrated embodiment, and lower bore AP7B has an 18 mm diameter in this embodiment, which makes the top well suited for small diameter syringe insertion, and the bottom well suited for larger vial attachment. Also the axial length of the top bore is preferably longer than the axial length of the lower bore as in 80% length in the top bore and 20% length in the lower bore or 75% length in the top bore and 25% length in the lower bore and points therebetween these two ranges.

In FIGS. set 117A and 117B collar 380 represents a collar well suited as a connecting collar between a vial and a syringe, with a collar thickness or height of 40 mm. As shown in the cross-section view of FIG. 117B, aperture AP8 is made up of a smaller diameter circular cylindrical bore AP8A that opens out into a larger diameter circular cylindrical bore AP8B. Upper bore AP8A has a 13 mm diameter in the illustrated embodiment, and lower bore AP8B has an 18 mm diameter in this embodiment, which makes the top well suited for intermediate diameter syringe insertion, and the bottom well suited for larger vial attachment. The same bore length ratio ranges as discussed above for FIG. 116B is applicable here.

In FIGS. set 118A and 118B collar 382 represents a collar well suited as a connecting collar between a vial and a syringe, with a collar thickness or height of 40 mm. As shown in the cross-section view of FIG. 118B, aperture AP9 is made up of a smaller diameter circular cylindrical bore AP9A that opens out into a larger diameter circular cylindrical bore AP9B. Upper bore AP9A has a 15.5 mm diameter in the illustrated embodiment, and lower bore AP9B has an 18 mm diameter in this embodiment, which makes the top well suited for intermediate to larger sized diameter syringe insertion, and the bottom well suited for larger vial attachment. The same bore length ratio ranges as discussed above for FIG. 116B is applicable here.

In FIGS. set 119A and 119B collar 384 represents a collar well suited as a connecting collar between a vial and a syringe, with a collar thickness or height of 31 mm. As shown in the cross-section view of FIG. 119B, aperture AP10 is made up of a smaller diameter circular cylindrical bore AP10A that opens out into a larger diameter circular cylindrical bore AP10B. Upper bore AP10A has a 13 mm diameter in the illustrated embodiment, and lower bore AP10B has an 18 mm diameter in this embodiment, which makes the top well suited for intermediate to larger sized diameter syringe insertion, and the bottom well suited for larger vial attachment. An additional feature of upper bore AP10A is that it has equally circumferentially spaced grooves GR providing a plurality of individual bore pads BP extending radially inward and which provided an added degree of flexing and accommodation for an object insertion as in the referenced syringe. In the embodiment described here and above featuring a syringe/vial combination, the collars are also adaptable to connecting different lower and upper components rather than the exemplified syringe and collar combination for connection. Also, the same bore length ratio ranges as discussed above for FIG. 116B is applicable here.

In FIGS. set 120A and 120B collar 386 represents a collar well suited as a connecting collar for a syringe's needle assembly, with a collar thickness or height of 22 mm. As shown in the cross-section view of FIG. 120B, aperture A11 is made up of a series of different diameter regions including a smaller diameter circular cylindrical bore AP11A that opens out into a larger diameter circular stacked, frusto-conical bore arrangement AP11B (similar to that described above for collar 314), followed by an intermediate diameter bore AP11C which in turn opens out into a larger diameter needle reception/insertion bore AP11D.

FIGS. set 121A and 121B shows collar 388 as being similar to that described above for FIGS. set 120A and 120B, but having a smaller diameter upper bore as for a finer diameter needle shaft. The aperture sections AP12A, AP12B, and AP12D share a common shape with that of FIG. 120B, but are designed for smaller needle assembly reception. Also, sloped wall SL provides for a controlled needle insertion angle as in 40° to 60° needle insertion.

FIGS. sets 122A and 122B as well as 123A and 123B (featuring collars 390 and 392), closely conform, respectively, to the above described collars in FIGS. 120A and 121A, but have a thinner body (14 mm rather than 22 mm). Also, sloped surface SP provides for a controlled needle insertion angle as in 15°-30°.

In FIGS. set 124A and 124B collar 394 represents a collar of the FIG. 11 configuration (and thus has the attributes described above for collars of the FIG. 11 configuration) and represents a collar well suited as a connecting collar between a vial and a syringe, with a vertical collar thickness or height of, for example, 10 to 30 mm (e.g., 20 mm). As shown in the cross-section view of FIG. 124B, aperture AP13 is made up of a smaller diameter circular cylindrical bore AP13A (e.g., 3 to 6 mm) that opens out into a larger diameter circular cylindrical bore AP13B (e.g., 8 to 20 mm). In this embodiment, upper bore AP13A has a 6 mm diameter, and lower bore AP13B has a 10 mm diameter, which makes the top well suited for syringe insertion, and the bottom well suited for vial (canister or bottle type) attachment. The bore length for each of the upper and lower bore sections is about equal as in 50/50 or (60/40 to 40/60 as representative relative bore length ratios for bores AP13A and AP13B).

In FIGS. set 125A and 125B collar 396 represents a collar of the FIG. 11 configuration (and thus has the attributes described above for collars of the FIG. 11 configuration) and represents a collar well suited as a connecting collar between a vial and a syringe, with a collar thickness or height of about 20 mm. As shown in the cross-section view of FIG. 125B, aperture AP14 is made up of a smaller diameter circular cylindrical bore AP14A that opens out into a larger diameter circular cylindrical bore AP14B. Upper bore AP14A has, for example, a 6 mm diameter in the illustrated embodiment, and lower bore AP14B has an 18.5 mm diameter (larger vial than FIG. 124A) in this embodiment, which makes the top well suited for syringe insertion, and the bottom well suited for vial (canister or bottle type) attachment. The bore length ratios here conform with that described in FIG. 124A).

In FIGS. set 126A and 126B collar 398 represents a collar of the FIG. 11 configuration (and thus has the attributes described above for collars of the FIG. 11 configuration) and represents a collar well suited as a connecting collar between a vial and a syringe, with a collar thickness or height of about 20 mm. As shown in the cross-section view of FIG. 126B, aperture AP15 is made up of a relatively smaller diameter circular cylindrical bore AP15A that opens out into a relatively larger diameter circular cylindrical bore AP15B. Upper bore AP15A has a "large mouth" 13 mm diameter well suited for syringe with grasping collar as described, for example, in the disclosure for FIGS. 59, 61 and 62 illustrated embodiment, and lower bore AP15B has an 18.7 mm diameter in this embodiment, which makes the top well suited for syringe insertion, and the bottom well suited for vial (canister or bottle type) attachment. The bore length for each of the upper and lower bore sections is about equal as in 50/50 or (60/40 to 40/60 as representative relative bore length rations for bores AP15A and AP15B).

In FIGS. set 127A and 127B collar 400 represents a closed top collar of the FIG. 11 configuration (and thus has the attributes described above for collars of the FIG. 11 configuration) and represents a collar well suited as a connecting collar between a vial and a syringe, with a collar thickness or height of about 20 mm. As shown in the cross-section view of FIG. 127B, aperture AP16 is in the bottom half only while the upper half is solid with the elastomeric material forming the collar of FIG. 11 configuration. This closed top can provide a cap embodiment (e.g., threaded or non-threaded) and can be provided, for example, with a lesser thickness that is more easily suited for needle puncture when access to the vial is desired. The vial is connected to collar 400 by way of aperture AP16 which in this embodiment has an 8 mm diameter. The FIG. 127A embodiment is well suited for smaller vial containers and thus has an upper solid (e.g., needle puncture) area of 8 mm and a larger exterior as in 11.8 mm, with 8.5 mm vial capture recess diameter and a height of 7.5 mm.

In FIGS. set 128A and 128B collar 402 represents an open top/closed bottom collar of the FIG. 11 configuration (and thus has the attributes described above for collars of the FIG. 11 configuration) and represents a collar well suited as an insertion location for the base of an object as in the plunger flange of a syringe, such as shown in FIG. 40. As shown in the cross-section view of FIG. 128B, aperture AP17 is in the upper half only while the lower half is solid (e.g., 2 mm thickness for a 7.5 mm height collar) with the elastomeric material forming the collar of FIG. 11 configuration. The open top has a diameter of, for example, 6 mm.

In FIGS. set 129A and 129B have collar 404 that represents a collar of the FIG. 11 configuration (and thus has the attributes described above for collars of the FIG. 11 configuration) and represents a collar well suited as a connecting collar between a vial and a syringe, with a collar thickness or height of about 18 mm. As shown in the cross-section view of FIG. 129D, aperture AP18 is made up of a smaller diameter circular cylindrical bore AP18A that opens out into a larger diameter circular cylindrical bore AP18B. Upper bore AP18A has a relatively small 2 mm diameter in the illustrated embodiment, and lower bore AP18B has an 18.5 mm diameter in this embodiment, which makes the top well suited for fine gauged needle insertion, and the bottom well suited for vial (canister or bottle type) attachment. The bore length for each of the upper and lower bore sections is about equal as in 50/50 or (60/40 to 40/60 as representative relative bore length ratios for bores AP18A and AP18B). Also, in the above and below described collars featuring what would otherwise be through-holes there can be featured an intermediate membrane as a seal blockage of what would otherwise be a through-hole in that collar (e.g., a intermediate in height positioned sealing membrane inside the collar's interior which is well suited for receiving a puncturing needle without concern of a slip off as might occur with an upper end membrane).

In FIGS. set 129C and 129D collar 406 represents a collar of the FIG. 11 configuration (and thus has the attributes described above for collars of the FIG. 11 configuration) and represents a collar well suited as a connecting collar between a vial and a syringe, with a collar thickness or overall height of 18 mm. As shown in the cross-section view of FIG. 129D, aperture AP19 is made up of a relatively smaller diameter circular cylindrical bore AP19A that opens out into a larger diameter circular cylindrical bore AP19B. Upper bore AP19A has a 10 mm syringe reception diameter in the illustrated embodiment, and lower bore AP19B has an 18.5 mm diameter in this embodiment, which makes the top well suited for syringe insertion, and the bottom well suited for vial (canister or bottle type) attachment. The bore length for each of the upper and lower bore sections is about equal as in 50/50 or (60/40 to 40/60 as representative relative bore length rations for bores AP19A and AP19B).

FIGS. 130A to 130C, provide an example of a combination 200 comprised of collar 202 (of FIG. 11 configuration) and mount 204 (of FIG. 3A configuration) being used to hold a needle cover 206 (following its insertion into the enlarged open end of collar 202 until becoming trapped in the smaller diameter portion of the collar cavity such as the cavity arrangement shown in FIG. 129B). With the needle cover 206 in position as shown in FIG. 130A and the collar frictionally retained on the support surface in a tilted up direction, the user can insert with one hand H the needle assembly 208, as shown in FIG. 130B, such that the needle shaft enters into the enlarged open end of collar 202. Once sufficiently inserted the user, with the same single hand, can then grasp the top end of collar 202, with needle casing extending there-away, and pull it toward the base mount 204 (or simultaneous toward each other or hold the collar and move the mount forward) to achieve a snapped engagement of the needle in the needle cover (as depicted in FIG. 130C).

The FIG. 130B embodiment also illustrates how, with the same single finger downward compression used to enter the needle, there can be achieved separation. That is, with collar 202 pinned to the surface with a single finger, the user can retract the vial with other fingers of that same hand to achieve separation of the needle assembly and collar 207.

FIGS. 131A to 131C show tray 210 with a set of different size mounts (212A and 212B) each of the FIG. 3A configuration. The different size mounts 212A and 212B are nested in a generally common plane arrangement with mount 212A circumferentially exterior, but engaging with the inward mount 212B. Mount 212A has its ridges received in the accommodating recesses 213 formed in aperture 216 of tray 210 (in similar fashion to the arrangement described above for the tray in FIG. 30), while mount 212B has its ribs contacting the annular core of mount 212A and with the ribs being retained between two adjacent ribs of mount 212A so as to be frictionally fixed in position. Thus, by this nesting arrangement, a utensil 218 (a specimen vial), that is too narrow for a good holding fit in collar 212A, but can be securely received in the appropriate sized (good friction retention of the vial without tilt) mount 212B. In this way, the tray has greater functionality and is able to handle a wider variety of sized utensils so as to make it more universal in use.

Also, FIG. 131A reveals a triple nested arrangement of mounts with mounts 214X (largest), 214Y (intermediate diameter), 214Z (smallest) arranged like the nested common plane arrangement shown for mounts 212A and 212B. As seen the diameter of collar 214X is larger than that of 212A making it suited for receipt in a larger aperture provided in tray 210 (see FIG. 39 as an example of different sized tray apertures). Thus, the set of mounts involving mount 214X can be retained in a larger aperture in the tray and still hold a smaller diameter vial as in vial in that are used to adjust the size of a tray aperture (e.g., see FIG. 39 example tray) such that a smaller utensil can fit in a larger aperture.

FIG. 131B shows vial 218 having been inserted into the appropriate sized mount 214Z such that it is frictionally retained in straight up-right position when properly inserted. FIG. 131B also shows that this stable positioning is present while the nested set involving mount 214Z is merely resting on a support surface and not yet inserted into the confining aperture provided by tray 210 (the aperture not shown in the cut-away tray but see again FIG. 39).

FIG. 131C shows the vial 218 in a one hand H transportation position while retained in the nested set involving mount 214Z, and with the user able to pick-up and move the vial without detachment of any of the three mounts in the nested set involving mount 214Z. Also, with the increased diameter base support there is provided a more stable platform with the X-Y-Z rested mounts, such that the vial can be placed on a vibrating surface (mix retention or anti-coagulation vibration means) without fear of knock over and without the need for a special vial holder for designated use with the vibration means.

FIG. 132A to 132C show a double set kit of mounts 220A and 220B (each of the FIG. 3A configuration; and, in this embodiment, of a common size). Mounts 220A and 220B are shown holding together an assemblage of different utensils (inclusive of utensil having additional components of the described embodiments). As seen, mounts 220A and 220B securely hold together a plurality of different sized and shaped components. In the example shown in FIG. 132A, there is held in place two bottles B1 and B2 and two syringes S1 and S2, each extending vertically within the interior of the respective annular collars featured in mounts 220A and 220B, and each held in a radial compression state by the annular collars and ribs of the respective collars. Also, mounts 220A and 220B are arranged in a vertical stack (with separation between the annular rings and ribs in this embodiment). Further, the mounts 220A and 220B have their ribs oriented such that the underling rib surface (see 228 in FIG. 133B below) designed to support the underside of a bottle of mount 220B, represents a downward compression surface in top mount 220A such that the downward force of the ribs in mount 220A work together with the upward force of the ribs in mount 220B. The combination of mounts 220A and 220B provides for ease in transport with one hand H of a user, either by holding one of the more upper regions of the trapped components (132a), holding one or more of the mounts (FIG. 132B); or holding the bottom region of the trapped components in the cup shaped exposed palm (FIG. 132C). Also, the ribs contact different items in the assembly as to help avoid both vertical shifting and rotation shifting within the rings 220A and 220B.

FIGS. 133A to 133D further show the versatility of the mount of FIG. 3A configuration, with FIG. 133A showing mount 222 mounted securely on cap C of bottle B3 (such as a soda bottle). FIGS. 133B and 133D show various cross-sectional views of mount 222. As seen and in similar fashion as to FIG. 3A, mount 222 comprises annular core 224 and a plurality of spaced ribs 226 shown equally spaced about the core. As further seen in FIGS. 133B to 133D, ribs 226 extend radially inward from their exterior to core position (preferably molded together as one unit with the annular core). FIG. 133B illustrates mount 222 in the top in the up position, while FIG. 133D shows the top of mount 222 in the down position. Thus, there is more efficiently seen the utensil bottom contact surface 228 in FIG. 133B which provides a planar surface (in combination with the other mutually common height positioned contact surfaces 228) for contact with the bottom of the utensil (or the top of the utensil depending upon orientation and usage, with FIG. 133A showing the more inwardly extending contact surfaces 228 placed flush on the top surface of the bottle cap as is also the arrangement for mount 220A in FIG. 132A). FIG. 133B further shows ribs 226 as having an edge 226E made possible by the downward extending, exterior curved slope 230 of ribs 226 and the upward and radially outward extending slope leading 232 away from the edge. As noted above, this point edge contact helps stably position in an upright manner utensils while accepting misalignment until radial compression amongst the various ribs settles, and also helps in the development of a radially horizontal compression force once a utensil is positioned.

FIG. 134 shows a view of a pliable mount of FIG. 3A configuration which also shows how the accommodating ribs 226 in combination with the twisting, pliable nature of core 224 are able to accommodate a large tilt due to missed insertion of a medicine dropper bottle, or an actual intended oblique bottle orientation.

FIG. 135A to 135D illustrate various views of turret collar combination 234 comprised of turret collar 236 and an underlying platform 238 (preferably a spin and lock platform to provide a turret rotation function support to collar 234). That is. FIG. 135A shows turret collar combination 234 comprised of a modified collar 236 (generally of the FIG. 10A configuration) that is combined/retained (frictional reception contact holding relationship with rotation possible until a desired lock position is reached) by underlying platform 238. As seen, platform 238 has a saucer like configuration with a disc main body 240 having a circular periphery with smooth, upper contoured outer edging 242. Main body 240 further includes a planar upper surface 244 having at its center a raised mound that is generally semi-spherical turret mound 246. As seen in FIG. 135B, turret mound 246 is designed for extension into a conforming recess 250 conveniently provided as part of a through-hole aperture APT that extends through the thickness of the collar. Platform 238 further includes a preferably channeled (preferably a plurality of concentric channels formed in the undersurface of platform 238 as represented by channels 252 shown in cross-section). Also, platform 238 is preferably a soft, pliable material such as silicone rubber as to provide for frictional position retainment as to provide a stable turret support and also for accommodating variations in body surface when used as a medical instrument. Mounting of the platform can also be made even more position secure via use of temporary adhesive as used in EKG pads such as those with removable non-adhesive cover sheeting). Suitable dimensions for platforms 238 includes a diameter of 15 to 30 mm as in 20 mm, a thickness plate of 1 mm to 4 mm as in 1.7 mm, a bulb 246 height of 3 to 7 mm (as in 4 mm) and a bulb diameter of 4 to 8 mm as in 6.3 mm.

Collar 236 is preferably provided with a sloped (long collar ridge side to opposing long collar ride side) through-hole 254 that is conical in shape and shown as slanting downward from its larger insertion end 254A to its narrower exit end 254B lying at the lower extremity of finger depression recess 256. Also, through-hole 254 also is bisected by aperture AP such that it opens at two interior points into aperture APT. In this way porting is provided vertically in aperture APT and also through the long length of collar 236 with aperture APT in communication with the through-hole. Some non-limiting illustrative dimensions for components of collar 236 include a thickness height of 10 to 15 mm as in 11 mm, an aperture 258 oval of 2 mm height, 5 mm length, and a maximum length (short ridge to short ridge) of about 20 to 30 mm (e.g., 26.2 mm).

Collar 236 is provided with additional porting via an oblong (e.g., oval) passageway 258 with open end 258A shown in FIG. 135A (and a full cross-sectional view provided in FIG. 136C which is described below). Passageway 258 extends the full length from short-ridge side to short-ridge side of the main body of collar 236 (see PR as short ridge example in FIG. 135D) and also bisects with the aperture APT such that each extension opens into the central aperture APT as also depicted in FIG. 136A. Passageway 258 is preferably arranged to pass in the lower portion of the main body of collar 236 (the lower quarter relative to the height of the collar), but is preferably not blocked off by the bulbous turret mound 246. In this way the smooth contour of the top of mound 246 can help in the feeding of elongated instruments through the desired porting including passageway 258 which opens into aperture APT in that region.

FIGS. 135E and 135F illustrate a modified turret collar 260 having similar features as described above for turret collar 236, but rather than a conical through-hole that is tilted, there is provided through-hole 262 that has a common diameter along its entire length (each extension thereof extending to opposite sides of aperture APT which is in communication with through hole 262) and is arranged in horizontal fashion. That is, opening 262A is at the same height level as opening 262B, with the latter opening out at the center of finger depression recess 256 rather than at its lower edge in the earlier embodiment. FIG. 135F also illustrates the turret recess 250 lying just below and in communication with passageway 258.

Figures 135G, 135H:
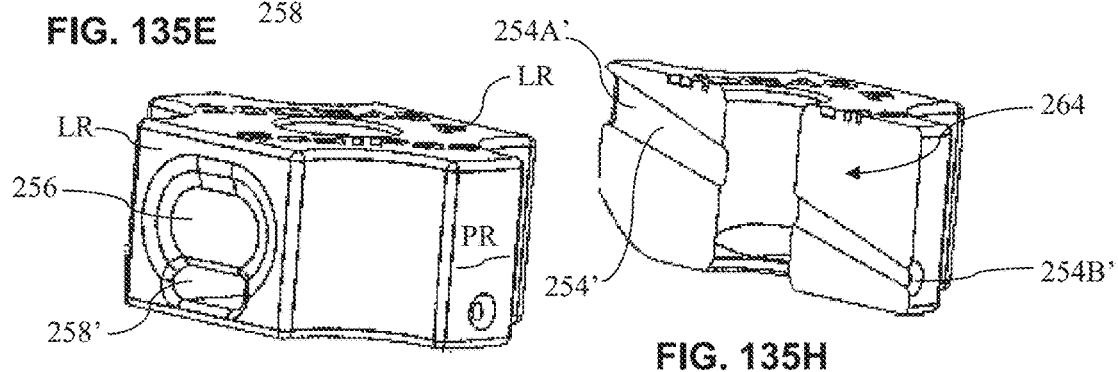

FIGS. 135G and 135H show a modified embodiment of the turret collar described above. In this embodiment turret collar 264 includes generally the same collar configuration but features the lower passageway 258' as passing not between the opposing short length ridges PR but between the opposing long side ridges LR. Thus, the oblong opening of passageway 258 opens out at the lower region of finger depression recess 256. Also, through-hole 254' is similar to through-hole 254 described above (sloped and conical), but instead extends through the collar body and aperture APT from short side ridge PR to its opposing ridge (PR). As seen from FIG. 135H, the slope results in opening 254B' being in the lower quarter of collar body height and the enlarged opening 254A' in the upper quarter of height of collar 264.

Figures 135I, 135J:
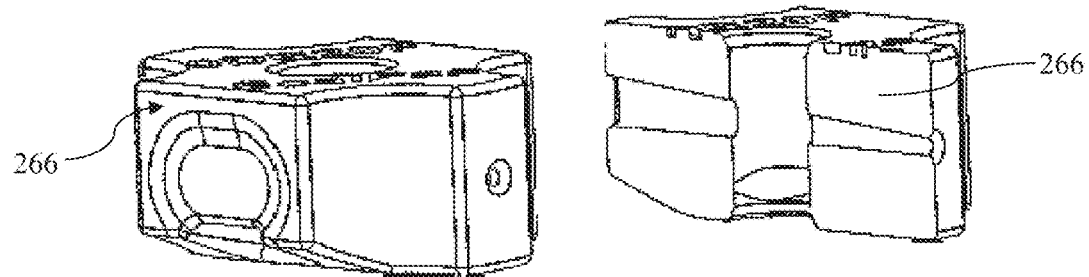

FIGS. 135I and 135J show turret collar 266 which has the same configuration as that of turret collar 264 but for rather than a tilting through-hole such as through-hole 254' in FIG. 135H it has a horizontal through-hole 268 (while also retaining the conical configuration featured in through-hole 254', however).

FIG. 136A to 136C illustrate collar 236 of FIG. 135A removed from its mount, with FIG. 136A showing a perspective view of the collar with an angled thin tool (e.g., a flexible or non-flexible tool as in one <3 mm in diameter and preferably less than 1 mm) inserted into through-hole 254, as in through opening 254A and down through to the opposite opening 254B whereupon the tool extends to both sides of collar 235 (e.g., a tool as in a needle, a sheath (e.g., a catheter sheath), a wire, a fluid tube, etc.). While turret collar 236 is mentioned for receipt of insert tooling or utensils, depending on the circumstances, any of the other above described turret collars can be utilized for insertion(s) of such tools or utensils.

FIG. 136B shows a front elevational view of that which is shown in FIGS. 136A, and 136C shows a cross-sectional view along cross-section A-A in FIG. 136B (which represents a horizontal bisect of passageway 258). As further seen from FIG. 136B inserted tool IT can extend above and below the respective top plane and bottom planes TP and BP of collar 236 (with the lower one potentially illustrating a below skin entry point).

FIG. 137 shows another embodiment of a turret collar 270 which is similar to collar 236 but for a different through-hole 272 that replaces through-hole 254 in collar 236. That is, through-hole 272 has an oval or oblong shape like passageway 258, but has its major diameter extending vertically rather than horizontally like for passageway 258 (e.g., 1 mm minor diameter and 3 mm major diameter). There is still retained a downward slope as seen by the IT ends being at different height in FIG. 137. As shown in the enlarged detail in FIG. 137A, through-hole opening 272A has a smooth lead in edge 274 which defines the IT insertion hole 276. The minor axis diameter for this insertion hole can be sized as to provide some frictional resistance from upward or downward adjustment in the IT relative to the maximum diameter direction for the oval shaped opening. In FIGS. 137 and 137A there is shown the tool IT in a shallow angle orientation wherein the IT tool contacts the bottom of the insertion opening 272 border.

FIGS. 138 and 138A depict the same turret collar 270 as in FIG. 137, but has the IT tool adjusted up to a maximum angle such that tool IT abuts the upper extremity of the border defining through-hole opening 272A.

FIG. 139 shows the same view as FIG. 136A, but show the utensil as being a combination utensil ITC, having IT as described above as a hollow sheath initially inserted through the collar plus a feed though instrument ITI. Such an arrangement can represent a useful relationship in a variety of fields both medical and non-medical, but is particularly useful in the medical field as once the turret collar is mounted on its platform after the platform is placed in position (or a simultaneous mounting) and the ITC placed, it can be held in place or rotated to a different desired orientation in turret fashion. Additionally, sheath IT will retain its position while the interior instrument ITI can be threaded in one direction or the other. Examples including sheathed wiring assemblies, catheter sheath and insert combinations, fiber optics and line-up sheathing, etc.

FIG. 140 shows the arrangement of FIG. 139 rotated so that the inlet side of opening 272A is more visible rather than the outlet side 272B of FIG. 139.

FIG. 141 shows a similar view as that of FIG. 140 but with a position retainer insert 278 added. In this way there is added assurance of the desired upward positioned tool IT is retained relative to collar 272. FIGS. 141A to 141C show different variants of the position retainer insert 278 designed to hold the tool at a desired orientation within the receiving oblong or oval shaped opening provided in the collar for tool positioning flexibility. Also, the base of insert 278 is provided with a hole for insertion of a tool facilitating removal.

FIGS. 142A and 142B show different views of the combination 234 comprising a turret collar and swivel mount as shown in FIG. 136A, but with a modified turret collar (236') featuring a pair of clamp down wings 280A and 280B with wing platforms extending out of short side ridges PR at their base and supporting clamps 282A and 282B within reception grooves/ridging 281A and 281B. Clamp down wings provide a useful location for securement of the turret collar in place once the rotation position of the turret collar relative to the base represented by spin platform 238 is chosen. For example, clamp down wings can be, for example, stapled in position to the recipient support surface such as a patient. Also, clamp down wings can be threaded into an existing aperture such as 258. The clamp down wings can also help in the retention relationship between dome 246 and the recovery aperture of the tunnel collar supported thereon.

FIG. 143 shows a swivel mounted collar 270 similar to FIG. 137 with an illustration of the numerous porting provided by passageways 258 and through-hole 272 and aperture APT communicating with all porting. Hence, a plurality of different utensils or one utensil having a plurality of different offshoots (e.g., instrument wiring or tubing) can be received therein and directed in a desired direction and slope (up or down) or horizontally. In FIG. 143 a series of wires are showing with five different exit points illustrated.

FIGS. 144 and 144A illustrate collar 270 of FIG. 137 further comprising plug device 284 just prior to insertion, with the plug device comprised of a base body 286 with a central aperture, a pin top 288 that is retained secured to base body 286 via tether 290. As shown, insertion of pin portion 287 of pin top 288 places its cap 289 in a closed state relative to the central aperture in the base body 286. As further shown in FIG. 144, pin top 288 has a central aperture CA, which can provide an insertion opening for a smaller instrument (a though-hole through the entire plug, for example) or a threading guide for an item retained in collar 270. The plug 284 also can close off and pin, if desired, instruments or tooling placed in aperture APT or though the various portings described above. FIG. 144A shows the collar and plug arrangement shown in FIG. 144 but from a side view. FIG. 144 also shows porting IP in the base body of the plug that can be used for threading of a thin instrument such as a flexible sheath, whereupon plug downward movement and/or rotation results in a crimping or braking function and/or a fluid blockage mode if fluid is passing through instrument IT.

FIGS. 144B to 144D show different length plug devices 284 (284' and 284") each with integrated pin caps that can be inserted to seal off the plug itself received by the collar. As shown, the base body can be adjusted in height so as to extend into aperture APT to a greater or lesser extent.

FIGS. 145 and 145A show the same collar 270 and plug device 284 featured in FIG. 144, but with the plug device 184 inserted into the aperture APT of collar 270 in sealing fashion. FIG. 145 also shows optional segregated porting XX that can be added if additional instruments are to be supported (e.g., those extending in generally common direction at least initially).

FIG. 146 shows a top plan view of another collar embodiment of the present invention featuring "split" collar 500 having the same general configuration as the collar outline shown in FIG. 109. With reference to FIG. 146 and the demarcations provided in FIG. 109, there can be seen that collar 500 has the same configuration as that presented in FIG. 109 and the solid body version of the collar shown in FIG. 109B. Thus, there is shown in FIG. 146 inner body D3 having the illustrated (top) surface, and out from which extends (in the Y-axis direction) the narrower width, but more radially elongated, "bow-tie" projections BT1 and BT2 with exposed end surfaces 339A and 339B. Along the X-axis there can be seen the wider parallel sides 338A and 338B, of the less radially extending projections PR1 and PR2.

There can also be seen in FIG. 146 the formation of reception slit 502 extending along the central X-axis for the full x-axis length of collar 500 (i.e., reception slit 502 extends to and fully between each of exposed surfaces 338A and 338B). Reception slit 502 is also shown as having a thinner reception slit width section 504 (e.g., a section with side walls that are split, but in contact with one another until separated as by flexing out away from each other) as well as, preferably, a wider slit section 506, with the latter being helpful in facilitating initial positioning and alignment of an instrument intended for receipt within the interior central region where slit 502 ends and through-hole 508 is provided (FIG. 147). Thus, slit 502 extends to an intermediate region in the Z-axis direction ("Z" FIG. 147) as in central point (50% of overall height) or a height that is 50+/−20% relative to the Z-axis height of collar 500 per the illustrated frame of reference. Wider slit section 506 is also shown as being less in X-axis length than thinner reception slit section 504, as in a 25 to 40% range of the overall slit length (e.g., an X-axis length that puts the interior end of the wider slit section 506 generally aligned with the deepest cut out points for the adjacent corner cut outs C1 and C2 shown).

With reference to FIG. 146 and the common shaped collar in FIG. 109B there can be seen that the projection PR2 has sloped surface SL that slopes outward away from border line 507 (extending lengthwise in the Y-axis direction) to the peripheral wall surface 338B. As further shown in FIG. 146, wider slit section 506 initiates in diverging fashion from its border point BP with thinner slit section 504. That is, there is a divergence applicable to wider slit walls 512A and 512B that diverge outward as they extend along the X-axis away from thinner slit section 504. Walls 512A and 512B also diverge in a direction upward from the deepest region of wider slit section within the body of collar 500 out to the surface of inner body D3. That is, there is a divergence in regard to the extension of walls 512A and 512B in the X-axis direction away from border point BP where those walls converge with the walls of the thinner section in a smooth contour fashion. As also seen in FIG. 146 the border point BP is just inward (e.g., within 5 mm) of border line 507. The other divergence in the wider slit section 506 is along the Z axis direction where the wider slit is narrowest at the border region with hole 508 and most spread apart in its natural state at the border surface region with the exposed (top in FIG. 146) surface of inner body D3.

Under many uses of the present invention the entire collar 500 is formed of a single material as in any of the aforementioned flexible polymers such as the aforementioned silicone elastomer (e.g., one having a Shore A hardness value in the previous noted ranges of 20 to 80 as in 30-40). The material also is preferably a material that can be sterilized as in medical grade silicone elastomer (or silicone rubber as sometimes referred to). Alternatively, the collar can be disposable which provides greater options as to the material that can be relied upon. As described in greater detail below, in view of the preferred flex and return characteristic of the present invention, the flexible material is one that avoids splitting despite numerous flexing outward and inward cycles (e.g., a minimum of 100's of cycles possible before interior body splitting at the pivot point, for example). Also, a latex elastomer is also featured under the present invention, although in recognition of some allergic reactions to Latex, a Latex free elastomer material is also featured.

To appreciate this flexing characteristic in collar 500 reference is made to the before and after flexing depictions in FIGS. 147 and 148. That is, FIG. 147 shows a side view of the collar shown in FIG. 146 being held in a non-flexed state; while FIG. 148 shows a side view of the collar 500 shown in FIG. 146 being held in a flexed state. As shown in FIG. 147, reception slit 502 extends down from the upper surface of inner body D3 and extends to a central region of hole 508. Hole 508 is shown as a through-hole that is generally Z-axis centrally positioned and extends in the X-axis direction together with slit 502 (preferably completely between the two exposed side surfaces 338A and 338B). A variety of through-hole configurations are featured under embodiments of the present invention, with hole 508 in FIG. 147 shown as a generally small diameter (e.g., a diameter range of 0.5 mm to 1.5 mm). In addition to being generally centered along the Z-axis height, hole 508 is also shown as being generally centrally positioned relative to the Y-axis direction extending surface 338A. This arrangement helps avoid splitting of the collar upon flexing and also provides mutually extending "wing" contact surfaces in the flexed down bow-tie projection BT1 and BT2.

FIG. 148 shows reception slit 502 (both the thinner slit section 504 and wider slit section 506) in a flexed outward state, which is a state suitable for receiving therebetween an instrument (such as instruments of the type described below). As also seen in FIG. 148 (wherein a user's fingers are shown as expanding the slit, although the slit can be instrument opened instead as featured below), the non-slit, lower surface 510 of the inner body assumes a concave shape as to present potential surface contact corner edges 510A and 510B provided at the underside of projections BT1 and BT2. Also, hole 508 can be seen as representing the pivot point for the two side walls forming slit 502 as they move apart from each other as to form a wider gap in the region of slit 502.

With reference to FIG. 149 and the perspective view of FIGS. 150 and 151 (as well as the bottom and side views 152 to 154), there can be seen that the tapered wall surface SL has a relatively shallow taper referenced by angle XT1 in FIG. 154, with a suitable range for many embodiments of the invention being of 12° to 60°.

Further, the wider gap region 506 of slit 502 (as shown in FIGS. 146 and 149) has a V-shaped notch region 512 formed by side wall regions 512A and 512B that extend down to a bottom vertex region 512C (FIG. 146). The wider slit section 506 is also inclusive of a lower region that communicates at vertex region 512C with the hole 508. Wall regions 512A and 512B extend from counterpart contacting side walls 504A and 504B (FIG. 148) forming thinner slit section 504 of which the noted lower region extends in respective common plane fashion and thus are shown in flush contact when not flexed apart.

The arrangement of the tapered wall surface 505 and V-shaped notch region in the wider slit section facilitates initial positioning of an instrument for insertion into collar 500. FIG. 149 shows an example of instrument 514 which is shown in this embodiment as an elongated sharpened tip object as in a needle shaft forming part of the below described needle assembly, although alternate instrument embodiments are featured in the present invention inclusive of other sharpened tip instruments, catheter instruments, as well as non-medical field instruments some of which are described below. FIG. 149 shows instrument 514 having a proximal region nested within the V-shaped notch region with an upward tilt generally conforming to angle XT1 of sloped surface SL. Upon further compression in the down Z-axis direction needle shaft 514 is consumed by the slit 502 as it slightly expands the slit walls apart to the diameter of the shaft in contact with the side walls of the slit 500. The interface between the V-shaped notch and the narrower slit section 504 ensures that upon downward compression the shaft extends down until it is safely received at the lower region of the slit and within the hole 508 (if appropriately sized relative to the instrument, receiving the instrument therein). FIG. 150 shows that hole 508 is appropriately sized in this embodiment as to safely receive all, or essentially all, of the entirety of the shaft diameter relative to the portion of the needle shaft received in collar 500, with the remainder shown extending out along the X-axis to its free, sharp distal end. In alternate embodiments, as in a collar being utilized with a hypodermic syringe needle assembly, the hub of the needle assembly is nestled between the widened slit side walls of slit 502 and still visibly exposed due to the relative instrument diameter and opened slit width spacing (FIG. 155 below shows an example of this relationship relative to a different collar embodiment).

The slit 502 can be formed in the collar 500 at the time of formation, as in a spacer insert in a flexible plastic injection molding of collar 500, or slit 502 can be later formed as in with a cutting of a wall with a suitable cutter or cutter instruments preferably capable of forming the two sectioned slit (different slit sections 504 and 506), although embodiments of the invention include a slit with a single configuration as in with slit formation 504 over the entirety of slit 502 (with reliance on a body periphery end edge cut location for a preferred initiation point which can be seen as less desirable than the more Z-axis downward compression of a stable, V-notched positioned instrument as provided by walls 512A and 512B of wider reception slit 506 (preferably also in conjunction with the downward tapered wall SL)). The slit depth and relative thickness height of the collar having the slit formed therein are designed relative to the collar material (e.g., how flexible without splitting) to achieve the desired insertion and securement relationship with or without added closing compression forces.

The hole 508 can also be formed in the collar 500 at the time of formation, as in a spacer insert in a flexible plastic injection molding of collar 500, or hole 508 can be later formed as in with a drill or the like.

FIGS. 150 and 151 provide a few examples as to how collar 500 can be readily grabbed with instrument 512 securely held and with the fingers well away from any sharp edges. That is, after safe insertion (see FIG. 149), an operator can readily slide fingers into the cavities between the projections and/or onto any of the four projections as in a pinching of opposing projection pairs. For example, either of the grasping states in FIGS. 150 and 151 can be utilized to enable ready operation to a desired angle of insertion, while retaining working security from needle pricks, etc. Further the Z-axis thickness of the collar 502 with an intermediate positioned instrument outward extension location on the distal working end also helps keep the instrument off from a potentially contaminated under surface until desired use.

In FIG. 150 there can be seen a four finger grasping of the combination of collar 500 and the fully received instrument 514 (the combination of collar 500 and instrument 514 being referred to as "instrument assembly" 511 hereafter). The four fingers involved in grasping instrument assembly 511 in FIG. 150 include the thumb, index finger, middle finger, and adjacent digit (i.e., all but the pinky finger are involved in direct collar contact) provide a stable grasping relationship, but also one that can be readily adjusted including a slide forward and back along a surface motion (note the manner in which edges of corner cut outs and peripheral edges adjacent the projection sides can provide a dig in relationship to ensure non-slippage and firm gripping in the flesh of the hand's fingers as noted, while flexed edging 510A and 510B can also provide for a sleigh-runner set slide capability once collar 500 is put into motion.

FIG. 150 also shows the smooth, solid or uninterrupted bottom surface 516 of collar 500 having a planar base section 518 (parallel with the non-tapered portion of the opposite "top" side of collar 500) as well as a tapered slide section 520 extending up from its base at the planar base section 518 and out and upward to the "underside" edge of surface 338A (in which surface the outlet of hole 508 is found, and out from which extends instrument 514). The tapered slide section further promotes the sleigh-ride capability when controlled forward and/or backward movement along the X-axis is desired. Tapered slide section 520 extends upward at an angle XT2 (FIG. 154) which is shown as being of a higher slope angle than the above described tapered wall SL. Thus, angle XT2>XT1 as in XT2/XT1 being in a ratio of 1.0 to 1.5.

FIG. 151 shows a two finger pinch holding of collar 500 via pressing inward on the surfaces 339A and 339B as to push bow-tie projections BT1, BT2 toward the center and which acts, at the same time, to place instrument 512 under compression as well as to achieve the greatest stability at the time of compression at the ends of surfaces, as during a time of needle tip insertion and needle plunging, while an operator can then release the pinch the grip to conserve energy and avoid finger strain, while instrument 512 is still in stable, nested position relative to receiving collar 500. Also, in the case of a needle assembly as in an IV needle, collar 500 can be taped or otherwise fixed in position as to retain the inserted needle in a desired orientation, with the aforementioned end edges 510A and 510B of the concave surface 510 providing a skin surface depression reception region that is both relatively comfortable and well suited for avoiding slippage of the instrument assembly once held down, as by taping.

Angle XT2 can be varied to suit the environment of use, with FIGS. 153 and 154 showing an example of tapered slide surface being flush with a surface such as a patient's skin surface 522 (e.g., an arm surface presented as an example). This arrangement provides for a smooth sliding forward (or back) as represented in FIGS. 153 and 154, as, for example, any skin build up in front of collar 500 is smoothed out by the tapered slide surface 520 as the collar rides along surface 522. While able to slide smoothly along the X-axis, as noted above, the peripheral edging PE as represented (in the bottom view of collar 500 in FIG. 152) by the lower edging of the corner cut out bottom surface and the lower region edging for each wall surface (339A and 338A) bites into the skin surface as to preclude rotation about the Z-axis. FIGS. 153 and 154 further show that the tilt angle of tapered slide surface places the needle shaft at a desirable angle for insertion (as in angle XT3 being in a range the above described needle angle orientation. Reference is also made to the above described advantages in such an angle of insertion of a needle shaft. FIG. 153 is shown with needle assembly 512A of instrument 512 prior to a syringe cylinder being locked in place and is illustrative of an additional needle assembly placement, as in a wrist region IV needle placement, and shows the aforementioned needle shaft positioned at a desired depth and with the needle assembly hub 512B defining locking means as in a LUER lock attachment featuring a conical reception hub.

FIG. 154 shows an assembly state involving syringe cylinder SY having been locked in place (LUER lock counterpart) to achieve a medicament source for syringe injection via a push down of an associated plunger (not shown in FIG. 154).

FIG. 155 shows a top plan view of instrument assembly 511 showing the top surface of collar 500 in a convex orientation with the opposite concave surface 510 (FIG. 148) on the opposite side (with FIG. 148 showing a similar concave flexing for collar 500). Opposite surface 510 thus has its outermost edging 510A and 510B (FIG. 148) arranged as to be in first and deepest contact in the skin surface which provides the benefit of non-rotation as well as preclusion form easy Y-axis slippage, until so desired upon, for example, finger lift out. This being particularly true as when there is a taping or other hold down means utilized as is often done, such as when an IV needle is positioned for multiple potential insertion of different syringes and feeding lines, etc. In addition, FIG. 155 also shows how for this embodiment there is the V-shaped cut out of slit 502 receiving the larger end of the truncated needle hub 512B with the border region providing a tight connection due to the highest level of tensioning of the side walls of slit 502, with the thinner region of the needle assembly hub being placed under less compression such that there is provided an option of a degree of finger forced trunnion minor rotation of the needle assembly which is still retained stably and at a desired insertion angle via tapered surface 520.

Additional retention means (to preclude an inadvertent lift out of a nested instrument) is inclusive of added retainers such as independent or integrated type retainers (e.g., velcro tabs (to opposite sides)), as well as other integrated retainer means as in a wedge and recess combination that represents means for further preventing instrument removal back out of the receiving slit (although the preferred materials are sufficient in many environments as to avoid the need for added instrument slit retention means).

FIG. 155 also illustrates an additional advantageous clamping feature of an embodiment of the present invention. That is, FIG. 155 shows an arching and splitting of section 338A that results in a stable surface contact that includes a hugging of the surface based on the arched wings sloping down away from the split central region. With illustrated embodiment showing needle hub 512B as well as needle shaft 512A nested within the split, the configuration provides for a taping to the surface over needle hub 512B (made secure by taping surface 500 and the needle hub received therein). Thus, for example, when 512B is jarred or shaken, the shock absorbing element or dampening means provided by the noted split wing configuration absorbs the shock. Thus, in this case featuring a needle as the instrument, the needle adjustment is damped which is considered to help prevent erosion of the vein.

FIG. 156 shows a receiving (or proximal) end view of a modified, "split" collar 524 that is generally of the type of collar shown in FIG. 120A. With reference to similar reference numbering for generally common features amongst these embodiments, there can be seen slit 502 with the larger slit width section 506 defined by the V-shaped gap walls 512A and 512B that extend to the initiation of thinner width section 504 (FIG. 159). Reception slit 502 is shown as being formed in the central region of the curvature defining corner cut out C3 as opposed to the earlier collar 500 embodiment wherein the slit was formed in one of the side walls. FIG. 156 further shows that slit 502 extends radially inward until opening into hole 508 (with the hole in this case having a minor taper in the X-axis direction with the larger opening 508E being at the receiving end 526 and the smaller diameter end 508I at the distal or working end 528). Hole 508 is also show as being at a central location from a Z-axis height standpoint as well as from a Y-axis width standpoint.

With reference to FIG. 157 to FIG. 159, there can be seen an insertion sequence for instrument 530, which is shown for this embodiment as being a curved end of a rod such as a catheter or other medical conduit or wire, or a non-medical instrument such as an electrical wire or some other conduit or tube either flexible or rigid. FIG. 157 shows a perspective view of the "split" collar 524 embodiment shown in FIG. 156 just prior to receipt of an instrument 530 (with the instrument being generally aligned in parallel with slit 502 and above it). The presence of slit 502 in the deepest portion of corner cut-out C3 provides assistance in initial guidance of instrument 530, as the curved side walls of corner cut-out C3 guide any misdirected insertion into the proper central region where the slit is located. The instrument 530 shown is illustrative of a variety of different types of instruments well-suited for use with the various collar embodiments described in the present application. For example, the aforementioned probe, a cutting instrument inclusive of a laser head, a precision drilling instrument, a catheter, stylet, and non-medical related instruments, etc.

The insertion of instrument 530 into larger slit width section 506 between walls 512A and 512B in section C3 can be achieved in an embodiment of a method of assembly under the present invention (not shown) by placing the collar 524 in a vertical position where the bottom arch C2 and the top arch C3 corresponds to a 180° top to bottom vertical direction, with the stability of arch C2 arching or spreading to receive a stable pressure, non-rotating element as insertion of 530 is single-handedly accomplished. That is, rather than the orientation shown in FIG. 156, the collar 524 is rotated clockwise until corner cut out C3 and slit 502 are each aligned along a vertical plane extending flush with the slit 502, which further places the X-axis elongated edging defining the outermost edges of corner cut out C2 in flexing surface contact with a supporting surface below. This orientation facilitates one hand insertion of an instrument in similar fashion to the insertion technique described for the alternate embodiment show in FIG. 149. FIG. 159 illustrates an additional alternative relationship for inserting an instrument that, depending on the instrument and collar material involved, can be carried out with only one hand or with two hands (rather than relying on surface friction to retain the collar in position, a second hand is used to hold the collar as the instrument is inserted).

FIG. 158 shows the same perspective view of the "split" collar embodiment shown in FIG. 157, but with the instrument 530 having just been pushed down by a single finger (with or without other fingers or palm region contact of the same hand with other regions of the instrument being inserted) and in the initial stages of reception within the collar 524. That is, the instrument, via its guidance initially within the larger gap region 506 of the slot 502, is shown as further expanding apart the side walls defining thinner reception slit width section 504 as the instrument 530 is frictionally slid therebetween.

FIG. 159 shows a working (or distal) end perspective view of the "split" collar 524 shown in FIG. 158 with the instrument having just been fully received in the collar and the walls defining the thin reception slit section 504 having closed fully back up as the diameter of the portion of the instrument 530 received is generally in conformance with the smaller diameter section 508I of hole 508, while the larger diameter section having edge 508E is sized as to be larger than the instrument (when the instrument has a common width with that received in the smaller diameter section). In alternate embodiments the receiving hole 508 can be of a larger diameter and/or the instruments of a smaller diameter than shown as to provide for a group of instruments inclusive of wires or cords to provide an organizing means. In use, collar 502 can be grasped in similar fashion as described above inclusive of a two finger pinch grasp as at the bow-tie projections BT1 and BT2 wherein there is provided a further clamping force on the received portion of the instrument 530. FIG. 157 also shows an optional sloped entrance slit ring 508R provided at one or both of the ends of collar (an interior directed sloped surface to facilitate axial insertion if so utilized or, in an alternate, embodiment an exterior directed slit-ring around the entrance). In still a further embodiment, smaller diameter section 5081 is smaller in diameter than the instrument resulting in a 502 slit spacing gap upon the instrument being fully inserted. Under such a relationship there is preferably still sufficient peripheral coverage or contact with the upper half portion of the instrument as to preclude ready pull out of the instrument from its final resting position. Still further, the interior structure for hole 508 may have varying diameter sections as by conical and/or stepped wall sections with FIGS. 120B, 122A, 122B, etc. of the present application being illustrated.

FIG. 160 shows a receiving end perspective (in use) of "split" collar 532 featuring a tapered through-hole 508 somewhat similar to that shown in FIG. 114B and the above described FIG. 156 embodiment only with a larger taper and larger receiving end hole 508L (shown also with an optional rim flange ring 508R which can be molded in monolithic integral fashion with the remainder of the collar 532 (with the monolithic common material molding technique also applicable to the above and below described collars with the slit pre-formed or formed after molding solidification)). Hole 508 in the configuration shown in FIG. 160 has a larger diameter end 508L that receives instrument 536 (e.g., a tool with a sharpened end or a needle shaft with a sharpened end as a few examples as to provide instrument assembly 535 of collar 532 and instrument 536) such that there is circumferential spacing at the proximal end 538 with the taper preferably being designed for no circumferential spacing (diameter of smaller diameter end of hole 508 generally conforming with the exterior diameter of the received portion of instrument 536—with a depiction of the same shown in below described FIG. 161). FIG. 160 illustrates a four finger pencil grip grasping for compression of the cavity defining hole 508 into instrument 536 contact for relative (instrument/collar) X-axis non-movement retention. As seen, finger contact includes two fingers received in adjacent corner cut outs and finger (pad and side finger contact) on the longer side walls 338A and 338B.

FIG. 161 shows the embodiment of FIG. 160 from an alternate working or distal end 540 view point. From this view point there can be seen the smaller diameter end 5081 of hole 508 in a generally conforming diameter relationship with the exterior of the received portion of instrument 536 (e.g., sufficiently conforming to provide friction retention positioning absent an X-axis slide force overcoming the static friction retention). There can also be seen in FIG. 161 the firm grasp potential which provides sufficient friction retention as in to provide for preclusion of X-axis instrument slip even when the instrument is utilized to generate forces at the tip along the X-axis (this retention level being possible still with dexterity potential as in instrument twisting about the long X-axis). This instrument usage gripping status is shown as being provided by the illustrated direct tool contact fingers F1 (thumb); F2 (index); F3 (middle); and F4 (ring)— with the pinky finger F5 providing compression contact to the adjacent ring finger F4. Thus, as seen from the various contact points with both corner edges and corner cut outs and side walls, there is provided a firm and stable grasping potential by the collar configuration while also providing for instrument holding compression by finger pressure directed radially inward (while relative to the illustrated contact between the exterior of the instrument and smaller diameter end of hole 508 there is retained relative retention of the instrument in the collar with only relaxed finger contact when only holding and not direct working (axial pressure on the tip) is involved). Thus, the instrument assembly represented in FIG. 161 as well as in the other described embodiments, allows for an operator to generate strong retention forces as upon one of the above described grasping techniques when it is desired to use the instrument as in a needle insertion into the skin, and once that step is completed the user can release the grasp as to have the benefit of a readily conformable and easily compressible collar when desired for direct use, while also enabling the user to hold the instrument assembly with a relaxed grasping state on that instrument assembly.

The above described instrument assembly 511 with collar 500 and instrument assembly 535 with collar 532 and instrument 536 are each also well suited for use when a two handed procedure applies. For example, each collar provides for controlled rotation of an instrument, as with one hand positioned above the wider diameter hole 508E, while the other hand is in a hold relationship with the exterior of the collar. Thus, a rotational two-handed skilled procedure can be very affective, especially when dealing with a smaller (instrument friction retention) 5081 diameter, whereby having a smaller diameter means a comfortable, controlled rotation can be achieved with two hands (second hand not shown). As further seen in FIG. 161 fingers could be shifted from the finger hold or a surface contact controlling or relaxing mode such that the instrument can be adjusted along the X-axis. For example, upon relaxing the grip the instrument can be adjusted relative to a friction contact state and thus retracted or extended with the working tip controlling length and exposure; and, if necessary, retracted completely inside the collar (not shown). The retracted instrument can then be reintroduced upon a further need arising. Again, a stepped interior (e.g., an Empire State Building shaped inner structure) with different diameters can provide both haptic feedback and greater control with sensitivities of the normal finger pad tri-pinch method, since fingers can slide up and down the grooves and rotate with a more comfortable skilled hold. As seen, instruments 514 and 536 have a very narrow diameter, which, in and of itself, can create physical spasms and grasping downsides (carpal tunnel syndrome, tendinitis, etc.) were it not for the benefit of collars 500 and 524 described above. In addition, collars under the present invention, provide for, after insertion, the collar acting as a security resting base, or breaking or tilting grasping element to help distance the instrument from the cutting surface, or could act as a very sensitive probing or cutting device where extremely sensitive moment is demanded. If, in addition, the collar can offer a very slight vibration where consistent sawing is essential, where consistent depth control must not be exaggerated, and once a breakthrough is imminent the forward force can be well controlled against over-puncture such as in skin layers, such as epidural layering.

FIGS. 162 to 164 show various views of the embodiment of FIG. 161 subject to a mechanical clamping assembly to help visualize the unique compression grasping quality of split collar embodiments of the present invention. That is, upon compression, as by way of the above described finger compression techniques, there is a degree of relative slit 502 side wall slippage that provides for even a greater wraparound of the hole surface relative to the instrument as to achieve even a greater strength relative retention. Such wraparound potential can also provide for accommodation of a degree of circumferential gaping between the smaller diameter hole 5081 and the received instrument 536. Each of FIGS. 162 to 164 illustrate clamp assembly 542 (the two end contact points of the compression pads 542A and 542B only being shown and the intermediate part of the C-clamp shown in cut-away). Each of FIGS. 162 to 164 also show the clamp assembly 542 in a clamping compression mode to illustrate an exaggerated finger grasp compression holding mode such as that shown above in FIGS. 160 and 161. With the compression pads in a "squash" mode, there can be seen, particularly in FIGS. 163 and 164 a wraparound of the surface defining smaller diameter hole 5081 about the received portion of instrument 536. This wraparound relationship is also shown in these figures to generate an offset or overhang 544 (within the protective confines of a corner cut out (C3 shown)) of one of the two slit 502 defining sidewalls relative to the other. As noted above this wraparound provides for a tighter retention gripping of the instrument when the collar is in a compressed state, and, where applicable, a lessening of any circumferential gaping between the exterior surface of the instrument and the interior receiving surface of hole 508 of collar 534. This capability accommodates both the need for security of anchoring, yet still provides for a non-cinching internal movement, which can be critical, as in when a catheter's internal cable has to move freely along the X-axis relative to the outer catheter sheath so that compression will not crimp the catheter's cable movement. FIGS. 162 to 164 emphasize that structural compression will not lead to a flattening or collapsing of the internal channel running through the collar. Further, parallel plates of 592A and 592B are also representative of pressure pads that under an embodiment of the invention are placed inside an internal structure to surround the collar and provide the desired degree of non-crimping retention.

Further the mechanical compression assembly shown in FIG. 162, for example, is also representative of an embodiment of the present invention wherein the compression application is carried out by mechanical means in place of hand manipulation and thus the collar can be included in a mechanical assembly that provides for retention an release inclusive of tool holding or product holding as when a product end is being sharpened, etc. Thus, the present collar is well suited for a variety of mechanical, industrial applications free of finger manipulation.

FIGS. 165 and 166 show the same split collar 534 of FIG. 157, but with a different instrument in both an initial contact state of insertion and a fully inserted state, respectively. That is, FIG. 165 shows an initial contact and an initial insertion state of instrument 546 relative to the reception slit 502. As seen, the surface contact portion of collar 534 is provided by the wider width (in Y-axis direction) surface 338A which helps avoid rotation of collar 534 about the X-axis during the illustrated insertion of tool 546 (e.g., a dental tool or a surgical catheter). The corner cut-out location of slit 502 also helps avoid rotation of collar 534 during instrument insertion as it is closer to the center of gravity than the exterior surfaces. In addition, the angle of corner cut-out C3 leads the instrument directly to the slit or gap regardless of gravitational limitations. As with the other embodiments, the V-shaped wider notch gap 506 helps in the initial insertion and subsequent reception as seen by a comparison of FIGS. 165 and 166.

In embodiments of the invention the collar is an independent unit that is not secured to the surface, although alternate embodiments include having adhesive or other fastening material such as Velcro, that enables collar 534 to be permanently or temporarily secured to a supporting surface as to provide a temporary instrument loading dock that maintains the instrument such as 546 suspended above the base supporting surface (e.g., a dental tray table or the like as well as the surface of a body). An example of securement can include fasteners such as Velcro combinations, fasteners, adhesion (noting that there are limitations on the types of adhesives that may be used with a silicone elastomeric material if so utilized.

FIG. 167 shows the enlarged end 506 of slit 502 before its parting (in conjunction with the parting the side walls of the thinner slit receipt portion 502) until the instrument 548 is received within the confines of hole 508. In view of the elongated and flexible nature of the illustrated instrument 548, rather than pushing down along the Z-axis with one direct insertion finger as in the other embodiments, there can be achieved receipt in similar fashion to dental floss insertion between teeth, wherein opposite ends of instrument 548 can be grasped and optionally rendered taut before initial contact with the instrument in the border region between slit sections 504 and 506 as at a slight tilt, followed by opposite end downward movement to place instrument 548 fully within the confines of hole 508. Accordingly, this is an illustration of an insertion wherein the collar can be applied and different sections of an instrument or apparatus, without cross through threading (pushing an instrument through the hole 508 along the X-axis) limitations.

As further shown in FIG. 168, instrument 548 may have an outer circumference that is smaller than hole 508 as to provide circumferential retention, but full freedom to slide along the slit elongation of axis. Further, the relative difference defining the gap 508G shown in FIG. 168 can be made large enough as to provide for the accommodation of multiple instruments (e.g., multiple wires of the same or different diameters) as to achieve a bundling of the same within the trapping confines of the biased shut slit side walls and the sufficiently sized hole 508.

FIGS. 167A and 168A show split collar embodiment (534A and 534B) similar to that of FIGS. 167 and 168, and thus similar components are referenced the same. Some differences include, relative to collar 534A, the inclusion of additional through-hole 508A, which is shown as being non-slit in this embodiment and provided in the central region of one of the longer projections 533P of collar 534 which is shorter in circumferential length as compared to the longer circumferential length but shorter or more squat adjacent projections 533S shown in FIG. 167A. This additional through-hole 508A is shown as extending longitudinally in generally parallel fashion and within which is provided another instrument 548A, as in an additional linear element having the same or different characteristic as element 548 received in the hole 508 in communication with slit 502. For example, the additional linear element can be an electronic wire, fluid (gas or liquid) conduit, added tooling such as more rigid probe linear elements, etc. The FIG. 167A and FIG. 168A embodiments also are illustrative of useful medical field collar embodiments, but also can take on non-medical usage forms as in wire organizing means such as in aircraft or computer station wire organizers or other multi-wire locations as in home wiring, and the like. The slit and non-slit sourced holes 508 and 508A are particularly adept at handling situations as where there are elongated elements that are more typically removed for review or replacement that can be provided in the slit sourced hole 508 while the less likely to be accessed instrument or one likely to have more permanent status is represented by instrument 508A received in its thread-through (rather than slit) insertion hole 508A.

FIG. 168A shows collar 534B which is similar to collar 534A but for additional through-holes like hole 508A in FIG. 167A. These additional through-holes are also all preferably parallel to the longitudinal extension of slit access hole 508 and are formed in both projection 533P of collar 534B and projection 533S of collar 534B. That is, as shown, there are provided in collar 534B through-holes 508X1, X2, X3, X4 and X5 (although more or less than the 5 shown are possible depending on the associated holding requirements). FIG. 168A further shows that within each of through-holes 508X1,X2,X3,X4 and X5 there is provided a respective elongated instrument or element as represented by 548X1, X2,X3,X4 and X5. Again, these different elongated instruments or elements can all be the same type or of the same type but different size or of a variety of different types and/or sizes. Also, in the embodiment shown in FIG. 168 there are still further added thread through-holes in the shorter height projection 533S as represented by holes 508Y1,Y2 that have threaded entirely there-through elongated instruments (elements) 548Y1, Y2.

Also, when collar 534 is formed of an insulating material such as insulative materials chosen from the above collar material listing options, the element received in the central slit accessed hole 508 is insulated despite being readily inserted and removed, as are any of the other added elements such as that received in through-holes 508X1, X2, X3, X4 and X5 due to the encompassing nature of collar 534. This encompassing nature also provides insulative protection between each received element at least along the length of the collar.

FIG. 170A shows a similarly configured collar 534E as that shown in FIG. 170 but with an added passageway 508A extending through shorter projection 533S of the illustrated collar 534E and which is shown as having received a threaded through instrument 550X which is shown of both a smaller size and different type than cable with plug end wire 550 (again preferably a differential in access requirement as where the cable plug can be plugged in and removed whereas the other instrument 550X can be a more permanently wired component as in a fixed in position electrical wire). Moreover, with appropriate sizing of hole 508A and the element received therein there can be seen that even under extreme compression the hole dimension remains closer to its original diameter than does the wrap around hole 508 defined by the slit accessed section of collar 534. As such there can be achieved a desirable clamping and position fixation on the element received in the central-slit access hole shown while the other hole 508A can receive a component for which there is a desire to avoid tight, potentially crimping clamping such as would be the case with a flexible fluid supply hose or conduit.

FIG. 170B shows as assembly featuring multiple collars (534X and 534Y) of the FIG. 170 type arranged (compressed friction retention fit via projections of the collar within the cavity) in a common reception area RA represented by an elongated cavity as might be formed in an interior housing area of a vehicle such as a dash board or side door panel in an automobile or a side wall or seat region in an airplane (see VP in FIG. 170D for an example). In FIG. 170B each collar is shown as receiving a common elongated instrument or element shown in the form of a cable wire CW with input end (e.g., an audio input jack for a headphone, ear bud, or the like or a cell phone charger insert) As further shown, the slit 502 in collar 534Y is arranged such that it can be readily pulled out by an intended user by an upward, outer quadrant slit location. The other collar 534X, however, has a downward, outer quadrant slit location such that upon pulling out from collar 534Y, collar 534X can provide at least a temporary blockage from pull out due to the receiving friction relationship between each of collars 534X and 534Y relative to cavity RA and also the noted slit orientation in the collar 534X. Also, the friction relationship between each of collars 534X and 534Y and their common reception cavity provides for longitudinal adjustment such as an extension of a separation distance DS to a larger length space difference represented by distance DL (DL>DS). Accordingly, a desired length of usage can be adjusted to suit the need for input while maintaining a generally taught wire extension and controlled location for the remainder of the cable.

FIG. 170D shows collar 534Y also having the FIG. 170 configuration and also shown received in a capture passageway RA as may be provided in the interior housing molding of a vehicle VP and with a different received instrument as in one having a free end ear plug (EPL) or an opposite (plug-in member) end of cable wire CW with the first end shown in FIG. 170A being a plug in jack of a common wire with ear plug. As seen from FIG. 170D the different size slit sections 502 and 504 with the enlarged slit section 504 being well suited for receiving and temporarily retaining in position the ear plug end of the cable wire CW. Also, just one collar of the type shown in FIG. 170D is useful in helping retain and position temporarily a received elongated instrument and thus FIG. 170D can represent the sole collar or there can be featured multiple collars in a common for spaced apart cavities for achieving different support locations along a length of a common instrument such as represented in FIGS. 170B and 170C. Furthermore, as can be seen by FIG. 170D the arrangement of the collar, received instrument and receiving cavity provides the advantage that the instrument (ear bud) can be readily grasped since it is not positioned deep within the cavity, but yet retains its position relative to the vehicle (e.g., does not fall between the seat and a sidewall). In this way, there can be gained quick access as where it is desired to put an ear bud in while traveling in the vehicle with minimum distraction and attention required.

FIGS. 169 to 171 show split collar 534 (previously shown in FIG. 157) with a different instrument 550 received therein. That is, these figures show the instrument 550 as a flexible line with a bulbous end portion (with an electrical cable line having a plug-in bulbous end being illustrative). FIG. 169 shows the instrument receiving collar 534 after slit 502 has been flexed to receive the cable portion within hole 508 and then returned under its natural bias to a closed state. In the FIG. 169 view, there is no mechanical or hand compression on going, and thus the slit 502 is shown having biased back into its natural contracted state (wherein the walls defining thinner reception slit width section 504 of the slit are placed in flush contact, or nearly in flush contact with any non-flush spacing narrow enough to still contain the cable in hole 508 as when the cable diameter is slightly larger than that of the hole 508).

FIG. 170 shows collar 534 under a mechanical compression assembly, while FIG. 171 shows the collar in a finger compression "two finger pinch" state. In both the mechanical and finger compression modes shown, there can be seen a degree of wrapping in that there is shown a slight overhang 544 of the upper slit forming wall over the underlying slit forming wall. Again, this wrapping helps enhance the relative fixation between the collar 534 and received instrument 550. Upon release of the finger compression, for example, the instrument 550 is still generally in a fixed in position interrelationship (e.g., due to the generally common diameter at the hole 508 outlet of the collar 534 with the cable section shown of the instrument 550). In this way, a user can clamp the instrument for ensured retainment of the fixed in position relationship (as when, for example, the plug end is to be inserted into a receptacle (not shown)), while upon release of the finger grasp (e.g., a two finger pinch involving fingers F1 and F2 at the parallel surfaces 338A and 338B)

there is retained a friction retention until X-axis forces provide for slippage of the cable within the confines of the hole. That is, in a holding, but not hard compression finger pinch relationship, there can be achieved a releasable slide friction relationship which is useful in other situations (e.g., a behind the wall feed of the cable while retained within the collar 534). Thus, in the state shown in FIG. 169, the collar plus the inclusion of fixing means to temporarily or permanently fix collar 534 to another surface (such as a wall or floor or Velcro connected to a rug or the like), provides for desirable placement of a cable and an added degree of organization as when running a cable along a baseboard between electrical components.

FIG. 170A shows its collar 534E having the same configuration as in collar 534 but with an added passageway (e.g., one that has a non-varying through diameter) well suited for receiving a linear element via threading (no slit provided for access) such as a wire. Again, the slit access passageway for receiving linear element 550 (e.g., a plug in electrical conduit) and the non-slit passageway receiving linear element 550X provides for a readily removed and inserted linear element (e.g., an electric wire) and one that can be more permanently retained once threaded in position. Also, although only one non-slit passageway is shown in FIG. 170A, two or more as in the 6 added non-slit passageways shown in FIG. 168A can be utilized as well.

FIG. 172 shows a top plan view of a modified, "split" collar 552 that is similar to that shown in FIG. 93 but with the inclusion of split 502 (as above, similar or the same features amongst embodiments have been referenced the same). As with the prior embodiments, split 502 has thinner reception slit width section 504 and wider slit section 506. FIG. 172 shows collar 552 and instrument 554 (e.g., a sharpened tool as in a needle shaft) in an initial stage of insertion (featuring, as in the above embodiments, a downward force applied, such as with finger F2, with the instrument received in the wider gap defined by wider slit section 506 and positioned at the border region between the thinner and wide slit sections 504 and 506 for controlled thinner slit section flexing outward as instrument 554 is frictionally slid down into its final position internally within the central region positioned hole 508 (see FIG. 158). Also, while the illustrated slit 502 is shown as being linear relative to the central axis of elongation of the collar along the X-axis (as well as central hole 508) the slit can be deviated from the central axis as by having a slight spiral configuration which provides still for insertion by pressing down as shown in FIG. 172 while providing enhanced capturing encirclement once the instrument is fully received in hole 508.

Figure 102A:
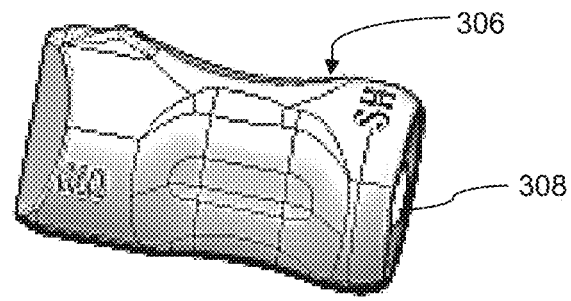
Figure 102B:
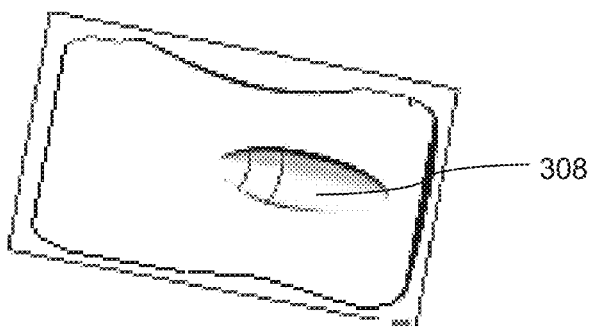
Figure 102C:
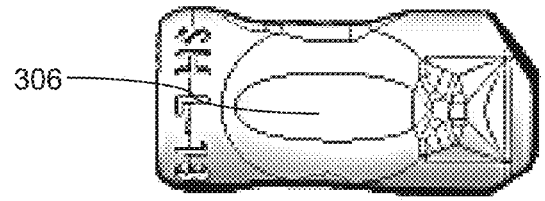
Figure 102D:
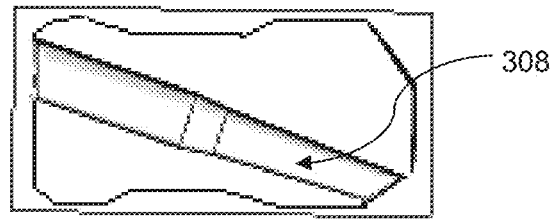

Also, embodiments of the invention include having an inclined hole 508, as in wherein hole 508 is arranged oblique to the central axis of elongation, with an example presented in FIG. 102D. Further, as with the other embodiments featuring hole 508, there is always the option of using a threading technique when the collar is an environment not well-suited for the insertion techniques such as represented in FIG. 172. For example, there is the potential for insertion of a collar into a surface hole as in a wall hole whereupon the collar can flex to provide retention within the surface hole, and if the wall surface covers the slit there is still a potential for threading the instrument (e.g., any electrical wires, etc.) through hole 508. Thus, the collar provides a more universal approach to instrument insertion and retention.

FIG. 173 shows that which is shown in FIG. 172, but with instrument 554 in a final stage of insertion relative to collar 552. As in the above embodiments, whether hole 508 is tapered or non-tapered there is preferably featured a light friction contact retainment relative to collar 552 in its non-compressed natural state. Alternate embodiments of the invention (which is also applicable to the other collar embodiments described herein), include both the resulting structure and technique of adhesively bonding the instrument within the confines of hole 508 when relative collar/instrument X-axis adjustment is not needed or involved after initial insertion.

FIG. 174 shows collar 552 in a user two finger (e.g., fingers F1 and F2) pinch mode which functions to lock the instrument in position as to preclude relative sliding or at least there is presented a higher friction retainment relationship between collar 552 and instrument 554. Also, as seen the pinching finger contact points are in opposing side wall depressions formed in the body of collar 552 (see the above discussion regarding U.S. Pat. No. 8,745,825 which is incorporated by reference in this application).

FIG. 175 shows that which is shown in FIG. 173 but in a three finger "pencil hold" mode (having some differences relative to the four finger contact mode described above as in FIG. 161 made possible by the deeper corner cut-outs and overall periphery as compared to the smoother contoured nature of collar 552). FIG. 175 also illustrates exit hole 508E in a relatively tight relationship with instrument 554 (with the wraparound potential for achieving a tighter fit as described above relative to overhang 544 shown in FIG. 171). As also seen in FIG. 175 the compression arrows and relative positioning of instrument 554 in hole 508 following slit close up (and potential wrap around) help insure that there is no return of instrument 554 back up through slit 502. In the three-finger pinch hold the thumb, index finger, and middle finger can present an uneven compression which will stymie sliding movement especially with the uneven grasping points when pressure is applied to (see FIGS. 87-90). At the same time, in FIG. 175 a retraction of a sharp tip 559 provides for the potential for the sharp tip to be slid back into the sleeve and can be secured, for example, by taping, or capping, or some other means for protection from sharps while being transported for disposal.

FIGS. 176 to 178 show split collar 552, which is the same as that of FIG. 172, but receiving a different instrument 556. Instrument 556 is shown as having a conical portion with a narrower distal end and a wider more proximal area with a portion of some of each being received within collar 552, with such shapes being found on instruments such as, for example, catheters, dental instruments, probes, etc. The narrower diameter received portion of instrument 556 is also relatively larger than the received portion of instrument 556 such that there is the potential for the diameter of the instrument being larger than the narrowest diameter of the hole 508. Also, since the more proximal area has even a larger diameter, when 508 is of a constant diameter there is the potential for the instrument to extend out of hole 508, but in a captured state with the biased closed side walls of slit 502.

Further, the instrumented generated expansion of the collar 552 results in opposite collar halves moving outward into wings as to provide for a wing shaped concave bottom surface in the collar that can also accommodate placement on a flat or concave surface without rotation (surface not shown). FIG. 176 shows an initial contact state of insertion of hand held instrument 556, while FIG. 177 shows a nearly fully inserted state of that instrument (i.e., the instrument fully received within the peripheral confines of the collar, but not yet received in its final resting state within hole 508). FIG. 178 shows a user two finger pinch mode with the instrument supported. FIG. 178 also shows the enlarged proximal end of instrument 556 (shown as having a knurled section) received within the confines of slit 502 inclusive of reception of the more proximal portion within the enlarged gap or wider slit section 506, while there is still fully or nearly fully closed thinner slit section 504. FIG. 178 also shows how the opposing finger reception depressions that are found on each side of slit 502 provide for a transverse force compression that provides a secure grasping relationship.

FIG. 179 shows the same split collar 552 shown in FIG. 172, but with the needle assembly 558 of a syringe 560 fully received by the collar. FIG. 179 also shows that the needle assembly includes a needle shaft 562 and hub 563 (e.g., a LUER™ lock hub as discussed above). Hub 563 is shown as having a larger diameter than the needle shaft and also a conical profile. The hub is received within wider section 506 of slit 502 and due to its relatively larger diameter than hole 508 features flexed outward walls in both sections 504 and 506 of slit 502. Despite this outward flex positioning of the walls defining slit 502, a (less than majority) portion of the thinner section 504 still remains entirely closed (side walls contacting) as to facilitate capture of the instrument beyond the friction retention forces already present on the exterior of the instrument (syringe).

FIG. 179 also shows how collar 552 provides a secure retention relationship between the instrument (syringe) 560 and collar 552 particularly upon finger compression such as the pinch relationship shown in FIG. 178 for a different instrument. Further, the collar 552 with its generally cylindrical configuration with finger depressions provides for a clear line of vision as the needle is inserted into a surface such as the skin surface shown at a desired angled orientation. The collar grasping relationship also provides a stable foundation that allows for a controlled plunger (not shown) push into the cylinder partially depicted while the needle is retained from moving forward deeper into a pre-positioned level as the plunger is pushed forward to release medicament or some other liquid. There is also shown a typical support as in the illustrated cotton roll cylinder to facilitate retention of a desired angle of insertion (and avoiding tension on the skin upon release by the needle). Accordingly, in FIG. 179 the instrument is fully inserted into its final resting state, but the gap is not closed for 360°, and thus the instrument remains visible while within the final position reception region of the collar. The instrument (in this case a hypodermic needle assembly) is thus in a snug friction state within the collar, while there is retained enough visibility to monitor flow.

FIG. 180 shows a different perspective view inclusive of a view of skin surface contact by the distal end of collar 552. FIG. 180 shows the split collar 552 shown in FIG. 179, but from a different view point wherein there can be seen the collar 552, needle assembly 558 and skin surface 564 relationship. This relationship is inclusive of a collar edge contact with skin surface 564 at a desirable angle orientation that is in common with the needle central axis orientation (an example being the illustrated angle XT4 such as one of the aforementioned angle orientations well suited for needle insertion (e.g., the above described angle range of 12° to 60° (or more)). Again there can be provided cotton roll cylinder or the like to help set up and retain a desired angle of needle extension in the receiving area of the person.

FIG. 181 shows a view of the split wing collar shown in FIG. 155, but from a different viewpoint. Also, the wing extensions of collar 500 can be further seen to provide a stable platform that precludes undesirable flipping or twisting of the needle or needle support assembly unless such action is desired by the operator. FIG. 181 further shows, however, by way of dashed lines optional hold down means 568 for securement and retention of the collar and needle combination from any undesired level of movement. FIG. 181 illustrates hold down means in the form of the aforementioned taping which tape secures instrument assembly 511 to the illustrated needle receiving surface 522 (e.g., the arm of a patient receiving an IV assembly).

In this embodiment truncated needle hub 512B is shown as being connected with needle cylinder 570 as via a standard LUER-Lok™ lock connection following or prior to an IV connection, if the needle is being utilized for IV purposes. The securement of split collar 500 of instrument assembly 511 shown in FIG. 181 provides the same benefits as described above for the embodiment shown in FIG. 155 (e.g., the border region providing a tight connection due to the highest level of tensioning of the side walls of slit 502, with the thinner region of the needle assembly hub being placed under less compression such that there is provided an option of a degree of finger forced trunnion minor rotation of the needle assembly which is still retained stably and at a desired insertion angle via tapered surface 520).

Instead of tape (or as a supplement to tape) alternate hold down means 568 can be utilized (e.g., to retain the collar in position and/or to preclude an inadvertent lift out of a nested instrument). Such alternate hold down means configurations are inclusive of added retainers such as independent or integrated type retainers (e.g., Velcro tabs (to opposite sides and/or across the slit)).

FIG. 181 also shows needle hub 512B as well as needle shaft 512A nested within the split of collar 500. This configuration provides for the option of taping to the surface over needle hub 512B (made secure by taping surface 500 and the needle hub received therein). Thus, for example, when 512B is jarred or shaken, the shock absorbing element or dampening means provided by the noted split wing configuration absorbs the shock. Thus, in this case featuring a needle as the instrument, the needle adjustment is damped which is considered to help prevent erosion of the vein.

Also, as can be seen FIG. 182 represents an alternate embodiment of the non-slit collar 298 show in FIGS. 101A to 101D. In the FIG. 182 embodiment the same exterior body configuration featured in FIGS. 101A to 101D is modified to include a slit along all (or a portion) of the collar's X-axis length to provide for the no axial (e.g., no threading) insertion described above (or a hybrid arrangement wherein only a minor portion of the total length of the collar needs to involve axial internal insertion (e.g., threading) with the remainder of proper insertion achieved by a slit separation; such as via separation of a modified slit 502 extending over a majority of the length of the collar). For example, upon insertion of a needle assembly there is achieved both a desired pre-established angling of the needle plus a pair of wings extending outward and down in wing fashion that can be readily taped down with the needle assembly in the desired position. In this way the sleeve and skin will have a more stable surface interfacing the sleeve and the skin, and the tape securing will be easier than those in FIGS. 179 and 189 of which are necessary when angle could be steeper without surface area available for this contact.

Accordingly, FIG. 182 shows a top perspective view of the split collar shown in FIG. 179 but with a more fully received needle hub configuration and at less of an angle XT4 (e.g., a 15 degree needle insertion relative to surface 522 as shown in FIG. 180). FIG. 182 also illustrates hold down means 568 (e.g., tape) used to maintain collar 552 in a flush arrangement over its entire length with surface 522 as better seen in the side view of split collar 552 shown in FIG. 183.

FIG. 183 also shows a side view of the split collar shown in FIG. 182 with received needle hub as well as the optional (dashed line showing) hold down means (tape in this instance or a portion of a strap that can extend entirely around the periphery of an arm or receiving body part) 568. When the holding means extends over the split it is readily positioned and held in a desired location due to the contouring of the split collar 552 (e.g., even if the adhesion breaks at the tape/collar interface location there is still a degree of positional retention due to the contouring of the collar receiving the hold down means 568). In addition, in light of the preferably flexible nature of collar 552 in FIG. 183 as well as the preferred surface concavity for finger pressing, there is also a natural tendency for a concave undersurface in collar 552 in which skin can be compressed to assist in positioning retention as in avoiding slippage backward or forward and avoiding side slippage as well once in a desired location and held down.

FIG. 184A shows the collar 552 shown in FIG. 179 but with a nail received therein. FIG. 184B shows the same collar 552 shown in FIG. 184A, but with a wrap 572 around the periphery of the collar. As with the previous embodiments, the ability of collar 552 to wrap tight around the object received in the slit (in this case a nail) enables for a tight fit that can further be enhanced and retained with wrap 572 such as an elastomeric wrap (an elastic band that is relatively wide as to cover but still be retained within the depressed central region of collar 552). Collar 552 with its received fastener can thus be both readily held safely (e.g., avoids hammer/finger contact) while also providing a convenient elastomeric holder that can be compressed and securely retained within a cavity of a layered material through which the fastener extends through as it is captured or retained by an underlying layer. The wrap can be avoided as well which provides for more easy insertion of the next nail after the former nail was sufficiently started to ensure alignment when the wrap is removed (or, for situations where a degree of nail body exposure is desired as in picture hanging the wrap can be retained in place after hammering is complete).

With reference to FIGS. 185A to 185F, there can be seen advantageous electrical wire and collar 552 combinations. For example, with collar 552 formed of an insulating, and also preferably compressible, material (e.g., any of the aforementioned elastomeric materials described above) there is provided the ability to protect the wire while the wire passes to opposite sides of a layer as in a metal layer with sharp edge hole reception regions or one where a protective ring in a receiving hole has broken or moved. For instance, relative to metallic components in airplanes and other machinery, there can be situations where vibrations or general movements of component(s) through or on which a wire extends can lead to a fraying of a wire own insulating coating. This contact can lead to metal wire exposure and shorts or the like upon the frayed region of the wire coming into contact with an adjacent metal surface inclusive of another wire.

With reference to FIG. 185A there can be seen wire 574 having insulating coating 576 as well as exposed (metal) wire region 578 where the insulating coating is lacking and the interior metal wire region is exposed. This can be due to a situation where there is desired a region of exposure in equipment set up or one where the exposed region has undesirably developed due to fraying or the like. In each situation the exposure can be insulated by collar 552 (which is sufficiently long enough in the longitudinal direction to entirely cover over the exposed region and preferably at least 3 mm or more beyond full coverage at each end. Also, in the latter situation where fraying has occurred due to use, the collar 552 can be implemented as a remedy to prevent undesired exposed wire contact that can lead to shorts in the like. For example, a wire extending through a hole in a plate, as in an airplane cabin plating, can be repaired by inserting the collar through the hole as to both insulate and provide a vibration dampening and fray prevention arrangement for that wire extending through the receiving hole in the plate. This is but one example, of the ability of the collar to both cover and protect from exposed wire contact and shorting.

FIG. 185B shows collar 552 that shown in FIG. 185A with exposed wire portion 578 fully received therein and after the natural collapse of the insulating material of collar 552. FIG. 185C shows the collar shown in FIG. 185A but with wrap 572 (an elastic band or a metal strap as collar 552 would still provide an insulating quality due to its helical wrap around the received wire within collar 552). FIG. 185D shows wire receiving collar 552 in the same manner shown in FIG. 185C from a different viewpoint such there can be seen how the wire is both covered over by collar 552 and also wrapped into place by wrap 572.

Another region where electrical shorts and the like can develop is regions of a wire that are joined together which traditionally have been capped or intended exposed wire regions. Sometimes such capped ends are not practical in tight spaces and can readily come off without knowledge if behind a wall or plate or the like as they are often formed of hard plastic with metal interiors and thus not well suited in damping vibration.

In this regard, FIG. 185E shows the same collar 552 receiving and covering over two wrapped free ends (574A and 580A) of two wires 574 and 580 that are joined together (with or without the additional wrap 572 shown in FIG. 185C).

FIG. 185F shows the same collar 552 receiving and covering over a non-exposed region of an insulated wire or other conduit (i.e., the insulation is still intact), with collar 552 being intended to provide an insulating and protective covering over that portion of wire, as in the situation where that portion would otherwise be potentially subject to abrasion and undesirable potential wire metal exposure.

As an example of this protective nature relative to positioning and usage of a wire or the like, reference is made to FIG. 185G wherein there is featured a metal plate 586 having a hole 588 intended for wire 574 passage therethough to opposite sides; but with that wire 574 in the protective confines of the elastomeric collar 552, which has been compressed into the hole and allowed to relax so both the collar is fixedly positioned and the wire is protectively received and retained in position. Thus the combination of wire 574 and collar 552 can be readily inserted and retained by compression in a plate or the like as to provide for wire passage through a hole with lessened concern for wire fraying. The helical wrap and tight confinement of the wires (and wire end wrapping) also enhances the longitudinal locking in place and the preferred elastomer material helps avoid undesired separation despite vibration or other environmental factors.

This protection (made available by the collar inserted into a desired position as in a hole of a plate and encompassing the received portion of the wire or other conduit type, with one example shown in FIG. 185G) is equally applicable to each of the various wire reception embodiments described above, as in the exposed wire embodiment of FIG. 185A, the twisted end wires arrangement in FIG. 185E, and the preemptive non-exposed wire (covering intact at the time of initial placement) embodiment of FIG. 185F. It is also noted that in addition to the split collar featured in FIG. 185G, an additional aspect of the invention is using a non-split collar as in the below described collar 590 in FIG. 190A in a similar plug-in-hole relationship (although there is a degree of insertion and retention enhancement in moving from a split to a non-split collar).

As described above collar 552 is advantageous in providing, when desired, both an insulating and vibration dampening and retention enhancement. As an example of a situation where vibration dampening is highly helpful in avoidance of disengagement of a fastener from its reception area can be seen in the use of cotter pin fasteners. That is, cotter pins can come loose and disengage due to vibration and/or shifting components without the ability to return to an original fastener state. FIG. 186A shows slit collar 552 prior to assembly with fastener 584 received therein and extending to opposite sides of collar 552. In this embodiment, collar 552 receives the straight portion of cotter pin 584 and the compressing wavy section of the cotter pin is compressed against the elastomeric collar as to both insulate and provide added dampening and longitudinal disengagement avoidance due to the elastomeric reception of the peaks of the wavy portion of the cotter pin into the surface of the collar. In other embodiments as in a trailer hitch cotter pin or the like, the collar can be inserted within the receiving aperture as to help dampen and retain the straight section while the wavy portion makes contact with the exterior of the pin or the like of the hitch.

FIG. 186B shows collar 552 shown in FIG. 186A following insertion and retention of the cotter pin 584 within the collar 552. FIG. 186C shows the collar shown in FIG. 186B, but from a different viewpoint. FIG. 186D shows collar 552 in a non-insulating, direct contact relationship with the straight section of the cotter pin and the peaks of the wavy portion of the cotter pin extending into the slit for direct contact therebetween. FIG. 186E shows the same arrangement as in FIG. 186D but from a different viewpoint'

FIG. 187A shows a fastener receiving slit or split collar 552 embodiment similar to that shown in FIG. 184A, but receiving screw fastener 584 instead of a nail. Screw fastener 582 is shown by itself in FIG. 187B and there can be seen the threading that advantageously can cut into the side wall of the enveloping collar 552 as can be seen in FIG. 187A that provides for additional retention (while still allowing for rotation retraction or rotation insertion adjustment relative to the preferably elastomeric material described above for use in collar 552, although an initial wrapping of the fastener can be done without longitudinal insertion).

It is noted that collar 552 referenced above is appropriately sized for its intended usage as in when the collar is to be inserted into a hole in a plate or wall and receive a fastener it is to be appropriately sized as in final diameter configuration to be received in that hole with a compression retention receipt (see FIG. 185G, for example), and has a length suited to its intended environment and its functional protective covering function. However, when there is made use of the preferred elastomeric material for collar 552, it can receive, and properly retain a range of sizes and types of fasteners, with the particular sized threaded screw depicted in FIG. 187B being one example. Thus, another aspect of collar 552 is it can be positioned inside an existing hole in similar fashion to wall "anchors" whereas a range of screws or other type fasteners of different diameters and thread type variations may be utilized due to the split collar design (which can expand or compress to better accommodate different sizes unlike existing anchors, where set sizes are relied upon. The material of collars such as collar 552 can be the aforementioned material as well as soft metals or alloys such as brass in addition to a variety of plastic composites of sufficient strength to handle this described hole insertion and fastener reception function.

FIGS. 188A and 188B show an alternate combination wherein collar 552 receives a threaded fastener 586 (non-pointed free end but having threads and a screw cap as but one example, with the illustrated machine screw 586 being one example). Again, it can be seen that the wrapping nature of collar 552 about the threads of the fastener provides a degree of control when the free end of the fastener is received within a receiving thread exterior to the collar 552 with the collar providing a damping function relative to that actual engagement point of the threaded fastener in that there is limited vibration due to the "upstream" engagement of the threads in the collar relative to the downstream actual main retention engagement at the free end of the fastener (not shown). The added friction provided by the wrap around collar and the received threads or exterior (smooth or otherwise) surface of the fastener further adds to the ability to retain the relative positioning and providing for controlled threading and de-threading alignment and forces.

FIG. 189 shows a group of suitable fasteners FA all of which can be received by an appropriately sized collar 552 despite the difference in types and threaded/non-threaded characteristics. There can also be seen from the group of fasteners that some common type but different sized fasteners can be received by a common collar size (although different collar sizes geared toward a particular fastener size are also featured in the present invention as in larger sized bolts that can be received by a larger size collar and smaller bolts received in a smaller version of the same configured collar such as collar 552).

FIG. 190A shows a non-split collar embodiment 590 similar to that shown in FIG. 86 but receiving a wire with exposed, non-insulated free end that is being manipulated with a tool. As seen in FIG. 190A a user's finger tips can provide a compressing force on the elastomeric (compressible) collar 590 that suitably retains the component received therein from internal sliding (particularly when considering the catch relationship in the step down from the insulating cover of wire 574 and the exposed free metal end 574A. The exposed free metal end 574A being similar to the free end shown in FIG. 185E prior to twisting engagement with a second wire's free, exposed end. This secure arrangement provides for a secure positioning of wire 574 such that controlled, desired manipulation can be done on the exposed end as in the illustrated crimping with tool 592 (shown as a vice grip wrench in this embodiment). There can also be drawn forward, in user controlled fashion, the wire away from a stationary collar as seen by a comparison of FIGS. 190A and 190B (with FIG. 190B showing manipulation being carried out and with the collar only on the insulated portion of the wire).

FIG. 191A shows non-split collar embodiment 590 similar to that shown in FIG. 86 but receiving a wire with exposed, non-insulated intermediate section 578. FIG. 191B shows the same collar as shown in FIG. 191A with the collar fully covering over the exposed intermediate section 578. The aperture 594 formed in collar 590 can take on a variety of configurations that enables threading of the wire through the aperture, a desired degree of slide manipulation and retention once positioned at a desired location (e.g., in similar fashion to the catheter slide and retention characteristics as described above for FIG. 97, for example, but designed for the appropriate size of the electrical wire received). Thus, collar 590 can be threaded over an undesired exposed section of wire (e.g., exposed as by rubbing friction with another wire, friction and/or scraping on a supporting surface or rodent chewing or the like) whereupon once properly positioned the frictional catch relationship will retain the position until a desired release (inclusive of the hole retention arrangement potential like that described for FIG. 185G albeit without the full wrap around tightening relationship provided by the slit configuration).

To help illustrate the unique position retention capability of winged collar 500 (e.g., see earlier embodiment of the same shown in FIG. 181) reference is made to FIGS. 192A and 192B showing collar received tool 598 having a knurled handle 600 leading to tapered section 602 and leading to a free end in the form of a tool working end 604 (e.g., a hooked, pinching, pointed, spooned, etc.). As shown in FIG. 192A receiving tool 598 is shown having free end 604 in engagement with a torsion introducing elastic band 605 that is shown in a wrapped state (potential torque energy generating state) relative to the engaged working end 604 of tool 598. In this illustration there is featured tray 601 such as that described in U.S. Pat. No. 9,179,975 to Eliot Robert Gitman (and thus sharing at least one common inventor as in the present case), and which patent is incorporated herein by reference in its entirety. This elastic coiling of energy is used to demonstrate the controlling factor provided by the collar of the present invention. For instance, this control function is of usage in a variety of fields as in those in industrial and medical usages, where controlling the physics of recoiling energy, while a procedure is taking place can be advantageous. For example, controlled corrections and modifications in tension of tendons of a body during or procedure or, on the industrial side, providing enhanced control over release of built up energy in a coiled body in an industrial setting (e.g., dampening function upon return or during coiling).

As seen in FIG. 192A, tray 601 features peripheral wall 601W with an upper peripheral ledge surface 603. Tray wall 601W defines an interior rectangular recess 601R within which sliding barrier 601S with projection 601B is received. Barrier 601S freely slides along the direction of elongation of the tray, but is otherwise retained from coming out of the tray. An interior wall projection 6011 is also featured in opposing fashion to projection 601B and the elastic band 605 is fixed within a hook region of each of the two, opposed projections.

As also seen in FIG. 192A the user's finger is compressed down on tool 598 as to retain the twisted elastic band torsion in a potential energy state. From a comparison of FIGS. 192A and 192B, there can be seen the effect on tool 598 upon finger release on tool 598 and the release of the potential energy of the wound elastic band, which causes the tool to spin and jump from its original position to the new position shown in FIG. 192B.

Winged collar 500 provides a means to preclude such undesirable adjustment despite similar torsion states as might be experienced when working with tool 598 in a variety of environments as in medical, woodworking, craft making, etc. This movement preclusion is available in situations with or without any additional hold-down means as in tape, with the discussion below focusing on the capability of split winged collar 500 performance capabilities alone. That is, as seen in FIG. 192C there is shown tool 598 received in the capturing collar 500. In the FIG. 192C illustration there is shown hand (single finger) "retention" of tool 598 in its relative position with respect to split collar 500 which is in surface contact with a periphery portion 601W of tray 601. As further seen in FIG. 192C, the finger depression of collar 500 with received tool 598 results in a tilting up action on the instrument end 604 against the periphery portion 601W of tray 601. The relationship between the collar's forward edge support provided below the slit end region in the collar in which the tool 598 is situated, also provides an advantageous fulcrum relationship in that the tool end can be rotated up and down relative to that fulcrum spot which is positioned relatively close to the working free end of the tool. Still further the finger pressure on the collar as shown in FIG. 192C, functions to also place pressure on the gap to help in inhibiting undesired, relative movement of the tool within the receiving gap provided in the collar.

FIG. 192D shows the same view as that in FIG. 192C, but for the finger of the user no longer in a "retention" state with respect to the collar 500 and received tool 598. As seen, despite the release of the finger(s) from the collar, collar 500 retains its original state (insofar as its front edge friction contact edge 500FE) as does the received tool 598 (but for a lift up with the rear end of the collar coming off the tray surface together with a similar up rotation in the tool). This retention of the collar in a fixed from sliding longitudinally state and/or rotating relative to the surface of the tray 601, despite the potential torque force provided by the tensioned elastic band on the end of the tool, allows for user freedom in using either hand with or without a tool. For instance, in the medical field this retention ability in collar 500 despite such environmental forces is a useful feature as it provides for greater flexibility in a surgeon or the like to access and work on areas (e.g., tool 598 is used to retain a body part or other surgical equipment component in a non-obstruction location until such time as a return or additional movement in location is desired). This greater flexibility is inclusive of the avoidance of a need for an assistant to hold a tool (e.g., forceps) while a surgeon is working on a different area as with a scalpel. Hence there is also avoided the potential of collisions between such personnel.

FIG. 192E provides a closer view of the retained collar status as shown in FIG. 192D and thus a closer view of the tool and collar interrelationship. That is, FIG. 192E shows an example of slit winged collar 500 having the same characteristics as described for collar 500 in the earlier embodiment of FIG. 181. In FIG. 192E there is shown how receiving tool 598 (shown having its knurled handle 600 leading to tapered section 602 and leading to a free end in the form of working end 604 (e.g., a hooked or spooned most distal end)) is received within collar 500. As seen, tapered section 602 is fully received within the collar slit and the knurled handle portion 600 is shown proximally to that engagement (although in alternate embodiments a knurled portion can be received which would increase the relative surface contact, but is not needed in the embodiment shown with collar 500 formed of one of the materials earlier described as in silicone rubber). Both a portion of tapered section 602 and working end 604 (a hooked grasping end) are shown extending freely away from collar 500 and into the noted engagement with the twisted elastic band 605 fixed at opposite ends to the noted projection 601B and 6011 of tray 601. Again, as seen from FIG. 192E, despite the release of finger contact, collar 500 is able to prevent longitudinal movement in tool 598; and, if desired, no movement including rotation (or the relative frictional relationship between the smooth tapered tool portion and the receiving region of collar can be arranged as to preclude the noted longitudinal movement while allowing for internal rotation only movement of the instrument in the receiving hole 508 and/or expanded slit 502 in the collar 500, with FIG. 192E showing a state after such rotation release of built up tension in elastic band 605).

FIG. 192F shows a further, different positioning of collar 500 with received tool 598 on periphery 601W of tray 601. In FIG. 192F there is shown collar 500 and tool 598 having been moved from a generally coincident to longitudinal (y-axis extension) location line of extension 606 of tray 601 to one moved about 30 degrees on both the horizontal plane (angle Ax) and also in height (angle Az) to the upper quadrant of the end region of ledge surface 603 of tray 601. Even in this position (representing an original position after twist connection with the elastic band or a position assumed by shifting following an earlier location as in that which is shown in FIG. 192E) there is retained the desired tool location without twisting or relative repositioning of that tool once placed in a desired setting within the collar. This provides the advantage of being able to maintain a tool is both a desired position and a desired working state (e.g., in a grasping relationship with a component being worked upon which in the illustrated embodiment, is a still torsioned elastic band). The close proximity in this arrangement provides more leverage than finger held tool 100 and thus a closer "fulcrum" relationship is provided with the collar 500.

FIG. 192G shows a still further, different positioning of collar 500 with received tool 598 on periphery 601W of tray 601. In FIG. 192G there is shown collar 500 and tool 598 having been moved from a generally coincident to longitudinal location line of extension 606 of tray 601 to one moved about 45 degrees (angle Ax1) along the horizontal plane extending through longitudinal extension line 606 as well as 30 degrees upward (angle Az1) above that plane (with front edge 601FE of the collar in friction retention on the tray periphery 601W. This is an example of how readily the tool 598 (any received form) and collar 500 combination featured in the present application can be adjusted to a new position without a flip over or sliding of collar 500 as, for example, to open up a new view line relative to the user's working at the noted worksite.

This added user flexibility relative to tool and collar positioning is illustrated in FIG. 192H wherein there is shown the same non-hand contact collar 500 holding tool 598 in a similar adjusted location as shown in FIG. 192G. There is further shown two hands manipulating two additional tools TO1 and TO2 (e.g., a tweezer tool and a scissor tool for a total of three tools shown in this embodiment), with one of the three tools shown with no hand contact and two shown in hand contact (although alternate embodiments include the potential of two or more tools with collar retention and no hand contact featured, as in switching out the tweezer shown with a forceps clamp with the thinner end of the forceps instrument held in a slit of another collar 500). Thus, the FIG. 192H illustration provides an example of what a worksite set up might feature as in a surgical set up, wherein the elastic banding can be representative of tissue, tendons, cartilage, etc. and the various tools being used to move, hold, cut, etc. the material at the worksite can be placed into a desired positon and retained there despite forces acting upon the working end of the tool during a procedure. Further, the potential of leaving collar 500 with a tool in tensioned state could be for purposes of lengthening or stretching the material for a desired period of time as in the referenced tendon example during an attachment procedure, or from an industrial product standpoint, an elastic member can be stretched and then glued in position with the collar holding the stretched elastic member in position until the glue hardens. Thus, with a scaling up in size of the collar shown there can be utilized the collar 500 for additional industrial uses as in band attachment in furniture production where positional retention until adhesive setting is desirable with the ability to rapidly insert and remove the band member (with recipient tool connector).

FIG. 192I shows a view similar to FIG. 192G, but with an added illustration of the ability to manually rotate the instrument while the collar retains its positioning as represented by the compression contact lines added into FIG. 192I. In this way a user (e.g., a surgeon or craftsman) can tighten up material (in this case a further winding of rubber band 605 about tool end 604).

FIGS. 192E, 192F, 192G, 192H and 192I show collar 500 having a slit "up" positioning and wings arranged to have their planar bottoms (or at least forward edge 500FE) generally flush with the underlying surface presented by the tray 601 (tray peripheral surface 601W being representative of what can take on a variety of different surface embodiments including skin or surgical cloth drape contact etc.). The versatility of collar 500, however, provides for alternate configurations or special relationships with a supporting surface. For example, as shown in FIG. 192J there is an arrangement where collar 500 has its split face down such that the non-slit opposite planer surface of collar 500 (which has portions defining the oppositely extending wings) has a central non-slit region directly over the tool received in the opposite side slit as to provide a retention function in that the tool is covered over in the slit region. This arrangement enables the collar 500 to retain its position despite the above described potential torsion relationship of tool 598 held in the collar slit and having a free end engaged with the twisted elastic band. This is made especially so when considering the larger number of contact edges that are in contact with the peripheral tray surface 601W as can be seen by a comparison of the added contact edge demarcations added in each of FIGS. 192I and 192J.

With reference to FIGS. 193A to 193E, the aforementioned corner cut-outs in collar 500 also provide an advantageous catch for when there is desired retention of tool 607 (a tool similar to tool 598 but having even a more elongated free end and a capture ring at the working end) while under a state of tension (or non-tension as in a simpler hold state). Tool 607 is received in collar 500 in similar fashion as tool 598 described above and has a hooked capture end as a working end while also in a state of having its free end in both a grasping and tensioned state relative to a workpiece. This relationship is shown in FIG. 193A to 193E, with FIG. 193A showing an initial grasp engagement of the working end of the tool with an object. There is illustrated a forward, strung elastic band 605F being received in forward tray notch 601N1. The received strung elastic band is illustrative of a forward tension generating component (see arrow Tf) which is a representative of other environments, as in a medical worksite where a tendon or cartilage strand or the like might be gently stretched to a new position to provide better access to a different component at the worksite.

FIG. 193A also shows a second tray notch 601N2 formed in an intermediate area of the tray in tray cavity 601C and receiving an intermediate tensioning member 605M which contacts the undersurface of the tool to generate an upward force on the tool which is absorbed by the slit tool 500 with its vertical "wings" orientation as shown in FIG. 193A. FIG. 193A still further shows rearward tension member 605R in the form of a third elastic band 605R that is placed in a state of tension as the sliding wall 601S slides forward against the return tension force of band 605R. Thus the finger grasping of collar allows the user to fine control both movement forward (e.g., pushing forward with the illustrated thumb), or drawing rearward as by the index finger received in the forward, upper notch of collar 500 with each having the added vertical maintenance control provided by the middle finger placed against the side of the collar as shown in FIG. 193A.

FIG. 193B provides an enlarged view of the working end region of tool 607 wherein there can be seen that the working end 604 is a hooking end that is engaged with the forward strand of the elastic band 605F received within tray notch 601N1. There is also shown an underlying strand represented by 605M. Again the various strands can be representative of a tool positioning implements as shown to help in positioning the end 604 of tool 607 as well as being representative of tendon or cartilage strands or the like that show the fineness manipulation possible via the tool grasped tool via collar 500. There can also be seen target area TG which is representative of for example a region of a body cavity where access is desired but for which viewing might be difficult were it not for the capability provided by the collar and instrument combination that enables retraction and retention is a desired location external to target region TG until a return of the moved component (e.g., a tendon or cartilage fiber moved out for target viewing and allowed to return in a controlled manner).

This control finesse capability and multi-functional adaptability provided by collar 500 is further illustrated in FIG. 193C which shows the resting position of collar 500 while still retaining tool 607 in a reception state in its slit region. That is, as seen from FIG. 193C one of the four corner cut-outs is engaged with the barrier wall 601S provided on tray 601 such that there can be hand released the collar once engaged as shown in FIG. 193D (despite the elastic tension state) while the hand is used for other uses as in the manner described for FIG. 192H. In addition, the slit engaged relationship with tool 607 as well as the enhanced gripping contouring of collar 500 provides for added flexibility in manipulation as in a pulling and/or pushing back relationship relative to the two way elastic band retention of barrier wall 601S in its sliding relationship within tray 601, while being in state of tension on opposite sides of that barrier wall 601S. This pull back or push forward adjustment can be carried out either at the collar site or at the more proximal region of the tool while retained by the collar (hence the collar moves with tool adjustment). An example of the ability to adjust the tool while the collar retains its relative position to the supporting tray is seen in FIG. 193C in that the notched bottom of collar 500 is held on to the corresponding shaped wall 601S with the assistance of a pushing forward index finger, while at the same time the thumb and middle finger of the same grasping hand can either push forward or pull back the tool via a sliding action in the interior of the collar as in within the central aperture 508 at the end of the slit 502.

In addition to the above described single hand forward and rearward tool adjustment, there can also be utilized a two hand manipulation (having alternatives during any procedure is helpful both from the standpoint of being able to better adjust to the environment presented but also from the standpoint of providing relief to the grasper which is provided, for example, from the standpoint of not having to continuously use the same motion, but allowing a variety of options that a grasper can switch between). This two hand fine forward and rearward adjustment (depending on the relative retention friction forces provided by the slit retained tool) can be undertaken with one hand used to hold the collar in position and (optionally) squeeze to put collar 500 in a more open concave wing state (see FIG. 148) at the same time, whereupon the other hand can readily shift the elongated tool either forward or back relative to a still fixed in longitudinal position collar 500 above barrier wall 601S. Hence there can be achieved tool adjustment relative to the collar in either direction and then upon release the tool and collar are reengaged and held in the current position.

FIG. 193E shows still another option for forward and rearward adjustment wherein the collar 500 is entirely released from hand contact and the forward and rearward adjustment is achieved via the tensioning devices themselves. That is as tool 607 is drawn backward against the added tensioning of forward strand 605F and lessening tension of rearward strand 605R, there is a corresponding sliding action in interior tray wall 601S. In this embodiment, the hand released (and vertically oriented) collar is again engaged via its underlying notch as shown in FIG. 193C with the corner cut out maintaining position on wall of the carrier tray and with the tool 607 (e.g., a relatively rigid wire or rod) alone being grasped to adjust the level of pull back or tension increase in the grasped band. Further fine control is provided in that, in addition to the index-thumb tool grasp, the ring finger can be placed in contact with the end of tray 601 as to provide additional overall support and hand-tool control.

FIG. 194A shows a user grasping another instrument in the form of a more flattened body as represented by fork 700. As seen, there is a three finger contact arrangement that is rendered relatively unstable in light of the thin edge contact requirement associated with the flattened body.

FIGS. 194B1 and B2 show the split collar like that of FIG. 172, but in a modified form inclusive of an enlarged interior reception cavity 508W for receipt of the flatter instrument 700 (in this case a flattened region of a fork shown in position to be inserted). The interior reception area can be configured to best accommodate the instrument intended for grasping. Accordingly, with this embodiment the reception cavity is configured as a relatively narrow rectangular cavity for snug reception of the fork's handle cross-section. Also, the slit configuration with the narrower and wider (insert start gap) described above, is also preferably provided; although under different aspects of the invention a single size and commonly shaped slit can be provided as in a linear one or one with a non-linear profile as to help avoid retraction until sufficient withdrawal force is applied.

FIG. 194C shows the split collar 500W of FIG. 194B1, but in a partially received stage of insertion of the collar on the instrument 700.

FIG. 194D shows the split collar 500W of FIG. 194B1, in a fully received stage of insertion and with the collar being held in a firm and highly stable three-point "pencil grip" grasp arrangement.

FIG. 194E shows a similar view as in FIG. 194D but in with a different viewpoint of the three-point "pencil grip" grasp arrangement.

It should be noted that features that are described with reference to one or more embodiments are described by way of example rather than by way of limitation to those embodiments. Thus, unless stated otherwise or unless particular combinations are clearly inadmissible, optional features that are described with reference to only some embodiments are assumed to be likewise applicable to all other embodiments also.

FIG. 195 shows an alternate embodiment of collar 630 having a substantially central axial through-hole (not visible in FIG. 195) with a slit 632 shown extending for the full longitudinal length of collar 630 so as to open out at the collar ends. Collar 630 is similar to that shown in FIG. 176 and thus slit 632 extends down into the centralized through-hole (also extending out to opposite ends). Collar 630 has a through-hole with either a constant diameter cross section or one that deviates as in the aforementioned collars such as those in FIGS. 90, 92 and 97. Slit 632 is different than its slit counterpart in FIG. 176 in that it has a non-linear configuration such as a sinusoidal pattern and thus assists in retention of an instrument such as instrument 634 (shown in this embodiment as a probing utensil such as used in the dental industry featuring a narrow tip and a tapering intermediate section extending to a handle or chuck like end (not shown)) until a desired time for removal. Also, alternate non-linear arrangements are also featured as aspects of the invention as in a shallow V or W shape or a zig-zag or saw tooth shape. Also, although the embodiment of FIG. 195 is shown free of a wider slit section (e.g., such as wider slit section 506 shown in FIG. 177), such a tool insertion facilitation configuration is also featured under the illustrated FIG. 195 collar, as in a wider slit section extending linear and over less than a third of the gap length shown in FIG. 195, the remainder preferably having the non-linear configuration.

FIG. 196 shows an example of usage of a collar under the present invention, such as the above referenced collar 630 (or collars such as those in FIGS. 90, 92 and 97), relative to instrument 627 that utilizes, for example, multiple collars 630A and 630B over a length of that instrument. In this regard, FIG. 196 depicts instrument 627 as the deep surgery medical instrument described in US Patent Pub. No. 2015/0148596 to Gitman ("US '596"), which publication is incorporated herein by reference. As described in US '596, deep surgical instrument 627 features rod 636 around which sleeves 630A and 630B extend, with preferably at least one of those sleeves (and optionally both) being a split sleeve (e.g., a collar 630 split sleeve) slideably supported along the length of rod 636. Further, instrument 627 includes handle 633 and working unit 635. To provide an example of a suitable working unit for the extended length instrument 627, FIG. 196 shows a deep surgical scalpel as the working unit 635.

Also, with reference again to FIG. 196, and the various embodiments described in US '596, there can be seen that slit collar usage such as described for sleeves 630A and 630B (representing sleeves 25, 26 in US '596) can also be used for sliding tube receptor purposes or other instrument holder sleeving (e.g., an extended mirror sleeve support). Examples of such additional sleeve configurations and uses can be seen in FIGS. 6 plus of US '596 (e.g., see reference 126 in US '596)). In addition, rather than a slit sleeve, usage of a non-slit collar with good haptic feedback such as the collar in FIG. 78 of the present application is also available for improved slide control and positioning of a collar received on the rod 636. Still further, the inclusion of a wrap of either a non-porous nature (such as the elastic band type wraps of FIG. 184B) or a porous wrap (embodiments of which are described below) is also representative of different aspects of the present invention.

In FIG. 196 each of sleeves 630A and 630B are split sleeves preferably with the non-linear slit configuration shown in FIG. 195; and with the slit preferably being on the underside as to facilitate retention on the rod as the sleeve(s) is/are slid to different positions along the rod 636. For example, the interior of the slit sleeve 630A and/or 630B can have a circular hole 508 as in the earlier embodiments or a non-circular cross-sectioned hole as in a polygonal (square or (elongated) rectangular hole such as hole 508W featured in the embodiment shown in FIG. 194B1, which hole preferably matches the cross sectional configuration of the rod 636. Thus, a square cross-sectioned rod 636 receiving a square sectioned hole of one or more of sleeves 630A and 630B, preferably with a non-linear slit, is an arrangement under the present invention. The frictional relationship between sleeve 630A and/or 630B relative to the exterior of rod (and thus the ease or difficulty in implementing sliding on the rod) is designed with the intended function in mind. Thus, if an instrument is of the nature where an easily slide, but fixed position retention capability (once not in hand forced sliding motion) is desired there is implemented a desired compression level relationship between the collar and the received rod. In other words, a collar, such as one that is adjusted multiple times during a medical procedure, is arranged as to have its preferably elastomeric sleeve interior appropriately sized for such easy sliding of the sleeve along the preferably metal exterior of the rod. If instead, sleeve adjustment is desired to be made more difficult, there can be implemented an even higher level of compression and frictional engagement between the sleeve through-hole (once sleeve closed) and the surface of the rod. Thus, with a sliding sleeve 630A and/or 630B there is made possible a gripping slide relationship along the rod and one that stays on until removal is desired (sanitizing cleaning), with the sinusoidal additional trapping benefit preferred in some embodiments (with or without added wrapping or banding around the sleeve(s) 630A and 630B).

FIGS. 197A to 197C illustrate an alternate technique for using collar 630 (or any of the aforementioned split collar embodiments) relative to a tool whereupon an added wrap is provided to facilitate retention and, for example, provide for a more comfortable and more easily controlled grasping location such as for fine work using the end of the instrument. For instance in FIG. 197A there is shown the same collar 630 of FIG. 195, but with an awl type craftsman instrument 634B which is shown as having a larger circumference received within the slit and through-hole of the collar and thus more of a slit gap is formed upon instrument receipt. Tool or instrument 634B features bulbous handle 638 out from which extends the tipped end extension 640. FIG. 197A also shows an example of a wrapping material which in this case is preferably one that can be readily removed (e.g., removed after the fine work is completed). That is, in FIG. 197A there is shown an example of a preferred wrapping material such as a porous wrapping material (inclusive of one that is self-adhering) such as that represented by the source roll 640 and ripped off segment 642 (collar and wrap kit combination) described above. Still further, rather than the generally cylindrical contoured collars like collars 634A and 634B, multi-wall/multi-recess slit collars such as that shown in FIG. 167A are featured, which in addition to a grasp slide function can also provide additional elongated instrument coupling and positioning control.

As an example of a suitable wrap material, reference is made to roll 640 in the form of a 3M™ VetRap™ Bandaging Tape with Hand Tear Technology Scissors-free application. This wrap has benefits of being a clean, straight tearing wrap material that is not made with natural rubber latex and which sticks to itself without pins or tape and conforms around contours that are difficult to bandage. This material also preferably has the nature of being porous as in the ability to absorb fluid such as an adhesive that provides for below described additional features.

FIG. 197B illustrates collar 630 in a state of being wrapped about tool 634B, while FIG. 197C shows a completed wrap state with the grasping collar shown closer to the free end tip of tool 634B. FIG. 197C also shows the wrapped collar in contact with workpiece WP as to facilitate fine working of the tool tip on the workpiece.

FIGS. 198A and 198B illustrate another advantageous function provided by collar 630 and the above described direct contact wrapping material 642. In the embodiment shown in FIG. 198A, rather than an awl as the slit recipient, there is depicted a part of an ear-bud head set device 644 (more fully shown in FIG. 198B) with ear-bud EB. In FIG. 198A there is shown wire 646 and an earphone unit 648 (e.g., one or more of a microphone, volume adjustment, on/off switch). As is well known, the interface between the wire and an attached unit such as an earphone unit is an area where the wire coating can be detached so as to expose interior wiring (often a common occurrence as well with the plug in the end of a charger wire or ear-bud head set, as in a phone plug (e.g., an I-Phone plug-in end as detailed more below)).

As seen in FIG. 198A, collar 630 bridges the insulated wire portion (that is still covering the interior metal wiring) and unit 648. With sufficiently flexible collar material, the received wire and unit can be positioned in a common configured hole section of the through-hole of the collar or there can be a stepped interior cavity, particularly if the drop down between unit 648 and non-exposed wire is large. This bridging arrangement, and received unit within the slit relationship, provides for a strengthening of what would normally be a weakened, and easily subject to further damage or breakage) region. That is, upon wrapping with tape section 642, which is flexible enough to follow the different contouring of the collar, the slit gap is closed and there is a large friction capture between the non-exposed wire section of wire 646 and the unit 648.

As further shown in FIG. 198B there can be placed insulating and/or waterproof tape TP over the combination of wrap section 642 and collar and received ear-bud assembly, as for waterproofing and/or further insulating purposes. Rather than waterproof tape TP, there can be utilized an applied coating material that can be adsorbed by the porous tape wrap (an example of a suitable coating material includes an adhesive material such as that described below relative to FIG. 200F).

FIG. 198C illustrates the aforementioned highly susceptible to damage area of a wire and phone PH plug-in insert (plug-in insert not shown, but received in the capture recess of the phone) associated with an phone ear-bud head set (in the illustrate example; with another common example being a charger device featuring the same phone plug-in end that often is damaged due to stretching etc. resulting in exposed frayed wiring that often precludes proper operation).

In somewhat similar fashion to the manner of repair described above for the earphone unit 648 of the ear-bud head set device 644, there is provided a collar and wrap combination 650 at another location of the ear-bud head set device 644. Combination 650 provides for a portion of a collar, like collar 630, to come into contact around both the frayed (or exposed) wire section and the non-frayed wire section, wherein the insulated original wire nature is recreated as to avoid further damage or electrical exposure. In other words, the bundle represented by reference number 650 in FIG. 198C is a wrapped collar with wire inserted in the slit and flexible wrapping about the slit collar in similar fashion to the arrangement shown in FIG. 198A. As described above relative to FIG. 198B, there can be applied a coating material over the porous material as in a waterproofing coating layer.

Also, if there is a need for continued access to a portion of the received instrument as in a micro-phone pick-up or a speaker output region, there can be maintained a non-coat region in the wrap such as that exemplified by the dashed zone 651 in FIG. 198C where sound reception and sound output (or any other type of access reason requirement) can be maintained, and only partially disrupted via the porous tape (which access would be not available with electrical tape and similar non-porous wrappings). Additionally, the maintained porous region can be set up so as not to be aligned with the slit/gap region of the collar, with the coating material also being potentially received within the gap region to close it off (and, if it is an adhesive suitable for collar material attachment, can also adhere the gap into a permanently closed state). The wrapping and collar covering of the frayed section (and adhesive coating if present) further strengthens the wiring against over tensioning.

FIG. 198D shows an enlarged view of the phone PH and received plug-in with outer collar-wrap cover combination 650 together with a showing of how readily the plug-in can be grasped (and thus collar-wrap cover combination 650 can also be asserted over a non-damaged wire section to facilitate plug-in and removal via a two finger pinching operation in addition to the repair purpose described).

FIG. 199 shows an alternate embodiment of the present invention featuring a larger collar 630L (e.g., of similar configuration to split sleeves such as those described above including sleeve 630) receiving, within its slit interior, a smaller diametered (and lower length) split sleeve 630S (also preferably having a similar split sleeve configuration like sleeve 630). As further seen in FIG. 199, there is received, within both collars, a wire assembly (e.g., the ear-bud device described above). FIG. 199 also shows an example of the above described damaged (exposed) wire section 646E at the interface of the ear-phone control unit 648L (or some other larger diametered portion of a common instrument). In FIG. 199 the slit of the smaller collar 630S is shown aligned with the slit of the larger collar 630L for viewing purposes. However, in many situations, the slit of the smaller collar 630S is preferably positioned as to be blocked off by the solid wall of the encapsulating larger collar 630L. Thus, a preferred collar 630L and 630S combination features non-aligned slits, as in larger collar 630L receiving collar 630L in a rotated state as compared to that shown in FIG. 199.

The arrangement of FIG. 199 is particularly useful for applications involving a stepped down situation, as where a wire extends into another unit that has a larger diameter and is a region ripe for separation (e.g., when the larger component gets caught and the wire is pulled upon, which tensioning can eventually generate the above noted exposed region of the wire 646E). With the combination featured in FIG. 199, however, there is provided a further damage prevention arrangement. For example (although shown shifted slightly left to show the frayed wire, smaller collar 630S is preferably designed to abut unit 648L at one end and to bridge the fray and contact the adjacent, non-frayed section of the wire 646. Further upon being encapsulated by the larger slit collar 630L, which bridges the smaller collar 630S and the larger ear-phone control unit 649L, there is avoided further stretching of the frayed area as to prolong the life of the wire assembly shown. Also, although not shown there can be provided a wrap over the larger slit collar 630L with a wrap segment such as segment 642 and/or a non-porous tape such as tape TP in FIG. 198B.

Figure 200A:
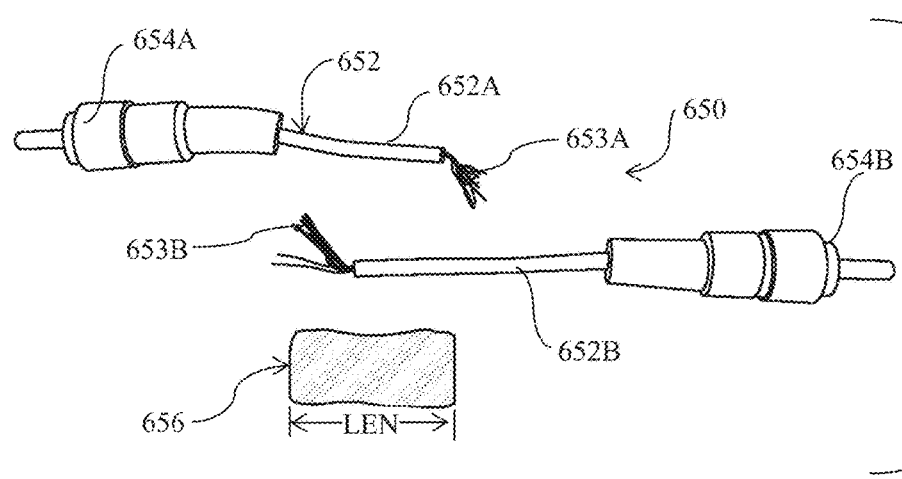

FIGS. 200A to 200F show a system and technique using, to start, a non-slit collar (such as that of FIG. 78 (as an example of a collar choice) which is then slit open to receive a wire assembly, with the combination then being porous material wrapped, and then stiffened/waterproofed with an adhesive or adsorbed coating material. In FIG. 200A there is featured wire assembly 650, which can take on a variety of forms, but in the illustrated embodiment is represented by an electronics communication wire assembly, with elongated insulated wire 652 (shown as having been broken apart as to have first and second wire segments 652A and 652B) and opposite male plugs 654A and 654B. Each of the respective wire segments 652A and 652B have corresponding frayed interior wire material free ends 653A and 653B. Also shown in FIG. 200A, is collar 656 which is non-slit in the condition shown in FIG. 200A. Non-slit collar 656 is shown as being of length LEN and is shown as being in similar form as shown in, for example, FIG. 78, FIG. 97, and FIG. 190A, and thus features a capturing through-hole sufficiently sized over a least a portion of its length to friction capture in a compression state a received wire segment such as 652A. This continuous through-hole can thus be of constant diameter over its length, or of varied cross-sectional diameter, as in a stepped up diameter over a portion of the through-hole length (well suited for attaching different diametered wires) or a varying contoured through-hole diameter, as in one with an intermediate reduction for higher compression on the twisted together exposed wire sections described below.

Figure 200B:
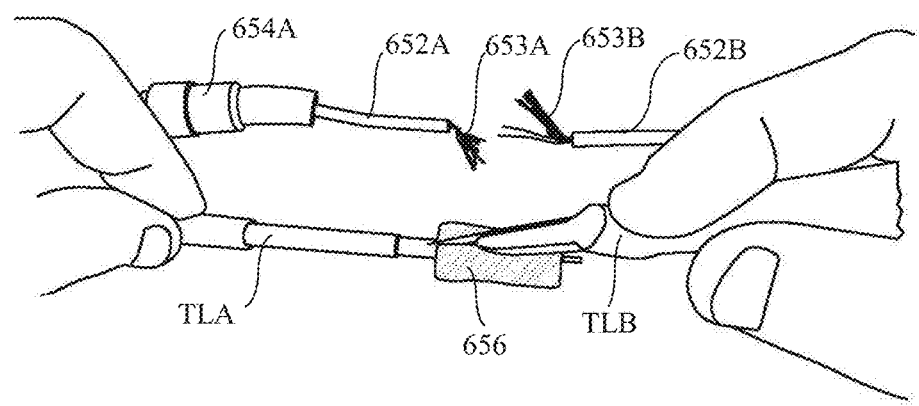

FIG. 200B shows wire assembly 650 still in a broken apart/detached state like that in FIG. 200A, as well as collar 656 being worked on through an operator's use of tools TLA and TLB. Tool TLA represents a collar hold down tool and thus features a tapered free end dimensioned for reception in the through-hole of the collar 656 such that the bottom region of the collar can be pressed down into a supporting surface. At the same time, there is shown tool TLB which is a cutting tool such as a scalpel that is utilized to form a through-slit radially into the collar 656 over its whole length so as to provide access to the full length of the through-hole in collar 656.

Figure 200C:
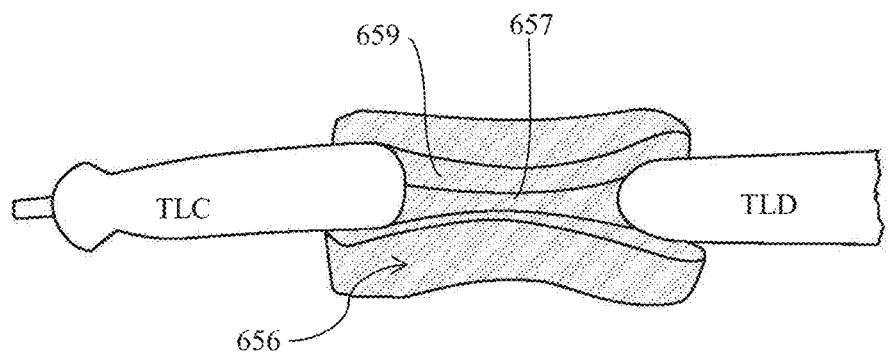
Figure 200D:
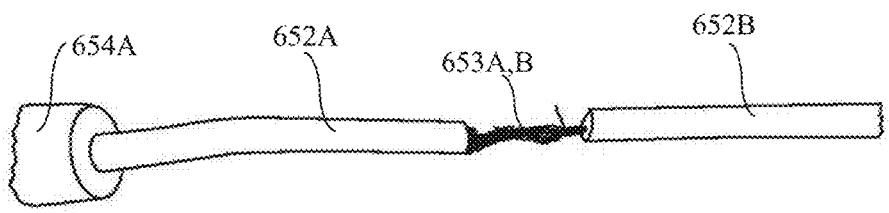

The through-slit formed in collar 656 is illustrated in FIG. 200C wherein opposing cut walls define slit 659, with slit 659 shown extending radially down to collar through-hole 657. In FIG. 200C, tools TLC and TLD are used just for the purpose of spreading apart the normally biased closed elastomeric slit collar (now slit) shown in FIG. 200C for visibility purposes, but can also be used (at least one to provide an easier start) for coupled wire insertion into the collar as explained below. Again, a slit widening as in section 506 in FIG. 177 is also an aspect of the present invention and provides for easier insertion of the coupled wire set into the collar as represented by FIG. 200D. That is, FIG. 200D shows the two previous independent/separated wire segments 652A and 652B now having been coupled together into an electricity passage state by the common twisting together of frayed interior wire material free ends 653A and 653B.

Figure 200E:
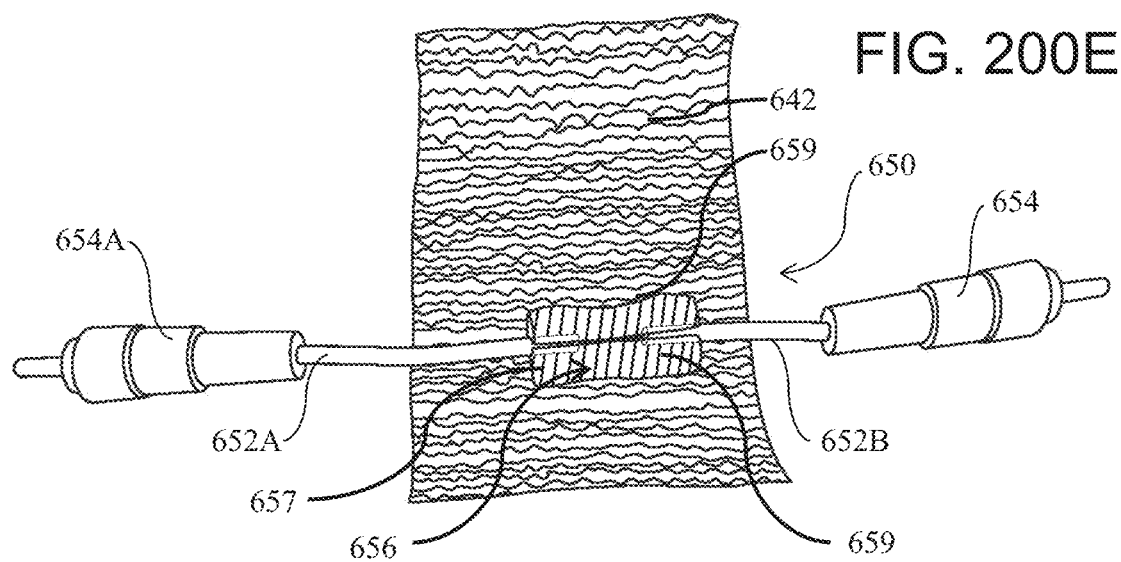

FIG. 200E shows coupled wire assembly 650 of FIG. 200D inserted into slit 659 of collar 656 (shown in cross-section in FIG. 200E). As further seen in FIG. 200E, the through-hole 657 formed in collar 656 has a stepped diameter cross-section arrangement design with larger diameter cavity ends (but still suited to clamp down to fix the insulated/inserted ends of respective wire segments) and a smaller diameter intermediate cavity section designed to extend a similar distance as the thickness of the insulation as to come into contact with the coupled frayed interior wire material free ends 653A and 653B (although there is featured a varying contoured through-hole in FIG. 200E, a non-varying, suitably sized through-hole for receiving the coupled wire ends is also another aspect of the invention). Collar 656 is further shown resting on the yet to be wrapped porous wrap 642 previously described relative to FIG. 197A.

Figure 200F:
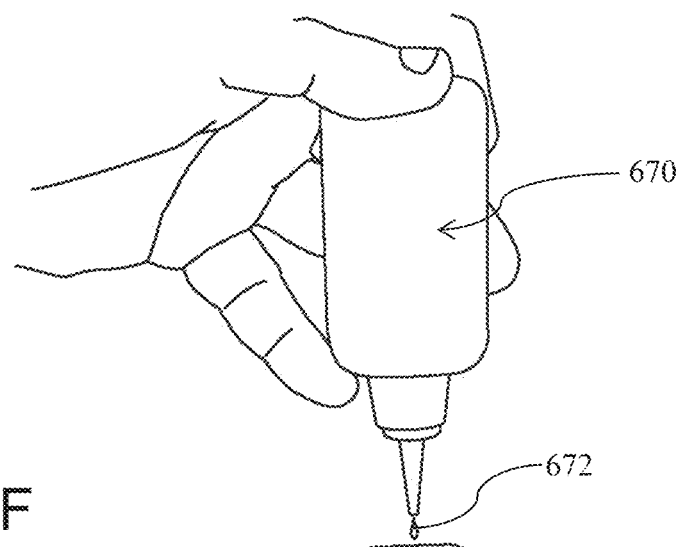

FIG. 200F shows both collar 656 and the received coupled portion of wire assembly 650 (in the condition shown in FIG. 200E) having been wrapped up within wrap 642, which wrap is shown as extending out away from each end of collar 656 such that when the wrap (e.g., an elastic self-adhesive wrap) is wrapped around the collar, it also wraps around wire segments 652A and 652B as to join the entire assembly within a fixing wrap state. Moreover in view of the flexible nature of the wrap it is possible to bend the wire into a desired state, as in the straight configuration shown, or one that has another angle (e.g., a right, an acute angle or an obtuse angle) better suited for the intended environment of use. FIG. 200F further shows a coating supply bottle 670 for supplying waterproofing and/or rigidity changing usage material 672, which material is also preferably non-conductive like the rest of the entire assembly components shown in FIG. 200F (except for the conducting portion of the wire itself represented by the interior wire material free ends 653A and 653B). With the use of the porous wrap 642, material 672 is readily absorbed along the wrap's exposed surface, as well as inward through the porous wrap as to close up any gaps left, for example, by slit 659. A suitable material 672, both relative to being non-conductive and of a setting adhesive for improved assembly bonding as well as a final angled (or not-linear) shape in assembly 650, is an adhesive such as cyanoacrylate adhesive.

Thus, there is provided a fully insulating enclosure for the coupled wire assembly 650 with a low profile as compared to many of the prior art devices which utilize screw clamps in a unitary plastic receiving body.

Thus, in an embodiment of the present invention there is provided a technique for combining previously detached components of an assembly, such as the illustrated respective wire components of wire assembly 650 in FIGS. 200A to 200D. Under this technique (no particular order being intended to be represented by the lettering in parenthesis) there is carried out steps of (a) slitting a non-slit collar as to provide access to a through-hole of the described collar (or if a collar is a slit collar already, this step can be skipped); (b) combining the detached components of an assembly, as in twisting together the noted frayed exposed wire ends; (c) inserting a portion (e.g., the coupled wire portion) of the combined (potentially formerly detached) assembly within the slit and into the through-hole of the collar; and, once the portion is received, (d) wrapping around the collar a wrap, as in a porous (preferably self-adhesive) wrap; once wrapped, (e) the wire assembly (with wrapped collar attachment) can optionally be further modified by supplying another layer or coating within and/or over the wrap material, as in a material that satisfies one or more (e.g., all) of the categories of being non-conducting, waterproof, capable of hardening into a fixed position, or adhesive.

Just some of the above method steps (a) to (e) can also be carried, as in relative to FIG. 197C wherein only the insertion into the collar of an instrument and the wrapping of the collar with contained instrument is carried out; while another example involves all but step (b), as in a situation such as shown in FIG. 198C where the inserted component of an assembly is damaged (but not yet in a separated state) into a collar, and the collar and the inserted instrument is then wrapped with wrapping material followed by adding material such as an adhesive or another layer (tape) applied about the prior wrap.

While the above methods are shown as being carried out on a mechanical (wire assembly), some of the above method techniques and associated systems can also be carried out for medical purposes. For instance, providing a tourniquet to a body part or providing an immobilizing devices such as a cast or splint to a body part. In each situation, an appropriate kit of present invention components is provided for carrying out the described tourniquet or immobilizing technique (e.g., cast or splint technique). As an example of tourniquet use, a split collar is provided in a region of a flesh cut that is bleeding so as to provide tourniquet application means. In an example of a cast or a splint application, a collar under the present invention is applied over a broken or fractured limb, digit or other broken, sprained or fractured body part. In this regard, reference is made to FIGS. 201A to 201D which show a system and technique for a tourniquet application and a system and technique for a cast or splint application providing means for immobilization and position retention.

Figure 201A:
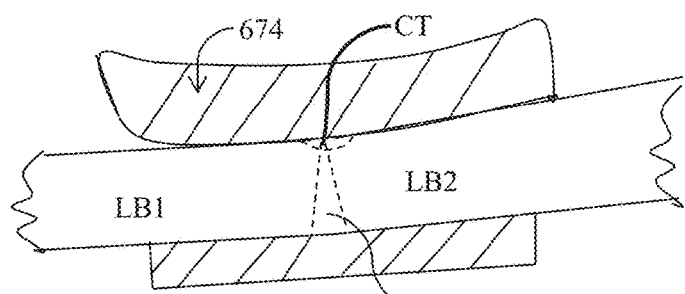

With reference to FIG. 201A there can be seen limb LB with a cut CT. Limb LB is shown received within collar 674 designed to receive limb LB as to preferably have, in its natural biased closed state, a minor degree of flesh compression that is not sufficient to stop blood flow within the encompassed body part (suitably elastomeric compression as to avoid internal blow flow stoppage while providing for friction contact over at least a majority (and preferably greater than 75% of the received body part)). Material, such as described above (e.g., a latex free silicon elastomeric material as in one with a range of 40 to 60 durometer, in similar fashion to that described above in other uses for collars of the present invention) can be used for collar 674.

In a situation where there is only a cut or some other manner of blood flow to the surface of the flesh, collar 674 is utilized as a tourniquet, by way of hand compression of the collar about the limb that is sufficient to achieve a stoppage of blood flow internally within the limb; and, in so doing, a stoppage of blood flow externally within the cut area (or a tightening band can be used in combination with collar 674 to achieve even a higher assurance of blood flow stoppage). Upon a desire to enable internal blood flow within the limb to avoid degradation of the limb until further treatment can be carried out, the compression can be stopped, but the collar generally retained in place, and in a state ready to repeat a rapid compression imposition when desired. Further the slit can be either positioned away from the cut region (wherein a solid wall of the collar extends into contact with the cut) or, more preferably under some situations, the slit can be aligned to extend over the cut or source of external bleeding as to provide more ready access (e.g., visibility and/or shots) to the cut region as well as avoidance of direct compression on a sensitive/nerve exposed area.

Collar 674 (or a similar equivalent to collar 674 designed for the size and configuration of the intended body part) can be used to immobilize a body part such as a limb (inclusive of limb joint areas as in ankles and wrists, etc.) or used as a foundation for a splint. This immobilization (or substantial immobilization in view of the preferably flexible material of collar 674 in the interior cavity surface of the collar that comes in contact with the body part) can be used to provide support for sprains and strains. In situations where a prolonged immobilization is desired, there is provided a cast featuring collar 674 as the foundation plus a wrap, as in the porous wrap described above, and for a firmer cast there is added firming material to the wrap as to harden it to the state of not being readily bent out of a preset configuration.

To illustrate such medical immobilization techniques, attention is again directed at FIG. 201A showing a fracture or break section FR relative to the limb LB received in collar 674. There is further referenced limb sections LB1 and LB2 to indicate the limb portions extending to opposite sides of a fracture or break line.

Figure 201B:
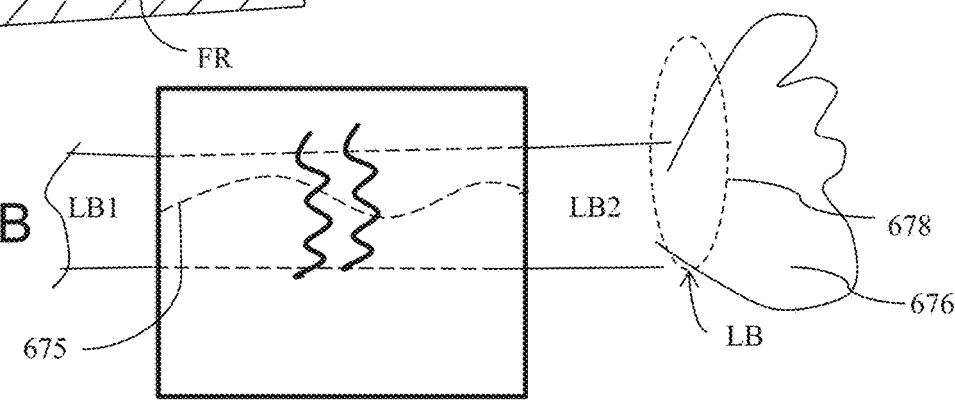
Figure 201C:
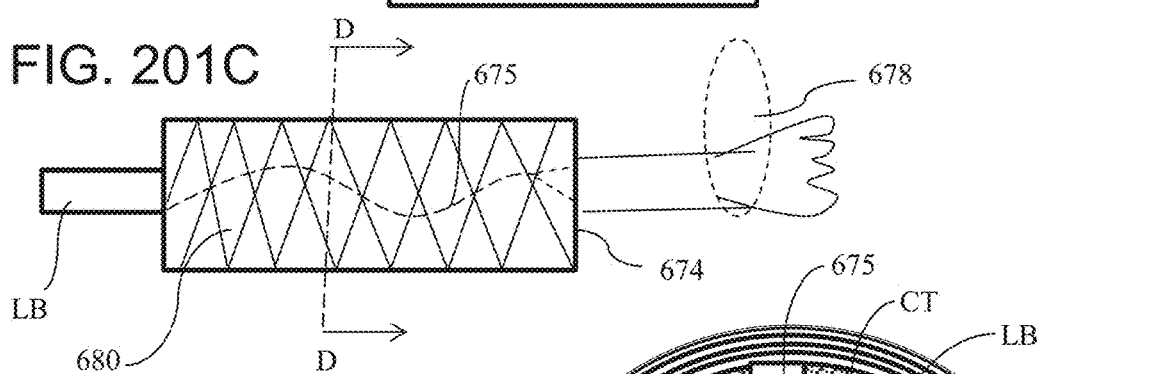

FIG. 201B illustrates the same limb sections LB1 and LB2, but with collar 674 not shown in cut-away view, but encircling each of LB1 and LB2, as in after those limb sections have been appropriately re-set in the event of a break and received with collar 674. FIG. 201B also shows slit 675 as being non-linear (similar to the arrangement shown in FIG. 195). Again, a variety of body parts can be placed within a casting or splint collar assembly under the present invention. FIG. 201C also shows a diverging slit section like gap 506 like that in FIG. 177, which facilitates an initial insertion of a limb within the confines of the collar by facilitating initiation of slit separation. Alternatively (or in addition) the slit extends both above and below the interior through-hole with such a deeper slit formation providing more of a clam shell clamping arrangement which also facilitates body part insertion with minimal pain.

To illustrate some of the choices in body part immobilization there is shown in FIG. 201B arm 676 positioned within collar 674 (or optionally a leg as represented by dashed foot depiction 678). An additional non-limiting collar immobilization body part region includes fingers and toes with the collar being appropriately modified in size relative to the typical range of size of the body part to be immobilized.

FIG. 201C illustrates another step in limb cast formation featuring the wrapping of collar 674 with wrap 680 which in a preferred embodiment is a porous, self-adhering wrap such as the wrap 642 material (e.g., the noted 3M™ VetRap™ Bandaging Tape material). Furthermore, depending upon the degree of immobilization (e.g., sprain vs break immobilization levels) there can be provided a hardening material such as one that soaks into a porous wrap and sets.

Figure 201D:
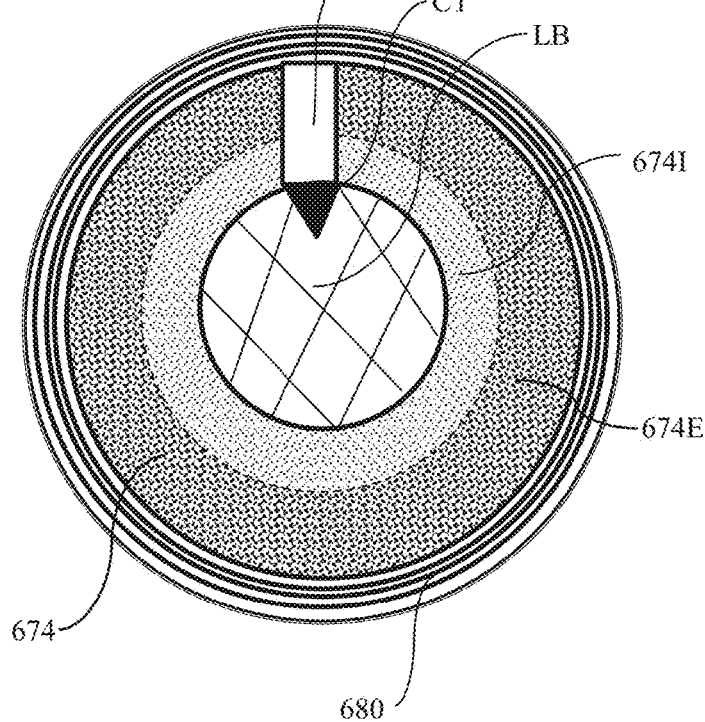

FIG. 201D provides a cross-section view taken at cross-section line D-D in FIG. 201C. As shown, collar 674 encircles limb LB and includes slit 675 (shown as lined up with cut CT in this embodiment). FIG. 201D also shows, by way of a darkness or density differential, an aspect of the invention wherein the preferably unitary (monolithic) formed collar (injection molded for example) has a varying hardness density in its radial depth. For example, there can be provided a softer interior material layer 6741 better suited for direct limb contact. The softer interior material layer 6741 can have a softer durometer material range (e.g., a lower end half of a 40 to 60 durometer range as in 40 to 50 durometer with 40 durometer being an example of a softer material value) for its interior collar body part contact material layer 6741. This softer material is shown in FIG. 201D as being encircled by a higher durometer level exterior collar material 674E (e.g., a value occupying the upper half range of 40 to 60 as in 50 to 60D value range, and preferably one having a 60 durometer value). Rather than the illustrated monolithic formation using different blends of elastomer in radial sequence (an injection molding sequenced injection), there can be also featured independent laminate layering of different (e.g., preformed layers) which are preferably adhered together layers, as in adhesive joined laminate layer build-up of similar type material as described from the monolithic body). While a generally 50/50 depth split in radial depth differential for hard and soft material is featured in the FIG. 201D embodiment, there can be provided a different percentage harder/softer split, as in a range of 20 to 80 radial coverage in the softer material (with the 20% softer material example being one that provides a firmer and more immobilizing cast embodiment). Alternatively, a continuous or more graduated approach in going from soft to hard material can be utilized in the radial depth of the collar.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims. Further any range presented in the present application is intended to encompass each value within that range relative to a common and appropriate level of unit specificity (e.g., 0.5 value increases and decreases relative to specific end point values within the above described durometer ranges (e.g., 40.0 to 40.5 and 50.0 to 49.5 durometer; and 0.1 increases and decreases in length ranges and 3.1 to 3.2 mm for referenced mm length ranges.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g., each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below. This completes the description of the preferred and alternate embodiments of the invention. Those skilled in the art may recognize other equivalents to the specific embodiment described herein which equivalents are intended to be encompassed by the claims attached hereto.

What is claimed is:

1. A grasping collar comprising:
a flexible body having an exterior surface with surface cavities configured for finger reception;
a hole extending within an interior region of the body along an X-axis direction and being a through-hole relative to the body;
an elongated slit extending in the X-axis direction, and in a radially inward direction from an exterior surface of the body into communication with the hole, the elongated slit including a thinner slit section extending in the X-axis direction for a portion of an overall length of the body as well as a wider slit section extending in the X-axis direction for a remaining portion of the overall length of the body, and wherein the surface cavities that are configured for finger reception are spaced circumferentially apart about an external periphery of the collar, and each of the surface cavities includes an area of maximum radial depression that extends at least within an intermediate area of the external periphery of the collar and between opposite, external ends of the overall length of the body, and wherein the surface cavities are inclusive of surface cavities that are most elongated in the X-axis direction.

2. The grasping collar of claim 1 wherein the wider slit section has side walls that diverge apart in going from a border region with the thinner slit section to a free end of the body.

3. The grasping collar of claim 1 wherein the thinner slit section is longer than the wider slit section.

4. The grasping collar of claim 1 wherein the wider slit section has converging walls that converge in an exterior to interior radial direction relative to the flexible body.

5. The grasping collar of claim 1 wherein walls of the body defining the thinner slit section are in contact when the collar is in a natural state.

6. The grasping collar of claim 1 wherein wall surfaces defining the thinner slit section extend into common side wall surfaces defining the wider slit section in a smooth, non-interrupted fashion.

7. The grasping collar of claim 1 wherein the collar is a monolithic component formed of a flexible material.

8. The grasping collar of claim 1 wherein the collar is monolithic as to be formed entirely of a single material selected from the group consisting of silicone rubber, natural rubber, PVC, polyurethane, PE, PP, polyester, PEEK, polyphenylsulfone, nylon, or a latex free rubber.

9. The grasping collar of claim 1 wherein the minimum diameter of the hole is larger than a gap thickness between opposing body walls defining the thinner slit section.

10. The grasping collar of claim 9 wherein the hole has a taper that converges in the X-axis direction from a proximal end of the collar to a distal, working end of the collar.

11. The grasping collar of claim 1 wherein the body has a pair of surface cavities to opposite sides of the slit formed in the body.

12. The grasping collar of claim 11 wherein the body has a circular or oval shaped cross-sectional configuration.

13. The grasping collar of claim 1 wherein the body has a first exposed surface in which is formed the slit and a second exposed surface opposing the first exposed surface in which the slit is not formed.

14. The grasping collar of claim 13 wherein the opposing first and second exposed surfaces include parallel sections.

15. The grasping collar of claim 1 wherein the hole extending in the X-axis direction slopes from a higher proximal collar end position to a lower distal collar end position.

16. A method of forming the grasping collar of claim 1 including molding the body and forming the slit therein.

17. The method of claim 16 wherein the slit is formed during the molding of the body.

18. A method of assembly an instrument assembly including inserting an instrument within the slit of the grasping collar of claim 1.

19. The method of claim 18 wherein the inserting of the instrument includes inserting a portion of the instrument within the wider gap and then further forcing the instrument as to separate side walls of the thinner slit section until the instrument is received partially or wholly within the hole of the body.

20. A method of providing a needle assembly securement to a surface, comprising: separating different regions of the collar of claim 1 to opposite sides of the collar to form a wing expansion configuration having spaced apart wing regions and a needle assembly positioned between the wing regions, and securing the wing regions to a surface as to retain a separation of the different regions of the collar with the needle assembly positioned between the different regions of the collar.

21. The grasping collar of claim 1 wherein the wider and thinner slits extend radially inward to intersect the hole which has a common diameter over the overall length of the body.

22. The grasping collar of claim 1 wherein the elongated slit is formed in one of the surface cavities.

23. The grasping collar of claim 1 wherein the hole extending within the interior region of the body has a non-circular, radially elongated cross-sectional configuration.

24. An assembly that comprises the grasping collar of claim 1 and a received component, and wherein the received component has a periphery or a peripheral portion that is configured to be larger than a periphery or a peripheral portion of the hole of the collar.

25. The grasping collar of claim 1 wherein walls of the body defining the thinner slit section are free from contact when the collar is in a natural state.

26. A grasping collar comprising:
a flexible body having an exterior surface with surface cavities configured for finger reception;
a hole extending within an interior region of the body along an X-axis direction and being a through-hole relative to the body;
an elongated slit extending in the X-axis direction, and in a radially inward direction from an exterior surface of the body into communication with the hole, the elongated slit including a thinner slit section extending in the X-axis direction for a portion of an overall length of the body as well as a wider slit section extending in the X-axis direction for a remaining portion of the overall length of the body, and wherein the body includes four surface cavities which are corner recesses, and between respective pairs of the corner recesses projections, with the projections including an opposing pair of first length side wall projections and an opposing pair of second length side wall projections, which second length side wall projections are shorter in length than first length side wall projections.

27. The grasping collar as recited in claim 26 wherein the slit extends along the X-axis and intersects the longer length side wall projections.

28. The grasping collar of claim 27 wherein the projections having longer side walls extend out from a center of the body to a lesser extent than the projections having shorter length side walls.

29. A grasping collar comprising:
a flexible body having an exterior surface with surface cavities configured for finger reception;
a hole extending within an interior region of the body along an X-axis direction and being a through-hole relative to the body;
an elongated slit extending in the X-axis direction, and in a radially inward direction from an exterior surface of the body into communication with the hole, the elongated slit including a thinner slit section extending in the X-axis direction for a portion of an overall length of the body as well as a wider slit section extending in the X-axis direction for a remaining portion of the overall length of the body,
wherein the body has a first exposed surface in which is formed the slit and a second exposed surface opposing the first exposed surface in which the slit is not formed,
wherein the opposing first and second exposed surfaces include parallel sections, and wherein the opposing first and second exposed surfaces include a tapered surface that slopes outward in the X-axis direction and radially inward to a free edge region of the body.

30. The grasping collar of claim 29 wherein each of the first and second exposed surfaces has a tapered surface that slopes outward and inward to respective free edge regions of the body.

31. A grasping collar comprising:
a flexible body having an exterior surface with surface cavities configured for finger reception;
a hole extending within an interior region of the body along an X-axis direction and being a through-hole relative to the body;
an elongated slit extending in the X-axis direction, and in a radially inward direction from an exterior surface of the body into communication with the hole, the elongated slit including a thinner slit section extending in the X-axis direction for a portion of an overall length of the body as well as a wider slit section extending in the X-axis direction for a remaining portion of the overall length of the body, and wherein the surface cavities that are configured for finger reception are spaced circumferentially apart about an external periphery of the collar, and each of the surface cavities includes an area of maximum radial depression that extends at least within an intermediate area of the external periphery of the collar and between opposite, external ends of the overall length of the body, and wherein the surface cavities configured for finger reception each have an annular border edge rim that is entirely positioned inward along the X-axis between the opposite ends of the overall length of the body.

32. A grasping collar comprising:
a flexible body having an exterior surface with surface cavities configured for finger reception;
a hole extending within an interior region of the body along an X-axis direction and being a through-hole relative to the body;
an elongated slit extending in the X-axis direction, and in a radially inward direction from an exterior surface of the body into communication with the hole, the elongated slit including a thinner slit section extending in the X-axis direction for a portion of an overall length of the body as well as a wider slit section extending in the X-axis direction for a remaining portion of the overall length of the body, and wherein the surface cavities that are configured for finger reception are spaced circumferentially apart about an external periphery of the collar, and each of the surface cavities includes an area of maximum radial depression that extends at least within an intermediate area of the external periphery of the collar and between opposite, external ends of the overall length of the body, and wherein the surface cavities configured for finger reception have a common radial depth over an entire extension along the X-axis.

33. The grasping collar of claim 32 wherein the surface cavities are formed at corners of opposing pairs of planar surfaces.

34. A grasping collar comprising:
a flexible body having an exterior surface with surface cavities configured for finger reception;

a hole extending within an interior region of the body along an X-axis direction and being a through-hole relative to the body;

an elongated slit extending in the X-axis direction, and in a radially inward direction from an exterior surface of the body into communication with the hole, the elongated slit including a thinner slit section extending in the X-axis direction for a portion of an overall length of the body as well as a wider slit section extending in the X-axis direction for a remaining portion of the overall length of the body, and wherein the surface cavities that are configured for finger reception are spaced circumferentially apart about an external periphery of the collar, and each of the surface cavities includes an area of maximum radial depression that extends at least within an intermediate area of the external periphery of the collar and between opposite, external ends of the overall length of the body, and wherein the surface cavities configured for finger reception extend for the full overall X-axis length of the collar.

35. A grasping collar comprising:
a flexible body having an exterior surface with surface cavities configured for finger reception;
a hole extending within an interior region of the body along an X-axis direction and being a through-hole relative to the body;
an elongated slit extending in the X-axis direction, and in a radially inward direction from an exterior surface of the body into communication with the hole, the elongated slit including a thinner slit section extending in the X-axis direction for a portion of an overall length of the body as well as a wider slit section extending in the X-axis direction for a remaining portion of the overall length of the body, and wherein the surface cavities that are configured for finger reception are spaced circumferentially apart about an external periphery of the collar, and each of the surface cavities includes an area of maximum radial depression that extends at least within an intermediate area of the external periphery of the collar and between opposite, external ends of the overall length of the body, and wherein the collar has, relative to the X-axis extension of the collar, an intermediate waist depression circumferentially extending about the collar.

36. The grasping collar of claim 35 wherein the surface cavities are circumferentially spaced apart within the intermediate waist depression of the collar.

37. A grasping collar comprising:
a flexible body having an exterior surface with surface cavities configured for finger reception;
a hole extending within an interior region of the body along an X-axis direction and being a through-hole relative to the body;
an elongated slit extending in the X-axis direction, and in a radially inward direction from an exterior surface of the body into communication with the hole, the elongated slit including a thinner slit section extending in the X-axis direction for a portion of an overall length of the body as well as a wider slit section extending in the X-axis direction for a remaining portion of the overall length of the body, and wherein the surface cavities that are configured for finger reception are spaced circumferentially apart about an external periphery of the collar, and each of the surface cavities includes an area of maximum radial depression that extends at least within an intermediate area of the external periphery of the collar and between opposite, external ends of the overall length of the body, and wherein at least the thinner slit section has a non-linear slit configuration along the X-axis direction.

38. A grasping collar assembly comprising a grasping collar comprising:
a flexible body having an exterior surface with surface cavities configured for finger reception;
a hole extending within an interior region of the body along an X-axis direction and being a through-hole relative to the body;
an elongated slit extending in the X-axis direction, and in a radially inward direction from an exterior surface of the body into communication with the hole, the elongated slit including a thinner slit section extending in the X-axis direction for a portion of an overall length of the body as well as a wider slit section extending in the X-axis direction for a remaining portion of the overall length of the body, and wherein the surface cavities that are configured for finger reception are spaced circumferentially apart about an external periphery of the collar, and each of the surface cavities includes an area of maximum radial depression that extends at least within an intermediate area of the external periphery of the collar and between opposite, external ends of the overall length of the body, and a wrap extending about the collar as to extend across the elongated slit.

\* \* \* \* \*